US012662686B2

(12) United States Patent
Wolfe et al.

(10) Patent No.: US 12,662,686 B2
(45) Date of Patent: Jun. 23, 2026

(54) COMPOSITIONS AND METHODS FOR MODIFYING EUKARYOTIC CELLS

(71) Applicant: Orchard Therapeutics (Europe) Limited, London (GB)

(72) Inventors: Jia Wolfe, Winchester, MA (US); Pervinder Sagoo, St Albans (GB)

(73) Assignee: Orchard Therapeutics (Europe) Limited, London (GB)

( * ) Notice: Subject to any disclaimer, the term of this patent is extended or adjusted under 35 U.S.C. 154(b) by 1144 days.

(21) Appl. No.: 17/615,773

(22) PCT Filed: Jun. 5, 2020

(86) PCT No.: PCT/US2020/036415

§ 371 (c)(1),
(2) Date: Dec. 1, 2021

(87) PCT Pub. No.: WO2020/247814

PCT Pub. Date: Dec. 10, 2020

(65) Prior Publication Data

US 2023/0002784 A1 Jan. 5, 2023

Related U.S. Application Data

(60) Provisional application No. 62/857,587, filed on Jun. 5, 2019.

(51) Int. Cl.

| | |
|---|---|
| ***C12N 15/86*** | (2006.01) |
| ***C07D 491/048*** | (2006.01) |
| ***C07D 491/052*** | (2006.01) |
| ***C07D 498/18*** | (2006.01) |

(52) U.S. Cl.

CPC ......... *C12N 15/86* (2013.01); *C07D 491/048* (2013.01); *C07D 491/052* (2013.01); *C07D 498/18* (2013.01)

(58) Field of Classification Search

None

See application file for complete search history.

(56) References Cited

U.S. PATENT DOCUMENTS

| | | | |
|---|---|---|---|
| 5,093,330 | A | 3/1992 | Caravatti et al. |
| 5,264,431 | A | 11/1993 | Wacker et al. |
| 5,461,146 | A | 10/1995 | Lewis et al. |
| 5,624,949 | A | 4/1997 | Heath, Jr. et al. |
| 5,756,494 | A | 5/1998 | Lewis et al. |
| 5,801,030 | A | 9/1998 | McVey et al. |
| 6,057,117 | A | 5/2000 | Harrison et al. |
| 6,080,398 | A | 6/2000 | Pelus et al. |
| 6,136,597 | A | 10/2000 | Hope et al. |
| 6,333,194 | B1 | 12/2001 | Levy et al. |
| 6,399,053 | B1 | 6/2002 | Pelus et al. |
| 6,447,766 | B1 | 9/2002 | Pelus et al. |
| 6,608,063 | B2 | 8/2003 | Nuss et al. |
| 6,610,719 | B2 | 8/2003 | Paralkar et al. |
| 6,747,037 | B1 | 6/2004 | Old et al. |
| 6,987,102 | B2 | 1/2006 | Bridger et al. |
| 7,897,590 | B2 | 3/2011 | Bridger et al. |
| 7,935,692 | B2 | 5/2011 | Bridger et al. |
| 8,927,281 | B2 | 1/2015 | Boitano et al. |
| 9,150,605 | B2 | 10/2015 | Allerson et al. |
| 9,272,043 | B2 | 3/2016 | Saltzman et al. |
| 9,409,906 | B2 | 8/2016 | Sauvageau et al. |
| 9,580,426 | B2 | 2/2017 | Boitano et al. |
| 2002/0019357 | A1 | 2/2002 | Braun |
| 2003/0206910 | A1 | 11/2003 | Nicol et al. |
| 2004/0092535 | A1 | 5/2004 | Barsanti et al. |
| 2004/0209878 | A1 | 10/2004 | Guzi et al. |
| 2005/0020570 | A1 | 1/2005 | Griffin et al. |

(Continued)

FOREIGN PATENT DOCUMENTS

| | | | |
|---|---|---|---|
| CN | 103958667 | A | 7/2014 |
| CN | 108713059 | A | 10/2018 |

(Continued)

OTHER PUBLICATIONS

Chang et al. (Transplant International, 2005, p. 871-878).*

Takahashi et al., "Induction of Pluripotent Stem Cells from Mouse Embryonic and Adult Fibroblast Cultures by Defined Factors," Cell. 126: 663-676 (2006).

Borel et al., "Recombinant AAV as a Platform for Translating the Therapeutic Potential of RNA Interference," Molecular Therapy. 22(4): 692-701 (2014).

Rao et al., "siRNA vs. shRNA: Similarities and differences," Advanced Drug Delivery Reviews. 61: 746-759 (2009).

Lam et al., "siRNA Versus miRNA as Therapeutics for Gene Silencing," Mol Ther Nucleic Acids. 4:e252:1-20 (2015) (20 pages).

O'Doherty et al., "Human Immunodeficiency Virus Type 1 Spinoculation Enhances Infection through Virus Binding," American Society for Microbiology Journal of Virology. 74(21): 10074-10080 (2000) (16 pages).

(Continued)

*Primary Examiner* — Agnieszka Boesen

(74) *Attorney, Agent, or Firm* — Clark & Elbing LLP

(57) ABSTRACT

Described herein are compositions and methods for modifying eukaryotic cells, for example, to express a transgene of interest and/or to produce an expanded population of cells ex vivo. Using the compositions and methods of the disclosure, a population of eukaryotic cells, such as a population of pluripotent cells (e.g., CD34+ hematopoietic stem or progenitor cells) may be transduced to express a gene of interest by contacting the cells with a viral vector, such as a lentiviral vector, and a poloxamer. Additionally, the compositions and methods described herein can be used to promote the proliferation or survival of a population of pluripotent cells (e.g., CD34+ hematopoietic stem or progenitor cells) ex vivo, for example, by contacting the cells with a poloxamer. Examples of poloxamers that may be used in conjunction with the compositions and methods of the disclosure are those having a molar mass in excess of 10,000 g/mol, as well as those having a molar mass of polyoxypropylene subunits greater than 2,000 g/mol and/or an ethylene oxide content of greater than 40% by mass.

20 Claims, 4 Drawing Sheets

Specification includes a Sequence Listing.

(56) References Cited

U.S. PATENT DOCUMENTS

| | | | | |
|---|---|---|---|---|
| 2006/0013883 | A1* | 1/2006 | Nicol | A61P 35/00 514/44 R |
| 2006/0247214 | A1 | 11/2006 | DeLong et al. | |
| 2010/0178271 | A1 | 7/2010 | Bridger et al. | |
| 2015/0064788 | A1 | 3/2015 | Anastasov et al. | |
| 2015/0307900 | A1 | 10/2015 | Johnston et al. | |
| 2017/0037047 | A1 | 2/2017 | Sauvageau et al. | |
| 2017/0087219 | A1 | 3/2017 | Bunting et al. | |
| 2017/0121454 | A1 | 5/2017 | Saltzman et al. | |

FOREIGN PATENT DOCUMENTS

| | | | |
|---|---|---|---|
| WO | WO-91/09034 | A1 | 6/1991 |
| WO | WO-93/07153 | A1 | 4/1993 |
| WO | WO-94/11026 | A2 | 5/1994 |
| WO | WO-00/23567 | A2 | 4/2000 |
| WO | WO-00/38663 | A2 | 7/2000 |
| WO | WO-00/47186 | A1 | 8/2000 |
| WO | WO-01/12596 | A1 | 2/2001 |
| WO | WO-01/34843 | A1 | 5/2001 |
| WO | WO-2004/044136 | A2 | 5/2004 |
| WO | WO-2004/050027 | A2 | 6/2004 |
| WO | WO-2004/104025 | A1 | 12/2004 |
| WO | WO-2006/086775 | A2 | 8/2006 |
| WO | WO-2007/071456 | A1 | 6/2007 |
| WO | WO-2007/112084 | A2 | 10/2007 |
| WO | WO-2010/108028 | A2 | 9/2010 |
| WO | WO-2013/127964 | A1 | 9/2013 |
| WO | WO-2015/162302 | A2 | 10/2015 |
| WO | WO-2017/139576 | A1 | 8/2017 |
| WO | WO-2018/046774 | A1 | 3/2018 |
| WO | WO-2018/183692 | A1 | 10/2018 |
| WO | WO-2020/247814 | A1 | 12/2020 |
| WO | WO-2021/076993 | A1 | 4/2021 |

OTHER PUBLICATIONS

Guo et al., "Spinoculation Triggers Dynamic Actin and Cofilin Activity That Facilitates HIV-1 Infection of Transformed and Resting CD4 T Cells," American Journal of Microbiology Journal of Virology. 85(19): 9824-9833 (2011) (15 pages).

Millington et al., "Towards a Clinically Relevant Lentiviral Transduction Protocol for Primary Human $CD34^+$ Hematopoietic Stem/Progenitor Cells," PLoS One. 4(7): e6461 (2009) (10 pages).

Delenda, "Lentiviral vectors: optimization of packaging, transduction and gene expression," J Gene Med. 6: S125-S138 (2004).

Osborn et al., "A Picornaviral 2A-Like Sequence-Based Tricistronic Vector Allowing for High-Level Therapeutic Gene Expression Coupled to a Dual-Reporter System," Molecular Therapy. 12(3): 569-574 (2005).

Klump et al., "Retroviral vector-mediated expression of HoxB4 in hematopoietic cells using a novel coexpression strategy," Gene Therapy. 8(10):811-817 (2001).

Yoder et al., "HIV Envelope-CXCR4 Signaling Activates Cofilin to Overcome Cortical Actin Restriction in Resting CD4 T Cells," Cell. 134: 782-792 (2008).

Lewis et al., "Staurosporine Increases Lentiviral Vector Transduction Efficiency of Human Hematopoietic Stem and Progenitor Cells," Mol Ther Methods Clin Dev. 9:313-322 (Apr. 2018).

Kim et al., "PEO-PPO Diblock Copolymers Protect Myoblasts from Hypo-Osmotic Stress In Vitro Dependent on Copolymer Size, Composition, and Architecture," Biomacromolecules. 18(7):2090-101 (2017).

International Search Report and Written Opinion for International Application No. PCT/US2020/056123, mailed Feb. 1, 2021 (13 pages).

International Preliminary Report on Patentability for International Application No. PCT/US2020/056123, issued Apr. 19, 2022 (5 pages).

International Search Report and Written Opinion for International Application No. PCT/US2020/036415 mailed Sep. 28, 2020 (13 pages).

International Preliminary Report on Patentability for International Application No. PCT/US2020/036415 issued Dec. 7, 2021 (5 pages).

Uchida et al., "High-Efficiency Lentiviral Transduction of Human $CD34^+$ Cells in High-Density Culture with Poloxamer and Prostaglandin E2," Mol Ther Methods Clin Dev. 13:187-196 (2019).

Dishart et al., "Third-generation lentivirus vectors efficiently transduce and phenotypically modify vascular cells: implications for gene therapy," J Mol Cell Cardiol. 35(7):739-48 (2003).

Strappe et al., "Delivery of a lentiviral vector in a Pluronic F127 gel to cells of the central nervous system," Eur J Pharm Biopharm. 61(3):126-33 (2005).

Alexandridis et al., "Poly(ethylene oxide)-poly(propylene oxide)-poly(ethylene oxide) block copolymer surfactants in aqueous solutions and at interfaces: thermodynamics, structure, dynamics, and modeling," Colloids and Surfaces A: Physiochemical and Engineering Aspects. 96:1-46 (1995).

Masiuk et al., "PGE2 and Poloxamer Synperonic F108 Enhance Transduction of Human HSPCs with a β-Globin Lentiviral Vector," Mol Ther Methods Clin Dev. 13:390-398 (Jun. 2019).

UniProt Database, Accession No. D9YZU5, <https://www.uniprot.org/uniprotkb/D9YZU5/entry> (Oct. 2010) (5 pages).

Petrillo et al., "Cyclosporin a and rapamycin relieve distinct lentiviral restriction blocks in hematopoietic stem and progenitor cells," Mol Ther. 23(2):352-62 (Feb. 2015).

Petrillo et al., "Cyclosporine H Overcomes Innate Immune Restrictions to Improve Lentiviral Transduction and Gene Editing In Human Hematopoietic Stem Cells," Cell Stem Cell. 23(6):820-832.e9 (Epub Nov. 2018) (34 pages).

* cited by examiner

COMPOSITIONS AND METHODS FOR MODIFYING EUKARYOTIC CELLS

SEQUENCE LISTING

The instant application contains a Sequence Listing which has been submitted electronically in ASCII format and is hereby incorporated by reference in its entirety. Said ASCII copy, created on Nov. 30, 2021, is named "51139-018002_Sequence_Listing_11_30_21_ST25" and is 2,355 bytes in size.

FIELD OF THE INVENTION

The disclosure relates to compositions and methods for the modification of eukaryotic cells, such as for genetically modifying eukaryotic cells to express a transgene of interest, as well as for promoting cell proliferation and survival.

BACKGROUND

Genetic diseases associated with protein deficiencies and loss-of-function mutations represent a challenging class of conditions that have historically been difficult to treat. Cell-based therapies represent a promising path forward, allowing a gene of interest to be functionally expressed in a patient in a stable manner. Preparing cells for this form of therapy often requires that the cells be genetically modified so as to express the desired gene. There exists a need for improved methods for enhancing the genetic modification of eukaryotic cells.

SUMMARY OF THE INVENTION

The present disclosure relates to compositions and methods for modifying eukaryotic cells, such as pluripotent cells, including hematopoietic stem cells (HSCs) and hematopoietic progenitor cells (HPCs). The compositions and methods described herein can be used to genetically modify such cells, for example, so as to promote the expression of a transgene of interest in the cells. For example, using the compositions and methods of the disclosure, a population of pluripotent cells, such as a population of HSCs and/or HPCs, may be contacted with a viral vector encoding a transgene of interest so as to transduce the cells to express a desired gene. The viral vector may be a retrovirus, such as a lentivirus. To stimulate viral transduction of the target cells, the cells may be contacted with the viral vector, as well as a poloxamer, such as a poloxamer having a molar mass in excess of 10,000 g/mol, a molar mass of polyoxypropylene subunits greater than 2,000 g/mol, and/or an ethylene oxide content of greater than 40% by mass. The compositions and methods of the disclosure provide a series of important medicinal benefits, as the cells prepared in accordance with the procedures described herein can be provided to a subject (e.g., a mammalian subject, such as a human patient) having a pathology associated with an endogenous deficiency in the gene of interest. By administration of the modified cells to the subject, the subject may experience restored expression of the deficient gene. Without being limited by mechanism, this therapeutic approach represents a means by which a subject having a genetic disorder may be treated, as well as a methodology for alleviating the symptoms of the disorder.

The compositions and methods of the disclosure are based, in part, on a series of surprising discoveries. It has presently been found, for example, that poloxamers, including those that have been shown previously to be ineffective at improving viral transduction efficiency, are indeed capable of promoting viral transduction when contacted with a target cell at a concentration of less than 10 μg/ml (e.g., a concentration of from about 10 ng/ml to about 9 μg/ml, such as a concentration of 10 ng/ml, 50 ng/ml, 100 ng/ml, 500 ng/ml, or 1 μg/ml, among other concentrations described herein). This unexpected observation engenders a variety of benefits. For example, by virtue of the transduction-enhancing activity of poloxamers at lower concentrations, a reduced quantity of poloxamer may be used to effectuate transduction of a target cell, while still maintaining robust genetic modification.

In a first aspect, the disclosure features a method of transducing a eukaryotic cell to express a transgene by contacting the cell with (i) a viral vector encoding the transgene, and (ii) a poloxamer.

In a further aspect, the disclosure features a method of expressing a transgene in a eukaryotic cell by contacting the cell with (i) a viral vector encoding the transgene, and (ii) a poloxamer.

In an additional aspect, the disclosure features a method of promoting migration of a viral vector encoding a transgene to the nucleus of a eukaryotic cell by contacting the cell with (i) the viral vector, and (ii) a poloxamer.

In some embodiments of any of the three preceding aspects of the disclosure, the method further includes contacting the cell with a substance that reduces activity and/or expression of protein kinase C (PKC).

In an additional aspect, the disclosure features a method of transducing a eukaryotic cell to express a transgene by contacting the cell with (i) a viral vector encoding the transgene, (ii) a substance that reduces activity and/or expression of PKC, and (iii) a poloxamer.

In a further aspect, the disclosure features a method of expressing a transgene in a eukaryotic cell by contacting the cell with (i) a viral vector encoding the transgene, (ii) a substance that reduces activity and/or expression of PKC, and (iii) a poloxamer.

In an additional aspect, the disclosure features a method of promoting migration of a viral vector encoding a transgene to the nucleus of a eukaryotic cell by contacting the cell with (i) the viral vector, (ii) a substance that reduces activity and/or expression of PKC, and (iii) a poloxamer.

In yet another aspect, the disclosure features a method of promoting actin depolymerization in a eukaryotic cell by contacting the cell with (i) a substance that reduces activity and/or expression of PKC, and (ii) a poloxamer.

In an additional aspect, the disclosure features a method of inhibiting cofilin phosphorylation in a eukaryotic cell by contacting the cell with (i) a substance that reduces activity and/or expression of PKC, and (ii) a poloxamer.

In a further aspect, the disclosure features a method of increasing the concentration of dephosphorylated cofilin in a eukaryotic cell, the method including contacting the cell with (i) a substance that reduces activity and/or expression of PKC, and (ii) a poloxamer.

Methods of measuring actin depolymerization, cofilin phosphorylation, and the amount of dephosphorylated cofilin in a eukaryotic cell are known in the art and include those described, e.g., in Yoder et al., Cell 134:782-792 (2008), the disclosure of which is incorporated herein by reference in its entirety.

In an additional aspect, the disclosure features a method of promoting survival and/or proliferation of a eukaryotic cell, the method including contacting the cell with (i) a substance that reduces activity and/or expression of PKC, and (ii) a poloxamer.

In some embodiments of any of the three preceding aspects of the disclosure, the method further includes contacting the cell with a viral vector encoding a transgene, thereby transducing the cell to express the transgene.

In some embodiments of any of the above aspects of the disclosure, the cell is a mammalian cell, such as a human cell. In some embodiments, the cell is a pluripotent cell. The cell may be a CD34+ cell.

In some embodiments, the cell is an embryonic stem cell or an induced pluripotent stem cell. In some embodiments, the cell is an HSC or HPC.

In some embodiments, the substance that reduces activity and/or expression of PKC activates Akt signal transduction. The substance that reduces activity and/or expression of PKC may be a PKC inhibitor or an agent that reduces translation of a ribonucleic acid (RNA) transcript encoding PKC (i.e., a messenger RNA transcript encoding PKC).

In some embodiments, the substance that reduces activity and/or expression of PKC is an agent that reduces translation of an RNA transcript encoding PKC. In some embodiments, the agent contains a nucleic acid. The nucleic acid may contain an interfering RNA, such as a short interfering RNA (siRNA), short hairpin RNA (shRNA), or micro RNA (miRNA). In some embodiments, the nucleic acid contains an antisense oligonucleotide.

In some embodiments, the nucleic acid anneals to an endogenous RNA transcript encoding PKC.

The nucleic acid may be, for example at least 85% complementary (e.g., 85%, 86%, 87%, 88%, 89%, 90%, 91%, 92%, 93%, 94%, 95%, 96%, 97%, 98%, 99%, or 100% complementary) to a region of the endogenous RNA transcript encoding PKC.

In some embodiments, the substance that reduces activity and/or expression of PKC is a PKC inhibitor. The PKC inhibitor may be staurosporine or a variant thereof. For example, the PKC inhibitor may be a compound represented by formula (I)

(I)

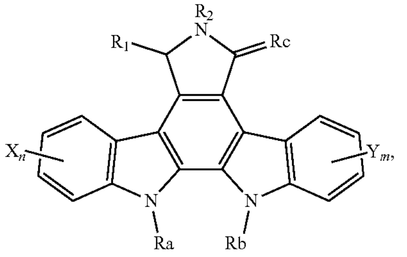

wherein $R_1$ is H, OH, optionally substituted alkoxy, optionally substituted acyloxy, optionally substituted amino, optionally substituted alkylamino, optionally substituted amido, halogen, optionally substituted $C_{1-6}$ alkyl, optionally substituted $C_{2-6}$ alkenyl, optionally substituted $C_{2-6}$ alkynyl, optionally substituted acyl, optionally substituted alkoxycarbonyl, oxo, thiocarbonyl, optionally substituted carboxy, or ureido;

$R_2$ is H, optionally substituted $C_{1-6}$ alkyl, optionally substituted $C_{2-6}$ alkenyl, optionally substituted $C_{2-6}$ alkynyl, or optionally substituted acyl;

$R_a$ and $R_b$ are each, independently, H, optionally substituted $C_{1-6}$ alkyl, optionally substituted $C_{2-6}$ alkenyl, or optionally substituted $C_{2-6}$ alkynyl, optionally substituted and optionally fused aryl, optionally substituted and optionally fused heteroaryl, optionally substituted and optionally fused cycloalkyl, or optionally substituted and optionally fused heterocycloalkyl, or $R_a$ and $R_b$, together with the atoms to which they are bound, are joined to form an optionally substituted and optionally fused heterocycloalkyl ring;

$R_c$ is O, $NR_d$, or S;

$R_d$ is H, optionally substituted $C_{1-6}$ alkyl, optionally substituted $C_{2-6}$ alkenyl, or optionally substituted $C_{2-6}$ alkynyl;

each X is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

each Y is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

--- represents a bond that is optionally present;

n is an integer from 0-4; and m is an integer from 0-4;

or a salt thereof.

In some embodiments, the PKC inhibitor is a compound represented by formula (II)

(II)

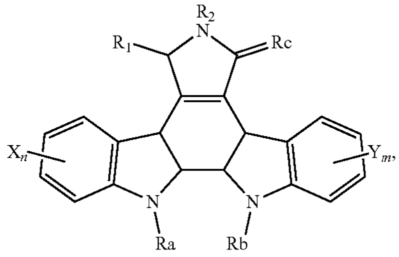

wherein $R_1$ is H, OH, optionally substituted alkoxy, optionally substituted acyloxy, optionally substituted amino, optionally substituted alkylamino, optionally substituted amido, halogen, oxo, or thiocarbonyl;

$R_2$ is H, optionally substituted $C_{1-6}$ alkyl, optionally substituted $C_{2-6}$ alkenyl, optionally substituted $C_{2-6}$ alkynyl, or optionally substituted acyl;

$R_a$ and $R_b$, together with the atoms to which they are bound, are joined to form an optionally substituted and optionally fused heterocycloalkyl ring;

$R_c$ is O or S;

each X is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

each Y is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

n is an integer from 0-4; and m is an integer from 0-4;

or a salt thereof.

In some embodiments, the PKC inhibitor is a compound represented by formula (III)

(III)

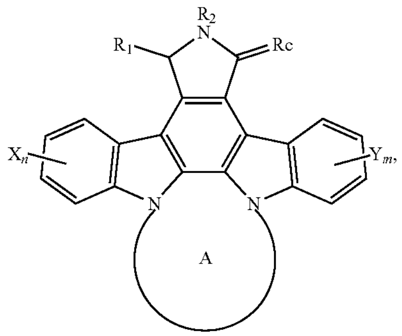

wherein $R_1$ is H, OH, oxo, or thiocarbonyl;

$R_2$ is H, optionally substituted $C_{1-6}$ alkyl, optionally substituted $C_{2-6}$ alkenyl, optionally substituted $C_{2-6}$ alkynyl, or optionally substituted acyl;

Ring A is an optionally substituted and optionally fused heterocycloalkyl ring;

$R_c$ is O or S;

each X is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

each Y is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

n is an integer from 0-4; and m is an integer from 0-4;

or a salt thereof.

In some embodiments, the PKC inhibitor is a compound represented by formula (IV)

(IV)

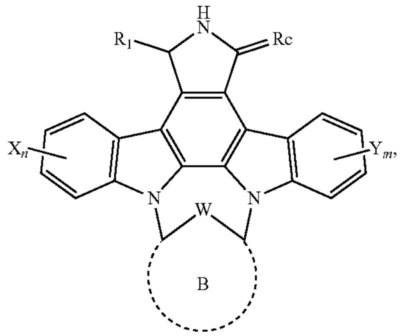

wherein $R_1$ is H, OH, or oxo;

Ring B is an optionally substituted heteroaryl or heterocycloalkyl ring;

$R_c$ is O or S;

W is O, NH, or S;

each X is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

each Y is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

n is an integer from 0-4; and m is an integer from 0-4;

or a salt thereof.

In some embodiments, the PKC inhibitor is a compound represented by formula (V)

(V)

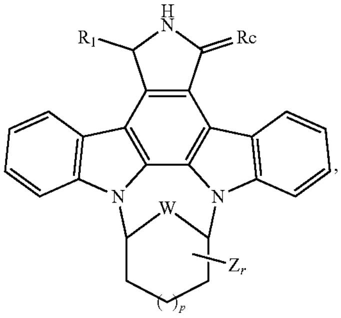

wherein $R_1$ is H, OH, or oxo;

$R_c$ is O or S;

W is O, NH, or S;

each Z is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl; and p is 0 or 1;

or a salt thereof.

In some embodiments, the PKC inhibitor is a compound represented by formula (VI)

(VI)

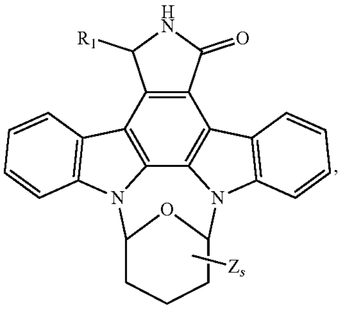

wherein $R_1$ is H, OH, or oxo;

each Z is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl; and s is an integer from 0-8;

or a salt thereof.

In some embodiments, the PKC inhibitor is a compound represented by formula (VII)

(VII)

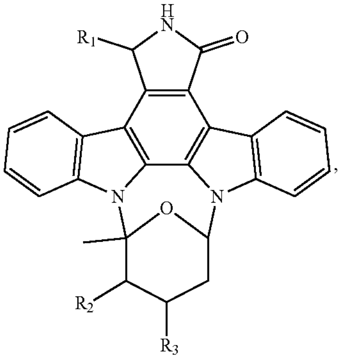

wherein $R_1$ is H, OH, or oxo;

$R_2$ is H, OH, optionally substituted alkoxy, or optionally substituted acyloxy; and $R_3$ is H, OH, optionally substituted alkoxy, optionally substituted acyloxy, optionally substituted amino, or optionally substituted amido or a salt thereof.

In some embodiments, the PKC inhibitor is a compound represented by formula (VIII)

(VIII)

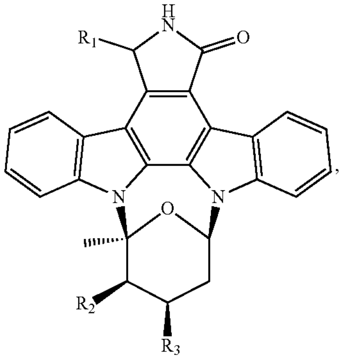

wherein $R_1$ is H, OH, or oxo;

$R_2$ is H, OH, optionally substituted alkoxy, or optionally substituted acyloxy; and $R_3$ is H, OH, optionally substituted alkoxy, optionally substituted acyloxy, optionally substituted amino, or optionally substituted amido or a salt thereof.

In some embodiments, the PKC inhibitor is a compound represented by formula (IX)

(IX)

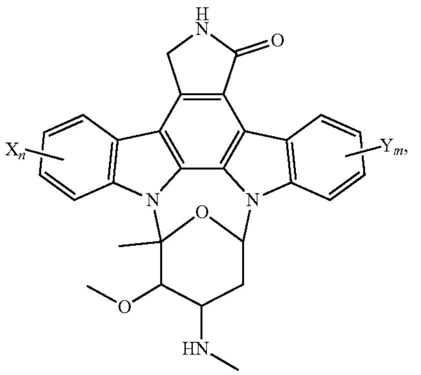

wherein each X is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

each Y is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

n is an integer from 0-4; and m is an integer from 0-4;

or a salt thereof.

In some embodiments, the PKC inhibitor is a compound represented by formula (I)

(1)

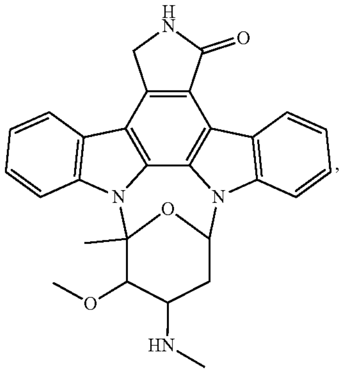

or a salt thereof.

In some embodiments, the PKC inhibitor is staurosporine, (2S,3R,4R,6R)-3-methoxy-2-methyl-4-(methylamino)-29-oxa-1,7,17-triazaoctacyclo[12.12.2.12,6.07,28.08,13.015,19.020,27.021,26]nonacosa-8,10,12,14,19,21,23,25,27-nonaen-16-one, represented by formula (2)

(2)

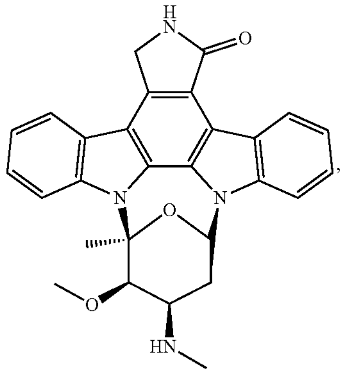

or a salt thereof.

In some embodiments, the PKC inhibitor is a compound represented by formula (X)

(X)

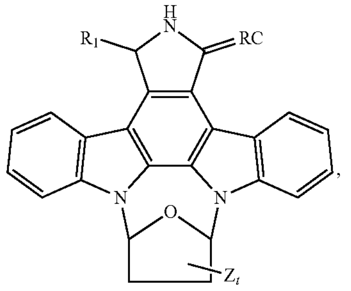

wherein $R_1$ is H, OH, or oxo;

each Z is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl; and t is an integer from 0-6;

or a salt thereof.

In some embodiments, the PKC inhibitor is a compound represented by formula (XI)

(XI)

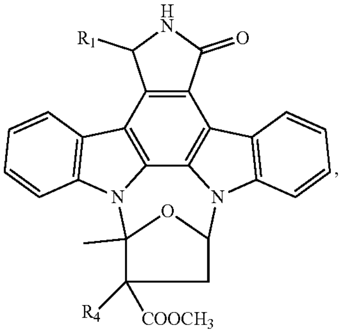

wherein $R_1$ is H, OH, or oxo; and $R_4$ is H, OH, optionally substituted alkoxy, or optionally substituted acyloxy;

or a salt thereof.

In some embodiments, the PKC inhibitor is a compound represented by formula (XII)

(XII)

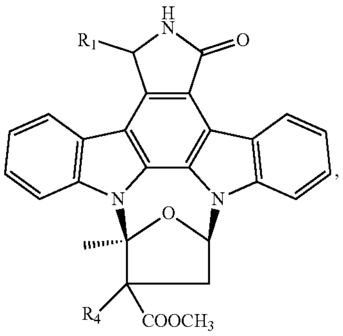

wherein $R_1$ is H, OH, or oxo; and $R_4$ is H, OH, optionally substituted alkoxy, or optionally substituted acyloxy;

or a salt thereof.

In some embodiments, the PKC inhibitor is a compound represented by formula (XIII)

(XIII)

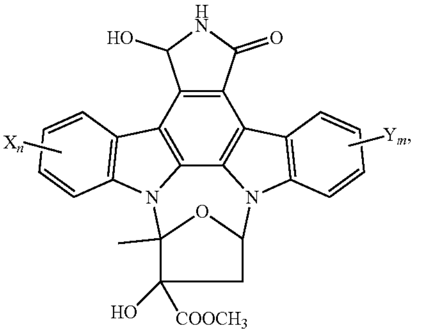

wherein each X is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

each Y is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

n is an integer from 0-4; and m is an integer from 0-4;

or a salt thereof.

In some embodiments, the PKC inhibitor is a compound represented by formula (3)

(3)

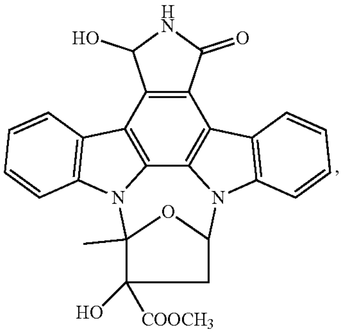

or a salt thereof.

In some embodiments, the PKC inhibitor is a compound represented by formula (4)

(4)
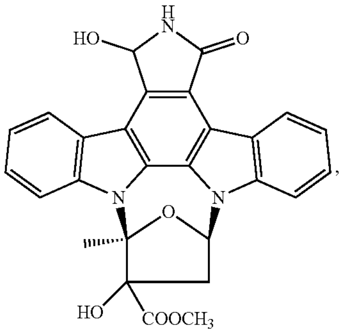
,
or a salt thereof.
In some embodiments the PKC inhibitor is a compound selected from:
(5)
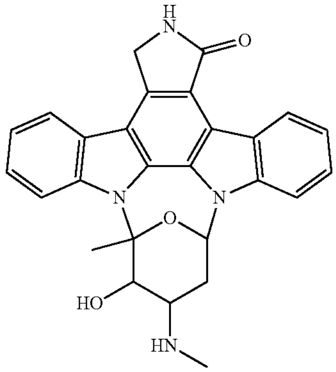
;
(6)
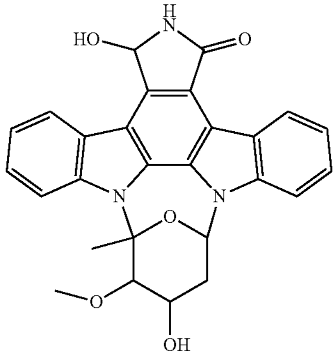
;
(7)
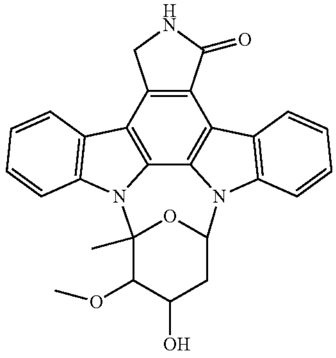
;
-continued
(8)
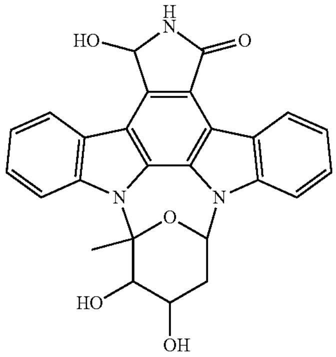
;
(9)
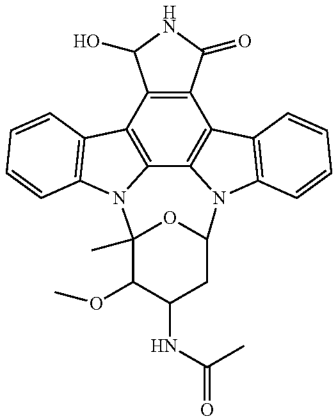
;
(10)
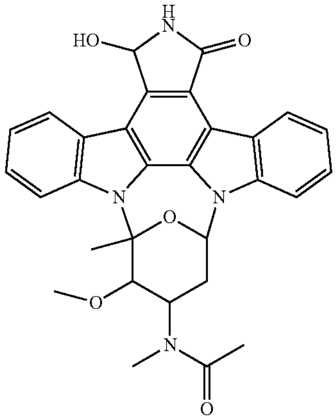
;
(11)
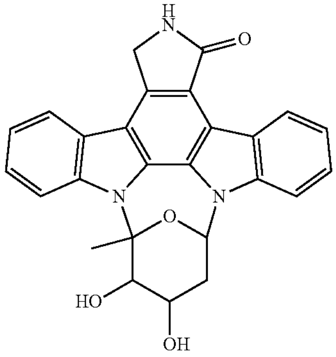
;

-continued (12)

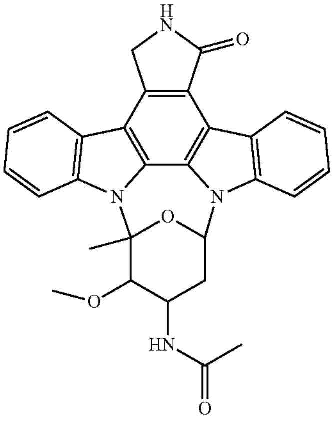

;

(13)

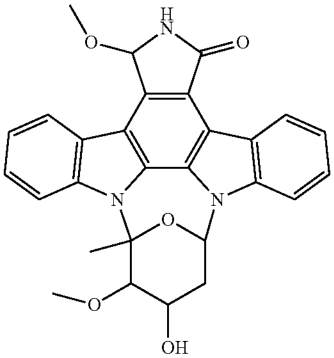

;

(14)

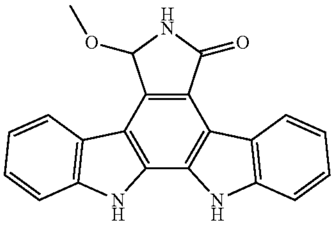

; and (15)

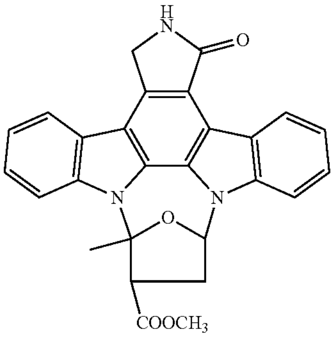

;

or a salt thereof.

In some embodiments, the PKC inhibitor is a compound represented by formula (XIV)

(XIV)

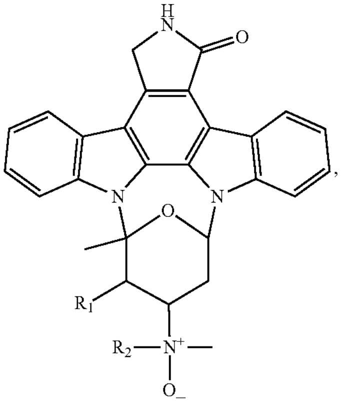

, wherein $R_1$ is H or optionally substituted $C_{1-6}$ alkyl; and $R_2$ is optionally substituted $C_{1-6}$ alkyl;

or a salt thereof.

In some embodiments, the PKC inhibitor is a compound represented by formula (XV)

(XV)

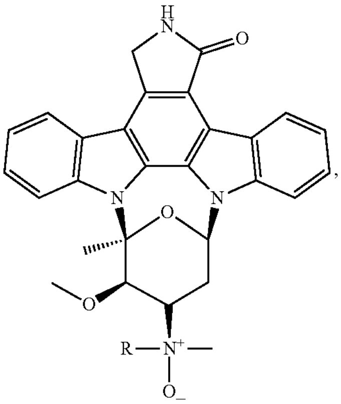

, wherein $R_1$ is H or optionally substituted $C_{1-6}$ alkyl; and $R_2$ is optionally substituted $C_{1-6}$ alkyl;

or a salt thereof.

In some embodiments, the PKC inhibitor is a compound selected from:

(16)

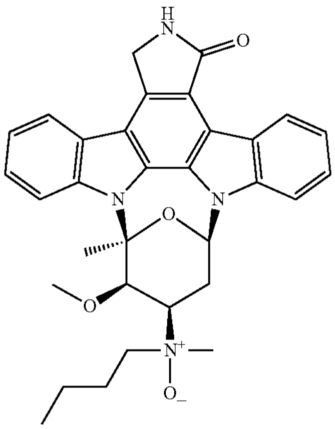

and

-continued (17)

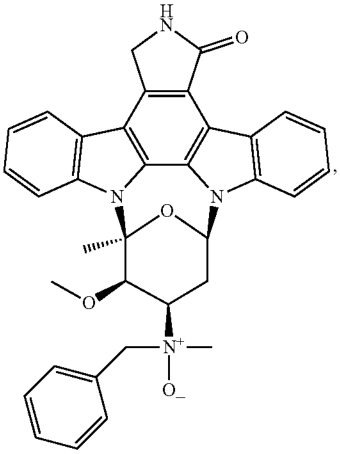, or a salt thereof.

In some embodiments, the PKC inhibitor is a compound represented by formula (XVI)

(XVI)

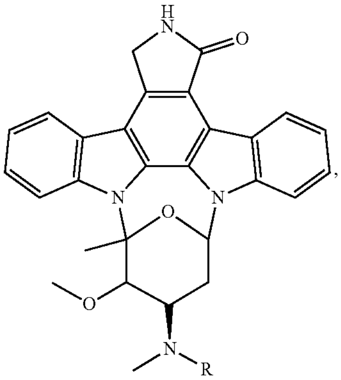, wherein R is H, optionally substituted alkyl, optionally substituted acyl, optionally substituted sulfonyl, optionally substituted sulfinyl, optionally substituted aryl, optionally substituted heteroaryl, optionally substituted cycloalkyl, and optionally substituted heterocycloalkyl;

or a salt or quaternized variant thereof.

In some embodiments, the PKC inhibitor is a compound represented by formula (XVII)

(XVII)

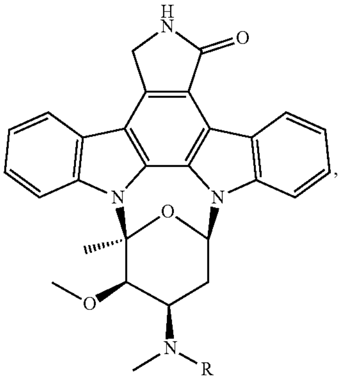, wherein R is H, optionally substituted alkyl, optionally substituted acyl, optionally substituted sulfonyl, optionally substituted sulfinyl, optionally substituted aryl, optionally substituted heteroaryl, optionally substituted cycloalkyl, and optionally substituted heterocycloalkyl;

or a salt or quaternized variant thereof.

In some embodiments, the PKC inhibitor is a compound selected from:

(18)

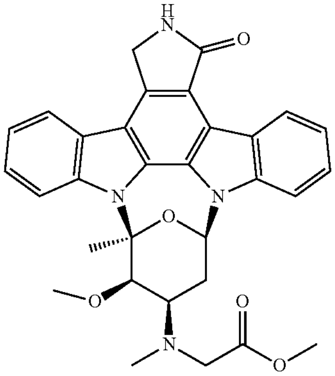;

(19)

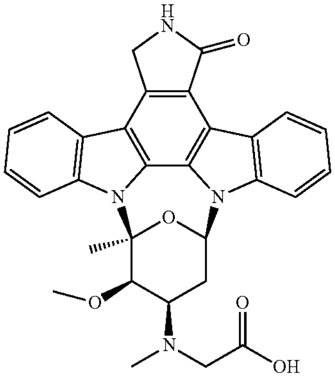;

(20)

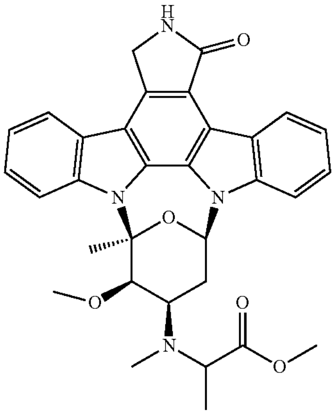;

-continued
(21)
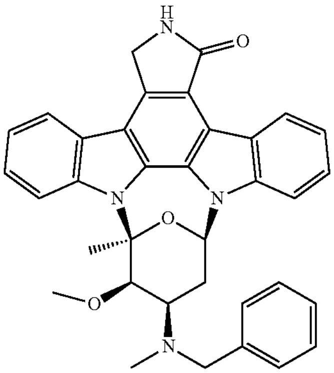
;
(22)
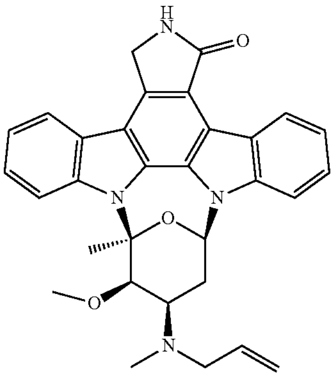
;
(23)
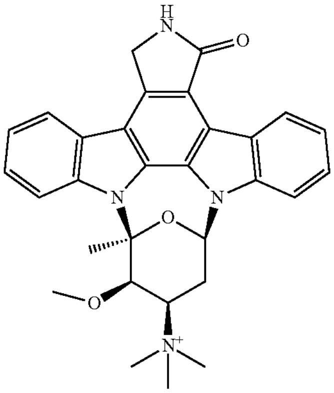
;
(24)
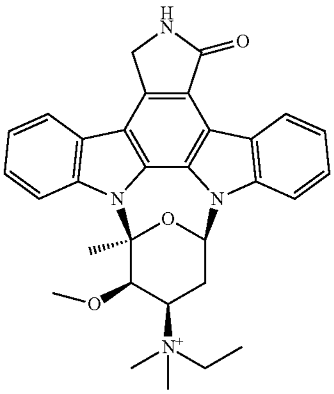
;
-continued
(25)
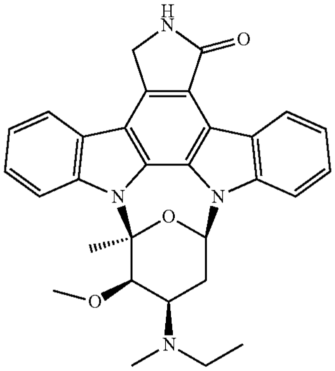
;
(26)
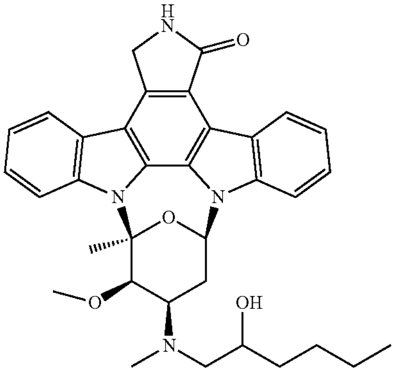
;
(27)
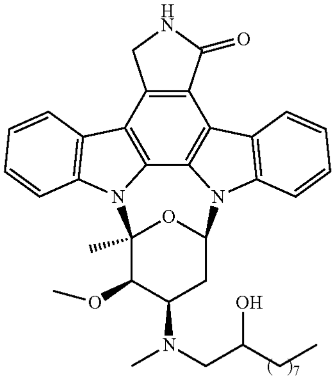
;
(28)
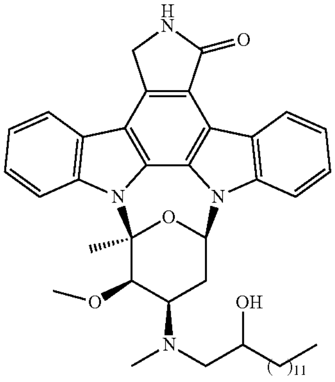
;

-continued
(29)
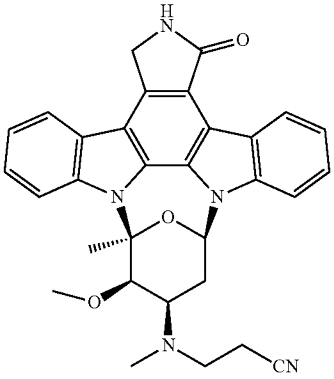
;
(30)
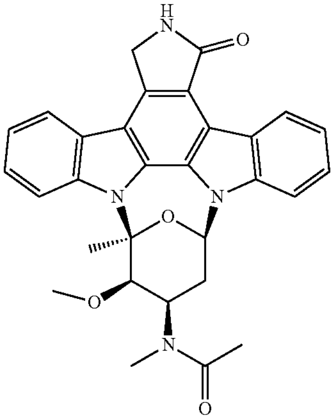
;
(31)
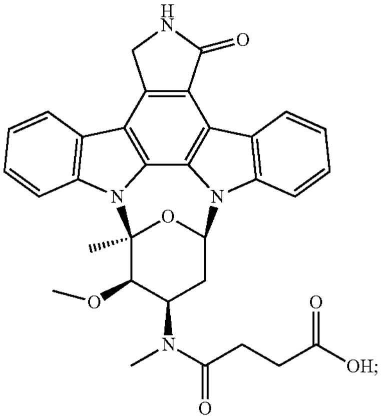
-continued
(32)
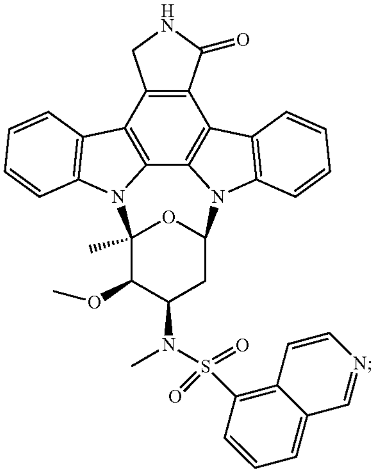
(33)
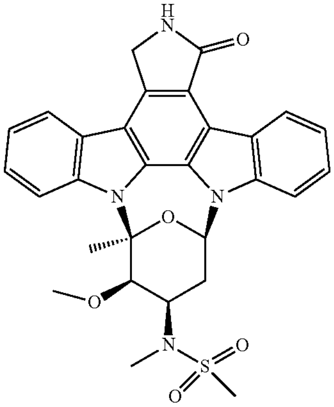
;
(34)
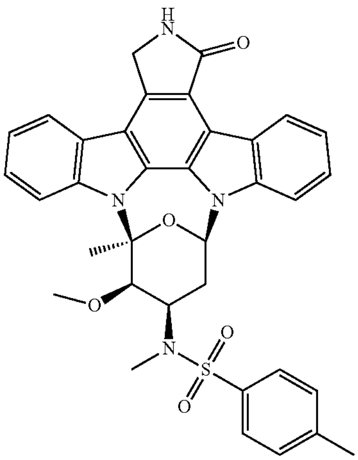
;

(35)
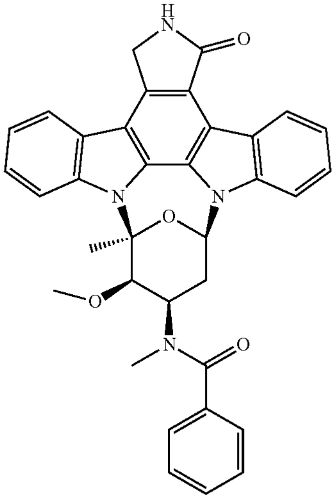
;
(36)
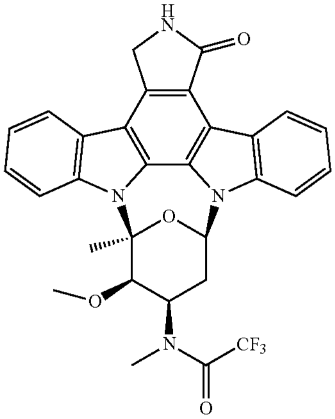
;
(37)
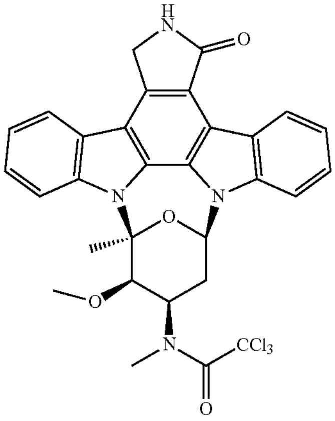
;
(38)
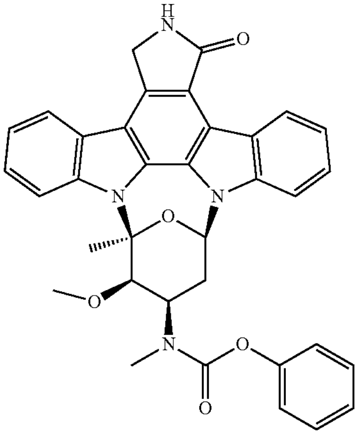
;
(39)
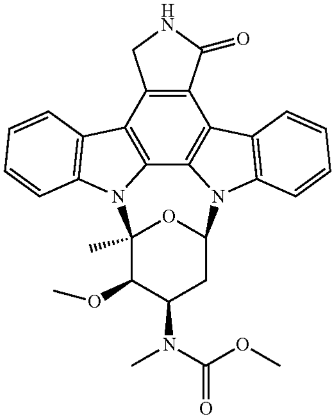
;
(40)
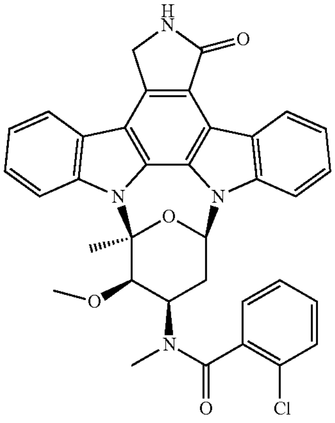
;

(41)
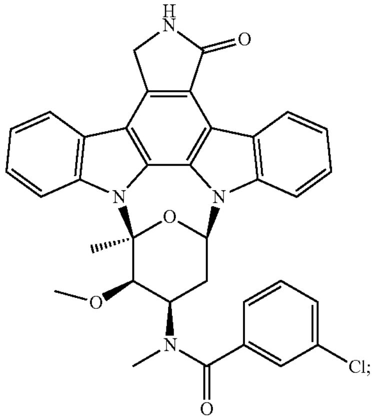
(42)
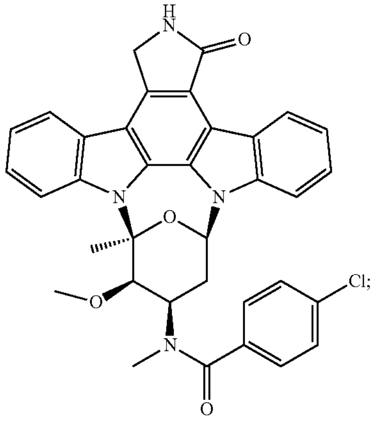
(43)
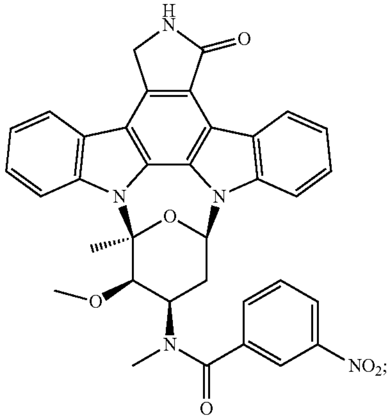
(44)
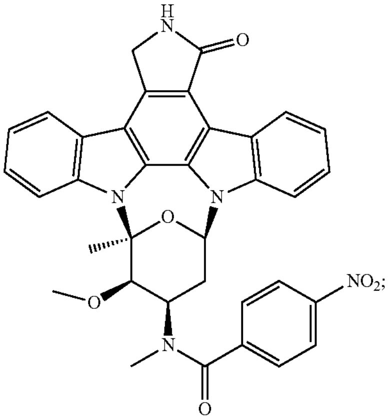
(45)
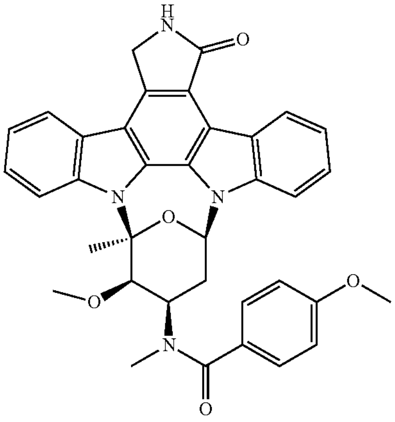
;
(46)
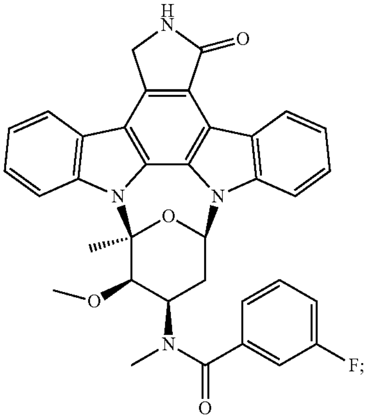

-continued
(47)
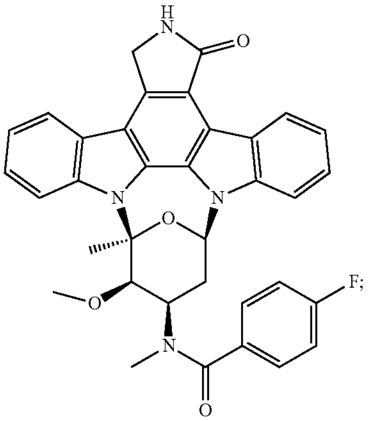
(48)
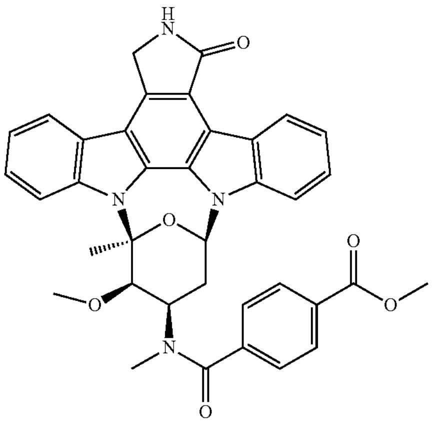
;
(49)
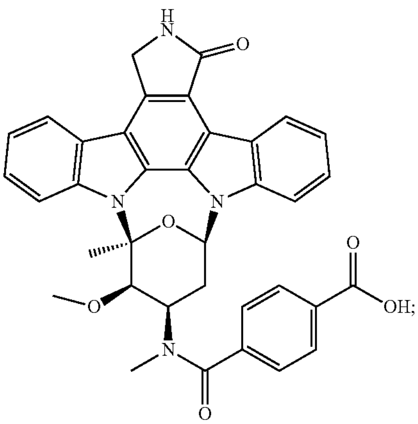
-continued
(50)
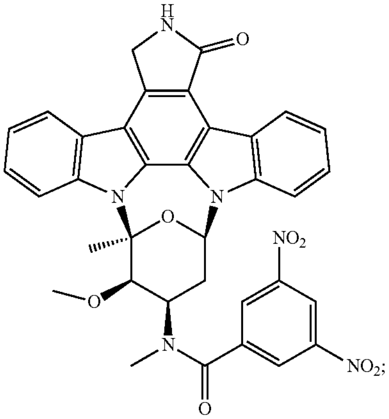
(51)
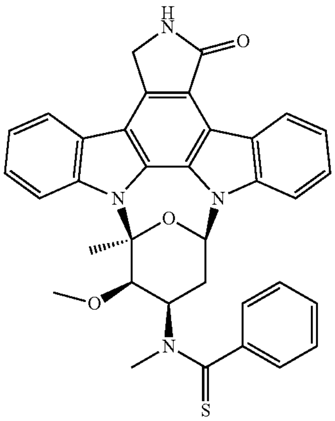
;
(52)
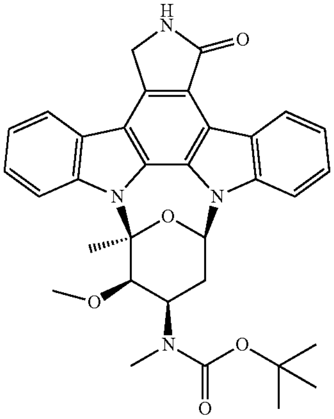
;

-continued
(53)
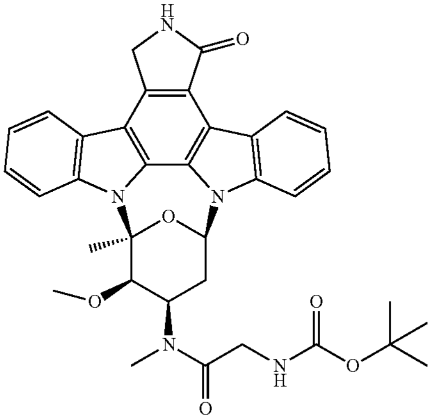
;
(54)
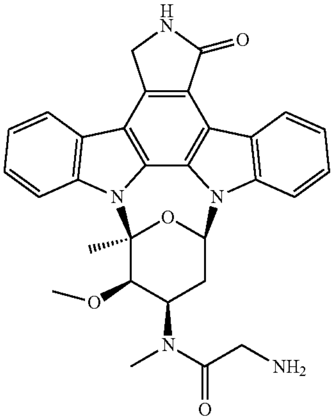
;
(55)
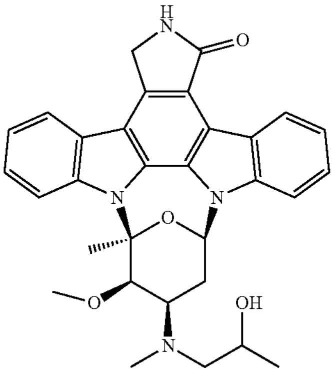
;
(56)
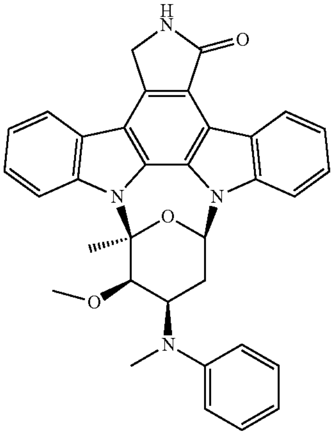
;
-continued
(57)
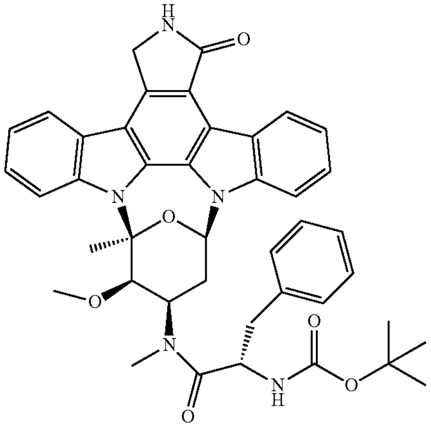
;
(58)
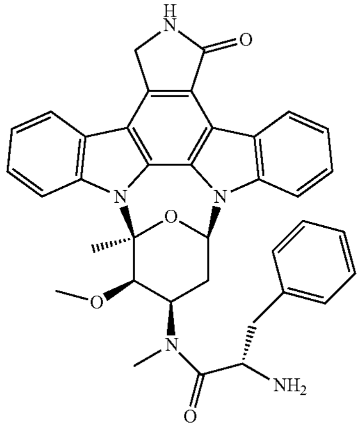
;
(59)
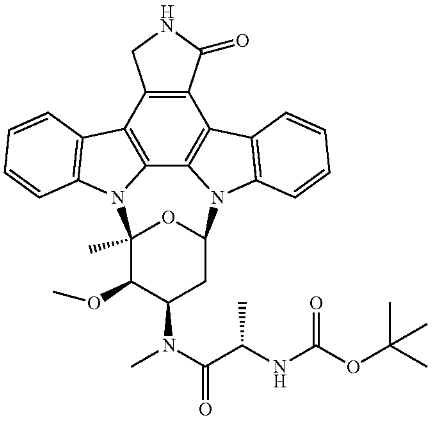
;

-continued
(60)
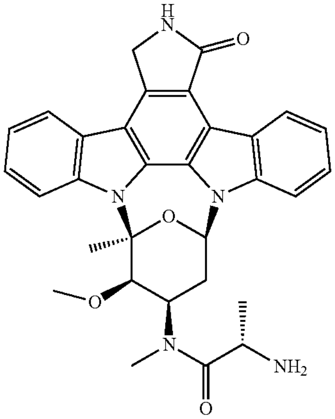
;
(61)
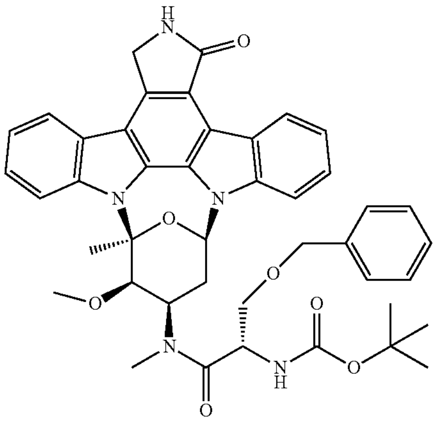
;
(62)
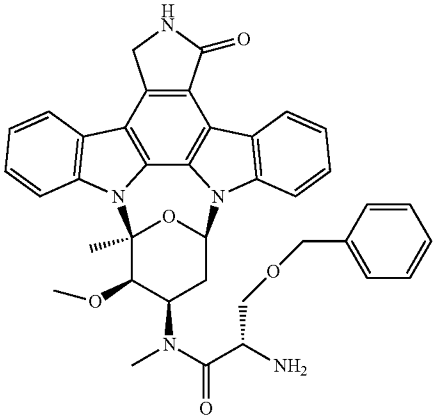
;
-continued
(63)
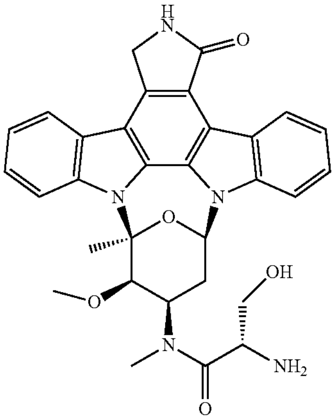
;
(64)
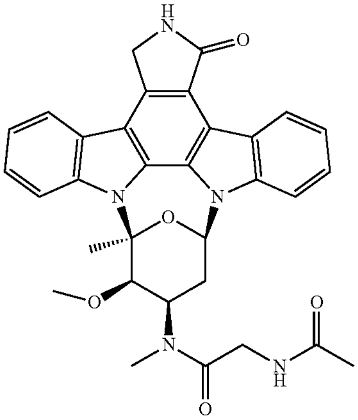
;
(65)
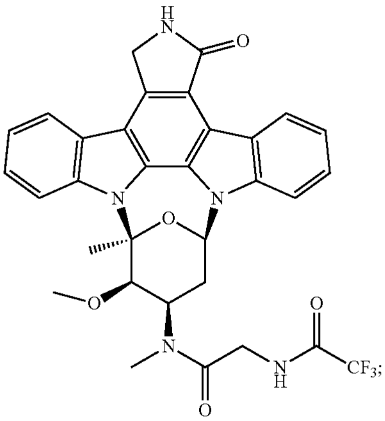
;

-continued
(66)
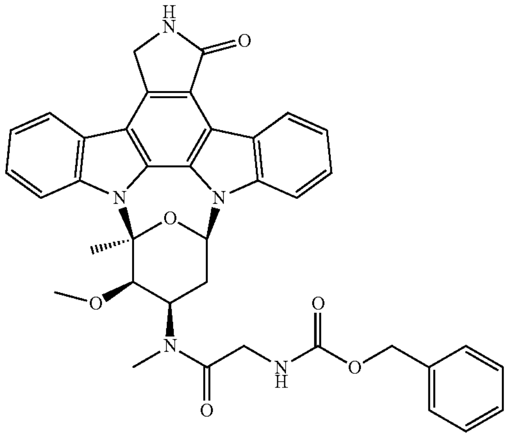
;
(67)
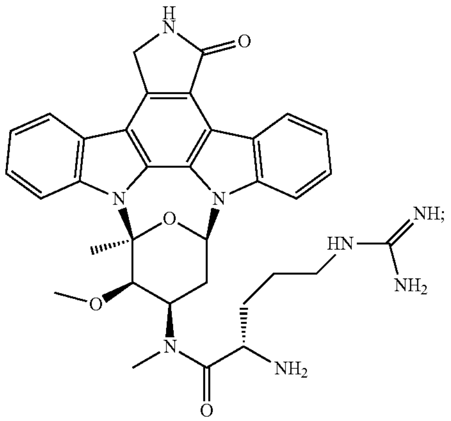
(68)
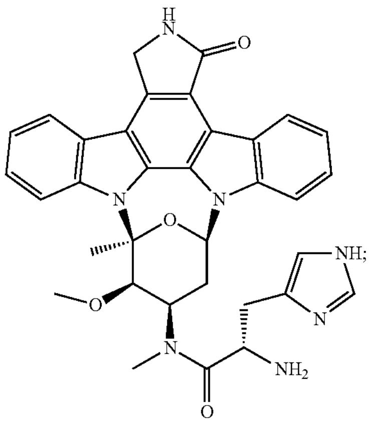
-continued
(69)
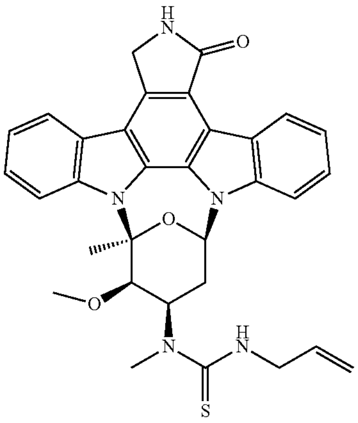
;
(70)
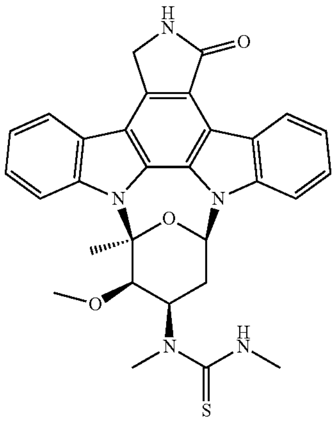
; and
(71)
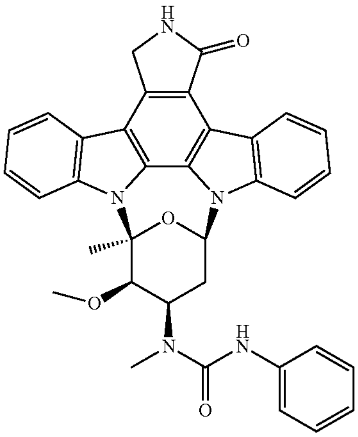
;
or a salt thereof.
In some embodiments, the PKC inhibitor is a compound represented by formula (XVIII)

(XVIII)

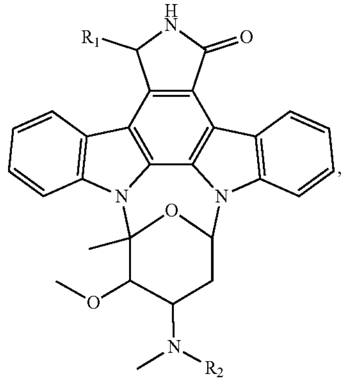

wherein R is H, OH, $C_{1-6}$ alkoxy, or oxo; and

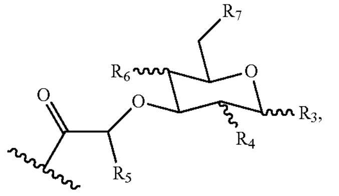

$R_2$ is, optionally wherein the configuration of the sugar moiety is derived from D-glucose, D-galactose, or D-mannose;

$R_3$ is H, OH, $C_{1-6}$ alkanoyloxy, $C_{1-6}$ alkoxy, benzyloxy, benzoyloxy or phenyloxy, each of which is optionally substituted in the phenyl moiety by halogen, hydroxyl, trifluoromethyl, $C_{1-6}$ alkyl, or $C_{1-6}$ alkoxy;

$R_4$ is OH, $C_{1-6}$ alkanoyloxy, benzoyloxy, benzyloxy, amino, $C_{1-6}$ alkylamino, di-$C_{1-6}$ alkylamino, $C_{1-6}$ alkoxycarbonylamino, $C_{2-20}$ alkanoylamino, benzoylamino, benzyloxycarbonylamino, or phenyloxycarbonylamino, each of which is optionally substituted in the phenyl moiety by halogen, hydroxyl, trifluoromethyl, $C_{1-6}$ alkyl, $C_{1-6}$ alkoxy;

$R_5$ is H or $C_{1-6}$ alkyl;

$R_6$ is hydroxyl which is free or esterified with an aliphatic $C_{2-22}$ carboxylic acid, or is $C_{1-6}$ alkoxycarbonyloxy, $C_{1-6}$ alkylsulfonyloxy, amino which is free or acylated with an aliphatic $C_{2-22}$ carboxylic acid, $C_{1-6}$ alkoxycarbonylamino, azido, benzoyloxy, benzyloxycarbonyloxy, benzoylamino, benzyloxycarbonylamino, or phenylsulfonyloxy, each of which is optionally substituted in the phenyl moiety by halogen, hydroxyl, trifluoromethyl, $C_{1-6}$ alkyl, or $C_{1-6}$ alkoxy; and $R_7$ is OH which is free or esterified with an aliphatic $C_{2-22}$ carboxylic acid, $C_{1-6}$ alkoxycarbonyloxy, $C_{1-6}$ alkylsulfonyloxy, azido, amino which is free or acylated with an aliphatic $C_{2-22}$ carboxylic acid, $C_{1-6}$ alkylamino, di-$C_{1-6}$ alkylamino, $C_{1-6}$ alkoxycarbonylamino, carbamoylamino, benzoyloxy, benzyloxycarbonyloxy, phenylsulfonyloxy, benzoylamino, benzylamino or benzyloxycarbonylamino, each of which is optionally substituted in the phenyl moiety by halogen, hydroxyl, trifluoromethyl, $C_{1-6}$ alkyl, $C_{1-6}$ alkoxy, or $C_{1-6}$ alkoxycarbonyl;

or a salt thereof.

In some embodiments, the PKC inhibitor is a compound represented by formula (XIX)

(XIX)

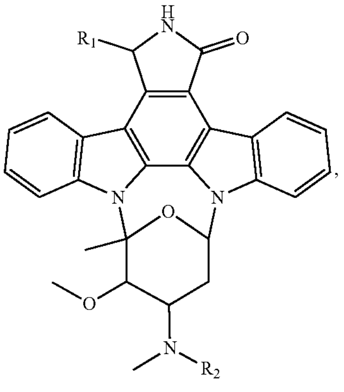

wherein R is H, OH, 1-6 alkoxy, or oxo; and $R_2$ is

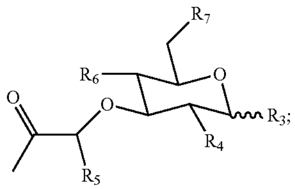

$R_3$ is H, OH, $C_{1-6}$ alkanoyloxy, $C_{1-6}$ alkoxy, benzyloxy, benzoyloxy or phenyloxy, each of which is optionally substituted in the phenyl moiety by halogen, hydroxyl, trifluoromethyl, $C_{1-6}$ alkyl, or $C_{1-6}$ alkoxy;

$R_4$ is OH, $C_{1-6}$ alkanoyloxy, benzoyloxy, benzyloxy, amino, $C_{1-6}$ alkylamino, di-$C_{1-6}$ alkylamino, $C_{1-6}$ alkoxycarbonylamino, $C_{2-20}$ alkanoylamino, benzoylamino, benzyloxycarbonylamino, or phenyloxycarbonylamino, each of which is optionally substituted in the phenyl moiety by halogen, hydroxyl, trifluoromethyl, $C_{1-6}$ alkyl, $C_{1-6}$ alkoxy;

$R_5$ is H or $C_{1-6}$ alkyl;

$R_6$ is hydroxyl which is free or esterified with an aliphatic $C_{2-22}$ carboxylic acid, or is $C_{1-6}$ alkoxycarbonyloxy, $C_{1-6}$ alkylsulfonyloxy, amino which is free or acylated with an aliphatic $C_{2-22}$ carboxylic acid, $C_{1-6}$ alkoxycarbonylamino, azido, benzoyloxy, benzyloxycarbonyloxy, benzoylamino, benzyloxycarbonylamino, or phenylsulfonyloxy, each of which is optionally substituted in the phenyl moiety by halogen, hydroxyl, trifluoromethyl, $C_{1-6}$ alkyl, or $C_{1-6}$ alkoxy; and $R_7$ is OH which is free or esterified with an aliphatic $C_{2-22}$ carboxylic acid, $C_{1-6}$ alkoxycarbonyloxy, $C_{1-6}$ alkylsulfonyloxy, azido, amino which is free or acylated with an aliphatic $C_{2-22}$ carboxylic acid, $C_{1-6}$ alkylamino, di-$C_{1-6}$ alkylamino, $C_{1-6}$ alkoxycarbonylamino, carbamoylamino, benzoyloxy, benzyloxycarbonyloxy, phenylsulfonyloxy, benzoylamino, benzylamino or benzyloxycarbonylamino, each of which is optionally substituted in the phenyl moiety by halogen, hydroxyl, trifluoromethyl, $C_{1-6}$ alkyl, $C_{1-6}$ alkoxy, or $C_{1-6}$ alkoxycarbonyl;

or a salt thereof.

In some embodiments, the PKC inhibitor is a compound selected from N-(1-α-O-Benzyl-2-N-acetylmuramyl)staurosporine, N-(2-N-Acetyl-muramyl)staurosporine, N-(6-O-Mesyl-1-α-O-benzyl-2-N-acetylmuramyl)staurosporine, N-(6-Azido-1-α-O-benzyl-2-N-acetyl-6-deoxymuramyl) staurosporine, N-(6-Amino-1-α-O-benzyl-2-N-acetyl-6-deoxymuramyl)staurosporine, N-(6-Amino-6-deoxy-2-N-acetylmuramyl)staurosporine, N-(6-O-Mesyl-2-N-acetylmuramyl)staurosporine, N-(2-N-Acetyl-demethylmuramyl)staurosporine, N-(1-α-O-Benzyl-2-N-acetylhomomuramyl)staurosporine, N-(1-α-O-Benzyl-2-N-acetyl-L-homomuramyl)staurosporine, the 1-α-anomer of N-(2-N-acetyl-L-homomuramyl)staurosporine, N-(1-α-O-Benzyl-4,6-O-diacetyl-2-N-acetylmuramyl)staurosporine, N-(1-α-O-Benzyl-4-O-acetyl-6-O-stearoyl-2-N-acetylmuramyl)staurosporin, N-(1-Deoxy-2-N-acetylmuramyl)staurosporine, the 1-α-anomer of N-(4-O-acetyl-6-O-stearoyl-2-N-acetylmuramyl)staurosporine, the 1-α-anomer of N-(4,6-O-diacetyl-2-N-acetylmuramyl)staurosporine, N-(1-α,4-O-diacetyl-6-O-stearoyl-2-N-acetylmuramyl)staurosporine, N-(1-α,4,6-O-Triacetyl-2-N-acetylmuramyl)staurosporine, N-(1-Deoxy-6-O-acetyl-2-N-acetylmuramyl)staurosporine, N-(1-Deoxy-6-O-mesyl-2-N-acetylmuramyl)staurosporine, N-(1-Deoxy-6-O-toluylsulfonyl-2-N-acetylmuramyl)staurosporine, N-(1-Deoxy-6-azido-2-N-acetylmuramyl)staurosporine, and N-(1-Deoxy-6-O-mesyl-2-N-acetylmuramyl) staurosporine, or a salt thereof.

In some embodiments, the PKC inhibitor is a compound represented by formula (XX)

(XX)

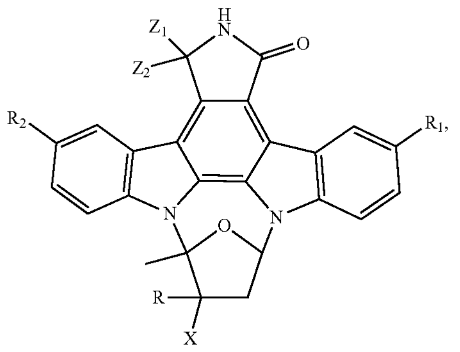

wherein $Z_1$ is H or OH;

$Z_2$ is H or OH;

$R_1$ is H, halogen, or optionally substituted alkyl;

$R_2$ is H or halogen;

R is OH or optionally substituted alkoxy; and

X is optionally substituted alkyl or optionally substituted acyl, optionally wherein X is $CH_2$—NH-serine, $CO_2CH_3$, $CH_2NHCO_2C_6H_5$, $CONHC_6H_5$, or $CH_2NHCO_2CH3$, wherein $C_6H_5$ denotes a phenyl moiety;

or a salt thereof.

In some embodiments, the PKC inhibitor is a compound represented by formula (XXI)

(XXI)

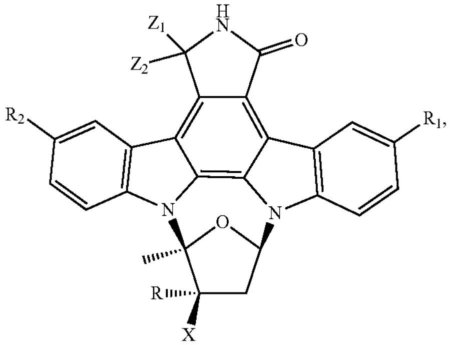

wherein $Z_1$ is H or OH;

$Z_2$ is H or OH;

$R_1$ is H, halogen, or optionally substituted alkyl;

$R_2$ is H or halogen;

R is OH or optionally substituted alkoxy; and

X is optionally substituted alkyl or optionally substituted acyl, optionally wherein X is $CH_2$—NH-serine, $CO_2CH_3$, $CH_2NHCO_2C_6H_5$, $CONHC_6H_5$, or $CH_2NHCO_2CH_3$, wherein $C_6H_5$ denotes a phenyl moiety;

or a salt thereof.

In some embodiments, the PKC inhibitor is a compound represented by formula (XXII), (XXIII), (XXIV), or (XXV)

(XXII)

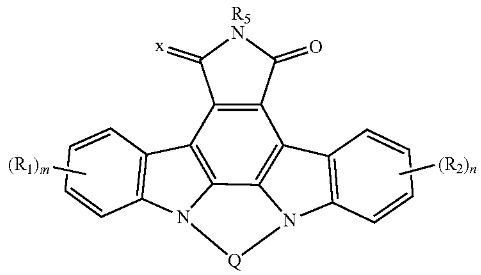

(XXIII)

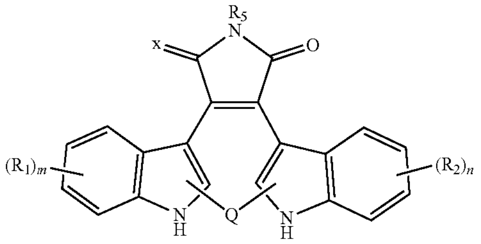

(XXIV)

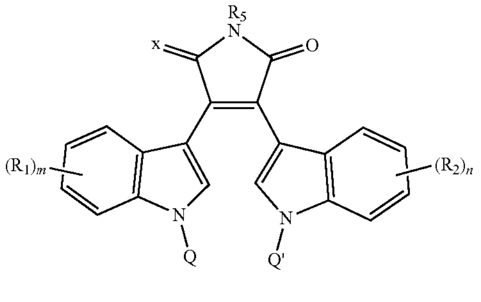

-continued (XXV)

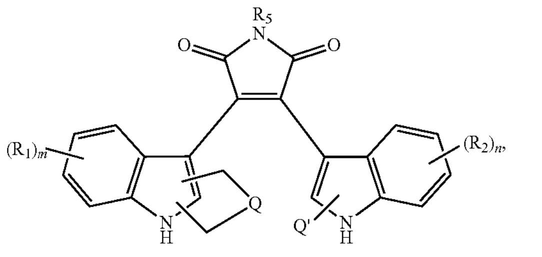

wherein each $R_1$ is, independently, optionally substituted alkyl, hydrogen, halogen, hydroxy, etherified or esterified hydroxy, amino, mono- or disubstituted amino, cyano, nitro, mercapto, substituted mercapto, carboxy, esterified carboxy, carbamoyl, N-mono- or N,N-di-substituted carbamoyl, sulfo, substituted sulfonyl, aminosulfonyl, or N-mono- or N,N-di-substituted aminosulfonyl;

each $R_2$ is, independently, optionally substituted alkyl, hydrogen, halogen, hydroxy, etherified or esterified hydroxy, amino, mono- or disubstituted amino, cyano, nitro, mercapto, substituted mercapto, carboxy, esterified carboxy, carbamoyl, N-mono- or N,N-di-substituted carbamoyl, sulfo, substituted sulfonyl, aminosulfonyl, or N-mono- or N,N-di-substituted aminosulfonyl;

each $R_5$ is, independently, H, an aliphatic, carbocyclic, or carbocyclic-aliphatic radical with up to 29 carbon atoms in each case, or a heterocyclic or heterocyclic-aliphatic radical with up to 20 carbon atoms in each case, and in each case up to 9 heteroatoms, or acyl with up to 30 carbon atoms; and each X is, independently, O, OH and H, or a pair of hydrogen atoms;

each Q is, independently, H, OH, halogen, etherified or esterified hydroxy, amino, mono- or disubstituted amino, cyano, nitro, mercapto, substituted mercapto, carboxy, esterified carboxy, carbamoyl, N-mono- or N,N-di-substituted carbamoyl, sulfo, substituted sulfonyl, aminosulfonyl or N-mono- or N,N-di-substituted aminosulfonyl;

each Q' is, independently, H, OH, halogen, etherified or esterified hydroxy, amino, mono- or disubstituted amino, cyano, nitro, mercapto, substituted mercapto, carboxy, esterified carboxy, carbamoyl, N-mono- or N,N-di-substituted carbamoyl, sulfo, substituted sulfonyl, aminosulfonyl or N-mono- or N,N-di-substituted aminosulfonyl;

each n is, independently, an integer from 0-4; and each m is, independently, an integer from 0-4;

or a salt thereof.

In some embodiments, the PKC inhibitor is a compound represented by formula (XXVI) or (XXVII)

(XXVI)

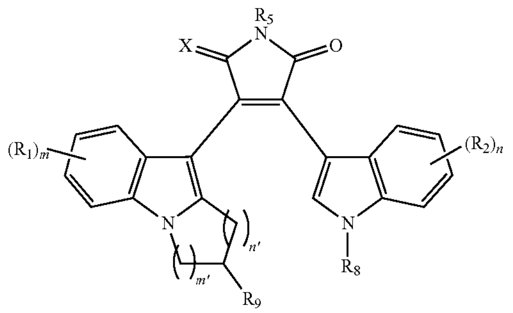

(XXVII)

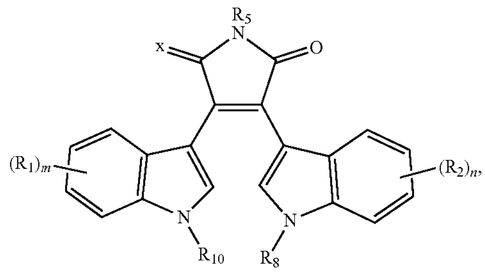

wherein each $R_1$ is, independently, optionally substituted alkyl, hydrogen, halogen, hydroxy, etherified or esterified hydroxy, amino, mono- or disubstituted amino, cyano, nitro, mercapto, substituted mercapto, carboxy, esterified carboxy, carbamoyl, N-mono- or N,N-di-substituted carbamoyl, sulfo, substituted sulfonyl, aminosulfonyl or N-mono- or N,N-di-substituted aminosulfonyl;

each $R_2$ is, independently, optionally substituted alkyl, hydrogen, halogen, hydroxy, etherified or esterified hydroxy, amino, mono- or disubstituted amino, cyano, nitro, mercapto, substituted mercapto, carboxy, esterified carboxy, carbamoyl, N-mono- or N,N-di-substituted carbamoyl, sulfo, substituted sulfonyl, aminosulfonyl or N-mono- or N,N-di-substituted aminosulfonyl;

each $R_5$ is, independently, H, an aliphatic, carbocyclic, or carbocyclic-aliphatic radical with up to 29 carbon atoms in each case, or a heterocyclic or heterocyclic-aliphatic radical with up to 20 carbon atoms in each case, and in each case up to 9 heteroatoms, or acyl with up to 30 carbon atoms;

each $R_8$ is, independently, acyl with up to 30 carbon atoms, an aliphatic, carbocyclic, or carbocyclic-aliphatic radical with up to 29 carbon atoms in each case, a heterocyclic or heterocyclic-aliphatic radical with up to 20 carbon atoms in each case, and in each case up to 9 heteroatoms;

each $R_9$ is, independently, optionally substituted acyl, optionally substituted alkyl, hydrogen, halogen, hydroxy, etherified or esterified hydroxy, amino, mono- or disubstituted amino, cyano, nitro, mercapto, substituted mercapto, carboxy, carbonyl, carbonyldioxy, esterified carboxy, carbamoyl, N-mono- or N,N-di-substituted carbamoyl, sulfo, substituted sulfonyl, aminosulfonyl or N-mono- or N,N-di-substituted aminosulfonyl;

each $R_{10}$ is, independently, acyl with up to 30 carbon atoms, an aliphatic, carbocyclic, or carbocyclic-aliphatic radical with up to 29 carbon atoms in each case, a heterocyclic or heterocyclic-aliphatic radical with up to 20 carbon atoms in each case, and in each case up to 9 heteroatoms;

each X is, independently, O, OH and H, or a pair of hydrogen atoms;

each n is, independently, an integer from 0-4;

each m is, independently, an integer from 0-4;

each n' is, independently, an integer from 0-4; and each m' is, independently, an integer from 0-4;

or a salt thereof.

In some embodiments, the PKC inhibitor is a compound represented by formula (XXVIII)

(XXVIII)

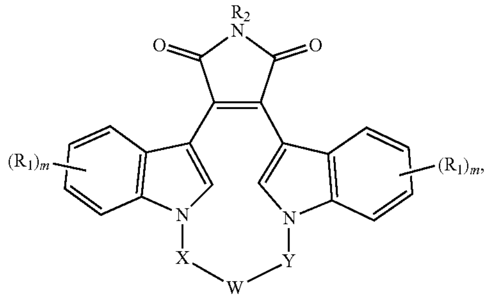

wherein $R_1$ is H or optionally substituted $C_{1-6}$ alkyl; and $R_2$ is optionally substituted $C_{1-6}$ alkyl;

or a salt thereof.

In some embodiments, the PKC inhibitor is a compound represented by formula (XXIX)

(XXIX)

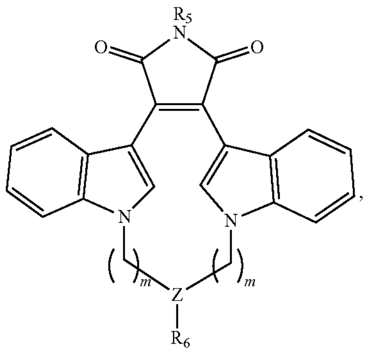

wherein $R_1$ is H or optionally substituted $C_{1-6}$ alkyl; and $R_2$ is optionally substituted $C_{1-6}$ alkyl;

or a salt thereof.

In some embodiments, the PKC inhibitor is a compound represented by formula (XXX)

(XXX)

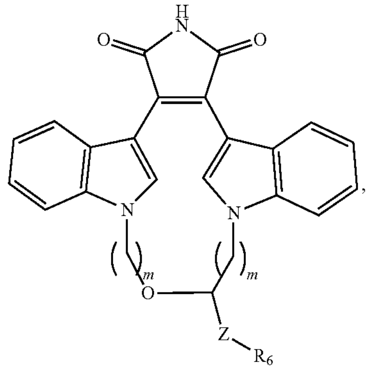

wherein $R_1$ is H or optionally substituted $C_{1-6}$ alkyl; and $R_2$ is optionally substituted $C_{1-6}$ alkyl;

or a salt thereof.

In some embodiments, the PKC inhibitor is a compound represented by formula (XXXI)

(XXXI)

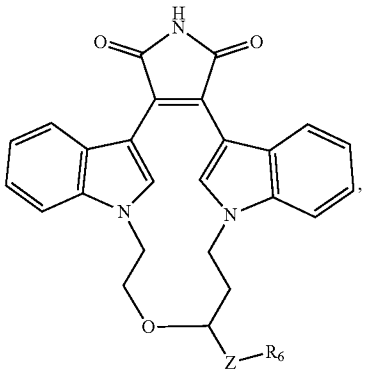

wherein $R_1$ is H or optionally substituted $C_{1-6}$ alkyl; and $R_2$ is optionally substituted $C_{1-6}$ alkyl;

or a salt thereof.

In some embodiments, the PKC inhibitor is a compound selected from:

(72)

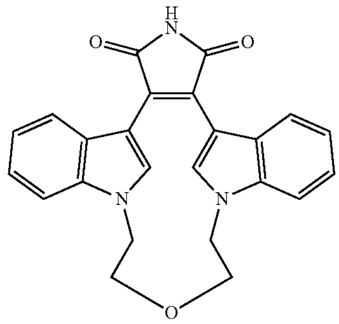

;

-continued
(73)
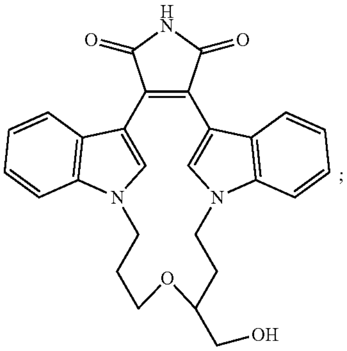
(74)
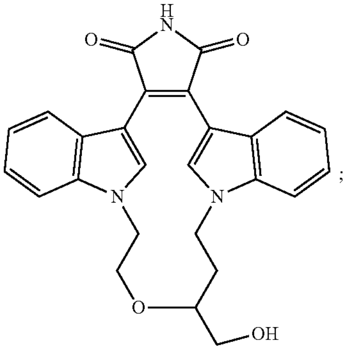
(75)
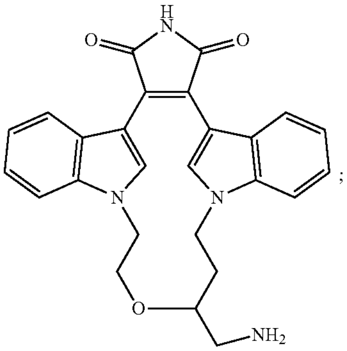
(76)
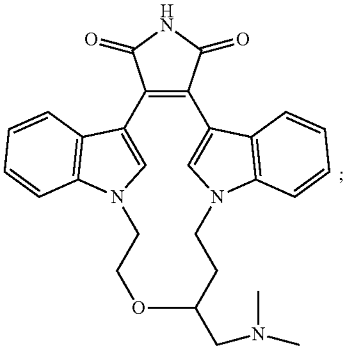
-continued
(77)
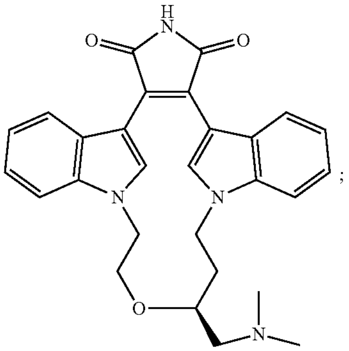
(78)
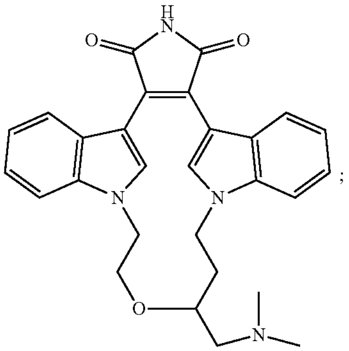
(79)
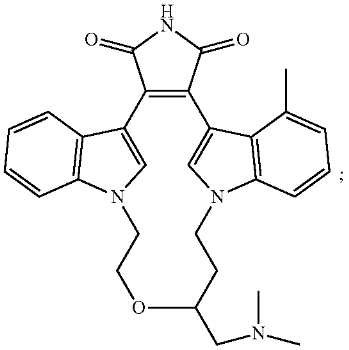
(80)
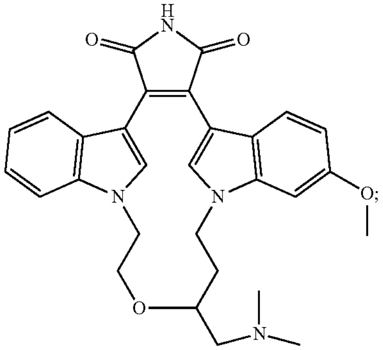

-continued
(81)
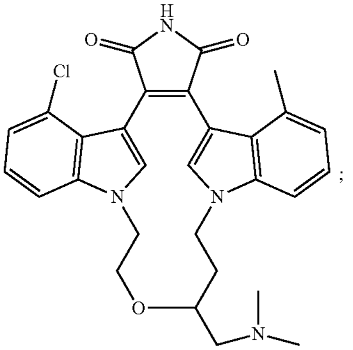
(82)
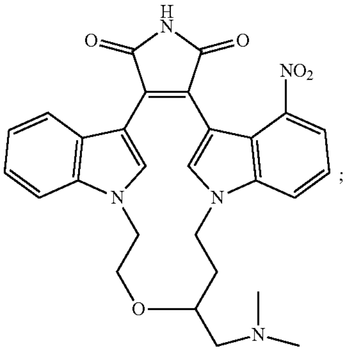
(83)
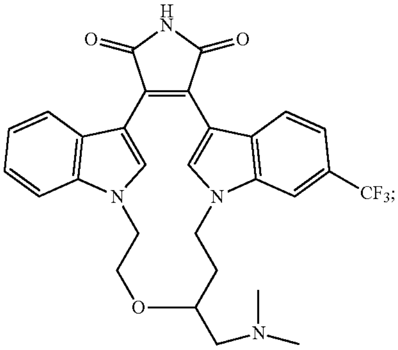
(84)
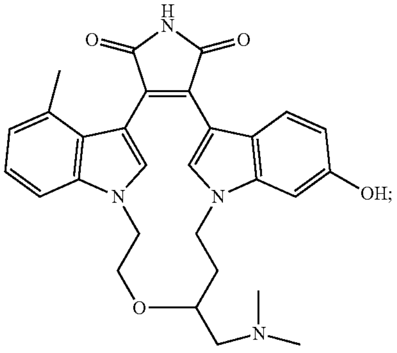
-continued
(85)
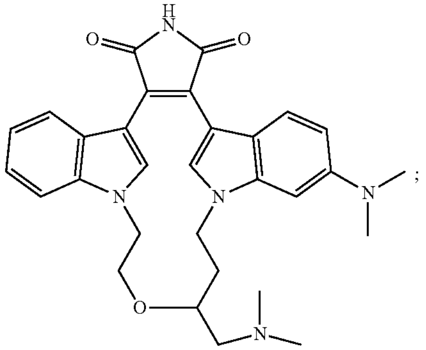
(86)
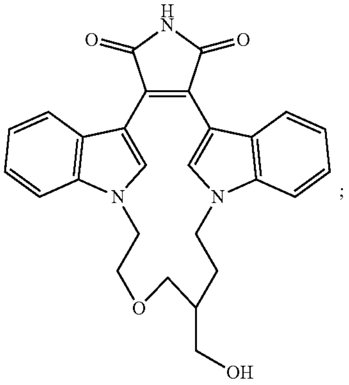
(87)
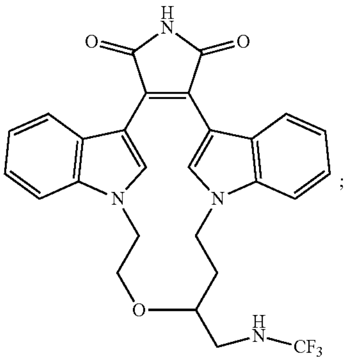
(88)
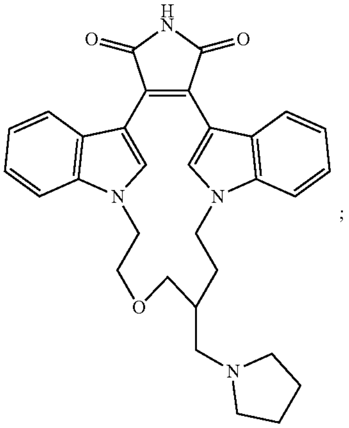

-continued
(89)
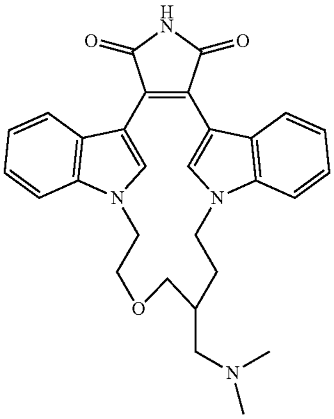
;
(90)
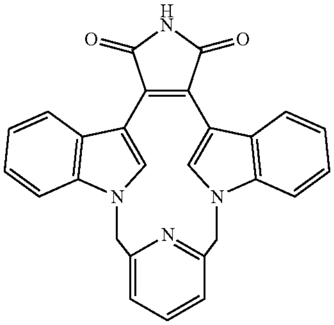
;
(91)
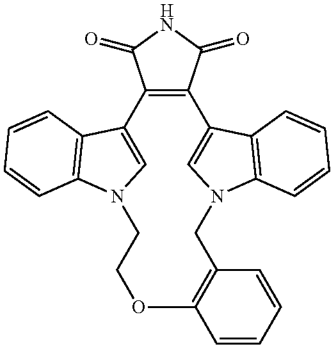
;
(92)
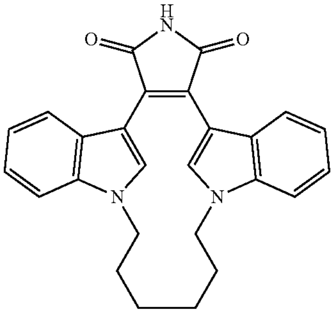
;
-continued
(93)
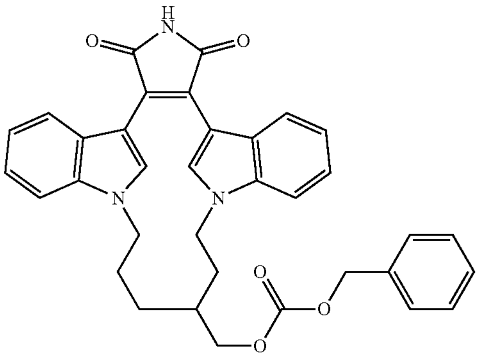
;
(94)
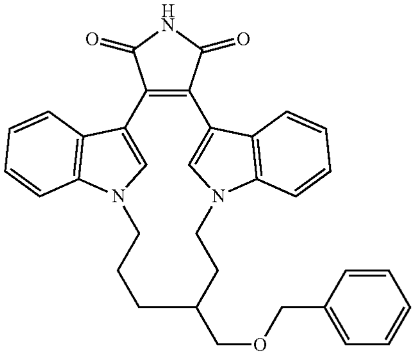
;
(95)
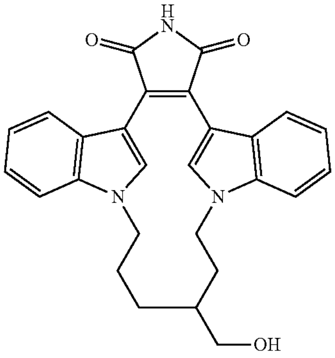
;
(96)
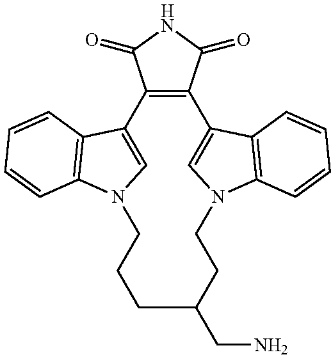
;

-continued
(97)
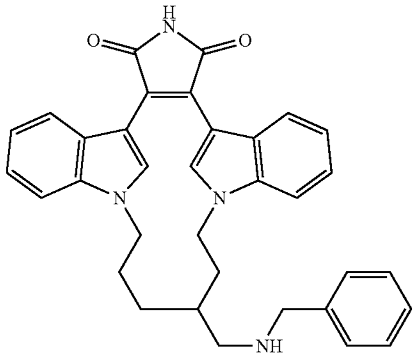
;
(98)
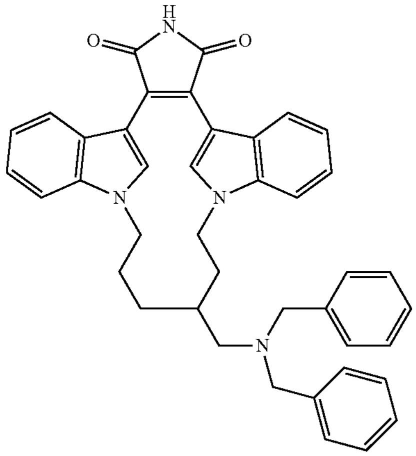
;
(99)
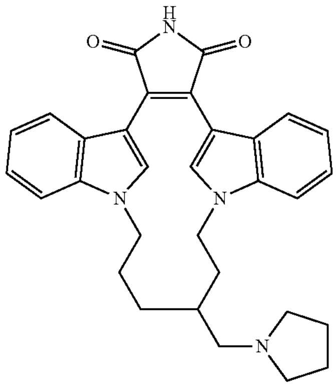
;
(100)
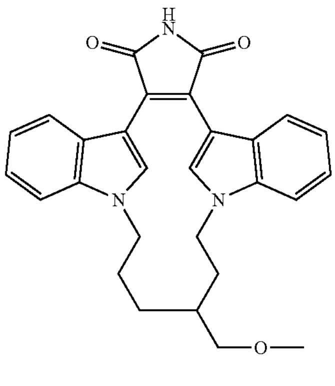
;
-continued
(101)
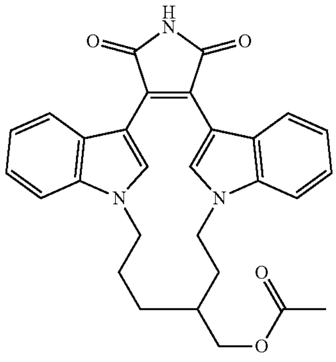
;
(102)
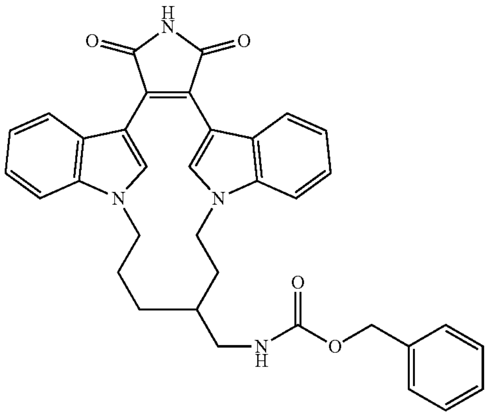
;
(103)
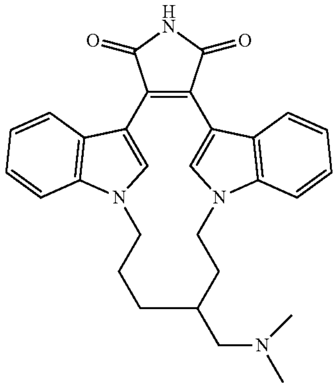
;
(104)
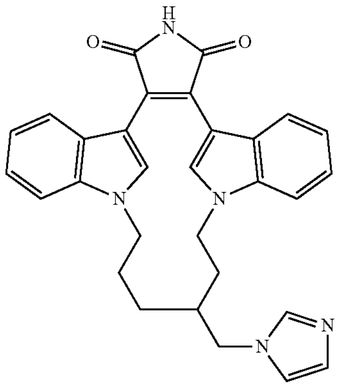
;

-continued (105)

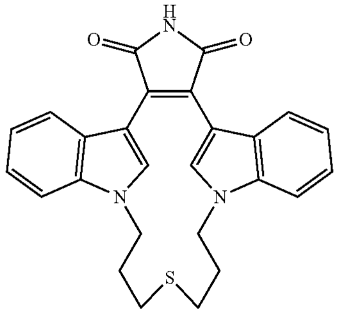

;

(106)

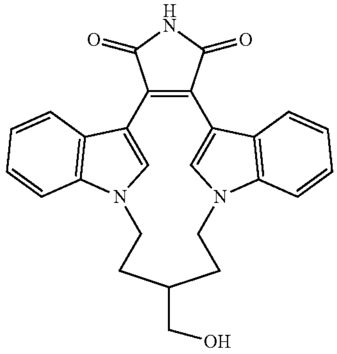

;

(107)

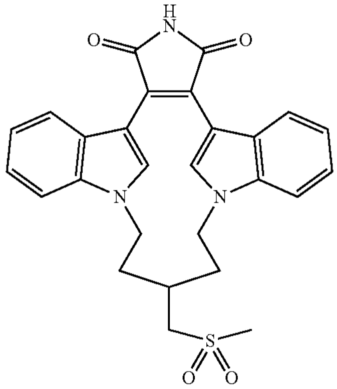

;

(108)

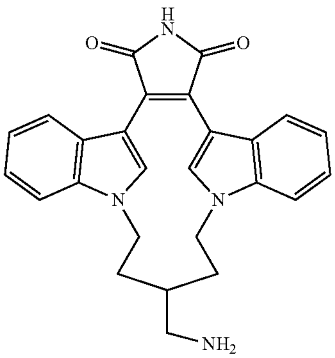

; and

-continued (109)

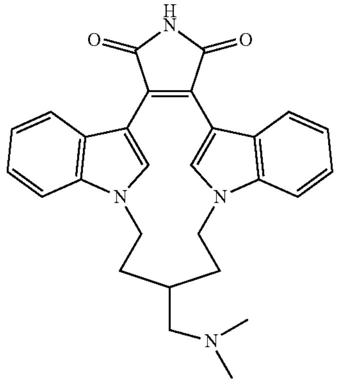

.

In some embodiments of any of the above aspects or embodiments of the disclosure, the concentration of the substance that reduces activity and/or expression of PKC, when contacted with the cell, is from about 100 μM to about 1 mM (e.g., about 100 μM, 105 μM, 110 μM, 115 μM, 120 μM, 125 μM, 130 μM, 135 μM, 140 μM, 145 μM, 150 μM, 155 μM, 160 μM, 165 μM, 170 μM, 175 μM, 180 μM, 185 μM, 190 μM, 195 μM, 200 μM, 205 μM, 210 μM, 215 μM, 220 μM, 225 μM, 230 μM, 235 μM, 240 μM, 245 μM, 250 μM, 255 μM, 260 μM, 265 μM, 270 μM, 275 μM, 280 μM, 285 μM, 290 μM, 295 μM, 300 μM, 305 μM, 310 μM, 315 μM, 320 μM, 325 μM, 330 μM, 335 μM, 340 μM, 345 μM, 350 μM, 355 μM, 360 μM, 365 μM, 370 μM, 375 μM, 380 μM, 385 μM, 390 μM, 395 μM, 400 μM, 405 μM, 410 μM, 415 μM, 420 μM, 425 μM, 430 μM, 435 μM, 440 μM, 445 μM, 450 μM, 455 μM, 460 μM, 465 μM, 470 μM, 475 μM, 480 μM, 485 μM, 490 μM, 495 μM, 500 μM, 505 μM, 510 μM, 515 μM, 520 μM, 525 μM, 530 μM, 535 μM, 540 μM, 545 μM, 550 μM, 555 μM, 560 μM, 565 μM, 570 μM, 575 μM, 580 μM, 585 μM, 590 μM, 595 μM, 600 μM, 605 μM, 610 μM, 615 μM, 620 μM, 625 μM, 630 μM, 635 μM, 640 μM, 645 μM, 650 μM, 655 μM, 660 μM, 665 μM, 670 μM, 675 μM, 680 μM, 685 μM, 690 μM, 695 μM, 700 μM, 705 μM, 710 μM, 715 μM, 720 μM, 725 μM, 730 μM, 735 μM, 740 μM, 745 μM, 750 μM, 755 μM, 760 μM, 765 μM, 770 μM, 775 μM, 780 μM, 785 μM, 790 μM, 795 μM, 800 μM, 805 μM, 810 μM, 815 μM, 820 μM, 825 μM, 830 μM, 835 μM, 840 μM, 845 μM, 850 μM, 855 μM, 860 μM, 865 μM, 870 μM, 875 μM, 880 μM, 885 μM, 890 μM, 895 μM, 900 μM, 905 μM, 910 μM, 915 μM, 920 μM, 925 μM, 930 μM, 935 μM, 940 μM, 945 μM, 950 μM, 955 μM, 960 μM, 965 μM, 970 μM, 975 μM, 980 μM, 985 μM, 990 μM, 995 μM, or 1 mM). In some embodiments, the concentration of the substance that reduces activity and/or expression of PKC, when contacted with the cell, is from about 200 μM to about 600 μM (e.g., about 200 μM, 205 μM, 210 μM, 215 μM, 220 μM, 225 μM, 230 μM, 235 μM, 240 μM, 245 μM, 250 μM, 255 μM, 260 μM, 265 μM, 270 μM, 275 μM, 280 μM, 285 μM, 290 μM, 295 μM, 300 μM, 305 μM, 310 μM, 315 μM, 320 μM, 325 μM, 330 μM, 335 μM, 340 μM, 345 μM, 350 μM, 355 μM, 360 μM, 365 μM, 370 μM, 375 μM, 380 μM, 385 μM, 390 μM, 395 μM, 400 μM, 405 μM, 410 μM, 415 μM, 420 μM, 425 μM, 430 μM, 435 μM, 440 μM, 445 μM, 450 μM, 455 μM, 460 μM, 465 μM, 470 μM, 475 μM, 480 μM, 485 μM, 490 μM, 495 μM, 500 μM, 505 μM, 510 μM, 515 μM, 520 μM, 525 μM, 530 μM, 535 μM, 540 μM, 545 μM, 550 μM, 555 μM, 560 μM, 565 μM, 570 μM, 575 μM, 580 μM, 585 μM, 590 μM, 595 μM, or 600 μM). In some embodiments, the concentration of the substance that reduces activity and/or expression of PKC, when contacted with the cell, is about 400 μM.

In some embodiments, the concentration of the poloxamer, when contacted with the cell, is from about 10 ng/ml to about 9.5 μg/ml (e.g., about 10 ng/ml, 15 ng/ml, 20 ng/ml, 25 ng/ml, 30 ng/ml, 35 ng/ml, 40 ng/ml, 45 ng/ml, 50 ng/ml, 55 ng/ml, 60 ng/ml, 65 ng/ml, 70 ng/ml, 75 ng/ml, 80 ng/ml, 85 ng/ml, 90 ng/ml, 95 ng/ml, 100 ng/ml, 105 ng/ml, 110 ng/ml, 115 ng/ml, 120 ng/ml, 125 ng/ml, 130 ng/ml, 135 ng/ml, 140 ng/ml, 145 ng/ml, 150 ng/ml, 155 ng/ml, 160 ng/ml, 165 ng/ml, 170 ng/ml, 175 ng/ml, 180 ng/ml, 185 ng/ml, 190 ng/ml, 195 ng/ml, 200 ng/ml, 205 ng/ml, 210 ng/ml, 215 ng/ml, 220 ng/ml, 225 ng/ml, 230 ng/ml, 235 ng/ml, 240 ng/ml, 245 ng/ml, 250 ng/ml, 255 ng/ml, 260 ng/ml, 265 ng/ml, 270 ng/ml, 275 ng/ml, 280 ng/ml, 285 ng/ml, 290 ng/ml, 295 ng/ml, 300 ng/ml, 305 ng/ml, 310 ng/ml, 315 ng/ml, 320 ng/ml, 325 ng/ml, 330 ng/ml, 335 ng/ml, 340 ng/ml, 345 ng/ml, 350 ng/ml, 355 ng/ml, 360 ng/ml, 365 ng/ml, 370 ng/ml, 375 ng/ml, 380 ng/ml, 385 ng/ml, 390 ng/ml, 395 ng/ml, 400 ng/ml, 405 ng/ml, 410 ng/ml, 415 ng/ml, 420 ng/ml, 425 ng/ml, 430 ng/ml, 435 ng/ml, 440 ng/ml, 445 ng/ml, 450 ng/ml, 455 ng/ml, 460 ng/ml, 465 ng/ml, 470 ng/ml, 475 ng/ml, 480 ng/ml, 485 ng/ml, 490 ng/ml, 495 ng/ml, 500 ng/ml, 505 ng/ml, 510 ng/ml, 515 ng/ml, 520 ng/ml, 525 ng/ml, 530 ng/ml, 535 ng/ml, 540 ng/ml, 545 ng/ml, 550 ng/ml, 555 ng/ml, 560 ng/ml, 565 ng/ml, 570 ng/ml, 575 ng/ml, 580 ng/ml, 585 ng/ml, 590 ng/ml, 595 ng/ml, 600 ng/ml, 605 ng/ml, 610 ng/ml, 615 ng/ml, 620 ng/ml, 625 ng/ml, 630 ng/ml, 635 ng/ml, 640 ng/ml, 645 ng/ml, 650 ng/ml, 655 ng/ml, 660 ng/ml, 665 ng/ml, 670 ng/ml, 675 ng/ml, 680 ng/ml, 685 ng/ml, 690 ng/ml, 695 ng/ml, 700 ng/ml, 705 ng/ml, 710 ng/ml, 715 ng/ml, 720 ng/ml, 725 ng/ml, 730 ng/ml, 735 ng/ml, 740 ng/ml, 745 ng/ml, 750 ng/ml, 755 ng/ml, 760 ng/ml, 765 ng/ml, 770 ng/ml, 775 ng/ml, 780 ng/ml, 785 ng/ml, 790 ng/ml, 795 ng/ml, 800 ng/ml, 805 ng/ml, 810 ng/ml, 815 ng/ml, 820 ng/ml, 825 ng/ml, 830 ng/ml, 835 ng/ml, 840 ng/ml, 845 ng/ml, 850 ng/ml, 855 ng/ml, 860 ng/ml, 865 ng/ml, 870 ng/ml, 875 ng/ml, 880 ng/ml, 885 ng/ml, 890 ng/ml, 895 ng/ml, 900 ng/ml, 905 ng/ml, 910 ng/ml, 915 ng/ml, 920 ng/ml, 925 ng/ml, 930 ng/ml, 935 ng/ml, 940 ng/ml, 945 ng/ml, 950 ng/ml, 955 ng/ml, 960 ng/ml, 965 ng/ml, 970 ng/ml, 975 ng/ml, 980 ng/ml, 985 ng/ml, 990 ng/ml, 995 ng/ml, 1 μg/ml, 1.1 μg/ml, 1.2 μg/ml, 1.3 μg/ml, 1.4 μg/ml, 1.5 μg/ml, 1.6 μg/ml, 1.7 μg/ml, 1.8 μg/ml, 1.9 μg/ml, 2 μg/ml, 2.1 μg/ml, 2.2 μg/ml, 2.3 μg/ml, 2.4 μg/ml, 2.5 μg/ml, 2.6 μg/ml, 2.7 μg/ml, 2.8 μg/ml, 2.9 μg/ml, 3 μg/ml, 3.1 μg/ml, 3.2 μg/ml, 3.3 μg/ml, 3.4 μg/ml, 3.5 μg/ml, 3.6 μg/ml, 3.7 μg/ml, 3.8 μg/ml, 3.9 μg/ml, 4 μg/ml, 4.1 μg/ml, 4.2 μg/ml, 4.3 μg/ml, 4.4 μg/ml, 4.5 μg/ml, 4.6 μg/ml, 4.7 μg/ml, 4.8 μg/ml, 4.9 μg/ml, 5 μg/ml, 5.1 μg/ml, 5.2 μg/ml, 5.3 μg/ml, 5.4 μg/ml, 5.5 μg/ml, 5.6 μg/ml, 5.7 μg/ml, 5.8 μg/ml, 5.9 μg/ml, 6 μg/ml, 6.1 μg/ml, 6.2 μg/ml, 6.3 μg/ml, 6.4 μg/ml, 6.5 μg/ml, 6.6 μg/ml, 6.7 μg/ml, 6.8 μg/ml, 6.9 μg/ml, 7 μg/ml, 7.1 μg/ml, 7.2 μg/ml, 7.3 μg/ml, 7.4 μg/ml, 7.5 μg/ml, 7.6 μg/ml, 7.7 μg/ml, 7.8 μg/ml, 7.9 μg/ml, 8 μg/ml, 8.1 μg/ml, 8.2 μg/ml, 8.3 μg/ml, 8.4 μg/ml, 8.5 μg/ml, 8.6 μg/ml, 8.7 μg/ml, 8.8 μg/ml, 8.9 μg/ml, 9 μg/ml, 9.1 μg/ml, 9.2 μg/ml, 9.3 μg/ml, 9.4 μg/ml, or 9.5 μg/ml).

In some embodiments, the concentration of the poloxamer, when contacted with the cell, is from about 10 ng/ml to about 9 μg/ml (e.g., about 10 ng/ml, 15 ng/ml, 20 ng/ml, 25 ng/ml, 30 ng/ml, 35 ng/ml, 40 ng/ml, 45 ng/ml, 50 ng/ml, 55 ng/ml, 60 ng/ml, 65 ng/ml, 70 ng/ml, 75 ng/ml, 80 ng/ml, 85 ng/ml, 90 ng/ml, 95 ng/ml, 100 ng/ml, 105 ng/ml, 110 ng/ml, 115 ng/ml, 120 ng/ml, 125 ng/ml, 130 ng/ml, 135 ng/ml, 140 ng/ml, 145 ng/ml, 150 ng/ml, 155 ng/ml, 160 ng/ml, 165 ng/ml, 170 ng/ml, 175 ng/ml, 180 ng/ml, 185 ng/ml, 190 ng/ml, 195 ng/ml, 200 ng/ml, 205 ng/ml, 210 ng/ml, 215 ng/ml, 220 ng/ml, 225 ng/ml, 230 ng/ml, 235 ng/ml, 240 ng/ml, 245 ng/ml, 250 ng/ml, 255 ng/ml, 260 ng/ml, 265 ng/ml, 270 ng/ml, 275 ng/ml, 280 ng/ml, 285 ng/ml, 290 ng/ml, 295 ng/ml, 300 ng/ml, 305 ng/ml, 310 ng/ml, 315 ng/ml, 320 ng/ml, 325 ng/ml, 330 ng/ml, 335 ng/ml, 340 ng/ml, 345 ng/ml, 350 ng/ml, 355 ng/ml, 360 ng/ml, 365 ng/ml, 370 ng/ml, 375 ng/ml, 380 ng/ml, 385 ng/ml, 390 ng/ml, 395 ng/ml, 400 ng/ml, 405 ng/ml, 410 ng/ml, 415 ng/ml, 420 ng/ml, 425 ng/ml, 430 ng/ml, 435 ng/ml, 440 ng/ml, 445 ng/ml, 450 ng/ml, 455 ng/ml, 460 ng/ml, 465 ng/ml, 470 ng/ml, 475 ng/ml, 480 ng/ml, 485 ng/ml, 490 ng/ml, 495 ng/ml, 500 ng/ml, 505 ng/ml, 510 ng/ml, 515 ng/ml, 520 ng/ml, 525 ng/ml, 530 ng/ml, 535 ng/ml, 540 ng/ml, 545 ng/ml, 550 ng/ml, 555 ng/ml, 560 ng/ml, 565 ng/ml, 570 ng/ml, 575 ng/ml, 580 ng/ml, 585 ng/ml, 590 ng/ml, 595 ng/ml, 600 ng/ml, 605 ng/ml, 610 ng/ml, 615 ng/ml, 620 ng/ml, 625 ng/ml, 630 ng/ml, 635 ng/ml, 640 ng/ml, 645 ng/ml, 650 ng/ml, 655 ng/ml, 660 ng/ml, 665 ng/ml, 670 ng/ml, 675 ng/ml, 680 ng/ml, 685 ng/ml, 690 ng/ml, 695 ng/ml, 700 ng/ml, 705 ng/ml, 710 ng/ml, 715 ng/ml, 720 ng/ml, 725 ng/ml, 730 ng/ml, 735 ng/ml, 740 ng/ml, 745 ng/ml, 750 ng/ml, 755 ng/ml, 760 ng/ml, 765 ng/ml, 770 ng/ml, 775 ng/ml, 780 ng/ml, 785 ng/ml, 790 ng/ml, 795 ng/ml, 800 ng/ml, 805 ng/ml, 810 ng/ml, 815 ng/ml, 820 ng/ml, 825 ng/ml, 830 ng/ml, 835 ng/ml, 840 ng/ml, 845 ng/ml, 850 ng/ml, 855 ng/ml, 860 ng/ml, 865 ng/ml, 870 ng/ml, 875 ng/ml, 880 ng/ml, 885 ng/ml, 890 ng/ml, 895 ng/ml, 900 ng/ml, 905 ng/ml, 910 ng/ml, 915 ng/ml, 920 ng/ml, 925 ng/ml, 930 ng/ml, 935 ng/ml, 940 ng/ml, 945 ng/ml, 950 ng/ml, 955 ng/ml, 960 ng/ml, 965 ng/ml, 970 ng/ml, 975 ng/ml, 980 ng/ml, 985 ng/ml, 990 ng/ml, 995 ng/ml, 1 μg/ml, 1.1 μg/ml, 1.2 μg/ml, 1.3 μg/ml, 1.4 μg/ml, 1.5 μg/ml, 1.6 μg/ml, 1.7 μg/ml, 1.8 μg/ml, 1.9 μg/ml, 2 μg/ml, 2.1 μg/ml, 2.2 μg/ml, 2.3 μg/ml, 2.4 μg/ml, 2.5 μg/ml, 2.6 μg/ml, 2.7 μg/ml, 2.8 μg/ml, 2.9 μg/ml, 3 μg/ml, 3.1 μg/ml, 3.2 μg/ml, 3.3 μg/ml, 3.4 μg/ml, 3.5 μg/ml, 3.6 μg/ml, 3.7 μg/ml, 3.8 μg/ml, 3.9 μg/ml, 4 μg/ml, 4.1 μg/ml, 4.2 μg/ml, 4.3 μg/ml, 4.4 μg/ml, 4.5 μg/ml, 4.6 μg/ml, 4.7 μg/ml, 4.8 μg/ml, 4.9 μg/ml, 5 μg/ml, 5.1 μg/ml, 5.2 μg/ml, 5.3 μg/ml, 5.4 μg/ml, 5.5 μg/ml, 5.6 μg/ml, 5.7 μg/ml, 5.8 μg/ml, 5.9 μg/ml, 6 μg/ml, 6.1 μg/ml, 6.2 μg/ml, 6.3 μg/ml, 6.4 μg/ml, 6.5 μg/ml, 6.6 μg/ml, 6.7 μg/ml, 6.8 μg/ml, 6.9 μg/ml, 7 μg/ml, 7.1 μg/ml, 7.2 μg/ml, 7.3 μg/ml, 7.4 μg/ml, 7.5 μg/ml, 7.6 μg/ml, 7.7 μg/ml, 7.8 μg/ml, 7.9 μg/ml, 8 μg/ml, 8.1 μg/ml, 8.2 μg/ml, 8.3 μg/ml, 8.4 μg/ml, 8.5 μg/ml, 8.6 μg/ml, 8.7 μg/ml, 8.8 μg/ml, 8.9 μg/ml, or 9 μg/ml).

In some embodiments, the concentration of the poloxamer, when contacted with the cell, is from about 50 ng/ml to about 8 μg/ml (e.g., about 50 ng/ml, 55 ng/ml, 60 ng/ml, 65 ng/ml, 70 ng/ml, 75 ng/ml, 80 ng/ml, 85 ng/ml, 90 ng/ml, 95 ng/ml, 100 ng/ml, 105 ng/ml, 110 ng/ml, 115 ng/ml, 120 ng/ml, 125 ng/ml, 130 ng/ml, 135 ng/ml, 140 ng/ml, 145 ng/ml, 150 ng/ml, 155 ng/ml, 160 ng/ml, 165 ng/ml, 170 ng/ml, 175 ng/ml, 180 ng/ml, 185 ng/ml, 190 ng/ml, 195 ng/ml, 200 ng/ml, 205 ng/ml, 210 ng/ml, 215 ng/ml, 220 ng/ml, 225 ng/ml, 230 ng/ml, 235 ng/ml, 240 ng/ml, 245 ng/ml, 250 ng/ml, 255 ng/ml, 260 ng/ml, 265 ng/ml, 270 ng/ml, 275 ng/ml, 280 ng/ml, 285 ng/ml, 290 ng/ml, 295 ng/ml, 300 ng/ml, 305 ng/ml, 310 ng/ml, 315 ng/ml, 320 ng/ml, 325 ng/ml, 330 ng/ml, 335 ng/ml, 340 ng/ml, 345 ng/ml, 350 ng/ml, 355 ng/ml, 360 ng/ml, 365 ng/ml, 370 ng/ml, 375 ng/ml, 380 ng/ml, 385 ng/ml, 390 ng/ml, 395 ng/ml, 400 ng/ml, 405 ng/ml, 410 ng/ml, 415 ng/ml, 420 ng/ml, 425 ng/ml, 430 ng/ml, 435 ng/ml, 440 ng/ml, 445 ng/ml, 450 ng/ml, 455 ng/ml, 460 ng/ml, 465 ng/ml, 470 ng/ml, 475 ng/ml, 480 ng/ml, 485 ng/ml, 490 ng/ml, 495 ng/ml, 500 ng/ml, 505 ng/ml, 510 ng/ml, 515 ng/ml, 520 ng/ml, 525 ng/ml, 530 ng/ml, 535 ng/ml, 540 ng/ml, 545 ng/ml, 550 ng/ml, 555 ng/ml, 560 ng/ml, 565 ng/ml, 570 ng/ml, 575 ng/ml, 580 ng/ml, 585 ng/ml, 590 ng/ml, 595 ng/ml, 600 ng/ml, 605 ng/ml, 610 ng/ml, 615 ng/ml, 620 ng/ml, 625 ng/ml, 630 ng/ml, 635 ng/ml, 640 ng/ml, 645 ng/ml, 650 ng/ml, 655 ng/ml, 660 ng/ml, 665 ng/ml, 670 ng/ml, 675 ng/ml, 680 ng/ml, 685 ng/ml, 690 ng/ml, 695 ng/ml, 700 ng/ml, 705 ng/ml, 710 ng/ml, 715 ng/ml, 720 ng/ml, 725 ng/ml, 730 ng/ml, 735 ng/ml, 740 ng/ml, 745 ng/ml, 750 ng/ml, 755 ng/ml, 760 ng/ml, 765 ng/ml, 770 ng/ml, 775 ng/ml, 780 ng/ml, 785 ng/ml, 790 ng/ml, 795 ng/ml, 800 ng/ml, 805 ng/ml, 810 ng/ml, 815 ng/ml, 820 ng/ml, 825 ng/ml, 830 ng/ml, 835 ng/ml, 840 ng/ml, 845 ng/ml, 850 ng/ml, 855 ng/ml, 860 ng/ml, 865 ng/ml, 870 ng/ml, 875 ng/ml, 880 ng/ml, 885 ng/ml, 890 ng/ml, 895 ng/ml, 900 ng/ml, 905 ng/ml, 910 ng/ml, 915 ng/ml, 920 ng/ml, 925 ng/ml, 930 ng/ml, 935 ng/ml, 940 ng/ml, 945 ng/ml, 950 ng/ml, 955 ng/ml, 960 ng/ml, 965 ng/ml, 970 ng/ml, 975 ng/ml, 980 ng/ml, 985 ng/ml, 990 ng/ml, 995 ng/ml, 1 μg/ml, 1.1 μg/ml, 1.2 μg/ml, 1.3 μg/ml, 1.4 μg/ml, 1.5 μg/ml, 1.6 μg/ml, 1.7 μg/ml, 1.8 μg/ml, 1.9 μg/ml, 2 μg/ml, 2.1 μg/ml, 2.2 μg/ml, 2.3 μg/ml, 2.4 μg/ml, 2.5 μg/ml, 2.6 μg/ml, 2.7 μg/ml, 2.8 μg/ml, 2.9 μg/ml, 3 μg/ml, 3.1 μg/ml, 3.2 μg/ml, 3.3 μg/ml, 3.4 μg/ml, 3.5 μg/ml, 3.6 μg/ml, 3.7 μg/ml, 3.8 μg/ml, 3.9 μg/ml, 4 μg/ml, 4.1 μg/ml, 4.2 μg/ml, 4.3 μg/ml, 4.4 μg/ml, 4.5 μg/ml, 4.6 μg/ml, 4.7 μg/ml, 4.8 μg/ml, 4.9 μg/ml, 5 μg/ml, 5.1 μg/ml, 5.2 μg/ml, 5.3 μg/ml, 5.4 μg/ml, 5.5 μg/ml, 5.6 μg/ml, 5.7 μg/ml, 5.8 μg/ml, 5.9 μg/ml, 6 μg/ml, 6.1 μg/ml, 6.2 μg/ml, 6.3 μg/ml, 6.4 μg/ml, 6.5 μg/ml, 6.6 μg/ml, 6.7 μg/ml, 6.8 μg/ml, 6.9 μg/ml, 7 μg/ml, 7.1 μg/ml, 7.2 μg/ml, 7.3 μg/ml, 7.4 μg/ml, 7.5 μg/ml, 7.6 μg/ml, 7.7 μg/ml, 7.8 μg/ml, 7.9 μg/ml, or 8 μg/ml).

In some embodiments, the concentration of the poloxamer, when contacted with the cell, is from about 100 ng/ml to about 7 μg/ml (e.g., about 100 ng/ml, 105 ng/ml, 110 ng/ml, 115 ng/ml, 120 ng/ml, 125 ng/ml, 130 ng/ml, 135 ng/ml, 140 ng/ml, 145 ng/ml, 150 ng/ml, 155 ng/ml, 160 ng/ml, 165 ng/ml, 170 ng/ml, 175 ng/ml, 180 ng/ml, 185 ng/ml, 190 ng/ml, 195 ng/ml, 200 ng/ml, 205 ng/ml, 210 ng/ml, 215 ng/ml, 220 ng/ml, 225 ng/ml, 230 ng/ml, 235 ng/ml, 240 ng/ml, 245 ng/ml, 250 ng/ml, 255 ng/ml, 260 ng/ml, 265 ng/ml, 270 ng/ml, 275 ng/ml, 280 ng/ml, 285 ng/ml, 290 ng/ml, 295 ng/ml, 300 ng/ml, 305 ng/ml, 310 ng/ml, 315 ng/ml, 320 ng/ml, 325 ng/ml, 330 ng/ml, 335 ng/ml, 340 ng/ml, 345 ng/ml, 350 ng/ml, 355 ng/ml, 360 ng/ml, 365 ng/ml, 370 ng/ml, 375 ng/ml, 380 ng/ml, 385 ng/ml, 390 ng/ml, 395 ng/ml, 400 ng/ml, 405 ng/ml, 410 ng/ml, 415 ng/ml, 420 ng/ml, 425 ng/ml, 430 ng/ml, 435 ng/ml, 440 ng/ml, 445 ng/ml, 450 ng/ml, 455 ng/ml, 460 ng/ml, 465 ng/ml, 470 ng/ml, 475 ng/ml, 480 ng/ml, 485 ng/ml, 490 ng/ml, 495 ng/ml, 500 ng/ml, 505 ng/ml, 510 ng/ml, 515 ng/ml, 520 ng/ml, 525 ng/ml, 530 ng/ml, 535 ng/ml, 540 ng/ml, 545 ng/ml, 550 ng/ml, 555 ng/ml, 560 ng/ml, 565 ng/ml, 570 ng/ml, 575 ng/ml, 580 ng/ml, 585 ng/ml, 590 ng/ml, 595 ng/ml, 600 ng/ml, 605 ng/ml, 610 ng/ml, 615 ng/ml, 620 ng/ml, 625 ng/ml, 630 ng/ml, 635 ng/ml, 640 ng/ml, 645 ng/ml, 650 ng/ml, 655 ng/ml, 660 ng/ml, 665 ng/ml, 670 ng/ml, 675 ng/ml, 680 ng/ml, 685 ng/ml, 690 ng/ml, 695 ng/ml, 700 ng/ml, 705 ng/ml, 710 ng/ml, 715 ng/ml, 720 ng/ml, 725 ng/ml, 730 ng/ml, 735 ng/ml, 740 ng/ml, 745 ng/ml, 750 ng/ml, 755 ng/ml, 760 ng/ml, 765 ng/ml, 770 ng/ml, 775 ng/ml, 780 ng/ml, 785 ng/ml, 790 ng/ml, 795 ng/ml, 800 ng/ml, 805 ng/ml, 810 ng/ml, 815 ng/ml, 820 ng/ml, 825 ng/ml, 830 ng/ml, 835 ng/ml, 840 ng/ml, 845 ng/ml, 850 ng/ml, 855 ng/ml, 860 ng/ml, 865 ng/ml, 870 ng/ml, 875 ng/ml, 880 ng/ml, 885 ng/ml, 890 ng/ml, 895 ng/ml, 900 ng/ml, 905 ng/ml, 910 ng/ml, 915 ng/ml, 920 ng/ml, 925 ng/ml, 930 ng/ml, 935 ng/ml, 940 ng/ml, 945 ng/ml, 950 ng/ml, 955 ng/ml, 960 ng/ml, 965 ng/ml, 970 ng/ml, 975 ng/ml, 980 ng/ml, 985 ng/ml, 990 ng/ml, 995 ng/ml, 1 μg/ml, 1.1 μg/ml, 1.2 μg/ml, 1.3 μg/ml, 1.4 μg/ml, 1.5 μg/ml, 1.6 μg/ml, 1.7 μg/ml, 1.8 μg/ml, 1.9 μg/ml, 2 μg/ml, 2.1 μg/ml, 2.2 μg/ml, 2.3 μg/ml, 2.4 μg/ml, 2.5 μg/ml, 2.6 μg/ml, 2.7 μg/ml, 2.8 μg/ml, 2.9 μg/ml, 3 μg/ml, 3.1 μg/ml, 3.2 μg/ml, 3.3 μg/ml, 3.4 μg/ml, 3.5 μg/ml, 3.6 μg/ml, 3.7 μg/ml, 3.8 μg/ml, 3.9 μg/ml, 4 μg/ml, 4.1 μg/ml, 4.2 μg/ml, 4.3 μg/ml, 4.4 μg/ml, 4.5 μg/ml, 4.6 μg/ml, 4.7 μg/ml, 4.8 μg/ml, 4.9 μg/ml, 5 μg/ml, 5.1 μg/ml, 5.2 μg/ml, 5.3 μg/ml, 5.4 μg/ml, 5.5 μg/ml, 5.6 μg/ml, 5.7 μg/ml, 5.8 μg/ml, 5.9 μg/ml, 6 μg/ml, 6.1 μg/ml, 6.2 μg/ml, 6.3 μg/ml, 6.4 μg/ml, 6.5 μg/ml, 6.6 μg/ml, 6.7 μg/ml, 6.8 μg/ml, 6.9 μg/ml, or 7 μg/ml).

In some embodiments, the concentration of the poloxamer, when contacted with the cell, is from about 250 ng/ml to about 6 μg/ml (e.g., about 250 ng/ml, 255 ng/ml, 260 ng/ml, 265 ng/ml, 270 ng/ml, 275 ng/ml, 280 ng/ml, 285 ng/ml, 290 ng/ml, 295 ng/ml, 300 ng/ml, 305 ng/ml, 310 ng/ml, 315 ng/ml, 320 ng/ml, 325 ng/ml, 330 ng/ml, 335 ng/ml, 340 ng/ml, 345 ng/ml, 350 ng/ml, 355 ng/ml, 360 ng/ml, 365 ng/ml, 370 ng/ml, 375 ng/ml, 380 ng/ml, 385 ng/ml, 390 ng/ml, 395 ng/ml, 400 ng/ml, 405 ng/ml, 410 ng/ml, 415 ng/ml, 420 ng/ml, 425 ng/ml, 430 ng/ml, 435 ng/ml, 440 ng/ml, 445 ng/ml, 450 ng/ml, 455 ng/ml, 460 ng/ml, 465 ng/ml, 470 ng/ml, 475 ng/ml, 480 ng/ml, 485 ng/ml, 490 ng/ml, 495 ng/ml, 500 ng/ml, 505 ng/ml, 510 ng/ml, 515 ng/ml, 520 ng/ml, 525 ng/ml, 530 ng/ml, 535 ng/ml, 540 ng/ml, 545 ng/ml, 550 ng/ml, 555 ng/ml, 560 ng/ml, 565 ng/ml, 570 ng/ml, 575 ng/ml, 580 ng/ml, 585 ng/ml, 590 ng/ml, 595 ng/ml, 600 ng/ml, 605 ng/ml, 610 ng/ml, 615 ng/ml, 620 ng/ml, 625 ng/ml, 630 ng/ml, 635 ng/ml, 640 ng/ml, 645 ng/ml, 650 ng/ml, 655 ng/ml, 660 ng/ml, 665 ng/ml, 670 ng/ml, 675 ng/ml, 680 ng/ml, 685 ng/ml, 690 ng/ml, 695 ng/ml, 700 ng/ml, 705 ng/ml, 710 ng/ml, 715 ng/ml, 720 ng/ml, 725 ng/ml, 730 ng/ml, 735 ng/ml, 740 ng/ml, 745 ng/ml, 750 ng/ml, 755 ng/ml, 760 ng/ml, 765 ng/ml, 770 ng/ml, 775 ng/ml, 780 ng/ml, 785 ng/ml, 790 ng/ml, 795 ng/ml, 800 ng/ml, 805 ng/ml, 810 ng/ml, 815 ng/ml, 820 ng/ml, 825 ng/ml, 830 ng/ml, 835 ng/ml, 840 ng/ml, 845 ng/ml, 850 ng/ml, 855 ng/ml, 860 ng/ml, 865 ng/ml, 870 ng/ml, 875 ng/ml, 880 ng/ml, 885 ng/ml, 890 ng/ml, 895 ng/ml, 900 ng/ml, 905 ng/ml, 910 ng/ml, 915 ng/ml, 920 ng/ml, 925 ng/ml, 930 ng/ml, 935 ng/ml, 940 ng/ml, 945 ng/ml, 950 ng/ml, 955 ng/ml, 960 ng/ml, 965 ng/ml, 970 ng/ml, 975 ng/ml, 980 ng/ml, 985 ng/ml, 990 ng/ml, 995 ng/ml, 1 μg/ml, 1.1 μg/ml, 1.2 μg/ml, 1.3 μg/ml, 1.4 μg/ml, 1.5 μg/ml, 1.6 μg/ml, 1.7 μg/ml, 1.8 μg/ml, 1.9 μg/ml, 2 μg/ml, 2.1 μg/ml, 2.2 μg/ml, 2.3 μg/ml, 2.4 μg/ml, 2.5 μg/ml, 2.6 μg/ml, 2.7 μg/ml, 2.8 μg/ml, 2.9 μg/ml, 3 μg/ml, 3.1 μg/ml, 3.2 μg/ml, 3.3 μg/ml, 3.4 μg/ml, 3.5 μg/ml, 3.6 μg/ml, 3.7 μg/ml, 3.8 μg/ml, 3.9 μg/ml, 4 μg/ml, 4.1 μg/ml, 4.2 μg/ml, 4.3 μg/ml, 4.4 μg/ml, 4.5 μg/ml, 4.6 μg/ml, 4.7 μg/ml, 4.8 μg/ml, 4.9 μg/ml, 5 μg/ml, 5.1 μg/ml, 5.2 μg/ml, 5.3 μg/ml, 5.4 μg/ml, 5.5 μg/ml, 5.6 μg/ml, 5.7 μg/ml, 5.8 μg/ml, 5.9 μg/ml, or 6 μg/ml).

In some embodiments, the concentration of the poloxamer, when contacted with the cell, is from about 500 ng/ml to about 5 μg/ml (e.g., about 500 ng/ml, 505 ng/ml, 510 ng/ml, 515 ng/ml, 520 ng/ml, 525 ng/ml, 530 ng/ml, 535 ng/ml, 540 ng/ml, 545 ng/ml, 550 ng/ml, 555 ng/ml, 560 ng/ml, 565 ng/ml, 570 ng/ml, 575 ng/ml, 580 ng/ml, 585 ng/ml, 590 ng/ml, 595 ng/ml, 600 ng/ml, 605 ng/ml, 610 ng/ml, 615 ng/ml, 620 ng/ml, 625 ng/ml, 630 ng/ml, 635 ng/ml, 640 ng/ml, 645 ng/ml, 650 ng/ml, 655 ng/ml, 660 ng/ml, 665 ng/ml, 670 ng/ml, 675 ng/ml, 680 ng/ml, 685 ng/ml, 690 ng/ml, 695 ng/ml, 700 ng/ml, 705 ng/ml, 710 ng/ml, 715 ng/ml, 720 ng/ml, 725 ng/ml, 730 ng/ml, 735 ng/ml, 740 ng/ml, 745 ng/ml, 750 ng/ml, 755 ng/ml, 760 ng/ml, 765 ng/ml, 770 ng/ml, 775 ng/ml, 780 ng/ml, 785 ng/ml, 790 ng/ml, 795 ng/ml, 800 ng/ml, 805 ng/ml, 810 ng/ml, 815 ng/ml, 820 ng/ml, 825 ng/ml, 830 ng/ml, 835 ng/ml, 840 ng/ml, 845 ng/ml, 850 ng/ml, 855 ng/ml, 860 ng/ml, 865 ng/ml, 870 ng/ml, 875 ng/ml, 880 ng/ml, 885 ng/ml, 890 ng/ml, 895 ng/ml, 900 ng/ml, 905 ng/ml, 910 ng/ml, 915 ng/ml, 920 ng/ml, 925 ng/ml, 930 ng/ml, 935 ng/ml, 940 ng/ml, 945 ng/ml, 950 ng/ml, 955 ng/ml, 960 ng/ml, 965 ng/ml, 970 ng/ml, 975 ng/ml, 980 ng/ml, 985 ng/ml, 990 ng/ml, 995 ng/ml, 1 μg/ml, 1.1 μg/ml, 1.2 μg/ml, 1.3 μg/ml, 1.4 μg/ml, 1.5 μg/ml, 1.6 μg/ml, 1.7 μg/ml, 1.8 μg/ml, 1.9 μg/ml, 2 μg/ml, 2.1 μg/ml, 2.2 μg/ml, 2.3 μg/ml, 2.4 μg/ml, 2.5 μg/ml, 2.6 μg/ml, 2.7 μg/ml, 2.8 μg/ml, 2.9 μg/ml, 3 μg/ml, 3.1 μg/ml, 3.2 μg/ml, 3.3 μg/ml, 3.4 μg/ml, 3.5 μg/ml, 3.6 μg/ml, 3.7 μg/ml, 3.8 μg/ml, 3.9 μg/ml, 4 μg/ml, 4.1 μg/ml, 4.2 μg/ml, 4.3 μg/ml, 4.4 μg/ml, 4.5 μg/ml, 4.6 μg/ml, 4.7 μg/ml, 4.8 μg/ml, 4.9 μg/ml, or 5 μg/ml).

In some embodiments, the concentration of the poloxamer, when contacted with the cell, is from about 750 ng/ml to about 3 μg/ml (e.g., about 750 ng/ml, 755 ng/ml, 760 ng/ml, 765 ng/ml, 770 ng/ml, 775 ng/ml, 780 ng/ml, 785 ng/ml, 790 ng/ml, 795 ng/ml, 800 ng/ml, 805 ng/ml, 810 ng/ml, 815 ng/ml, 820 ng/ml, 825 ng/ml, 830 ng/ml, 835 ng/ml, 840 ng/ml, 845 ng/ml, 850 ng/ml, 855 ng/ml, 860 ng/ml, 865 ng/ml, 870 ng/ml, 875 ng/ml, 880 ng/ml, 885 ng/ml, 890 ng/ml, 895 ng/ml, 900 ng/ml, 905 ng/ml, 910 ng/ml, 915 ng/ml, 920 ng/ml, 925 ng/ml, 930 ng/ml, 935 ng/ml, 940 ng/ml, 945 ng/ml, 950 ng/ml, 955 ng/ml, 960 ng/ml, 965 ng/ml, 970 ng/ml, 975 ng/ml, 980 ng/ml, 985 ng/ml, 990 ng/ml, 995 ng/ml, 1 μg/ml, 1.1 μg/ml, 1.2 μg/ml, 1.3 μg/ml, 1.4 μg/ml, 1.5 μg/ml, 1.6 μg/ml, 1.7 μg/ml, 1.8 μg/ml, 1.9 μg/ml, 2 μg/ml, 2.1 μg/ml, 2.2 μg/ml, 2.3 μg/ml, 2.4 μg/ml, 2.5 μg/ml, 2.6 μg/ml, 2.7 μg/ml, 2.8 μg/ml, 2.9 μg/ml, or 3 μg/ml).

In some embodiments, the concentration of the poloxamer, when contacted with the cell, is from about 800 ng/ml to about 2 μg/ml (e.g., about 800 ng/ml, 805 ng/ml, 810 ng/ml, 815 ng/ml, 820 ng/ml, 825 ng/ml, 830 ng/ml, 835 ng/ml, 840 ng/ml, 845 ng/ml, 850 ng/ml, 855 ng/ml, 860 ng/ml, 865 ng/ml, 870 ng/ml, 875 ng/ml, 880 ng/ml, 885 ng/ml, 890 ng/ml, 895 ng/ml, 900 ng/ml, 905 ng/ml, 910 ng/ml, 915 ng/ml, 920 ng/ml, 925 ng/ml, 930 ng/ml, 935 ng/ml, 940 ng/ml, 945 ng/ml, 950 ng/ml, 955 ng/ml, 960 ng/ml, 965 ng/ml, 970 ng/ml, 975 ng/ml, 980 ng/ml, 985 ng/ml, 990 ng/ml, 995 ng/ml, 1 μg/ml, 1.1 μg/ml, 1.2 μg/ml, 1.3 μg/ml, 1.4 μg/ml, 1.5 μg/ml, 1.6 μg/ml, 1.7 μg/ml, 1.8 μg/ml, 1.9 μg/ml, or 2 μg/ml).

In some embodiments, the concentration of the poloxamer, when contacted with the cell, is from about 900 ng/ml to about 1.1 μg/ml (e.g., about 900 ng/ml, 905 ng/ml, 910 ng/ml, 915 ng/ml, 920 ng/ml, 925 ng/ml, 930 ng/ml, 935 ng/ml, 940 ng/ml, 945 ng/ml, 950 ng/ml, 955 ng/ml, 960 ng/ml, 965 ng/ml, 970 ng/ml, 975 ng/ml, 980 ng/ml, 985 ng/ml, 990 ng/ml, 995 ng/ml, 1 μg/ml, 1.01 μg/ml, 1.02 μg/ml, 1.03 μg/ml, 1.04 μg/ml, 1.05 μg/ml, 1.06 μg/ml, 1.07 μg/ml, 1.08 μg/ml, 1.09 μg/ml, or 1.1 μg/ml). In some embodiments, the concentration of the poloxamer, when contacted with the cell, is about 1 μg/ml.

In some embodiments, the poloxamer has an average molar mass of polyoxypropylene subunits of greater than 2,050 g/mol (e.g., an average molar mass of polyoxypropylene subunits of about 2,055 g/mol, 2,060 g/mol, 2,075 g/mol, 2,080 g/mol, 2,085 g/mol, 2,090 g/mol, 2,095 g/mol, 2,100 g/mol, 2,200 g/mol, 2,300 g/mol, 2,400 g/mol, 2,500 g/mol, 2,600 g/mol, 2,700 g/mol, 2,800 g/mol, 2,900 g/mol, 3,000 g/mol, 3,100 g/mol, 3,200 g/mol, 3,300 g/mol, 3,400 g/mol, 3,500 g/mol, 3,600 g/mol, 3,700 g/mol, 3,800 g/mol, 3,900 g/mol, 4,000 g/mol, 4,100 g/mol, 4,200 g/mol, 4,300 g/mol, 4,400 g/mol, 4,500 g/mol, 4,600 g/mol, 4,700 g/mol, 4,800 g/mol, 4,900 g/mol, or 5,000 g/mol, or more).

In some embodiments, the poloxamer has an average molar mass of polyoxypropylene subunits of greater than 2,250 g/mol (e.g., an average molar mass of polyoxypropylene subunits of about 2,300 g/mol, 2,400 g/mol, 2,500 g/mol, 2,600 g/mol, 2,700 g/mol, 2,800 g/mol, 2,900 g/mol, 3,000 g/mol, 3,100 g/mol, 3,200 g/mol, 3,300 g/mol, 3,400 g/mol, 3,500 g/mol, 3,600 g/mol, 3,700 g/mol, 3,800 g/mol, 3,900 g/mol, 4,000 g/mol, 4,100 g/mol, 4,200 g/mol, 4,300 g/mol, 4,400 g/mol, 4,500 g/mol, 4,600 g/mol, 4,700 g/mol, 4,800 g/mol, 4,900 g/mol, or 5,000 g/mol, or more).

In some embodiments, the poloxamer has an average molar mass of polyoxypropylene subunits of greater than 2,750 g/mol (e.g., an average molar mass of polyoxypropylene subunits of about 2,800 g/mol, 2,900 g/mol, 3,000 g/mol, 3,100 g/mol, 3,200 g/mol, 3,300 g/mol, 3,400 g/mol, 3,500 g/mol, 3,600 g/mol, 3,700 g/mol, 3,800 g/mol, 3,900 g/mol, 4,000 g/mol, 4,100 g/mol, 4,200 g/mol, 4,300 g/mol, 4,400 g/mol, 4,500 g/mol, 4,600 g/mol, 4,700 g/mol, 4,800 g/mol, 4,900 g/mol, or 5,000 g/mol, or more).

In some embodiments, the poloxamer has an average molar mass of polyoxypropylene subunits of greater than 3,250 g/mol (e.g., an average molar mass of polyoxypropylene subunits of about 3,300 g/mol, 3,400 g/mol, 3,500 g/mol, 3,600 g/mol, 3,700 g/mol, 3,800 g/mol, 3,900 g/mol, 4,000 g/mol, 4,100 g/mol, 4,200 g/mol, 4,300 g/mol, 4,400 g/mol, 4,500 g/mol, 4,600 g/mol, 4,700 g/mol, 4,800 g/mol, 4,900 g/mol, or 5,000 g/mol, or more).

In some embodiments, the poloxamer has an average molar mass of polyoxypropylene subunits of greater than 3,625 g/mol (e.g., an average molar mass of polyoxypropylene subunits of about 3,700 g/mol, 3,800 g/mol, 3,900 g/mol, 4,000 g/mol, 4,100 g/mol, 4,200 g/mol, 4,300 g/mol, 4,400 g/mol, 4,500 g/mol, 4,600 g/mol, 4,700 g/mol, 4,800 g/mol, 4,900 g/mol, or 5,000 g/mol, or more).

In some embodiments, the poloxamer has an average molar mass of polyoxypropylene subunits of from about 2,050 g/mol to about 4,000 g/mol (e.g., about 2,050 g/mol, 2,055 g/mol, 2,060 g/mol, 2,065 g/mol, 2,070 g/mol, 2,075 g/mol, 2,080 g/mol, 2,085 g/mol, 2,090 g/mol, 2,095 g/mol, 2,100 g/mol, 2,105 g/mol, 2,110 g/mol, 2,115 g/mol, 2,120 g/mol, 2,125 g/mol, 2,130 g/mol, 2,135 g/mol, 2,140 g/mol, 2,145 g/mol, 2,150 g/mol, 2,155 g/mol, 2,160 g/mol, 2,165 g/mol, 2,170 g/mol, 2,175 g/mol, 2,180 g/mol, 2,185 g/mol, 2,190 g/mol, 2,195 g/mol, 2,200 g/mol, 2,205 g/mol, 2,210 g/mol, 2,215 g/mol, 2,220 g/mol, 2,225 g/mol, 2,230 g/mol, 2,235 g/mol, 2,240 g/mol, 2,245 g/mol, 2,250 g/mol, 2,255 g/mol, 2,260 g/mol, 2,265 g/mol, 2,270 g/mol, 2,275 g/mol, 2,280 g/mol, 2,285 g/mol, 2,290 g/mol, 2,295 g/mol, 2,300 g/mol, 2,305 g/mol, 2,310 g/mol, 2,315 g/mol, 2,320 g/mol, 2,325 g/mol, 2,330 g/mol, 2,335 g/mol, 2,340 g/mol, 2,345 g/mol, 2,350 g/mol, 2,355 g/mol, 2,360 g/mol, 2,365 g/mol, 2,370 g/mol, 2,375 g/mol, 2,380 g/mol, 2,385 g/mol, 2,390 g/mol, 2,395 g/mol, 2,400 g/mol, 2,405 g/mol, 2,410 g/mol, 2,415 g/mol, 2,420 g/mol, 2,425 g/mol, 2,430 g/mol, 2,435 g/mol, 2,440 g/mol, 2,445 g/mol, 2,450 g/mol, 2,455 g/mol, 2,460 g/mol, 2,465 g/mol, 2,470 g/mol, 2,475 g/mol, 2,480 g/mol, 2,485 g/mol, 2,490 g/mol, 2,495 g/mol, 2,500 g/mol, 2,505 g/mol, 2,510 g/mol, 2,515 g/mol, 2,520 g/mol, 2,525 g/mol, 2,530 g/mol, 2,535 g/mol, 2,540 g/mol, 2,545 g/mol, 2,550 g/mol, 2,555 g/mol, 2,560 g/mol, 2,565 g/mol, 2,570 g/mol, 2,575 g/mol, 2,580 g/mol, 2,585 g/mol, 2,590 g/mol, 2,595 g/mol, 2,600 g/mol, 2,605 g/mol, 2,610 g/mol, 2,615 g/mol, 2,620 g/mol, 2,625 g/mol, 2,630 g/mol, 2,635 g/mol, 2,640 g/mol, 2,645 g/mol, 2,650 g/mol, 2,655 g/mol, 2,660 g/mol, 2,665 g/mol, 2,670 g/mol, 2,675 g/mol, 2,680 g/mol, 2,685 g/mol, 2,690 g/mol, 2,695 g/mol, 2,700 g/mol, 2,705 g/mol, 2,710 g/mol, 2,715 g/mol, 2,720 g/mol, 2,725 g/mol, 2,730 g/mol, 2,735 g/mol, 2,740 g/mol, 2,745 g/mol, 2,750 g/mol, 2,755 g/mol, 2,760 g/mol, 2,765 g/mol, 2,770 g/mol, 2,775 g/mol, 2,780 g/mol, 2,785 g/mol, 2,790 g/mol, 2,795 g/mol, 2,800 g/mol, 2,805 g/mol, 2,810 g/mol, 2,815 g/mol, 2,820 g/mol, 2,825 g/mol, 2,830 g/mol, 2,835 g/mol, 2,840 g/mol, 2,845 g/mol, 2,850 g/mol, 2,855 g/mol, 2,860 g/mol, 2,865 g/mol, 2,870 g/mol, 2,875 g/mol, 2,880 g/mol, 2,885 g/mol, 2,890 g/mol, 2,895 g/mol, 2,900 g/mol, 2,905 g/mol, 2,910 g/mol, 2,915 g/mol, 2,920 g/mol, 2,925 g/mol, 2,930 g/mol, 2,935 g/mol, 2,940 g/mol, 2,945 g/mol, 2,950 g/mol, 2,955 g/mol, 2,960 g/mol, 2,965 g/mol, 2,970 g/mol, 2,975 g/mol, 2,980 g/mol, 2,985 g/mol, 2,990 g/mol, 2,995 g/mol, 3,000 g/mol, 3,005 g/mol, 3,010 g/mol, 3,015 g/mol, 3,020 g/mol, 3,025 g/mol, 3,030 g/mol, 3,035 g/mol, 3,040 g/mol, 3,045 g/mol, 3,050 g/mol, 3,055 g/mol, 3,060 g/mol, 3,065 g/mol, 3,070 g/mol, 3,075 g/mol, 3,080 g/mol, 3,085 g/mol, 3,090 g/mol, 3,095 g/mol, 3,100 g/mol, 3,105 g/mol, 3,110 g/mol, 3,115 g/mol, 3,120 g/mol, 3,125 g/mol, 3,130 g/mol, 3,135 g/mol, 3,140 g/mol, 3,145 g/mol, 3,150 g/mol, 3,155 g/mol, 3,160 g/mol, 3,165 g/mol, 3,170 g/mol, 3,175 g/mol, 3,180 g/mol, 3,185 g/mol, 3,190 g/mol, 3,195 g/mol, 3,200 g/mol, 3,205 g/mol, 3,210 g/mol, 3,215 g/mol, 3,220 g/mol, 3,225 g/mol, 3,230 g/mol, 3,235 g/mol, 3,240 g/mol, 3,245 g/mol, 3,250 g/mol, 3,255 g/mol, 3,260 g/mol, 3,265 g/mol, 3,270 g/mol, 3,275 g/mol, 3,280 g/mol, 3,285 g/mol, 3,290 g/mol, 3,295 g/mol, 3,300 g/mol, 3,305 g/mol, 3,310 g/mol, 3,315 g/mol, 3,320 g/mol, 3,325 g/mol, 3,330 g/mol, 3,335 g/mol, 3,340 g/mol, 3,345 g/mol, 3,350 g/mol, 3,355 g/mol, 3,360 g/mol, 3,365 g/mol, 3,370 g/mol, 3,375 g/mol, 3,380 g/mol, 3,385 g/mol, 3,390 g/mol, 3,395 g/mol, 3,400 g/mol, 3,405 g/mol, 3,410 g/mol, 3,415 g/mol, 3,420 g/mol, 3,425 g/mol, 3,430 g/mol, 3,435 g/mol, 3,440 g/mol, 3,445 g/mol, 3,450 g/mol, 3,455 g/mol, 3,460 g/mol, 3,465 g/mol, 3,470 g/mol, 3,475 g/mol, 3,480 g/mol, 3,485 g/mol, 3,490 g/mol, 3,495 g/mol, 3,500 g/mol, 3,505 g/mol, 3,510 g/mol, 3,515 g/mol, 3,520 g/mol, 3,525 g/mol, 3,530 g/mol, 3,535 g/mol, 3,540 g/mol, 3,545 g/mol, 3,550 g/mol, 3,555 g/mol, 3,560 g/mol, 3,565 g/mol, 3,570 g/mol, 3,575 g/mol, 3,580 g/mol, 3,585 g/mol, 3,590 g/mol, 3,595 g/mol, 3,600 g/mol, 3,605 g/mol, 3,610 g/mol, 3,615 g/mol, 3,620 g/mol, 3,625 g/mol, 3,630 g/mol, 3,635 g/mol, 3,640 g/mol, 3,645 g/mol, 3,650 g/mol, 3,655 g/mol, 3,660 g/mol, 3,665 g/mol, 3,670 g/mol, 3,675 g/mol, 3,680 g/mol, 3,685 g/mol, 3,690 g/mol, 3,695 g/mol, 3,700 g/mol, 3,705 g/mol, 3,710 g/mol, 3,715 g/mol, 3,720 g/mol, 3,725 g/mol, 3,730 g/mol, 3,735 g/mol, 3,740 g/mol, 3,745 g/mol, 3,750 g/mol, 3,755 g/mol, 3,760 g/mol, 3,765 g/mol, 3,770 g/mol, 3,775 g/mol, 3,780 g/mol, 3,785 g/mol, 3,790 g/mol, 3,795 g/mol, 3,800 g/mol, 3,805 g/mol, 3,810 g/mol, 3,815 g/mol, 3,820 g/mol, 3,825 g/mol, 3,830 g/mol, 3,835 g/mol, 3,840 g/mol, 3,845 g/mol, 3,850 g/mol, 3,855 g/mol, 3,860 g/mol, 3,865 g/mol, 3,870 g/mol, 3,875 g/mol, 3,880 g/mol, 3,885 g/mol, 3,890 g/mol, 3,895 g/mol, 3,900 g/mol, 3,905 g/mol, 3,910 g/mol, 3,915 g/mol, 3,920 g/mol, 3,925 g/mol, 3,930 g/mol, 3,935 g/mol, 3,940 g/mol, 3,945 g/mol, 3,950 g/mol, 3,955 g/mol, 3,960 g/mol, 3,965 g/mol, 3,970 g/mol, 3,975 g/mol, 3,980 g/mol, 3,985 g/mol, 3,990 g/mol, 3,995 g/mol, or 4,000 g/mol).

In some embodiments, the poloxamer has an average molar mass of polyoxypropylene subunits of from about 2,750 g/mol to about 4,000 g/mol (e.g., about 2,750 g/mol, 2,755 g/mol, 2,760 g/mol, 2,765 g/mol, 2,770 g/mol, 2,775 g/mol, 2,780 g/mol, 2,785 g/mol, 2,790 g/mol, 2,795 g/mol, 2,800 g/mol, 2,805 g/mol, 2,810 g/mol, 2,815 g/mol, 2,820 g/mol, 2,825 g/mol, 2,830 g/mol, 2,835 g/mol, 2,840 g/mol, 2,845 g/mol, 2,850 g/mol, 2,855 g/mol, 2,860 g/mol, 2,865 g/mol, 2,870 g/mol, 2,875 g/mol, 2,880 g/mol, 2,885 g/mol, 2,890 g/mol, 2,895 g/mol, 2,900 g/mol, 2,905 g/mol, 2,910 g/mol, 2,915 g/mol, 2,920 g/mol, 2,925 g/mol, 2,930 g/mol, 2,935 g/mol, 2,940 g/mol, 2,945 g/mol, 2,950 g/mol, 2,955 g/mol, 2,960 g/mol, 2,965 g/mol, 2,970 g/mol, 2,975 g/mol, 2,980 g/mol, 2,985 g/mol, 2,990 g/mol, 2,995 g/mol, 3,000 g/mol, 3,005 g/mol, 3,010 g/mol, 3,015 g/mol, 3,020 g/mol, 3,025 g/mol, 3,030 g/mol, 3,035 g/mol, 3,040 g/mol, 3,045 g/mol, 3,050 g/mol, 3,055 g/mol, 3,060 g/mol, 3,065 g/mol, 3,070 g/mol, 3,075 g/mol, 3,080 g/mol, 3,085 g/mol, 3,090 g/mol, 3,095 g/mol, 3,100 g/mol, 3,105 g/mol, 3,110 g/mol, 3,115 g/mol, 3,120 g/mol, 3,125 g/mol, 3,130 g/mol, 3,135 g/mol, 3,140 g/mol, 3,145 g/mol, 3,150 g/mol, 3,155 g/mol, 3,160 g/mol, 3,165 g/mol, 3,170 g/mol, 3,175 g/mol, 3,180 g/mol, 3,185 g/mol, 3,190 g/mol, 3,195 g/mol, 3,200 g/mol, 3,205 g/mol, 3,210 g/mol, 3,215 g/mol, 3,220 g/mol, 3,225 g/mol, 3,230 g/mol, 3,235 g/mol, 3,240 g/mol, 3,245 g/mol, 3,250 g/mol, 3,255 g/mol, 3,260 g/mol, 3,265 g/mol, 3,270 g/mol, 3,275 g/mol, 3,280 g/mol, 3,285 g/mol, 3,290 g/mol, 3,295 g/mol, 3,300 g/mol, 3,305 g/mol, 3,310 g/mol, 3,315 g/mol, 3,320 g/mol, 3,325 g/mol, 3,330 g/mol, 3,335 g/mol, 3,340 g/mol, 3,345 g/mol, 3,350 g/mol, 3,355 g/mol, 3,360 g/mol, 3,365 g/mol, 3,370 g/mol, 3,375 g/mol, 3,380 g/mol, 3,385 g/mol, 3,390 g/mol, 3,395 g/mol, 3,400 g/mol, 3,405 g/mol, 3,410 g/mol, 3,415 g/mol, 3,420 g/mol, 3,425 g/mol, 3,430 g/mol, 3,435 g/mol, 3,440 g/mol, 3,445 g/mol, 3,450 g/mol, 3,455 g/mol, 3,460 g/mol, 3,465 g/mol, 3,470 g/mol, 3,475 g/mol, 3,480 g/mol, 3,485 g/mol, 3,490 g/mol, 3,495 g/mol, 3,500 g/mol, 3,505 g/mol, 3,510 g/mol, 3,515 g/mol, 3,520 g/mol, 3,525 g/mol, 3,530 g/mol, 3,535 g/mol, 3,540 g/mol, 3,545 g/mol, 3,550 g/mol, 3,555 g/mol, 3,560 g/mol, 3,565 g/mol, 3,570 g/mol, 3,575 g/mol, 3,580 g/mol, 3,585 g/mol, 3,590 g/mol, 3,595 g/mol, 3,600 g/mol, 3,605 g/mol, 3,610 g/mol, 3,615 g/mol, 3,620 g/mol, 3,625 g/mol, 3,630 g/mol, 3,635 g/mol, 3,640 g/mol, 3,645 g/mol, 3,650 g/mol, 3,655 g/mol, 3,660 g/mol, 3,665 g/mol, 3,670 g/mol, 3,675 g/mol, 3,680 g/mol, 3,685 g/mol, 3,690 g/mol, 3,695 g/mol, 3,700 g/mol, 3,705 g/mol, 3,710 g/mol, 3,715 g/mol, 3,720 g/mol, 3,725 g/mol, 3,730 g/mol, 3,735 g/mol, 3,740 g/mol, 3,745 g/mol, 3,750 g/mol, 3,755 g/mol, 3,760 g/mol, 3,765 g/mol, 3,770 g/mol, 3,775 g/mol, 3,780 g/mol, 3,785 g/mol, 3,790 g/mol, 3,795 g/mol, 3,800 g/mol, 3,805 g/mol, 3,810 g/mol, 3,815 g/mol, 3,820 g/mol, 3,825 g/mol, 3,830 g/mol, 3,835 g/mol, 3,840 g/mol, 3,845 g/mol, 3,850 g/mol, 3,855 g/mol, 3,860 g/mol, 3,865 g/mol, 3,870 g/mol, 3,875 g/mol, 3,880 g/mol, 3,885 g/mol, 3,890 g/mol, 3,895 g/mol, 3,900 g/mol, 3,905 g/mol, 3,910 g/mol, 3,915 g/mol, 3,920 g/mol, 3,925 g/mol, 3,930 g/mol, 3,935 g/mol, 3,940 g/mol, 3,945 g/mol, 3,950 g/mol, 3,955 g/mol, 3,960 g/mol, 3,965 g/mol, 3,970 g/mol, 3,975 g/mol, 3,980 g/mol, 3,985 g/mol, 3,990 g/mol, 3,995 g/mol, or 4,000 g/mol).

In some embodiments, the poloxamer has an average molar mass of polyoxypropylene subunits of from about 3,250 g/mol to about 4,000 g/mol (e.g., about 3,250 g/mol, 3,255 g/mol, 3,260 g/mol, 3,265 g/mol, 3,270 g/mol, 3,275 g/mol, 3,280 g/mol, 3,285 g/mol, 3,290 g/mol, 3,295 g/mol, 3,300 g/mol, 3,305 g/mol, 3,310 g/mol, 3,315 g/mol, 3,320 g/mol, 3,325 g/mol, 3,330 g/mol, 3,335 g/mol, 3,340 g/mol, 3,345 g/mol, 3,350 g/mol, 3,355 g/mol, 3,360 g/mol, 3,365 g/mol, 3,370 g/mol, 3,375 g/mol, 3,380 g/mol, 3,385 g/mol, 3,390 g/mol, 3,395 g/mol, 3,400 g/mol, 3,405 g/mol, 3,410 g/mol, 3,415 g/mol, 3,420 g/mol, 3,425 g/mol, 3,430 g/mol, 3,435 g/mol, 3,440 g/mol, 3,445 g/mol, 3,450 g/mol, 3,455 g/mol, 3,460 g/mol, 3,465 g/mol, 3,470 g/mol, 3,475 g/mol, 3,480 g/mol, 3,485 g/mol, 3,490 g/mol, 3,495 g/mol, 3,500 g/mol, 3,505 g/mol, 3,510 g/mol, 3,515 g/mol, 3,520 g/mol, 3,525 g/mol, 3,530 g/mol, 3,535 g/mol, 3,540 g/mol, 3,545 g/mol, 3,550 g/mol, 3,555 g/mol, 3,560 g/mol, 3,565 g/mol, 3,570 g/mol, 3,575 g/mol, 3,580 g/mol, 3,585 g/mol, 3,590 g/mol, 3,595 g/mol, 3,600 g/mol, 3,605 g/mol, 3,610 g/mol, 3,615 g/mol, 3,620 g/mol, 3,625 g/mol, 3,630 g/mol, 3,635 g/mol, 3,640 g/mol, 3,645 g/mol, 3,650 g/mol, 3,655 g/mol, 3,660 g/mol, 3,665 g/mol, 3,670 g/mol, 3,675 g/mol, 3,680 g/mol, 3,685 g/mol, 3,690 g/mol, 3,695 g/mol, 3,700 g/mol, 3,705 g/mol, 3,710 g/mol, 3,715 g/mol, 3,720 g/mol, 3,725 g/mol, 3,730 g/mol, 3,735 g/mol, 3,740 g/mol, 3,745 g/mol, 3,750 g/mol, 3,755 g/mol, 3,760 g/mol, 3,765 g/mol, 3,770 g/mol, 3,775 g/mol, 3,780 g/mol, 3,785 g/mol, 3,790 g/mol, 3,795 g/mol, 3,800 g/mol, 3,805 g/mol, 3,810 g/mol, 3,815 g/mol, 3,820 g/mol, 3,825 g/mol, 3,830 g/mol, 3,835 g/mol, 3,840 g/mol, 3,845 g/mol, 3,850 g/mol, 3,855 g/mol, 3,860 g/mol, 3,865 g/mol, 3,870 g/mol, 3,875 g/mol, 3,880 g/mol, 3,885 g/mol, 3,890 g/mol, 3,895 g/mol, 3,900 g/mol, 3,905 g/mol, 3,910 g/mol, 3,915 g/mol, 3,920 g/mol, 3,925 g/mol, 3,930 g/mol, 3,935 g/mol, 3,940 g/mol, 3,945 g/mol, 3,950 g/mol, 3,955 g/mol, 3,960 g/mol, 3,965 g/mol, 3,970 g/mol, 3,975 g/mol, 3,980 g/mol, 3,985 g/mol, 3,990 g/mol, 3,995 g/mol, or 4,000 g/mol).

In some embodiments, the poloxamer has an average molar mass of polyoxypropylene subunits of from about 3,625 g/mol to about 4,000 g/mol (e.g., about 3,625 g/mol, 3,630 g/mol, 3,635 g/mol, 3,640 g/mol, 3,645 g/mol, 3,650 g/mol, 3,655 g/mol, 3,660 g/mol, 3,665 g/mol, 3,670 g/mol, 3,675 g/mol, 3,680 g/mol, 3,685 g/mol, 3,690 g/mol, 3,695 g/mol, 3,700 g/mol, 3,705 g/mol, 3,710 g/mol, 3,715 g/mol, 3,720 g/mol, 3,725 g/mol, 3,730 g/mol, 3,735 g/mol, 3,740 g/mol, 3,745 g/mol, 3,750 g/mol, 3,755 g/mol, 3,760 g/mol, 3,765 g/mol, 3,770 g/mol, 3,775 g/mol, 3,780 g/mol, 3,785 g/mol, 3,790 g/mol, 3,795 g/mol, 3,800 g/mol, 3,805 g/mol, 3,810 g/mol, 3,815 g/mol, 3,820 g/mol, 3,825 g/mol, 3,830 g/mol, 3,835 g/mol, 3,840 g/mol, 3,845 g/mol, 3,850 g/mol, 3,855 g/mol, 3,860 g/mol, 3,865 g/mol, 3,870 g/mol, 3,875 g/mol, 3,880 g/mol, 3,885 g/mol, 3,890 g/mol, 3,895 g/mol, 3,900 g/mol, 3,905 g/mol, 3,910 g/mol, 3,915 g/mol, 3,920 g/mol, 3,925 g/mol, 3,930 g/mol, 3,935 g/mol, 3,940 g/mol, 3,945 g/mol, 3,950 g/mol, 3,955 g/mol, 3,960 g/mol, 3,965 g/mol, 3,970 g/mol, 3,975 g/mol, 3,980 g/mol, 3,985 g/mol, 3,990 g/mol, 3,995 g/mol, or 4,000 g/mol).

In some embodiments, the poloxamer has an average ethylene oxide content of greater than 40% by mass (e.g., about 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, or more).

In some embodiments, the poloxamer has an average ethylene oxide content of greater than 50% by mass (e.g., about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, or more).

In some embodiments, the poloxamer has an average ethylene oxide content of greater than 60% by mass (e.g., about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, or more).

In some embodiments, the poloxamer has an average ethylene oxide content of greater than 70% by mass (e.g., about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, or more).

In some embodiments, the poloxamer has an average ethylene oxide content of from about 40% to about 90% (e.g., about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90%).

In some embodiments, the poloxamer has an average ethylene oxide content of from about 50% to about 85% (e.g., about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, or 85%).

In some embodiments, the poloxamer has an average ethylene oxide content of from about 60% to about 80% (e.g., about 60%, 61%, 62%, 63%, 64%, 65%, 66%, 67%, 68%, 69%, 70%, 71%, 72%, 73%, 74%, 75%, 76%, 77%, 78%, 79%, 80%).

In some embodiments, the poloxamer has an average molar mass of greater than 10,000 g/mol (e.g., about 10,100 g/mol, 10,200 g/mol, 10,300 g/mol, 10,400 g/mol, 10,500 g/mol, 10,600 g/mol, 10,700 g/mol, 10,800 g/mol, 10,900 g/mol, 11,000 g/mol, 11,100 g/mol, 11,200 g/mol, 11,300 g/mol, 11,400 g/mol, 11,500 g/mol, 11,600 g/mol, 11,700 g/mol, 11,800 g/mol, 11,900 g/mol, 12,000 g/mol, 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of greater than 11,000 g/mol (e.g., about 11,100 g/mol, 11,200 g/mol, 11,300 g/mol, 11,400 g/mol, 11,500 g/mol, 11,600 g/mol, 11,700 g/mol, 11,800 g/mol, 11,900 g/mol, 12,000 g/mol, 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of greater than 12,000 g/mol (e.g., about 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of greater than 12,500 g/mol (e.g., about 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of from about 10,000 g/mol to about 15,000 g/mol (e.g., about 10,000 g/mol, 10,100 g/mol, 10,200 g/mol, 10,300 g/mol, 10,400 g/mol, 10,500 g/mol, 10,600 g/mol, 10,700 g/mol, 10,800 g/mol, 10,900 g/mol, 11,000 g/mol, 11,100 g/mol, 11,200 g/mol, 11,300 g/mol, 11,400 g/mol, 11,500 g/mol, 11,600 g/mol, 11,700 g/mol, 11,800 g/mol, 11,900 g/mol, 12,000 g/mol, 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of from about 11,000 g/mol to about 15,000 g/mol (e.g., about 11,000 g/mol, 11,100 g/mol, 11,200 g/mol, 11,300 g/mol, 11,400 g/mol, 11,500 g/mol, 11,600 g/mol, 11,700 g/mol, 11,800 g/mol, 11,900 g/mol, 12,000 g/mol, 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of from about 11,500 g/mol to about 15,000 g/mol (e.g., about 11,500 g/mol, 11,600 g/mol, 11,700 g/mol, 11,800 g/mol, 11,900 g/mol, 12,000 g/mol, 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of from about 12,000 g/mol to about 15,000 g/mol (e.g., about 12,000 g/mol, 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of from about 12,500 g/mol to about 15,000 g/mol (e.g., about 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer is P407.

In some embodiments, the poloxamer is P338.

In some embodiments, the poloxamer is P288.

In some embodiments, the poloxamer is P188.

In some embodiments, the viral vector is selected from the group consisting of a Retroviridae family virus, an adeno-associated virus, an adenovirus, a parvovirus, a coronavirus, a rhabdovirus, a paramyxovirus, a picornavirus, an alphavirus, a herpes virus, and a poxvirus. The viral vector may be, for example, a Retroviridae family viral vector, such as a lentiviral vector, an alpharetroviral vector, or a gammaretroviral vector. In some embodiments, the Retroviridae family viral vector includes a central polypurine tract, a woodchuck hepatitis virus post-transcriptional regulatory element, a 5'-LTR, HIV signal sequence, HIV Psi signal 5'-splice site, delta-GAG element, 3'-splice site, and a 3'-self inactivating LTR.

In some embodiments, the viral vector is a pseudotyped viral vector that contains a viral genome originating from one type of virus and one or more viral capsid or envelope proteins that derive from a different type of virus. The pseudotyped viral vector may contain, for example, one or more viral envelope proteins from a virus selected from vesicular stomatitis virus (VSV), RD114 virus, murine leukemia virus (MLV), feline leukemia virus (FeLV), Venezuelan equine encephalitis virus (VEE), human foamy virus (HFV), walleye dermal sarcoma virus (WDSV), Semliki Forest virus (SFV), Rabies virus, avian leukosis virus (ALV), bovine immunodeficiency virus (BIV), bovine leukemia virus (BLV), Epstein-Barr virus (EBV), Caprine arthritis encephalitis virus (CAEV), Sin Nombre virus (SNV), Cherry Twisted Leaf virus (ChTLV), Simian T-cell leukemia virus (STLV), Mason-Pfizer monkey virus (MPMV), squirrel monkey retrovirus (SMRV), Rous-associated virus (RAV), Fujinami sarcoma virus (FuSV), avian carcinoma virus (MH2), avian encephalomyelitis virus (AEV), Alfa mosaic virus (AMV), avian sarcoma virus CT10, and equine infectious anemia virus (EIAV).

In some embodiments, the contacting of the cell with the one or more agents described above or herein occurs ex vivo. The cell may have been freshly cultured prior to the contacting or may have been cryopreserved and thawed prior to the contacting.

In some embodiments, the cell is first contacted with the substance that reduces activity and/or expression of PKC before the cell is contacted with the poloxamer. For example, the cell may first be contacted with the substance that reduces activity and/or expression of PKC for from about 30 minutes to about 6 hours before the cell is contacted with the poloxamer (e.g., about 30 minutes, 1 hour, 2 hours, 3 hours, 4 hours, 5 hours, or 6 hours before the cell is contacted with the poloxamer). In some embodiments, the cell is first contacted with the substance that reduces activity and/or expression of PKC for from about 1 hour to about 3 hours before the cell is contacted with the poloxamer (e.g., about 1 hour, 2 hours, or 3 hours before the cell is contacted with the poloxamer). In some embodiments, the cell is first contacted with the substance that reduces activity and/or expression of PKC about 2 hours before the cell is contacted with the poloxamer.

In some embodiments, when the cell is first contacted with the substance that reduces activity and/or expression of PKC before the cell is contacted with the poloxamer, the cell is washed to remove the substance that reduces activity and/or expression of PKC before the cell is contacted with the poloxamer.

In some embodiments, the cell is simultaneously contacted with the substance that reduces activity and/or expression of PKC and with the poloxamer. For example, the cell may be simultaneously contacted with the substance that reduces activity and/or expression of PKC, with the poloxamer, and with the viral vector.

In some embodiments, the cell is contacted with the viral vector after having been exposed to the substance that reduces PKC activity and/or expression. In these instances, the cell may be simultaneously contacted with the viral vector and the poloxamer. Alternatively, the cell may be contacted with the poloxamer before being contacted with the viral vector. In some embodiments, the cell is contacted with the viral vector before being contacted with the poloxamer.

Thus, in some embodiments of the disclosure, the cell is first contacted with the substance that reduces PKC activity and/or expression, is next contacted with the poloxamer, and is subsequently contacted with the viral vector. In some embodiments, the cell is first contacted with the substance that reduces PKC activity and/or expression, is next contacted with the viral vector, and is subsequently contacted with the poloxamer.

In some embodiments, the cell is further contacted with a cyclosporine, such as cyclosporine A (CsA) or cyclosporine H (CsH). The cell may be contacted with the poloxamer and with the cyclosporine simultaneously. Alternatively, the cell may be contacted with the poloxamer before being contacted with the staurosporine. In some embodiments, the cell is contacted with the cyclosporine before being contacted with the poloxamer.

In some embodiments, the concentration of the cyclosporine, when contacted with the cell, is from about 1 μM to about 10 μM (e.g., about 1 μM, 1.1 μM, 1.2 μM, 1.3 μM, 1.4 μM, 1.5 μM, 1.6 μM, 1.7 μM, 1.8 μM, 1.9 μM, 2 μM, 2.1 μM, 2.2 μM, 2.3 μM, 2.4 μM, 2.5 μM, 2.6 μM, 2.7 μM, 2.8 μM, 2.9 μM, 3 μM, 3.1 μM, 3.2 μM, 3.3 μM, 3.4 μM, 3.5 μM, 3.6 μM, 3.7 μM, 3.8 μM, 3.9 μM, 4 μM, 4.1 μM, 4.2 μM, 4.3 μM, 4.4 μM, 4.5 μM, 4.6 μM, 4.7 μM, 4.8 μM, 4.9 μM, 5 μM, 5.1 μM, 5.2 μM, 5.3 μM, 5.4 μM, 5.5 μM, 5.6 μM, 5.7 μM, 5.8 μM, 5.9 μM, 6 μM, 6.1 μM, 6.2 μM, 6.3 μM, 6.4 μM, 6.5 μM, 6.6 μM, 6.7 μM, 6.8 μM, 6.9 μM, 7 μM, 7.1 μM, 7.2 μM, 7.3 μM, 7.4 μM, 7.5 μM, 7.6 μM, 7.7 μM, 7.8 μM, 7.9 μM, 8 μM, 8.1 μM, 8.2 μM, 8.3 μM, 8.4 μM, 8.5 μM, 8.6 μM, 8.7 μM, 8.8 μM, 8.9 μM, 9 μM, 9.1 μM, 9.2 μM, 9.3 μM, 9.4 μM, 9.5 μM, 9.6 μM, 9.7 μM, 9.8 μM, 9.9 μM, or 10 μM). In some embodiments, the cyclosporine is CsA and the concentration of the cyclosporine, when contacted with the cell, is about 6 μM. In some embodiments, the cyclosporine is CsH and the concentration of the cyclosporine, when contacted with the cell, is about 8 μM.

In some embodiments, the cell is further contacted with an activator of prostaglandin E receptor signaling. The cell may be contacted with the poloxamer and with the activator of prostaglandin E receptor signaling simultaneously. Alternatively, the cell may be contacted with the poloxamer before being contacted with the activator of prostaglandin E receptor signaling. In some embodiments, the cell is contacted with the activator of prostaglandin E receptor signaling before being contacted with the poloxamer.

In some embodiments, the activator of prostaglandin E receptor signaling is a small molecule, such as a compound described in WO 2007/112084 or WO 2010/108028, the disclosures of each of which are incorporated herein by reference as they pertain to prostaglandin E receptor signaling activators.

In some embodiments, the activator of prostaglandin E receptor signaling is a small molecule, such as a small organic molecule, a prostaglandin, a Wnt pathway agonist, a cAMP/PI3K/AKT pathway agonist, a $Ca^{2+}$ second messenger pathway agonist, a nitric oxide (NO)/angiotensin signaling agonist, or another compound known to stimulate the prostaglandin signaling pathway, such as a compound selected from Mebeverine, Flurandrenolide, Atenolol, Pindolol, Gaboxadol, Kynurenic Acid, Hydralazine, Thiabendazole, Bicuculline, Vesamicol, Peruvoside, Imipramine, Chlorpropamide, 1,5-Pentamethylenetetrazole, 4-Aminopyridine, Diazoxide, Benfotiamine, 12-Methoxydodecenoic acid, N-Formyl-Met-Leu-Phe, Gallamine, IAA 94, Chlorotrianisene, and or a derivative of any of these compounds.

In some embodiments, the activator of prostaglandin E receptor signaling is a naturally-occurring or synthetic chemical molecule or polypeptide that binds to and/or interacts with a prostaglandin E receptor, typically to activate or increase one or more of the downstream signaling pathways associated with a prostaglandin E receptor.

In some embodiments, the activator of prostaglandin E receptor signaling is selected from the group consisting of: prostaglandin (PG) A2 (PGA2), PGB2, PGD2, PGE1 (Alprostadil), PGE2, PGF2, PGI2 (Epoprostenol), PGH2, PGJ2, and derivatives and analogs thereof.

In some embodiments, the activator of prostaglandin E receptor signaling is 15d-PGJ2, deltaI2-PGJ2, 2-hydroxyheptadecatrienoic acid (HHT), Thromboxane (TXA2 and TXB2), PG12 analogs, e.g., Iloprost and Treprostinil, PGF2 analogs, e.g., Travoprost, Carboprost tromethamine, Tafluprost, Latanoprost, Bimatoprost, Unoprostone isopropyl, Cloprostenol, Oestrophan, and Superphan, PGE1 analogs, e.g., 11-deoxy PGE1, Misoprostol, and Butaprost, and Corey alcohol-A ([3aa,4a,5,6aa]-(−)-[Hexahydro-4-(hydroxymethyl)-2-oxo-2H-cyclopenta/b/furan-5-yl][1,1'-biphenyl]-4-carboxylate), Corey alcohol-B (2H-Cyclopenta[b]furan-2-on,5-(benzoyloxy)hexahydro-4-(hydroxymethyl)[3aR-(3aa,4a,5,6aa)]), and Corey diol ((3aR,4S,5R,6aS)-hexahydro-5-hydroxy-4-(hydroxymethyl)-2H-cyclopenta[b]furan-2-one).

In some embodiments, the activator of prostaglandin E receptor signaling is a prostaglandin E receptor ligand, such as prostaglandin E2 (PGE2), or an analogs or derivative thereof. Prostaglandins refer generally to hormone-like molecules that are derived from fatty acids containing 20 carbon atoms, including a 5-carbon ring, as described herein and known in the art. Illustrative examples of PGE2 "analogs" or "derivatives" include, but are not limited to, 16,16-dimethyl PGE2, 16-16 dimethyl PGE2 p-(p-acetamidobenzamido) phenyl ester, I I-deoxy-16,16-dimethyl PGE2, 9-deoxy-9-methylene-16, 16-dimethyl PGE2, 9-deoxy-9-methylene PGE2, 9-keto Fluprostenol, 5-trans PGE2, 17-phenyl-omega-trinor PGE2, PGE2 serinol amide, PGE2 methyl ester, 16-phenyl tetranor PGE2, 15(S)-15-methyl PGE2, 15 (R)-15-methyl PGE2, 8-iso-15-keto PGE2, 8-iso PGE2 isopropyl ester, 20-hydroxy PGE2, nocloprost, sulprostone, butaprost, 15-keto PGE2, and 19 (R) hydroxy PGE2.

In some embodiments, the activator of prostaglandin E receptor signaling is a prostaglandin analog or derivative having a similar structure to PGE2 that is substituted with halogen at the 9-position (see, e.g., WO 2001/12596, herein incorporated by reference in its entirety), as well as 2-decarboxy-2-phosphinico prostaglandin derivatives, such as those described in US 2006/0247214, herein incorporated by reference in its entirety).

In some embodiments, the activator of prostaglandin E receptor signaling is a non-PGE2-based ligand. In some embodiments, the activator of prostaglandin E receptor signaling is CAY10399, ONO_8815Ly, ONO-AE1-259, or CP-533,536. Additional examples of non-PGE2-based EP2 agonists include the carbazoles and fluorenes disclosed in WO 2007/071456, herein incorporated by reference for its disclosure of such agents. Illustrative examples of non-PGE2-based $EP_3$ agonist include, but are not limited to, AE5-599, MB28767, GR 63799X, ONO-NT012, and ONO-AE-248. Illustrative examples of non-PGE2-based EP4 agonist include, but are not limited to, ONO-4819, APS-999 Na, AH23848, and ONO-AE 1-329. Additional examples of non-PGE2-based EP4 agonists can be found in WO 2000/038663; U.S. Pat. Nos. 6,747,037; and 6,610,719, each of which are incorporated by reference for their disclosure of such agonists In some embodiments, the activator of prostaglandin E receptor signaling is a Wnt agonist. Illustrative examples of Wnt agonists include, but are not limited to, Wnt polypeptides and glycogen synthase kinase 3 (GSK3) inhibitors. Illustrative examples of Wnt polypeptides suitable for use as compounds that stimulate the prostaglandin EP receptor signaling pathway include, but are not limited to, Wnt1, Wnt2, Wnt2b/13, Wnt3, Wnt3a, Wnt4, Wnt5a, Wnt5b, Wnt6, Wnt7a, Wnt7b, Wnt7c, Wnt8, Wnt8a, Wnt8b, Wnt8c, Wnt1 Oa, Wnt1 Ob, Wnt11, Wnt14, Wnt15, or biologically active fragments thereof. GSK3 inhibitors suitable for use as agents that stimulate the prostaglandin EP receptor signaling pathway bind to and decrease the activity of GSK3a, or GSK3. Illustrative examples of GSK3 inhibitors include, but are not limited to, BIO (6-bromoindirubin-3'-oxime), LiCl or other GSK-3 inhibitors, as exemplified in U.S. Pat. Nos. 6,057,117 and 6,608,063, as well as US 2004/0092535 and US 2004/0209878, and ATP-competitive, selective GSK-3 inhibitors CHIR-911 and CHIR-837 (also referred to as CT-99021 and CT-98023 respectively) (Chiron Corporation (Emeryville, CA)).

In some embodiments, the activator of prostaglandin E receptor signaling is an agent that increases signaling through the cAMP/P13K/AKT second messenger pathway, such as an agent selected from the group consisting of dibutyryl cAMP (DBcAMP), phorbol ester, forskolin, sclareline, 8-bromo-cAMP, cholera toxin (CTx), aminophylline, 2,4 dinitrophenol (DNP), norepinephrine, epinephrine, isoproterenol, isobutylmethylxanthine (IBMX), caffeine, theophylline (dimethylxanthine), dopamine, rolipram, iloprost, pituitary adenylate cyclase activating polypeptide (PACAP), and vasoactive intestinal polypeptide (VIP), and derivatives of these agents.

In some embodiments, the activator of prostaglandin E receptor signaling is an agent that increases signaling through the $Ca^{2+}$ second messenger pathway, such as an agent selected from the group consisting of Bapta-AM, Fendiline, Nicardipine, and derivatives of these agents.

In some embodiments, the activator of prostaglandin E receptor signaling is an agent that increases signaling through the NO/Angiotensin signaling, such as an agent selected from the group consisting of L-Arg, Sodium Nitroprusside, Sodium Vanadate, Bradykinin, and derivatives thereof.

In some embodiments, the cell is further contacted with a polycationic polymer. The cell may be contacted with the poloxamer and with the polycationic polymer simultaneously. Alternatively, the cell may be contacted with the poloxamer before being contacted with the polycationic polymer. In some embodiments, the cell is contacted with the polycationic polymer before being contacted with the poloxamer.

In some embodiments, the polycationic polymer is polybrene, protamine sulfate, polyethylenimine, or a polyethylene glycol/poly-L-lysine block copolymer.

In some embodiments, the cell is further contacted with an expansion agent during the transduction procedure. The cell may be, for example, a hematopoietic stem cell and the expansion agent may be a hematopoietic stem cell expansion agent, such as a hematopoietic stem cell expansion agent known in the art or described herein.

In some embodiments, during the transduction procedure, the cell is further contacted with an agent that inhibits mTor signalling. The agent that inhibits mTor signaling may be, for example, rapamycin, among other suppressors of mTor signaling.

In some embodiments, the cell is incubated with the viral vector (e.g., in combination with the one or more agents described above) for a period of from about 6 hours to about 48 hours (e.g., about 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, or 48 hours). In some embodiments, the cell is incubated with the viral vector (e.g., in combination with the one or more agents described above) for a period of from about 12 hours to about 24 hours (e.g., about 12 hours, 13 hours, 14 hours, 15 hours, 16 hours, 17 hours, 18 hours, 19 hours, 20 hours, 21 hours, 22 hours, 23 hours, or 24 hours). In some embodiments, the cell is incubated with the viral vector (e.g., in combination with the one or more agents described above) for a period of from about 16 hours to about 22 hours (e.g., about 16 hours, 17 hours, 18 hours, 19 hours, 20 hours, 21 hours, or 22 hours). In some embodiments, the cell is incubated with the viral vector (e.g., in combination with the one or more agents described above) for a period of from about 17 hours to about 19 hours (e.g., about 17 hours, 18 hours, or 19 hours). In some embodiments, the cell is incubated with the viral vector (e.g., in combination with the one or more agents described above) for a period of about 18 hours.

In some embodiments, the cell is spun (e.g., by centrifugation, i.e., "centrifuged") while being contacted with the viral vector (e.g., in combination with the one or more agents described above). This process, referred to herein as "spinoculation," may occur with a centripetal force of, e.g., from about 200×g to about 2,000×g. In some embodiments, the cell is spun at a centripetal force of from about 300×g to about 1,200×g while being contacted with the viral vector (e.g., in combination with the one or more agents described above). For example, the cell may be spun at a centripetal force of about 300×g, 400×g, 500×g, 600×g, 700×g, 800×g, 900×g, 1,000×g, 1,100×g, or 1,200×g while being contacted with the viral vector (e.g., in combination with the one or more agents described above). In some embodiments, the cell is spun for from about 10 minutes to about 3 hours (e.g., about 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, 120 minutes, 125 minutes, 130 minutes, 135 minutes, 140 minutes, 145 minutes, 150 minutes, 155 minutes, 160 minutes, 165 minutes, 170 minutes, 175 minutes, 180 minutes, or more). In some embodiments, the cell is spun at room temperature, such as at a temperature of about 25° C.

In an additional aspect, the disclosure features a method of expressing a transgene in a subject (e.g., a mammalian subject, such as a human) by administering to the subject a population of cells that have been modified in accordance with the method of any of the above aspects or embodiments of the disclosure, or progeny thereof.

In a further aspect, the disclosure features a method of delivering a population of genetically modified cells to a subject (e.g., a mammalian subject, such as a human) by administering to the subject a population of cells that have been modified in accordance with the method of any of the above aspects or embodiments of the disclosure, or progeny thereof.

In yet another aspect, the disclosure features a method of providing cell therapy to a subject in need thereof (e.g., a mammalian subject, such as a human) by administering to the subject a population of cells that have been modified in accordance with the method of any of the above aspects or embodiments of the disclosure, or progeny thereof.

In some embodiments of the three preceding aspects of the disclosure, the cells are allogeneic with respect to the subject. In some embodiments, the cells are HLA-matched to the subject. In some embodiments, the cells are autologous with respect to the subject.

In some embodiments, prior to contacting the cells with the one or more agents described above or herein, a population of precursor cells is isolated from the subject (e.g., in the case of an autologous cell population) or a donor (e.g., in the case of an allogeneic cell population). The precursor cells may then be expanded ex vivo, for example, by incubating the precursor cells with one or more cell expansion substances described herein or known in the art to promote cell proliferation, thereby yielding the population of cells being administered to the subject. For example, the expansion agent may be StemRegenin 1, also known in the art as compound SR1, represented by formula (110), below.

(110)

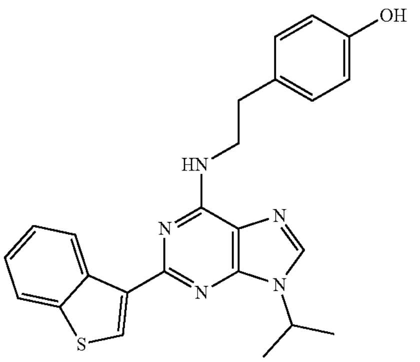

SR1 and other expansion agents are described, for example, in U.S. Pat. Nos. 8,927,281 and 9,580,426, the disclosures of each of which are incorporated herein by reference in their entirety.

Additional expansion agents that may be used in conjunction with the compositions and methods of the disclosure include compound UM-171, which is described in U.S. Pat. No. 9,409,906, the disclosure of which is incorporated herein by reference in its entirety. Expansion agents that may be used herein further include structural or stereoisomeric variants of compound UM-171, such as the compounds described in US 2017/0037047, the disclosure of which is incorporated herein by reference in its entirety. The structure of compound UM-171 is shown in formula (111), below.

(111)

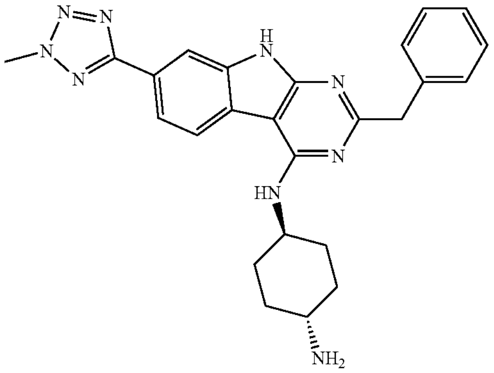

In some embodiments, the expansion agent is a bromide salt of compound (111), such as a compound represented by formula (112), below.

(112)

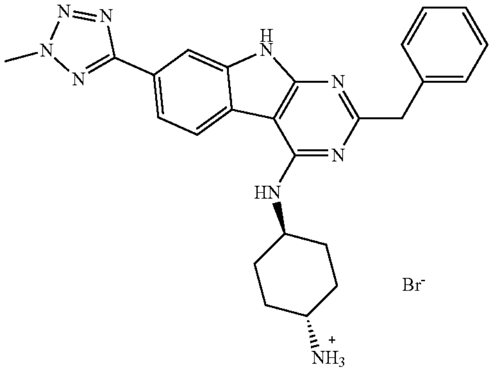

Additional expansion agents that may be used in conjunction with the compositions and methods of the disclosure include histone deacetylase (HDAC) inhibitors, as described, for example, in WO 2000/023567, the disclosure of which is incorporated herein by reference. Exemplary agents that may be used to expand a population of precursor cells as described herein are trichostatin A, trapoxin, trapoxin A, chlamydocin, sodium butyrate, dimethyl sulfoxide, suberanilohydroxamic acid, m-carboxycinnamic acid bishydroxamide, HC-toxin, Cyl-2, WF-3161, depudecin, and radicicol, among others.

In some embodiments, the precursor cells are CD34+ HSCs. Using HSC expansion agents described herein and known in the art, the precursor cells may be expanded without loss of HSC functional potential.

In some embodiments, prior to isolation of the precursor cells from the subject (e.g., in the case of an autologous cell population) or donor (e.g., in the case of an allogeneic cell population), the subject or donor is administered one or more mobilization agents that stimulate the migration of pluripotent cells (e.g., CD34+ HSCs and HPCs) from a stem cell niche, such as the bone marrow, to peripheral circulation.

Exemplary cell mobilization agents that may be used in conjunction with the compositions and methods of the disclosure are described herein and known in the art. For example, the mobilization agent may be a C—X—C motif chemokine receptor (CXCR) 2 (CXCR2) agonist. The CXCR2 agonist may be Gro-beta, or a truncated variant thereof. Gro-beta and variants thereof are described, for example, in U.S. Pat. Nos. 6,080,398; 6,447,766; and 6,399, 053, the disclosures of each of which are incorporated herein by reference in their entirety. Additionally or alternatively, the mobilization agent may include a CXCR4 antagonist, such as plerixafor or a variant thereof. Plerixafor and structurally similar compounds are described, for example, in U.S. Pat. Nos. 6,987,102; 7,935,692; and 7,897,590, the disclosures of each of which are incorporated herein by reference. Additionally or alternatively, the mobilization agent may include granulocyte colony-stimulating factor (G-CSF). The use of G-CSF as an agent to induce mobilization of pluripotent cells (e.g., CD34+ HSCs and/or HPCs) from a stem cell niche to peripheral circulation is described, for example, in US 2010/0178271, the disclosure of which is incorporated herein by reference in its entirety.

In some embodiments, prior to administering the population of cells to the subject, a population of endogenous pluripotent cells (e.g., a population of endogenous CD34+ HSCs or HPCs) is ablated in the subject by administration of one or more conditioning agents to the subject. In some embodiments, the method includes ablating a population of endogenous pluripotent cells (e.g., a population of endogenous CD34+ HSCs or HPCs) in the subject by administering to the subject one or more conditioning agents prior to administering to the subject the population of cells. The one or more conditioning agents may be myeloablative conditioning agents that deplete a wide variety of hematopoietic cells from the bone marrow of the subject. In some embodiments, the one or more conditioning agents are non-myeloablative conditioning agents that selectively target and ablate a specific population of endogenous pluripotent cells, such as a population of endogenous CD34+ HSCs or HPCs.

In some embodiments, upon administration of the population of cells to the subject, the administered cells, or progeny thereof, differentiate into one or more cell types selected from megakaryocytes, thrombocytes, platelets, erythrocytes, mast cells, myeloblasts, basophils, neutrophils, eosinophils, microglia, granulocytes, monocytes, osteoclasts, antigen-presenting cells, macrophages, dendritic cells, natural killer cells, T-lymphocytes, and B-lymphocytes.

In some embodiments, the subject has been diagnosed as having a deficiency of an endogenous protein encoded by the transgene. The subject may have been diagnosed, for example, as having a disease set forth in Table 2. In some embodiments, the subject has been diagnosed as having beta thalassemia.

In some embodiments of any of the above aspects or embodiments of the disclosure, the transgene encodes a beta-globin protein. The transgene may contain, for example, a nucleic acid having at least 85% sequence identity (e.g., 85%, 86%, 87%, 88%, 89%, 90%, 91%, 92%, 93%, 94%, 95%, 96%, 97%, 98%, 99%, or 100% sequence identity) to the nucleic acid sequence of SEQ ID NO: 1. In some embodiments, the transgene contains a nucleic acid having at least 90% sequence identity (e.g., 90%, 91%, 92%, 93%, 94%, 95%, 96%, 97%, 98%, 99%, or 100% sequence identity) to the nucleic acid sequence of SEQ ID NO: 1. In some embodiments, the transgene contains a nucleic acid having at least 95% sequence identity (e.g., 95%, 96%, 97%, 98%, 99%, or 100% sequence identity) to the nucleic acid sequence of SEQ ID NO: 1. In some embodiments, the transgene contains a nucleic acid having the nucleic acid sequence of SEQ ID NO: 1.

In some embodiments, the beta-globin protein has an amino acid sequence that is at least 85% identical (e.g., 85%, 86%, 87%, 88%, 89%, 90%, 91%, 92%, 93%, 94%, 95%, 96%, 97%, 98%, 99%, or 100% identical) to the amino acid sequence of SEQ ID NO: 2. In some embodiments, the beta-globin protein has an amino acid sequence that is at least 90% identical (e.g., 90%, 91%, 92%, 93%, 94%, 95%, 96%, 97%, 98%, 99%, or 100% identical) to the amino acid sequence of SEQ ID NO: 2. In some embodiments, the beta-globin protein has an amino acid sequence that is at least 95% identical (e.g., 95%, 96%, 97%, 98%, 99%, or 100% identical) to the amino acid sequence of SEQ ID NO: 2. In some embodiments, the beta-globin protein the amino acid sequence of SEQ ID NO: 2.

In some embodiments, the beta-globin protein has an amino acid sequence that differs from that of SEQ ID NO: 2 by way of one or more amino acid substitutions, insertions, and/or deletions. For example, the beta-globin protein may have an amino acid sequence that differs from that of SEQ ID NO: 2 by way of one or more conservative amino acid substitutions or nonconservative amino acid substitutions. The beta-globin protein may have an amino acid sequence that differs from that of SEQ ID NO: 2 by way, for example, of from 1 to 50 conservative amino acid substitutions, from 1 to 40 conservative amino acid substitutions, from 1 to 30 conservative amino acid substitutions, from 1 to 20 conservative amino acid substitutions, or from 1 to 10 conservative amino acid substitutions, optionally in combination with one or more nonconservative amino acid substitutions.

In another aspect, the disclosure features a composition containing a mixture formed by modifying a eukaryotic cell in accordance with the method of any of the above aspects or embodiments of the disclosure.

In a further aspect, the disclosure features a cell culture medium containing the composition of the preceding aspect.

In yet another aspect, the disclosure features a population of eukaryotic cells that have been modified in accordance with the method of any of the above aspects or embodiments of the disclosure.

In another aspect, the disclosure features a pharmaceutical composition containing the population of cells of the preceding aspect. The pharmaceutical composition may further contain one or more excipients, diluents, and/or carriers. In some embodiments, the pharmaceutical composition is formulated for administration, such as by way of intravenous infusion, to a subject, such as a mammalian subject (e.g., a human).

In another aspect, the disclosure features a kit containing a composition containing a mixture formed by modifying a eukaryotic cell in accordance with the method of any of the above aspects or embodiments of the disclosure. Additionally or alternatively, the kit may contain a cell culture medium containing this composition. The kit may additionally contain a package insert that includes instructions for using the contents of the kit to transduce a target cell.

In another aspect, the disclosure features a kit containing a population of eukaryotic cells that have been modified in accordance with the method of any of the above aspects or embodiments of the disclosure. Additionally or alternatively, the kit may contain a pharmaceutical composition containing a population of eukaryotic cells that have been modified in accordance with the method of any of the above aspects or embodiments of the disclosure. The kit may additionally contain a package insert instructing a user to administer the population of cells to a subject in accordance with any of the cell administration methods described above or herein.

Definitions

As used herein, the terms "ablate," "ablating," "ablation," and the like refer to the depletion of one or more cells in a population of cells in vivo or ex vivo. In some embodiments of the present disclosure, it may be desirable to ablate endogenous cells within a patient (e.g., a patient undergoing treatment for a disease described herein) before administering a therapeutic composition, such as a therapeutic population of cells, to the patient. This can be beneficial, for example, in order to provide newly-administered cells with an environment within which the cells may engraft. Ablation of a population of endogenous cells can be performed in a manner that selectively targets a specific cell type, for example, using antibody-drug conjugates that bind to an antigen expressed on the target cell and subsequently engender the killing of the target cell. Additionally or alternatively, ablation may be performed in a non-specific manner using cytotoxins that do not localize to a particular cell type, but are instead capable of exerting their cytotoxic effects on a variety of different cells. Examples of ablation include depletion of at least 5% of cells (e.g., at least 5%, 10%, 15%, 20%, 25%, 30%, 35%, 40%, 45%, 50%, or more) in a population of cells in vivo or in vitro. Quantifying cell counts within a sample of cells can be performed using a variety of cell-counting techniques, such as through the use of a counting chamber, a Coulter counter, flow cytometry, or other cell-counting methods known in the art.

As used herein, the term "about" refers to a quantity that varies by as much as 30% (e.g., 25%, 20%, 25%, 10%, 9%, 8%, 7%, 6%, 5%, 4%, 3%, 2% or 1%) relative to a reference quantity.

As used herein in the context of a protein of interest, the term "activity" refers to the biological functionality that is associated with a wild-type form of the protein. For example, in the context of an enzyme, the term "activity" refers to the ability of the protein to effectuate substrate turnover in a manner that yields the product of a corresponding chemical reaction. Activity levels of enzymes can be detected and quantitated, for example, using substrate turnover assays known in the art. As another example, in the context of a membrane-bound receptor, the term "activity" may refer to signal transduction initiated by the receptor, e.g., upon binding to its cognate ligand. Activity levels of receptors involved in signal transduction pathways can be detected and quantitated, for example, by observing an increase in the outcome of receptor signaling, such as an increase in the transcription of one or more genes (which may be detected, e.g., using polymerase chain reaction techniques known in the art).

As used herein, the terms "administering," "administration," and the like refer to directly giving a patient a therapeutic agent (e.g., a population of cells, such as a population of pluripotent cells (e.g., embryonic stem cells, induced pluripotent stem cells, or CD34+ cells)) by any effective route. Exemplary routes of administration are described herein and include systemic administration routes, such as intravenous injection, among others.

As used herein, the term "allogeneic" refers to cells, tissues, nucleic acid molecules, or other substances obtained or derived from a different subject of the same species. For example, in the context of a population of cells (e.g., a population of pluripotent cells) expressing one or more proteins described herein, allogeneic cells include those that are (i) obtained from a subject that is not undergoing therapy and are then (ii) transduced or transfected with a vector that directs the expression of one or more desired proteins. The phrase "directs expression" refers to the inclusion of one or more polynucleotides encoding the one or more proteins to be expressed. The polynucleotide may contain additional sequence motifs that enhances expression of the protein of interest.

As used herein, the term "anneal" refers to the formation of a stable duplex of nucleic acids by way of hybridization mediated by inter-strand hydrogen bonding, for example, according to Watson-Crick base pairing. The nucleic acids of the duplex may be, for example, at least 50% complementary to one another (e.g., about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 80%, 81%, 82%, 83%, 84%, 85%, 86%, 87%, 88%, 89%, 90%, 91%, 92%, 93%, 94%, 95%, 96%, 97%, 98%, 99%, 99.9%, or 100% complementary to one another. The "stable duplex" formed upon the annealing of one nucleic acid to another is a duplex structure that is not denatured by a stringent wash. Exemplary stringent wash conditions are known in the art and include temperatures of about 5° C. less than the melting temperature of an individual strand of the duplex and low concentrations of monovalent salts, such as monovalent salt concentrations (e.g., NaCl concentrations) of less than 0.2 M (e.g., 0.2 M, 0.19 M, 0.18 M, 0.17 M, 0.16 M, 0.15 M, 0.14 M, 0.13 M, 0.12 M, 0.11 M, 0.1 M, 0.09 M, 0.08 M, 0.07 M, 0.06 M, 0.05 M, 0.04 M, 0.03 M, 0.02 M, 0.01 M, or less).

As used herein, the term "autologous" refers to cells, tissues, nucleic acid molecules, or other substances obtained or derived from an individual's own cells, tissues, nucleic acid molecules, or the like. For example, in the context of a population of cells (e.g., a population of pluripotent cells) expressing one or more proteins described herein, autologous cells include those that are obtained from the patient undergoing therapy that are then transduced or transfected with a vector that directs the expression of one or more proteins of interest.

As used herein, the term "cell type" refers to a group of cells sharing a phenotype that is statistically separable based on gene expression data. For example, cells of a common cell type may share similar structural and/or functional characteristics, such as similar gene activation patterns and antigen presentation profiles. Cells of a common cell type may include those that are isolated from a common tissue (e.g., epithelial tissue, neural tissue, connective tissue, or muscle tissue) and/or those that are isolated from a common organ, tissue system, blood vessel, or other structure and/or region in an organism.

As used herein, the terms "condition" and "conditioning" refer to processes by which a subject is prepared for receipt of a transplant containing a population of cells (e.g., a population of pluripotent cells, such as CD34+ cells). Such procedures promote the engraftment of a cell transplant, for example, by selectively depleting endogenous cells (e.g., endogenous CD34+ cells, among others) thereby creating a vacancy which is in turn filled by the exogenous cell transplant. According to the methods described herein, a subject may be conditioned for cell transplant procedure by administration to the subject of one or more agents capable of ablating endogenous cells (e.g., CD34+ cells, among others), radiation therapy, or a combination thereof. Conditioning regimens useful in conjunction with the compositions and methods of the disclosure may be myeloablative or non-myeloablative. Other cell-ablating agents and methods well known in the art (e.g., antibody-drug conjugates) may also be used.

As used herein, the terms "conservative mutation," "conservative substitution," "conservative amino acid substitution," and the like refer to a substitution of one or more amino acids for one or more different amino acids that exhibit similar physicochemical properties, such as polarity, electrostatic charge, and steric volume. These properties are summarized for each of the twenty naturally-occurring amino acids in Table 1 below.

TABLE 1

Representative physicochemical properties of naturally occurring amino acids

| Amino Acid | 3 Letter Code | 1 Letter Code | Side-chain Polarity | Electrostatic character at physiological pH (7.4) | Steric Volume† |
|---|---|---|---|---|---|
| Alanine | Ala | A | nonpolar | neutral | small |
| Arginine | Arg | R | polar | cationic | large |
| Asparagine | Asn | N | polar | neutral | intermediate |
| Aspartic acid | Asp | D | polar | anionic | intermediate |
| Cysteine | Cys | C | nonpolar | neutral | intermediate |
| Glutamic acid | Glu | E | polar | anionic | intermediate |
| Glutamine | Gln | Q | polar | neutral | intermediate |
| Glycine | Gly | G | nonpolar | neutral | small |
| Histidine | His | H | polar | Both neutral and cationic forms in equilibrium at pH 7.4 | large |
| Isoleucine | Ile | I | nonpolar | neutral | large |
| Leucine | Leu | L | nonpolar | neutral | large |
| Lysine | Lys | K | polar | cationic | large |
| Methionine | Met | M | nonpolar | neutral | large |
| Phenylalanine | Phe | F | nonpolar | neutral | large |
| Proline | Pro | P | non-polar | neutral | intermediate |
| Serine | Ser | S | polar | neutral | small |
| Threonine | Thr | T | polar | neutral | intermediate |
| Tryptophan | Trp | W | nonpolar | neutral | bulky |
| Tyrosine | Tyr | Y | polar | neutral | large |
| Valine | Val | V | nonpolar | neutral | intermediate |

†based on volume in $A^3$: 50-100 is small, 100-150 is intermediate, 150-200 is large, and >200 is bulky From this table it is appreciated that the conservative amino acid families include (i) G, A, V, L and I; (ii) D and E; (iii) C, S and T; (iv) H, K and R; (v) N and Q; and (vi) F, Y and W. A conservative mutation or substitution is therefore one that substitutes one amino acid for a member of the same amino acid family (e.g., a substitution of Ser for Thr or Lys for Arg).

As used herein, the terms "embryonic stem cell" and "ES cell" refer to an embryo-derived totipotent or pluripotent stem cell, derived from the inner cell mass of a blastocyst that can be maintained in an in vitro culture under suitable conditions. ES cells are capable of differentiating into cells of any of the three vertebrate germ layers, e.g., the endoderm, the ectoderm, or the mesoderm. ES cells are also characterized by their ability propagate indefinitely under suitable in vitro culture conditions. ES cells are described, for example, in Thomson et al., Science 282:1145 (1998), the disclosure of which is incorporated herein by reference as it pertains to the structure and functionality of embryonic stem cells.

As used herein, the term "endogenous" describes a molecule (e.g., a polypeptide, nucleic acid, or cofactor) that is found naturally in a particular organism (e.g., a human) or in a particular location within an organism (e.g., an organ, a tissue, or a cell, such as a human cell).

As used herein, the term "expansion agent" refers to a substance capable of promoting the proliferation of a given cell type ex vivo. Accordingly, a "hematopoietic stem cell expansion agent" or an "HSC expansion agent" refers to a substance capable of promoting the proliferation of a population of hematopoietic stem cells ex vivo. Hematopoietic stem cell expansion agents include those that effectuate the proliferation of a population of hematopoietic stem cells such that the cells retain hematopoietic stem cell functional potential. Exemplary hematopoietic stem cell expansion agents that may be used in conjunction with the compositions and methods of the disclosure include, without limitation, aryl hydrocarbon receptor antagonists, such as those described in U.S. Pat. Nos. 8,927,281 and 9,580,426, the disclosures of each of which are incorporated herein by reference in their entirety, and, in particular, compound SR1. Additional hematopoietic stem cell expansion agents that may be used in conjunction with the compositions and methods of the disclosure include compound UM-171 and other compounds described in U.S. Pat. No. 9,409,906, the disclosure of which is incorporated herein by reference in its entirety. Hematopoietic stem cell expansion agents further include structural and/or stereoisomeric variants of compound UM-171, such as the compounds described in US 2017/0037047, the disclosure of which is incorporated herein by reference in its entirety. Additional hematopoietic stem cell expansion agents suitable for use in the instant disclosure include histone deacetylase (HDAC) inhibitors, such as trichostatin A, trapoxin, trapoxin A, chlamydocin, sodium butyrate, dimethyl sulfoxide, suberanilohydroxamic acid, m-carboxycinnamic acid bishydroxamide, HC-toxin, Cyl-2, WF-3161, depudecin, and radicicol, among others described, for example, in WO 2000/023567, the disclosure of which is incorporated herein by reference.

As used herein, the term "express" refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein. In the context of a gene that encodes a protein product, the terms "gene expression" and the like are used interchangeably with the terms "protein expression" and the like. Expression of a gene or protein of interest in a subject can manifest, for example, by detecting: an increase in the quantity or concentration of mRNA encoding corresponding protein (as assessed, e.g., using RNA detection procedures described herein or known in the art, such as quantitative polymerase chain reaction (qPCR) and RNA seq techniques), an increase in the quantity or concentration of the corresponding protein (as assessed, e.g., using protein detection methods described herein or known in the art, such as enzyme-linked immunosorbent assays (ELISA), among others), and/or an increase in the activity of the corresponding protein (e.g., in the case of an enzyme, as assessed using an enzymatic activity assay described herein or known in the art) in a sample obtained from the subject. As used herein, a cell is considered to "express" a gene or protein of interest if one or more, or all, of the above events can be detected in the cell or in a medium in which the cell resides. For example, a gene or protein of interest is considered to be "expressed" by a cell or population of cells if one can detect (i) production of a corresponding RNA transcript, such as an mRNA template, by the cell or population of cells (e.g., using RNA detection procedures described herein); (ii) processing of the RNA transcript (e.g., splicing, editing, 5' cap formation, and/or 3' end processing, such as using RNA detection procedures described herein); (iii) translation of the RNA template into a protein product (e.g., using protein detection procedures described herein); and/or (iv) post-translational modification of the protein product (e.g., using protein detection procedures described herein).

As used herein, the term "functional potential" as it pertains to a pluripotent cell, such as a hematopoietic stem cell, refers to the functional properties of stem cells which include: 1) multi-potency (which refers to the ability to differentiate into multiple different blood lineages including, but not limited to granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells); 2) self-renewal (which refers to the ability of stem cells to give rise to daughter cells that have equivalent potential as the mother cell, and further that this ability can repeatedly occur throughout the lifetime of an individual without exhaustion); and 3) the ability of stem cells or progeny thereof to be reintroduced into a transplant recipient whereupon they home to the stem cell niche and re-establish productive and sustained cell growth and differentiation.

As used herein, the terms "hematopoietic stem cells" and "HSCs" refer to immature blood cells having the capacity to self-renew and to differentiate into mature blood cells of diverse lineages including but not limited to granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). It is known in the art that such cells may or may not include CD34+ cells. CD34+ cells are immature cells that express the CD34 cell surface marker. In humans, CD34+ cells are believed to include a subpopulation of cells with the stem cell properties defined above, whereas in mice, HSCs are CD34-. In addition, HSCs also refer to long term repopulating HSC (LT-HSC) and short-term repopulating HSC (ST-HSC). LT-HSC and ST-HSC are differentiated, based on functional potential and on cell surface marker expression. For example, human HSC are a CD34+, CD38−, CD45RA−, CD90+, CD49F+, and lin− (negative for mature lineage markers including CO2, CD3, CD4, CD7, CD8, CD10, CD11B, CD19, CD20, CD56, CD235A). In mice, bone marrow LT-HSC are CD34−, SCA-1+, C-kit+, CD135−, Slamf1/CD150+, CD48−, and lin− (negative for mature lineage markers including Ter119, CD11b, Gr1, CD3, CD4, CD8, B220, IL-7ra), whereas ST-HS Care CD34+, SCA-1+, C-kit+, CD135−, Slamf1/CD150+, and lin− (negative for mature lineage markers including Ter119, CD11b, Gr1, CD3, CD4, CD8, B220, IL-7ra). In addition, ST-HSC are less quiescent (i.e., more active) and more proliferative than L T-HSC under homeostatic conditions. However, LT-HSC have greater self-renewal potential (i.e., they survive throughout adulthood, and can be serially transplanted through successive recipients), whereas ST-HSC have limited self-renewal (i.e., they survive for only a limited period of time, and do not possess serial transplantation potential). Any of these HSCs can be used in any of the methods described herein. Optionally, ST-HSCs are useful because they are highly proliferative and thus, can more quickly give rise to differentiated progeny.

As used herein, the term "HLA-matched" refers to a donor-recipient pair in which none of the HLA antigens are mismatched between the donor and recipient, such as a donor providing a hematopoietic stem cell graft to a recipient in need of hematopoietic stem cell transplant therapy. HLA-matched (i.e., where all of the 6 alleles are matched) donor-recipient pairs have a decreased risk of graft rejection, as endogenous T cells and NK cells are less likely to recognize the incoming graft as foreign, and are thus less likely to mount an immune response against the transplant.

As used herein, the term "HLA-mismatched" refers to a donor-recipient pair in which at least one HLA antigen, in particular with respect to HLA-A, HLA-B, HLA-C, and HLA-DR, is mismatched between the donor and recipient, such as a donor providing a hematopoietic stem cell graft to a recipient in need of hematopoietic stem cell transplant therapy. In some embodiments, one haplotype is matched and the other is mismatched. HLA-mismatched donor-recipient pairs may have an increased risk of graft rejection relative to HLA-matched donor-recipient pairs, as endogenous T cells and NK cells are more likely to recognize the incoming graft as foreign in the case of an HLA-mismatched donor-recipient pair, and such T cells and NK cells are thus more likely to mount an immune response against the transplant.

As used herein, the terms "induced pluripotent stem cell," "iPS cell," and "iPSC" refer to a pluripotent stem cell that can be derived directly from a differentiated somatic cell. Human iPS cells can be generated by introducing specific sets of reprogramming factors into a non-pluripotent cell that can include, for example, Oct3/4, Sox family transcription factors (e.g., Sox1, Sox2, Sox3, SoxI5), Myc family transcription factors (e.g., c-Myc, 1-Myc, n-Myc), Kruppel-like family (KLF) transcription factors (e.g., KLF1, KLF2, KLF4, KLF5), and/or related transcription factors, such as NANOG, LIN28, and/or Glis1. Human iPS cells can also be generated, for example, by the use of miRNAs, small molecules that mimic the actions of transcription factors, or lineage specifiers. Human iPS cells are characterized by their ability to differentiate into any cell of the three vertebrate germ layers, e.g., the endoderm, the ectoderm, or the mesoderm. Human iPS cells are also characterized by their ability propagate indefinitely under suitable in vitro culture conditions. Human iPS cells are described, for example, in Takahashi and Yamanaka, Cell 126:663 (2006), the disclosure of which is incorporated herein by reference as it pertains to the structure and functionality of iPS cells.

As used herein, the terms “interfering ribonucleic acid” and “interfering RNA” refer to a RNA, such as a short interfering RNA (siRNA), micro RNA (miRNA), or short hairpin RNA (shRNA) that suppresses the expression of a target RNA transcript by way of (i) annealing to the target RNA transcript, thereby forming a nucleic acid duplex; and (ii) promoting the nuclease-mediated degradation of the RNA transcript and/or (iii) slowing, inhibiting, or preventing the translation of the RNA transcript, such as by sterically precluding the formation of a functional ribosome-RNA transcript complex or otherwise attenuating formation of a functional protein product from the target RNA transcript. Interfering RNAs as described herein may be provided to a patient in the form of, for example, a single- or double-stranded oligonucleotide, or in the form of a vector (e.g., a viral vector) containing a transgene encoding the interfering RNA. Exemplary interfering RNA platforms are described, for example, in Lam et al., Molecular Therapy—Nucleic Acids 4:e252 (2015); Rao et al., Advanced Drug Delivery Reviews 61:746-769 (2009); and Borel et al., Molecular Therapy 22:692-701 (2014), the disclosures of each of which are incorporated herein by reference in their entirety.

As used herein in the context of a viral transduction protocol, the term “multiplicity of infection” or “MOI” refers to the ratio of (i) virions added to a population of cells being targeted for transduction to (ii) the quantity of cells in the population. As an example, a transduction protocol in which a population of $1\times10^6$ cells being targeted for transduction is contacted with $1\times10^7$ virions (e.g., lentiviral virions, such as a lentiviral virion described herein) would be characterized by a multiplicity of infection of 10.

As used herein in the context of hematopoietic stem and/or progenitor cells, the term “mobilization” refers to release of such cells from a stem cell niche where the cells typically reside (e.g., the bone marrow) into peripheral circulation. “Mobilization agents” are agents that are capable of inducing the release of hematopoietic stem and/or progenitor cells from a stem cell niche into peripheral circulation.

As used herein, the term “myeloablative” or “myeloablation” refers to a conditioning regiment that substantially impairs or destroys the hematopoietic system, typically by exposure to a cytotoxic agent or radiation. Myeloablation encompasses complete myeloablation brought on by high doses of cytotoxic agent or total body irradiation that destroys the hematopoietic system.

As used herein, the term “non-myeloablative” or “myelosuppressive” refers to a conditioning regiment that does not eliminate substantially all hematopoietic cells of host origin.

As used herein, the term “poloxamer” refers to a nonionic triblock copolymer composed of a central hydrophobic chain of polyoxypropylene flanked by two hydrophilic chains of polyoxyethylene.

Poloxamers are also known by the trade name of “Pluronics” or “Synperonics” (BASF). The block copolymer can be represented by the following formula: $HO(C_2H_4O)_x(C_3H_6O)_y(C_2H_4O)_zH$. The lengths of the polymer blocks can be customized. As a result, many different poloxamers exist. Poloxamers suitable for use in conjunction with the compositions and methods of the present disclosure include those having an average molecular weight of at least about 10,000 g/mol, at least about 11,400 g/mol, at least about 12,600 g/mol, at least about 13,000 g/mol, at least about 14,600 g/mol, or at least about 15,000 g/mol. Since the synthesis of block copolymers is associated with a natural degree of variation from one batch to another, the numerical values recited above (and those used herein to characterize a given poloxamer) may not be precisely achievable upon synthesis, and the average value will differ to a certain extent. Thus, the term “poloxamer” as used herein can be used interchangeably with the term “poloxamers” (representing an entity of several poloxamers, also referred to as mixture of poloxamers) if not explicitly stated otherwise. The term “average” in relation to the number of monomer units or molecular weight of (a) poloxamer(s) as used herein is a consequence of the technical inability to produce poloxamers all having the identical composition and thus the identical molecular weight. Poloxamers produced according to state of the art methods will be present as a mixture of poloxamers each showing a variability as regards their molecular weight, but the mixture as a whole averaging the molecular weight specified herein. BASF and Sigma Aldrich are suitable sources of poloxamers for use in conjunction with the compositions and methods of the disclosure.

As used herein, the term “pluripotent cell” refers to a cell that possesses the ability to develop into more than one differentiated cell type, such as a cell type of the hematopoietic lineage (e.g., granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). Examples of pluripotent cells are ESCs, iPSCs, and CD34+ cells.

As used herein, the term “promoter” refers to a recognition site on DNA that is bound by an RNA polymerase. The polymerase drives transcription of the transgene. Exemplary promoters suitable for use with the compositions and methods described herein are described, for example, in Sandelin et al., Nature Reviews Genetics 8:424 (2007), the disclosure of which is incorporated herein by reference as it pertains to nucleic acid regulatory elements. Additionally, the term “promoter” may refer to a synthetic promoter, which are regulatory DNA sequences that do not occur naturally in biological systems. Synthetic promoters contain parts of naturally occurring promoters combined with polynucleotide sequences that do not occur in nature and can be optimized to express recombinant DNA using a variety of transgenes, vectors, and target cell types.

“Percent (%) sequence complementarity” with respect to a reference polynucleotide sequence is defined as the percentage of nucleic acids in a candidate sequence that are complementary to the nucleic acids in the reference polynucleotide sequence, after aligning the sequences and introducing gaps, if necessary, to achieve the maximum percent sequence complementarity. A given nucleotide is considered to be “complementary” to a reference nucleotide as described herein if the two nucleotides form canonical Watson-Crick base pairs. For the avoidance of doubt, Watson-Crick base pairs in the context of the present disclosure include adenine-thymine, adenine-uracil, and cytosine-guanine base pairs. A proper Watson-Crick base pair is referred to in this context as a "match," while each unpaired nucleotide, and each incorrectly paired nucleotide, is referred to as a "mismatch." Alignment for purposes of determining percent nucleic acid sequence complementarity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal complementarity over the full length of the sequences being compared. As an illustration, the percent sequence complementarity of a given nucleic acid sequence, A, to a given nucleic acid sequence, B, (which can alternatively be phrased as a given nucleic acid sequence, A that has a certain percent complementarity to a given nucleic acid sequence, B) is calculated as follows:

100 multiplied by (the fraction $X/Y$)

where X is the number of complementary base pairs in an alignment (e.g., as executed by computer software, such as BLAST) of A and B, and where Y is the total number of nucleic acids in B. It will be appreciated that where the length of nucleic acid sequence A is not equal to the length of nucleic acid sequence B, the percent sequence complementarity of A to B will not equal the percent sequence complementarity of B to A. As used herein, a query nucleic acid sequence is considered to be "completely complementary" to a reference nucleic acid sequence if the query nucleic acid sequence has 100% sequence complementarity to the reference nucleic acid sequence.

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

100 multiplied by (the fraction $X/Y$)

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

As used herein, the term "pharmaceutically acceptable" refers to those compounds, materials, compositions and/or dosage forms, which are suitable for contact with the tissues of a subject, such as a mammal (e.g., a human) without excessive toxicity, irritation, allergic response and other problem complications commensurate with a reasonable benefit/risk ratio.

As used herein, the term "regulatory sequence" includes promoters, enhancers and other expression control elements (e.g., polyadenylation signals) that control the transcription or translation of the antibody chain genes. Such regulatory sequences are described, for example, in Perdew et al., Regulation of Gene Expression (Humana Press, New York, NY, (2014)); incorporated herein by reference.

As used herein, the terms "stem cell" and "undifferentiated cell" refer to a cell in an undifferentiated or partially differentiated state that has the developmental potential to differentiate into multiple cell types. A stem cell is capable of proliferation and giving rise to more such stem cells while maintaining its functional potential. Stem cells can divide asymmetrically, which is known as obligatory asymmetrical differentiation, with one daughter cell retaining the functional potential of the parent stem cell and the other daughter cell expressing some distinct other specific function, phenotype and/or developmental potential from the parent cell. The daughter cells themselves can be induced to proliferate and produce progeny that subsequently differentiate into one or more mature cell types, while also retaining one or more cells with parental developmental potential. A differentiated cell may derive from a multipotent cell, which itself is derived from a multipotent cell, and so on. Alternatively, some of the stem cells in a population can divide symmetrically into two stem cells. Accordingly, the term "stem cell" refers to any subset of cells that have the developmental potential, under particular circumstances, to differentiate to a more specialized or differentiated phenotype, and which retain the capacity, under certain circumstances, to proliferate without substantially differentiating. In some embodiments, the term stem cell refers generally to a naturally occurring parent cell whose descendants (progeny cells) specialize, often in different directions, by differentiation, e.g., by acquiring completely individual characters, as occurs in progressive diversification of embryonic cells and tissues. Some differentiated cells also have the capacity to give rise to cells of greater developmental potential. Such capacity may be natural or may be induced artificially upon treatment with various factors. Cells that begin as stem cells might proceed toward a differentiated phenotype, but then can be induced to "reverse" and re-express the stem cell phenotype, a term often referred to as "dedifferentiation" or "reprogramming" or "retrodifferentiation" by persons of ordinary skill in the art.

As used herein, the term "transgene" refers to a recombinant nucleic acid (e.g., DNA or cDNA) encoding a gene product (e.g., a gene product described herein). The gene product may be an RNA, peptide, or protein. In addition to the coding region for the gene product, the transgene may include or be operably linked to one or more elements to facilitate or enhance expression, such as a promoter, enhancer(s), destabilizing domain(s), response element(s), reporter element(s), insulator element(s), polyadenylation signal(s), and/or other functional elements. Embodiments of the disclosure may utilize any known suitable promoter, enhancer(s), destabilizing domain(s), response element(s), reporter element(s), insulator element(s), polyadenylation signal(s), and/or other functional elements.

As used herein, the terms "subject" and "patient" are used interchangeably and refer to an organism (e.g., a mammal, such as a human) that has been diagnosed as having, and/or is undergoing treatment for, a disease, such as a disease characterized by a gene or protein deficiency described herein.

As used herein, the terms "transduction" and "transduce" refer to a method of introducing a viral vector construct or a part thereof into a cell and subsequent expression of a transgene encoded by the vector construct or part thereof in the cell.

As used herein, the term "transduction efficiency" refers to the proportion of cells in a given population that are transduced with at least one copy of a vector (e.g., a viral vector, such as a lentiviral vector described herein). For example, if $1\times10^6$ cells are exposed to a virus (e.g., a lentivirus) and $0.5\times10^6$ cells are determined to have a least one copy of the viral vector in their genome following a transduction procedure, then the transduction efficiency for that procedure is 50%. Exemplary methods for determining transduction efficiency include polymerase chain reaction (PCR) procedures and flow cytometry.

As used herein, "treatment" and "treating" refer to an approach for obtaining beneficial or desired results, e.g., clinical results. Beneficial or desired results can include, but are not limited to, alleviation or amelioration of one or more symptoms or conditions; diminishment of extent of disease or condition; stabilized (i.e., not worsening) state of disease, disorder, or condition; preventing spread of disease or condition; delay or slowing the progress of the disease or condition; amelioration or palliation of the disease or condition; and remission (whether partial or total), whether detectable or undetectable. "Ameliorating" or "palliating" a disease or condition means that the extent and/or undesirable clinical manifestations of the disease, disorder, or condition are lessened and/or time course of the progression is slowed or lengthened, as compared to the extent or time course in the absence of treatment. "Treatment" can also mean prolonging survival as compared to expected survival if not receiving treatment. Those in need of treatment include those already with the condition or disorder, as well as those prone to or at risk of developing the condition or disorder, as well as those in which the condition or disorder is to be prevented.

As used herein, the term "vector" includes a nucleic acid vector, e.g., a DNA vector, such as a plasmid, a RNA vector, virus, or other suitable replicon (e.g., viral vector). A variety of vectors have been developed for the delivery of polynucleotides encoding exogenous proteins into a prokaryotic or eukaryotic cell. Examples of such expression vectors are disclosed in, e.g., WO 1994/011026; incorporated herein by reference as it pertains to vectors suitable for the expression of a gene of interest. Expression vectors suitable for use with the compositions and methods described herein contain a polynucleotide sequence as well as, e.g., additional sequence elements used for the expression of proteins and/or the integration of these polynucleotide sequences into the genome of a mammalian cell. Vectors that can be used for the expression of a protein or proteins described herein include plasmids that contain regulatory sequences, such as promoter and enhancer regions, which direct gene transcription. Additionally, useful vectors for expression of a protein or proteins described herein may contain polynucleotide sequences that enhance the rate of translation of the corresponding gene or genes, or improve the stability or nuclear export of the mRNA that results from gene transcription. Examples of such sequence elements are 5' and 3' untranslated regions, an IRES, and a polyadenylation signal site in order to direct efficient transcription of a gene or genes carried on an expression vector. Expression vectors suitable for use with the compositions and methods described herein may also contain a polynucleotide encoding a marker for selection of cells that contain such a vector. Examples of a suitable marker are genes that encode resistance to antibiotics, such as ampicillin, chloramphenicol, kanamycin, nourseothricin, or zeocin, among others.

As used herein, the term "vector copy number" or "VCN" refers to the quantity of copies of a vector, or portion thereof (e.g., a portion that encodes a transgene of interest), in the genome of a cell. The average VCN may be determined for a population of cells or for individual cell colonies. Exemplary methods for measuring VCN include PCR procedures and flow cytometry.

As used herein, the term "beta-globin," along with the names of other genes or proteins recited in the present disclosure, include wild-type forms of the corresponding gene or protein, as well as variants (e.g., splice variants, truncations, concatemers, and fusion constructs, among others) thereof. In the context of beta-globin, examples of such variants are proteins having at least 70% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.9% identity, or more) to any of the amino acid sequences of a wild-type beta-globin protein (e.g., SEQ ID NO: 2), provided, for example, that the beta-globin variant retains the functionality of a wild-type beta-globin.

As used herein, the term "alkyl" refers to monovalent, optionally branched alkyl groups, such as those having from 1 to 6 carbon atoms, or more. This term is exemplified by groups such as methyl, ethyl, n-propyl, isopropyl, n-butyl, isobutyl, tert-butyl, n-hexyl and the like.

As used herein, the term "lower alkyl" refers to alkyl groups having from 1 to 6 carbon atoms.

As used herein, the term "aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenanthrenyl and the like.

As used herein, the terms "aralkyl" and "aryl alkyl" are used interchangeably and refer to an alkyl group containing an aryl moiety. Similarly, the terms "aryl lower alkyl" and the like refer to lower alkyl groups containing an aryl moiety.

As used herein, the term "alkyl aryl" refers to alkyl groups having an aryl substituent, including benzyl, phenethyl and the like.

As used herein, the term "heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, I,3,4-oxadiazolyl,I,3,4-triazinyl, 1,2,3-triazinyl, benzofuryl, [2,3-dihydrobenzofuryl, isobenzofuryl, benzothienyl, benzotriazolyl, isobenzothienyl, indolyl, isoindolyl, 3H-indolyl, benzimidazolyl, imidazo[I,2-a]pyridyl, benzothiazolyl, benzoxa-zolyl, quinolizinyl, quinazolinyl, phthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl, benzoquinolyl, and the like.

As used herein, the term “alkyl heteroaryl” refers to alkyl groups having a heteroaryl substituent, including 2-furylmethyl, 2-thienylmethyl, 2-(1H-indol-3-yl)ethyl and the like.

As used herein, the term “lower alkenyl” refers to alkenyl groups preferably having from 2 to 6 carbon atoms and having at least 1 or 2 sites of alkenyl unsaturation. Exemplary alkenyl groups are ethenyl ($—CH{=}CH_2$), n-2-propenyl (allyl, $—CH_2CH{=}CH_2$) and the like.

As used herein, the term “alkenyl aryl” refers to alkenyl groups having an aryl substituent, including 2-phenylvinyl and the like.

As used herein, the term “alkenyl heteroaryl” refers to alkenyl groups having a heteroaryl substituent, including 2-(3-pyridinyl)vinyl and the like.

As used herein, the term “lower alkynyl” refers to alkynyl groups preferably having from 2 to 6 carbon atoms and having at least 1-2 sites of alkynyl unsaturation, preferred alkynyl groups include ethynyl ($—C{\equiv}CH$), propargyl ($—CH_2C{\equiv}CH$), and the like.

As used herein, the term “alkynyl aryl” refers to alkynyl groups having an aryl substituent, including phenylethynyl and the like.

As used herein, the term “alkynyl heteroaryl” refers to alkynyl groups having a heteroaryl substituent, including 2-thienylethynyl and the like.

As used herein, the term “cycloalkyl” refers to a monocyclic cycloalkyl group having from 3 to 8 carbon atoms, such as cyclopropyl, cyclobutyl, cyclopentyl, cyclohexyl, cycloheptyl, cyclooctyl, and the like.

As used herein, the term “lower cycloalkyl” refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

As used herein, the term “heterocycloalkyl” refers to a cycloalkyl group in which one or more ring carbon atoms are replaced with a heteroatom, such as a nitrogen atom, an oxygen atom, a sulfur atom, and the like. Exemplary heterocycloalkyl groups are pyrrolidinyl, piperidinyl, oxopiperidinyl, morpholinyl, piperazinyl, oxopiperazinyl, thiomorpholinyl, azepanyl, diazepanyl, oxazepanyl, thiazepanyl, dioxothiazepanyl, azokanyl, tetrahydrofuranyl, tetrahydropyranyl, and the like.

As used herein, the term “alkyl cycloalkyl” refers to alkyl groups having a cycloalkyl substituent, including cyclohexylmethyl, cyclopentylpropyl, and the like.

As used herein, the term “alkyl heterocycloalkyl” refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

As used herein, the term “carboxy” refers to the group —C(O)OH.

As used herein, the term “alkyl carboxy” refers to $C_1$-$C_5$-alkyl groups having a carboxy substituent, including 2-carboxyethyl and the like.

As used herein, the term “acyl” refers to the group —C(O)R, wherein R may be, for example, $C_1$-$C_6$-alkyl, aryl, heteroaryl, $C_1$-$C_6$-alkyl aryl, or $C_1$-$C_6$-alkyl heteroaryl, among other substituents.

As used herein, the term “acyloxy” refers to the group —OC(O)R, wherein R may be, for example, $C_1$-$C_6$-alkyl, aryl, heteroaryl, $C_1$-$C_6$-alkyl aryl, or $C_1$-$C_6$-alkyl heteroaryl, among other substituents.

As used herein, the term “alkoxy” refers to the group —O—R, wherein R is, for example, an optionally substituted alkyl group, such as an optionally substituted $C_1$-$C_6$-alkyl, aryl, heteroaryl, $C_1$-$C_6$-alkyl aryl, or $C_1$-$C_6$-alkyl heteroaryl, among other substituents. Exemplary alkoxy groups include by way of example, methoxy, ethoxy, phenoxy, and the like.

As used herein, the term “alkoxycarbonyl” refers to the group —C(O)OR, wherein R is, for example, hydrogen, $C_1$-$C_6$-alkyl, aryl, heteroaryl, $C_1$-$C_6$-alkyl aryl, or $C_1$-$C_6$-alkyl heteroaryl, among other possible substituents.

As used herein, the term “alkyl alkoxycarbonyl” refers to alkyl groups having an alkoxycarbonyl substituent, including 2-(benzyloxycarbonyl)ethyl and the like.

As used herein, the term “aminocarbonyl” refers to the group —C(O)NRR', wherein each of R and R' may independently be, for example, hydrogen, $C_1$-$C_6$-alkyl, aryl, heteroaryl, $C_1$-$C_6$-alkyl aryl, or $C_1$-$C_6$-alkyl heteroaryl, among other substituents.

As used herein, the term “alkyl aminocarbonyl” refers to alkyl groups having an aminocarbonyl substituent, including 2-(dimethylaminocarbonyl)ethyl and the like.

As used herein, the term “acylamino” refers to the group —NRC(O)R', wherein each of R and R' may independently be, for example, hydrogen, $C_1$-$C_6$-alkyl, aryl, heteroaryl, $C_1$-$C_6$-alkyl aryl, or $C_1$-$C_6$-alkyl heteroaryl, among other substituents.

As used herein, the term “alkyl acylamino” refers to alkyl groups having an acylamino substituent, including 2-(propionylamino)ethyl and the like.

As used herein, the term “ureido” refers to the group —NRC(O)NR'R", wherein each of R, R', and R" may independently be, for example, hydrogen, $C_1$-$C_6$-alkyl, aryl, heteroaryl, $C_1$-$C_6$-alkyl aryl, $C_1$-$C_6$-alkyl heteroaryl, cycloalkyl, or heterocycloalkyl, among other substituents. Exemplary ureido groups further include moieties in which R' and R", together with the nitrogen atom to which they are attached, form a 3-8-membered heterocycloalkyl ring.

As used herein, the term “alkyl ureido” refers to alkyl groups having an ureido substituent, including 2-(N'-methylureido)ethyl and the like.

As used herein, the term “amino” refers to the group —NRR', wherein each of R and R' may independently be, for example, hydrogen, $C_1$-$C_6$-alkyl, aryl, heteroaryl, $C_1$-$C_6$-alkyl aryl, $C_1$-$C_6$-alkyl heteroaryl, cycloalkyl, or heterocycloalkyl, among other substituents. Exemplary amino groups further include moieties in which R and R', together with the nitrogen atom to which they are attached, can form a 3-8-membered heterocycloalkyl ring.

As used herein, the term “alkyl amino” refers to alkyl groups having an amino substituent, including 2-(1-pyrrolidinyl)ethyl and the like.

As used herein, the term “ammonium” refers to a positively charged group $—N^+RR'R"$, wherein each of R, R', and R" may independently be, for example, $C_1$-$C_6$-alkyl, $C_1$-$C_6$-alkyl aryl, $C_1$-$C_6$-alkyl heteroaryl, cycloalkyl, or heterocycloalkyl, among other substituents. Exemplary ammonium groups further include moieties in which R and R', together with the nitrogen atom to which they are attached, form a 3-8-membered heterocycloalkyl ring.

As used herein, the term “halogen” refers to fluoro, chloro, bromo and iodo atoms.

As used herein, the term “sulfonyloxy” refers to a group $—OSO_2—R$ wherein R is selected from hydrogen, $C_1$-$C_6$-alkyl, $C_1$-$C_6$-alkyl substituted with halogens, e.g., an $—OSO_2—CF_3$ group, aryl, heteroaryl, $C_1$-$C_6$-alkyl aryl, and $C_1$-$C_6$-alkyl heteroaryl.

As used herein, the term “alkyl sulfonyloxy” refers to alkyl groups having a sulfonyloxy substituent, including 2-(methylsulfonyloxy)ethyl and the like.

As used herein, the term "sulfonyl" refers to group "—$SO_2$—R" wherein R is selected from hydrogen, aryl, heteroaryl, $C_1$-$C_6$-alkyl, $C_1$-$C_6$-alkyl substituted with halogens, e.g., an —$SO_2$—$CF_3$ group, $C_1$-$C_6$-alkyl aryl or $C_1$-$C_6$-alkyl heteroaryl.

As used herein, the term "alkyl sulfonyl" refers to alkyl groups having a sulfonyl substituent, including 2-(methylsulfonyl)ethyl and the like.

As used herein, the term "sulfinyl" refers to a group "—S(O)—R" wherein R is selected from hydrogen, $C_1$-$C_6$-alkyl, $C_1$-$C_6$-alkyl substituted with halogens, e.g., a —SO—$CF_3$ group, aryl, heteroaryl, $C_1$-$C_6$-alkyl aryl or $C_1$-$C_6$-alkyl heteroaryl.

As used herein, the term "alkyl sulfinyl" refers to $C_1$-$C_5$-alkyl groups having a sulfinyl substituent, including 2-(methylsulfinyl)ethyl and the like.

As used herein, the term "sulfanyl" refers to groups —S—R, wherein R is, for example, alkyl, aryl, heteroaryl, $C_1$-$C_6$-alkyl aryl, or $C_1$-$C_6$-alkyl heteroaryl, among other substituents. Exemplary sulfanyl groups are methylsulfanyl, ethylsulfanyl, and the like.

As used herein, the term "alkyl sulfanyl" refers to alkyl groups having a sulfanyl substituent, including 2-(ethylsulfanyl)ethyl and the like.

As used herein, the term "sulfonylamino" refers to a group —$NRSO_2$—R', wherein each of R and R' may independently be hydrogen, $C_1$-$C_6$-alkyl, aryl, heteroaryl, $C_1$-$C_6$-alkyl aryl, or $C_1$-$C_6$-alkyl heteroaryl, among other substituents.

As used herein, the term "alkyl sulfonylamino" refers to alkyl groups having a sulfonylamino substituent, including 2-(ethylsulfonylamino)ethyl and the like.

Unless otherwise constrained by the definition of the individual substituent, the above set out groups, like "alkyl", "alkenyl", "alkynyl", "aryl" and "heteroaryl" etc. groups can optionally be substituted, for example, with one or more substituents, as valency permits, such as a substituent selected from alkyl (e.g., $C_1$-$C_6$-alkyl), alkenyl (e.g., $C_2$-$C_6$-alkenyl), alkynyl (e.g., $C_2$-$C_6$-alkynyl), cycloalkyl, heterocycloalkyl, alkyl aryl (e.g., $C_1$-$C_6$-alkyl aryl), alkyl heteroaryl (e.g., $C_1$-$C_6$-alkyl heteroaryl, alkyl cycloalkyl (e.g., $C_1$-$C_6$-alkyl cycloalkyl), alkyl heterocycloalkyl (e.g., $C_1$-$C_6$-alkyl heterocycloalkyl), amino, ammonium, acyl, acyloxy, acylamino, aminocarbonyl, alkoxycarbonyl, ureido, aryl, heteroaryl, sulfinyl, sulfonyl, alkoxy, sulfanyl, halogen, carboxy, trihalomethyl, cyano, hydroxy, mercapto, nitro, and the like. In some embodiments, the substitution is one in which neighboring substituents have undergone ring closure, such as situations in which vicinal functional substituents are involved, thus forming, e.g., lactams, lactones, cyclic anhydrides, acetals, thioacetals, and aminals, among others.

As used herein, the term "optionally fused" refers to a cyclic chemical group that may be fused with a ring system, such as cycloalkyl, heterocycloalkyl, aryl, or heteroaryl. Exemplary ring systems that may be fused to an optionally fused chemical group include, e.g., indolyl, isoindolyl, benzofuranyl, isobenzofuranyl, benzothiophenyl, benzoxazolyl, benzothiazolyl, benzoisoxazolyl, benzoisothiazolyl, indazolyl, benzimidazolyl, quinolinyl, isoquinolinyl, phthalazinyl, quinoxalinyl, quinazolinyl, cinnolinyl, indolizinyl, naphthyridinyl, pteridinyl, indanyl, naphtyl, 1,2,3,4-tetrahydronaphthyl, indolinyl, isoindolinyl, 2,3,4,5-tetrahydrobenzo[b]oxepinyl, 6,7,8,9-tetrahydro-5H-benzocycloheptenyl, chromanyl, and the like.

As used herein, the term "pharmaceutically acceptable salt" refers to a salt, such as a salt of a compound described herein, that retains the desired biological activity of the non-ionized parent compound from which the salt is formed. Examples of such salts include, but are not restricted to acid addition salts formed with inorganic acids (e.g., hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. The compounds can also be administered as pharmaceutically acceptable quaternary salts, such as quaternary ammonium salts of the formula —NR, R',R"+Z—, wherein each of R, R', and R" may independently be, for example, hydrogen, alkyl, benzyl, $C_1$-$C_6$-alkyl, $C_2$-$C_6$-alkenyl, $C_2$-$C_6$-alkynyl, $C_1$-$C_6$-alkyl aryl, $C_1$-$C_6$-alkyl heteroaryl, cycloalkyl, heterocycloalkyl, or the like, and Z is a counterion, such as chloride, bromide, iodide, —O-alkyl, toluenesulfonate, methyl sulfonate, sulfonate, phosphate, carboxylate (such as benzoate, succinate, acetate, glycolate, maleate, malate, fumarate, citrate, tartrate, ascorbate, cinnamoate, mandeloate, and diphenylacetate), or the like.

As used herein, for example, in the context of a protein kinase C (PKC) inhibitor, such as staurosporine, the term "variant" refers to an agent containing one or more modifications relative to a reference agent and that (i) retains a functional property of the reference agent (e.g., the ability to inhibit PKC activity) and/or (ii) is converted within a cell (e.g., a cell of a type described herein, such as a CD34+ cell) into the reference agent. In the context of small molecule PKC inhibitors, such as staurosporine, structural variants of a reference compound include those that differ from the reference compound by the inclusion and/or location of one or more substituents, as well as variants that are isomers of a reference compound, such as structural isomers (e.g., regioisomers) or stereoisomers (e.g., enantiomers or diastereomers), as well as prodrugs of a reference compound. In the context of an interfering RNA molecule, a variant may contain one or more nucleic acid substitutions relative to a parent interfering RNA molecule.

The structural compositions described herein also include the tautomers, geometrical isomers (e.g., E/Z isomers and cis/trans isomers), enantiomers, diastereomers, and racemic forms, as well as pharmaceutically acceptable salts thereof. Such salts include, e.g., acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

As used herein, chemical structural formulas that do not depict the stereochemical configuration of a compound having one or more stereocenters will be interpreted as encompassing any one of the stereoisomers of the indicated compound, or a mixture of one or more such stereoisomers (e.g., any one of the enantiomers or diastereomers of the indicated compound, or a mixture of the enantiomers (e.g., a racemic mixture) or a mixture of the diastereomers). As used herein, chemical structural formulas that do specifically depict the stereochemical configuration of a compound having one or more stereocenters will be interpreted as referring to the substantially pure form of the particular stereoisomer shown. "Substantially pure" forms refer to compounds having a purity of greater than 85%, such as a purity of from 85% to 99%, 85% to 99.9%, 85% to 99.99%, or 85% to 100%, such as a purity of 85%, 86%, 87%, 88%, 89%, 90%, 91%, 92%, 93%, 94%, 95%, 96%, 97%, 98%, 99%, 99.9%, 99.99%, 99.999%, or 100%, as assessed, for example, using chromatography and nuclear magnetic resonance techniques known in the art.

BRIEF DESCRIPTION OF THE FIGURES

FIG. 2A is a plot summarizing the percentage of viable cells 18-24 hours post-transduction, as determined by flow cytometry detection of 7AAD-AnnexinV-cells. FIG. 2B is a plot summarizing the fold change in percentage of transduced cells induced by the addition of P407 or P338, relative to cells treated with vector alone. The percentage of transduced cells was assessed by flow cytometry detection of transgene expression 12 days post-transduction. FIG. 2C is a plot summarizing the fold change in mean transgene copy number (VCN) relative to cells treated with vector alone. VCN was determined by droplet digital PCR detection of integrated transgene sequences in genomic DNA harvested from cell cultures 12 days post-transduction. The data shown are mean±SEM for n=3-9 (FIGS. 2A and 2B) and n=3-6 (FIG. 2C) independent experiments with healthy human donor cells. Statistical analysis was conducted using a paired T-test of test conditions relative to vector and poloxamer vehicle treated cells, where "ns" indicates no statistical significance was ($p<0.05$).

DETAILED DESCRIPTION

Figure 1B:
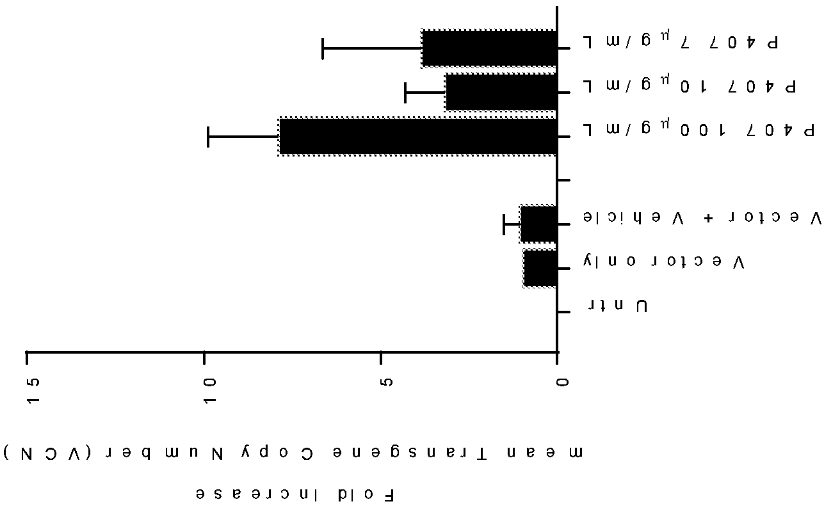
FIG. 1B is a graph showing the effect of poloxamer P407, when incubated with CD34+ hematopoietic stem cells at various concentrations, on lentiviral vector copy number, as described in Example One, below. CD34+ cells were transduced with a lentiviral vector containing a transgene encoding GFP. Cells were either untreated ("Untr") or incubated with the lentivirus alone ("Vector only"), the lentivirus in combination with vehicle ("Vector+Vehicle"), or the lentivirus in combination with particular concentrations of P407, as indicated along the x axis. Values along the y axis represent fold increase in vector copy number of cells 12 days after exposure to each of the specified conditions relative to vector copy number of cells 12 days after exposure to lentiviral vector alone ("Vector only"). Values along the y axis denote the mean±standard error of the mean (SEM) for n=3 independent experiments.

The compositions and methods described herein can be used, for example, to modify eukaryotic cells, such as pluripotent cells, including hematopoietic stem cells (HSCs) and hematopoietic progenitor cells (HPCs). Using the compositions and methods of the disclosure, such cells may be engineered to express a gene of interest, and/or manipulated so as to proliferate ex vivo. In some embodiments of the disclosure, a population of pluripotent cells, such as a population of HSCs and/or HPCs, is contacted with a viral vector encoding a transgene. The transgene may encode a protein product or a regulatory ribonucleic acid (RNA) molecule that modulates the expression of a different gene. In some embodiments, the transgene encodes a protein that is deficient or non-functional in a patient (e.g., a mammalian patient, such as a human) suffering from a genetic disease for example, a genetic disease characterized by a loss-of-function mutation. The cell may be contacted with the virus in a manner that promotes transduction of the cell so as to express the desired transgene. In some embodiments, the cell is then administered to a patient suffering from a disease described above, thereby restoring gene expression in the individual.

A variety of viral vectors can be used in conjunction with the compositions and methods of the disclosure. For examples, the viral vector may be a retrovirus, such as a lentivirus. Other viral vectors that may be used to achieve transduction of a target cell are described herein.

To augment the extent of transduction and/or the rate at which the target cell is transduced, the cell may be contacted with a poloxamer, such as a poloxamer having a molar mass in excess of 10,000 g/mol, a molar mass of polyoxypropylene subunits greater than 2,000 g/mol, and/or an ethylene oxide content of greater than 40% by mass.

The sections that follow describe the use of various viral vectors and agents that can be used to augment viral transduction of a target cell and an array of therapeutic uses of the transduced cells.

Poloxamers

Poloxamers that may be used in conjunction with the compositions and methods of the disclosure include those having an average molar mass of polyoxypropylene subunits of greater than 2,050 g/mol (e.g., an average molar mass of polyoxypropylene subunits of about 2,055 g/mol, 2,060 g/mol, 2,075 g/mol, 2,080 g/mol, 2,085 g/mol, 2,090 g/mol, 2,095 g/mol, 2,100 g/mol, 2,200 g/mol, 2,300 g/mol, 2,400 g/mol, 2,500 g/mol, 2,600 g/mol, 2,700 g/mol, 2,800 g/mol, 2,900 g/mol, 3,000 g/mol, 3,100 g/mol, 3,200 g/mol, 3,300 g/mol, 3,400 g/mol, 3,500 g/mol, 3,600 g/mol, 3,700 g/mol, 3,800 g/mol, 3,900 g/mol, 4,000 g/mol, 4,100 g/mol, 4,200 g/mol, 4,300 g/mol, 4,400 g/mol, 4,500 g/mol, 4,600 g/mol, 4,700 g/mol, 4,800 g/mol, 4,900 g/mol, or 5,000 g/mol).

In some embodiments, the poloxamer has an average molar mass of polyoxypropylene subunits of greater than 2,250 g/mol (e.g., an average molar mass of polyoxypropylene subunits of about 2,300 g/mol, 2,400 g/mol, 2,500 g/mol, 2,600 g/mol, 2,700 g/mol, 2,800 g/mol, 2,900 g/mol, 3,000 g/mol, 3,100 g/mol, 3,200 g/mol, 3,300 g/mol, 3,400 g/mol, 3,500 g/mol, 3,600 g/mol, 3,700 g/mol, 3,800 g/mol, 3,900 g/mol, 4,000 g/mol, 4,100 g/mol, 4,200 g/mol, 4,300 g/mol, 4,400 g/mol, 4,500 g/mol, 4,600 g/mol, 4,700 g/mol, 4,800 g/mol, 4,900 g/mol, or 5,000 g/mol).

In some embodiments, the poloxamer has an average molar mass of polyoxypropylene subunits of greater than 2,750 g/mol (e.g., an average molar mass of polyoxypropylene subunits of about 2,800 g/mol, 2,900 g/mol, 3,000 g/mol, 3,100 g/mol, 3,200 g/mol, 3,300 g/mol, 3,400 g/mol, 3,500 g/mol, 3,600 g/mol, 3,700 g/mol, 3,800 g/mol, 3,900 g/mol, 4,000 g/mol, 4,100 g/mol, 4,200 g/mol, 4,300 g/mol, 4,400 g/mol, 4,500 g/mol, 4,600 g/mol, 4,700 g/mol, 4,800 g/mol, 4,900 g/mol, or 5,000 g/mol).

In some embodiments, the poloxamer has an average molar mass of polyoxypropylene subunits of greater than 3,250 g/mol (e.g., an average molar mass of polyoxypropylene subunits of about 3,300 g/mol, 3,400 g/mol, 3,500 g/mol, 3,600 g/mol, 3,700 g/mol, 3,800 g/mol, 3,900 g/mol, 4,000 g/mol, 4,100 g/mol, 4,200 g/mol, 4,300 g/mol, 4,400 g/mol, 4,500 g/mol, 4,600 g/mol, 4,700 g/mol, 4,800 g/mol, 4,900 g/mol, or 5,000 g/mol).

In some embodiments, the poloxamer has an average molar mass of polyoxypropylene subunits of greater than 3,625 g/mol (e.g., an average molar mass of polyoxypropylene subunits of about 3,700 g/mol, 3,800 g/mol, 3,900 g/mol, 4,000 g/mol, 4,100 g/mol, 4,200 g/mol, 4,300 g/mol, 4,400 g/mol, 4,500 g/mol, 4,600 g/mol, 4,700 g/mol, 4,800 g/mol, 4,900 g/mol, or 5,000 g/mol).

In some embodiments, the poloxamer has an average molar mass of polyoxypropylene subunits of from about 2,050 g/mol to about 4,000 g/mol (e.g., about 2,050 g/mol, 2,055 g/mol, 2,060 g/mol, 2,065 g/mol, 2,070 g/mol, 2,075 g/mol, 2,080 g/mol, 2,085 g/mol, 2,090 g/mol, 2,095 g/mol, 2,100 g/mol, 2,105 g/mol, 2,110 g/mol, 2,115 g/mol, 2,120 g/mol, 2,125 g/mol, 2,130 g/mol, 2,135 g/mol, 2,140 g/mol, 2,145 g/mol, 2,150 g/mol, 2,155 g/mol, 2,160 g/mol, 2,165 g/mol, 2,170 g/mol, 2,175 g/mol, 2,180 g/mol, 2,185 g/mol, 2,190 g/mol, 2,195 g/mol, 2,200 g/mol, 2,205 g/mol, 2,210 g/mol, 2,215 g/mol, 2,220 g/mol, 2,225 g/mol, 2,230 g/mol, 2,235 g/mol, 2,240 g/mol, 2,245 g/mol, 2,250 g/mol, 2,255 g/mol, 2,260 g/mol, 2,265 g/mol, 2,270 g/mol, 2,275 g/mol, 2,280 g/mol, 2,285 g/mol, 2,290 g/mol, 2,295 g/mol, 2,300 g/mol, 2,305 g/mol, 2,310 g/mol, 2,315 g/mol, 2,320 g/mol, 2,325 g/mol, 2,330 g/mol, 2,335 g/mol, 2,340 g/mol, 2,345 g/mol, 2,350 g/mol, 2,355 g/mol, 2,360 g/mol, 2,365 g/mol, 2,370 g/mol, 2,375 g/mol, 2,380 g/mol, 2,385 g/mol, 2,390 g/mol, 2,395 g/mol, 2,400 g/mol, 2,405 g/mol, 2,410 g/mol, 2,415 g/mol, 2,420 g/mol, 2,425 g/mol, 2,430 g/mol, 2,435 g/mol, 2,440 g/mol, 2,445 g/mol, 2,450 g/mol, 2,455 g/mol, 2,460 g/mol, 2,465 g/mol, 2,470 g/mol, 2,475 g/mol, 2,480 g/mol, 2,485 g/mol, 2,490 g/mol, 2,495 g/mol, 2,500 g/mol, 2,505 g/mol, 2,510 g/mol, 2,515 g/mol, 2,520 g/mol, 2,525 g/mol, 2,530 g/mol, 2,535 g/mol, 2,540 g/mol, 2,545 g/mol, 2,550 g/mol, 2,555 g/mol, 2,560 g/mol, 2,565 g/mol, 2,570 g/mol, 2,575 g/mol, 2,580 g/mol, 2,585 g/mol, 2,590 g/mol, 2,595 g/mol, 2,600 g/mol, 2,605 g/mol, 2,610 g/mol, 2,615 g/mol, 2,620 g/mol, 2,625 g/mol, 2,630 g/mol, 2,635 g/mol, 2,640 g/mol, 2,645 g/mol, 2,650 g/mol, 2,655 g/mol, 2,660 g/mol, 2,665 g/mol, 2,670 g/mol, 2,675 g/mol, 2,680 g/mol, 2,685 g/mol, 2,690 g/mol, 2,695 g/mol, 2,700 g/mol, 2,705 g/mol, 2,710 g/mol, 2,715 g/mol, 2,720 g/mol, 2,725 g/mol, 2,730 g/mol, 2,735 g/mol, 2,740 g/mol, 2,745 g/mol, 2,750 g/mol, 2,755 g/mol, 2,760 g/mol, 2,765 g/mol, 2,770 g/mol, 2,775 g/mol, 2,780 g/mol, 2,785 g/mol, 2,790 g/mol, 2,795 g/mol, 2,800 g/mol, 2,805 g/mol, 2,810 g/mol, 2,815 g/mol, 2,820 g/mol, 2,825 g/mol, 2,830 g/mol, 2,835 g/mol, 2,840 g/mol, 2,845 g/mol, 2,850 g/mol, 2,855 g/mol, 2,860 g/mol, 2,865 g/mol, 2,870 g/mol, 2,875 g/mol, 2,880 g/mol, 2,885 g/mol, 2,890 g/mol, 2,895 g/mol, 2,900 g/mol, 2,905 g/mol, 2,910 g/mol, 2,915 g/mol, 2,920 g/mol, 2,925 g/mol, 2,930 g/mol, 2,935 g/mol, 2,940 g/mol, 2,945 g/mol, 2,950 g/mol, 2,955 g/mol, 2,960 g/mol, 2,965 g/mol, 2,970 g/mol, 2,975 g/mol, 2,980 g/mol, 2,985 g/mol, 2,990 g/mol, 2,995 g/mol, 3,000 g/mol, 3,005 g/mol, 3,010 g/mol, 3,015 g/mol, 3,020 g/mol, 3,025 g/mol, 3,030 g/mol, 3,035 g/mol, 3,040 g/mol, 3,045 g/mol, 3,050 g/mol, 3,055 g/mol, 3,060 g/mol, 3,065 g/mol, 3,070 g/mol, 3,075 g/mol, 3,080 g/mol, 3,085 g/mol, 3,090 g/mol, 3,095 g/mol, 3,100 g/mol, 3,105 g/mol, 3,110 g/mol, 3,115 g/mol, 3,120 g/mol, 3,125 g/mol, 3,130 g/mol, 3,135 g/mol, 3,140 g/mol, 3,145 g/mol, 3,150 g/mol, 3,155 g/mol, 3,160 g/mol, 3,165 g/mol, 3,170 g/mol, 3,175 g/mol, 3,180 g/mol, 3,185 g/mol, 3,190 g/mol, 3,195 g/mol, 3,200 g/mol, 3,205 g/mol, 3,210 g/mol, 3,215 g/mol, 3,220 g/mol, 3,225 g/mol, 3,230 g/mol, 3,235 g/mol, 3,240 g/mol, 3,245 g/mol, 3,250 g/mol, 3,255 g/mol, 3,260 g/mol, 3,265 g/mol, 3,270 g/mol, 3,275 g/mol, 3,280 g/mol, 3,285 g/mol, 3,290 g/mol, 3,295 g/mol, 3,300 g/mol, 3,305 g/mol, 3,310 g/mol, 3,315 g/mol, 3,320 g/mol, 3,325 g/mol, 3,330 g/mol, 3,335 g/mol, 3,340 g/mol, 3,345 g/mol, 3,350 g/mol, 3,355 g/mol, 3,360 g/mol, 3,365 g/mol, 3,370 g/mol, 3,375 g/mol, 3,380 g/mol, 3,385 g/mol, 3,390 g/mol, 3,395 g/mol, 3,400 g/mol, 3,405 g/mol, 3,410 g/mol, 3,415 g/mol, 3,420 g/mol, 3,425 g/mol, 3,430 g/mol, 3,435 g/mol, 3,440 g/mol, 3,445 g/mol, 3,450 g/mol, 3,455 g/mol, 3,460 g/mol, 3,465 g/mol, 3,470 g/mol, 3,475 g/mol, 3,480 g/mol, 3,485 g/mol, 3,490 g/mol, 3,495 g/mol, 3,500 g/mol, 3,505 g/mol, 3,510 g/mol, 3,515 g/mol, 3,520 g/mol, 3,525 g/mol, 3,530 g/mol, 3,535 g/mol, 3,540 g/mol, 3,545 g/mol, 3,550 g/mol, 3,555 g/mol, 3,560 g/mol, 3,565 g/mol, 3,570 g/mol, 3,575 g/mol, 3,580 g/mol, 3,585 g/mol, 3,590 g/mol, 3,595 g/mol, 3,600 g/mol, 3,605 g/mol, 3,610 g/mol, 3,615 g/mol, 3,620 g/mol, 3,625 g/mol, 3,630 g/mol, 3,635 g/mol, 3,640 g/mol, 3,645 g/mol, 3,650 g/mol, 3,655 g/mol, 3,660 g/mol, 3,665 g/mol, 3,670 g/mol, 3,675 g/mol, 3,680 g/mol, 3,685 g/mol, 3,690 g/mol, 3,695 g/mol, 3,700 g/mol, 3,705 g/mol, 3,710 g/mol, 3,715 g/mol, 3,720 g/mol, 3,725 g/mol, 3,730 g/mol, 3,735 g/mol, 3,740 g/mol, 3,745 g/mol, 3,750 g/mol, 3,755 g/mol, 3,760 g/mol, 3,765 g/mol, 3,770 g/mol, 3,775 g/mol, 3,780 g/mol, 3,785 g/mol, 3,790 g/mol, 3,795 g/mol, 3,800 g/mol, 3,805 g/mol, 3,810 g/mol, 3,815 g/mol, 3,820 g/mol, 3,825 g/mol, 3,830 g/mol, 3,835 g/mol, 3,840 g/mol, 3,845 g/mol, 3,850 g/mol, 3,855 g/mol, 3,860 g/mol, 3,865 g/mol, 3,870 g/mol, 3,875 g/mol, 3,880 g/mol, 3,885 g/mol, 3,890 g/mol, 3,895 g/mol, 3,900 g/mol, 3,905 g/mol, 3,910 g/mol, 3,915 g/mol, 3,920 g/mol, 3,925 g/mol, 3,930 g/mol, 3,935 g/mol, 3,940 g/mol, 3,945 g/mol, 3,950 g/mol, 3,955 g/mol, 3,960 g/mol, 3,965 g/mol, 3,970 g/mol, 3,975 g/mol, 3,980 g/mol, 3,985 g/mol, 3,990 g/mol, 3,995 g/mol, or 4,000 g/mol).

In some embodiments, the poloxamer has an average molar mass of polyoxypropylene subunits of from about 2,750 g/mol to about 4,000 g/mol (e.g., about 2,750 g/mol, 2,755 g/mol, 2,760 g/mol, 2,765 g/mol, 2,770 g/mol, 2,775 g/mol, 2,780 g/mol, 2,785 g/mol, 2,790 g/mol, 2,795 g/mol, 2,800 g/mol, 2,805 g/mol, 2,810 g/mol, 2,815 g/mol, 2,820 g/mol, 2,825 g/mol, 2,830 g/mol, 2,835 g/mol, 2,840 g/mol, 2,845 g/mol, 2,850 g/mol, 2,855 g/mol, 2,860 g/mol, 2,865 g/mol, 2,870 g/mol, 2,875 g/mol, 2,880 g/mol, 2,885 g/mol, 2,890 g/mol, 2,895 g/mol, 2,900 g/mol, 2,905 g/mol, 2,910 g/mol, 2,915 g/mol, 2,920 g/mol, 2,925 g/mol, 2,930 g/mol, 2,935 g/mol, 2,940 g/mol, 2,945 g/mol, 2,950 g/mol, 2,955 g/mol, 2,960 g/mol, 2,965 g/mol, 2,970 g/mol, 2,975 g/mol, 2,980 g/mol, 2,985 g/mol, 2,990 g/mol, 2,995 g/mol, 3,000 g/mol, 3,005 g/mol, 3,010 g/mol, 3,015 g/mol, 3,020 g/mol, 3,025 g/mol, 3,030 g/mol, 3,035 g/mol, 3,040 g/mol, 3,045 g/mol, 3,050 g/mol, 3,055 g/mol, 3,060 g/mol, 3,065 g/mol, 3,070 g/mol, 3,075 g/mol, 3,080 g/mol, 3,085 g/mol, 3,090 g/mol, 3,095 g/mol, 3,100 g/mol, 3,105 g/mol, 3,110 g/mol, 3,115 g/mol, 3,120 g/mol, 3,125 g/mol, 3,130 g/mol, 3,135 g/mol, 3,140 g/mol, 3,145 g/mol, 3,150 g/mol, 3,155 g/mol, 3,160 g/mol, 3,165 g/mol, 3,170 g/mol, 3,175 g/mol, 3,180 g/mol, 3,185 g/mol, 3,190 g/mol, 3,195 g/mol, 3,200 g/mol, 3,205 g/mol, 3,210 g/mol, 3,215 g/mol, 3,220 g/mol, 3,225 g/mol, 3,230 g/mol, 3,235 g/mol, 3,240 g/mol, 3,245 g/mol, 3,250 g/mol, 3,255 g/mol, 3,260 g/mol, 3,265 g/mol, 3,270 g/mol, 3,275 g/mol, 3,280 g/mol, 3,285 g/mol, 3,290 g/mol, 3,295 g/mol, 3,300 g/mol, 3,305 g/mol, 3,310 g/mol, 3,315 g/mol, 3,320 g/mol, 3,325 g/mol, 3,330 g/mol, 3,335 g/mol, 3,340 g/mol, 3,345 g/mol, 3,350 g/mol, 3,355 g/mol, 3,360 g/mol, 3,365 g/mol, 3,370 g/mol, 3,375 g/mol, 3,380 g/mol, 3,385 g/mol, 3,390 g/mol, 3,395 g/mol, 3,400 g/mol, 3,405 g/mol, 3,410 g/mol, 3,415 g/mol, 3,420 g/mol, 3,425 g/mol, 3,430 g/mol, 3,435 g/mol, 3,440 g/mol, 3,445 g/mol, 3,450 g/mol, 3,455 g/mol, 3,460 g/mol, 3,465 g/mol, 3,470 g/mol, 3,475 g/mol, 3,480 g/mol, 3,485 g/mol, 3,490 g/mol, 3,495 g/mol, 3,500 g/mol, 3,505 g/mol, 3,510 g/mol, 3,515 g/mol, 3,520 g/mol, 3,525 g/mol, 3,530 g/mol, 3,535 g/mol, 3,540 g/mol, 3,545 g/mol, 3,550 g/mol, 3,555 g/mol, 3,560 g/mol, 3,565 g/mol, 3,570 g/mol, 3,575 g/mol, 3,580 g/mol, 3,585 g/mol, 3,590 g/mol, 3,595 g/mol, 3,600 g/mol, 3,605 g/mol, 3,610 g/mol, 3,615 g/mol, 3,620 g/mol, 3,625 g/mol, 3,630 g/mol, 3,635 g/mol, 3,640 g/mol, 3,645 g/mol, 3,650 g/mol, 3,655 g/mol, 3,660 g/mol, 3,665 g/mol, 3,670 g/mol, 3,675 g/mol, 3,680 g/mol, 3,685 g/mol, 3,690 g/mol, 3,695 g/mol, 3,700 g/mol, 3,705 g/mol, 3,710 g/mol, 3,715 g/mol, 3,720 g/mol, 3,725 g/mol, 3,730 g/mol, 3,735 g/mol, 3,740 g/mol, 3,745 g/mol, 3,750 g/mol, 3,755 g/mol, 3,760 g/mol, 3,765 g/mol, 3,770 g/mol, 3,775 g/mol, 3,780 g/mol, 3,785 g/mol, 3,790 g/mol, 3,795 g/mol, 3,800 g/mol, 3,805 g/mol, 3,810 g/mol, 3,815 g/mol, 3,820 g/mol, 3,825 g/mol, 3,830 g/mol, 3,835 g/mol, 3,840 g/mol, 3,845 g/mol, 3,850 g/mol, 3,855 g/mol, 3,860 g/mol, 3,865 g/mol, 3,870 g/mol, 3,875 g/mol, 3,880 g/mol, 3,885 g/mol, 3,890 g/mol, 3,895 g/mol, 3,900 g/mol, 3,905 g/mol, 3,910 g/mol, 3,915 g/mol, 3,920 g/mol, 3,925 g/mol, 3,930 g/mol, 3,935 g/mol, 3,940 g/mol, 3,945 g/mol, 3,950 g/mol, 3,955 g/mol, 3,960 g/mol, 3,965 g/mol, 3,970 g/mol, 3,975 g/mol, 3,980 g/mol, 3,985 g/mol, 3,990 g/mol, 3,995 g/mol, or 4,000 g/mol).

In some embodiments, the poloxamer has an average molar mass of polyoxypropylene subunits of from about 3,250 g/mol to about 4,000 g/mol (e.g., about 3,250 g/mol, 3,255 g/mol, 3,260 g/mol, 3,265 g/mol, 3,270 g/mol, 3,275 g/mol, 3,280 g/mol, 3,285 g/mol, 3,290 g/mol, 3,295 g/mol, 3,300 g/mol, 3,305 g/mol, 3,310 g/mol, 3,315 g/mol, 3,320 g/mol, 3,325 g/mol, 3,330 g/mol, 3,335 g/mol, 3,340 g/mol, 3,345 g/mol, 3,350 g/mol, 3,355 g/mol, 3,360 g/mol, 3,365 g/mol, 3,370 g/mol, 3,375 g/mol, 3,380 g/mol, 3,385 g/mol, 3,390 g/mol, 3,395 g/mol, 3,400 g/mol, 3,405 g/mol, 3,410 g/mol, 3,415 g/mol, 3,420 g/mol, 3,425 g/mol, 3,430 g/mol, 3,435 g/mol, 3,440 g/mol, 3,445 g/mol, 3,450 g/mol, 3,455 g/mol, 3,460 g/mol, 3,465 g/mol, 3,470 g/mol, 3,475 g/mol, 3,480 g/mol, 3,485 g/mol, 3,490 g/mol, 3,495 g/mol, 3,500 g/mol, 3,505 g/mol, 3,510 g/mol, 3,515 g/mol, 3,520 g/mol, 3,525 g/mol, 3,530 g/mol, 3,535 g/mol, 3,540 g/mol, 3,545 g/mol, 3,550 g/mol, 3,555 g/mol, 3,560 g/mol, 3,565 g/mol, 3,570 g/mol, 3,575 g/mol, 3,580 g/mol, 3,585 g/mol, 3,590 g/mol, 3,595 g/mol, 3,600 g/mol, 3,605 g/mol, 3,610 g/mol, 3,615 g/mol, 3,620 g/mol, 3,625 g/mol, 3,630 g/mol, 3,635 g/mol, 3,640 g/mol, 3,645 g/mol, 3,650 g/mol, 3,655 g/mol, 3,660 g/mol, 3,665 g/mol, 3,670 g/mol, 3,675 g/mol, 3,680 g/mol, 3,685 g/mol, 3,690 g/mol, 3,695 g/mol, 3,700 g/mol, 3,705 g/mol, 3,710 g/mol, 3,715 g/mol, 3,720 g/mol, 3,725 g/mol, 3,730 g/mol, 3,735 g/mol, 3,740 g/mol, 3,745 g/mol, 3,750 g/mol, 3,755 g/mol, 3,760 g/mol, 3,765 g/mol, 3,770 g/mol, 3,775 g/mol, 3,780 g/mol, 3,785 g/mol, 3,790 g/mol, 3,795 g/mol, 3,800 g/mol, 3,805 g/mol, 3,810 g/mol, 3,815 g/mol, 3,820 g/mol, 3,825 g/mol, 3,830 g/mol, 3,835 g/mol, 3,840 g/mol, 3,845 g/mol, 3,850 g/mol, 3,855 g/mol, 3,860 g/mol, 3,865 g/mol, 3,870 g/mol, 3,875 g/mol, 3,880 g/mol, 3,885 g/mol, 3,890 g/mol, 3,895 g/mol, 3,900 g/mol, 3,905 g/mol, 3,910 g/mol, 3,915 g/mol, 3,920 g/mol, 3,925 g/mol, 3,930 g/mol, 3,935 g/mol, 3,940 g/mol, 3,945 g/mol, 3,950 g/mol, 3,955 g/mol, 3,960 g/mol, 3,965 g/mol, 3,970 g/mol, 3,975 g/mol, 3,980 g/mol, 3,985 g/mol, 3,990 g/mol, 3,995 g/mol, or 4,000 g/mol).

In some embodiments, the poloxamer has an average molar mass of polyoxypropylene subunits of from about 3,625 g/mol to about 4,000 g/mol (e.g., about 3,625 g/mol, 3,630 g/mol, 3,635 g/mol, 3,640 g/mol, 3,645 g/mol, 3,650 g/mol, 3,655 g/mol, 3,660 g/mol, 3,665 g/mol, 3,670 g/mol, 3,675 g/mol, 3,680 g/mol, 3,685 g/mol, 3,690 g/mol, 3,695 g/mol, 3,700 g/mol, 3,705 g/mol, 3,710 g/mol, 3,715 g/mol, 3,720 g/mol, 3,725 g/mol, 3,730 g/mol, 3,735 g/mol, 3,740 g/mol, 3,745 g/mol, 3,750 g/mol, 3,755 g/mol, 3,760 g/mol, 3,765 g/mol, 3,770 g/mol, 3,775 g/mol, 3,780 g/mol, 3,785 g/mol, 3,790 g/mol, 3,795 g/mol, 3,800 g/mol, 3,805 g/mol, 3,810 g/mol, 3,815 g/mol, 3,820 g/mol, 3,825 g/mol, 3,830 g/mol, 3,835 g/mol, 3,840 g/mol, 3,845 g/mol, 3,850 g/mol, 3,855 g/mol, 3,860 g/mol, 3,865 g/mol, 3,870 g/mol, 3,875 g/mol, 3,880 g/mol, 3,885 g/mol, 3,890 g/mol, 3,895 g/mol, 3,900 g/mol, 3,905 g/mol, 3,910 g/mol, 3,915 g/mol, 3,920 g/mol, 3,925 g/mol, 3,930 g/mol, 3,935 g/mol, 3,940 g/mol, 3,945 g/mol, 3,950 g/mol, 3,955 g/mol, 3,960 g/mol, 3,965 g/mol, 3,970 g/mol, 3,975 g/mol, 3,980 g/mol, 3,985 g/mol, 3,990 g/mol, 3,995 g/mol, or 4,000 g/mol).

In some embodiments, the poloxamer has an average ethylene oxide content of greater than 40% by mass (e.g., about 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, or more).

In some embodiments, the poloxamer has an average ethylene oxide content of greater than 50% by mass (e.g., about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, or more).

In some embodiments, the poloxamer has an average ethylene oxide content of greater than 60% by mass (e.g., about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, or more).

In some embodiments, the poloxamer has an average ethylene oxide content of greater than 70% by mass (e.g., about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, or more).

In some embodiments, the poloxamer has an average ethylene oxide content of from about 40% to about 90% (e.g., about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90%).

In some embodiments, the poloxamer has an average ethylene oxide content of from about 50% to about 85% (e.g., about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, or 85%).

In some embodiments, the poloxamer has an average ethylene oxide content of from about 60% to about 80% (e.g., about 60%, 61%, 62%, 63%, 64%, 65%, 66%, 67%, 68%, 69%, 70%, 71%, 72%, 73%, 74%, 75%, 76%, 77%, 78%, 79%, 80%).

In some embodiments, the poloxamer has an average molar mass of greater than 10,000 g/mol (e.g., about 10,100 g/mol, 10,200 g/mol, 10,300 g/mol, 10,400 g/mol, 10,500 g/mol, 10,600 g/mol, 10,700 g/mol, 10,800 g/mol, 10,900 g/mol, 11,000 g/mol, 11,100 g/mol, 11,200 g/mol, 11,300 g/mol, 11,400 g/mol, 11,500 g/mol, 11,600 g/mol, 11,700 g/mol, 11,800 g/mol, 11,900 g/mol, 12,000 g/mol, 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of greater than 11,000 g/mol (e.g., about 11,100 g/mol, 11,200 g/mol, 11,300 g/mol, 11,400 g/mol, 11,500 g/mol, 11,600 g/mol, 11,700 g/mol, 11,800 g/mol, 11,900 g/mol, 12,000 g/mol, 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of greater than 12,000 g/mol (e.g., about 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of greater than 12,500 g/mol (e.g., about 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of from about 10,000 g/mol to about 15,000 g/mol (e.g., about 10,000 g/mol, 10,100 g/mol, 10,200 g/mol, 10,300 g/mol, 10,400 g/mol, 10,500 g/mol, 10,600 g/mol, 10,700 g/mol, 10,800 g/mol, 10,900 g/mol, 11,000 g/mol, 11,100 g/mol, 11,200 g/mol, 11,300 g/mol, 11,400 g/mol, 11,500 g/mol, 11,600 g/mol, 11,700 g/mol, 11,800 g/mol, 11,900 g/mol, 12,000 g/mol, 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of from about 11,000 g/mol to about 15,000 g/mol (e.g., about 11,000 g/mol, 11,100 g/mol, 11,200 g/mol, 11,300 g/mol, 11,400 g/mol, 11,500 g/mol, 11,600 g/mol, 11,700 g/mol, 11,800 g/mol, 11,900 g/mol, 12,000 g/mol, 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of from about 11,500 g/mol to about 15,000 g/mol (e.g., about 11,500 g/mol, 11,600 g/mol, 11,700 g/mol, 11,800 g/mol, 11,900 g/mol, 12,000 g/mol, 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of from about 12,000 g/mol to about 15,000 g/mol (e.g., about 12,000 g/mol, 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of from about 12,500 g/mol to about 15,000 g/mol (e.g., about 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

Poloxamers P288, P335, P338, and P407

Poloxamers that may be used in conjunction with the compositions and methods of the disclosure include "poloxamer 288" (also referred to in the art as "P 288" and poloxamer "F98") having the approximate chemical formula $HO(C_2H_4O)_x(C_3H_6O)_y(C_2H_4O)_zH$, wherein the sum of x and y is about 236.36, and z is about 44.83. The average molecular weight of P288 is about 13,000 g/mol.

In some embodiments, the poloxamer is a variant of P288, such as a variant of the formula $HO(C_2H_4O)_x(C_3H_6O)_y(C_2H_4O)_zH$, wherein the sum of x and y is from about 220 to about 250, and z is from about 40 to about 50. In some embodiments, the average molecular weight of the poloxamer is from about 12,000 g/mol to about 14,000 g/mol.

Poloxamers that may be used in conjunction with the compositions and methods of the disclosure further include "poloxamer 335" (also referred to in the art as "P 335" and poloxamer "P105"), having the approximate chemical formula $HO(C_2H_4O)_x(C_3H_6O)_y(C_2H_4O)_zH$, wherein the sum of x and y is about 73.86, and z is about 56.03. The average molecular weight of P335 is about 6,500 g/mol.

In some embodiments, the poloxamer is a variant of P335, such as a variant of the formula $HO(C_2H_4O)_x(C_3H_6O)_y(C_2H_4O)_zH$, wherein the sum of x and y is from about 60 to about 80, and z is from about 50 to about 60. In some embodiments, the average molecular weight of the poloxamer is from about 6,000 g/mol to about 7,000 g/mol.

Poloxamers that may be used in conjunction with the compositions and methods of the disclosure further include "poloxamer 338" (also referred to in the art as "P 338" and poloxamer "F108"), having the approximate chemical formula $HO(C_2H_4O)_x(C_3H_6O)_y(C_2H_4O)_zH$, wherein the sum of x and y is about 265.45, and z is about 50.34. The average molecular weight of P335 is about 14,600 g/mol.

In some embodiments, the poloxamer is a variant of P338, such as a variant of the formula $HO(C_2H_4O)_x(C_3H_6O)_y(C_2H_4O)_zH$, wherein the sum of x and y is from about 260 to about 270, and z is from about 45 to about 55. In some embodiments, the average molecular weight of the poloxamer is from about 14,000 g/mol to about 15,000 g/mol.

Poloxamers that may be used in conjunction with the compositions and methods of the disclosure further include "poloxamer 407" (also referred to in the art as "P 407" and poloxamer "F127"), having the approximate chemical formula $HO(C_2H_4O)_x(C_3H_6O)_y(C_2H_4O)_zH$, wherein the sum of x and y is about 200.45, and z is about 65.17. The average molecular weight of P335 is about 12,600 g/mol.

In some embodiments, the poloxamer is a variant of P407, such as a variant of the formula $HO(C_2H_4O)_x(C_3H_6O)_y(C_2H_4O)_zH$, wherein the sum of x and y is from about 190 to about 210, and z is from about 60 to about 70. In some embodiments, the average molecular weight of the poloxamer is from about 12,000 g/mol to about 13,000 g/mol.

For clarity, the terms "average molar mass" and "average molecular weight" are used interchangeable herein to refer to the same quantity. The average molar mass, ethylene oxide content, and propylene oxide content of a poloxamer, as described herein, can be determined using methods disclosed in Alexandridis and Hatton, Colloids and Surfaces A: Physicochemical and Engineering Aspects 96:1-46 (1995), the disclosure of which is incorporated herein by reference in its entirety.

PKC Modulating Agents

A variety of agents can be used to reduce PKC activity and/or expression. Without being limited by mechanism, such agents can augment viral transduction by stimulating Akt signal transduction and/or maintaining cofilin in a dephosphorylated state, thereby promoting actin depolymerization. This actin depolymerization event may serve to remove a physical barrier that hinders entry of a viral vector into the nucleus of a target cell.

Staurosporine and Variants Thereof

In some embodiments, the substance that reduces activity and/or expression of PKC is a PKC inhibitor. The PKC inhibitor may be staurosporine or a variant thereof. For example, the PKC inhibitor may be a compound represented by formula (I)

(I)

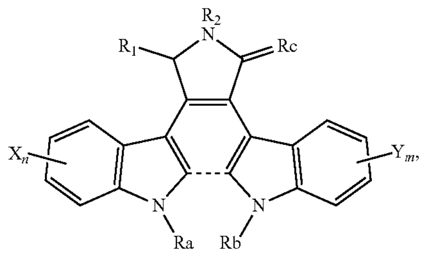

wherein $R_1$ is H, OH, optionally substituted alkoxy, optionally substituted acyloxy, optionally substituted amino, optionally substituted alkylamino, optionally substituted amido, halogen, optionally substituted $C_{1-6}$ alkyl, optionally substituted $C_{2-6}$ alkenyl, optionally substituted $C_{2-6}$ alkynyl, optionally substituted acyl, optionally substituted alkoxycarbonyl, oxo, thiocarbonyl, optionally substituted carboxy, or ureido;

$R_2$ is H, optionally substituted $C_{1-6}$ alkyl, optionally substituted $C_{2-6}$ alkenyl, optionally substituted $C_{2-6}$ alkynyl, or optionally substituted acyl;

$R_a$ and $R_b$ are each, independently, H, optionally substituted $C_{1-6}$ alkyl, optionally substituted $C_{2-6}$ alkenyl, or optionally substituted $C_{2-6}$ alkynyl, optionally substituted and optionally fused aryl, optionally substituted and optionally fused heteroaryl, optionally substituted and optionally fused cycloalkyl, or optionally substituted and optionally fused heterocycloalkyl, or $R_a$ and $R_b$, together with the atoms to which they are bound, are joined to form an optionally substituted and optionally fused heterocycloalkyl ring;

$R_c$ is O, $NR_d$, or S;

$R_d$ is H, optionally substituted $C_{1-6}$ alkyl, optionally substituted $C_{2-6}$ alkenyl, or optionally substituted $C_{2-6}$ alkynyl;

each X is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

each Y is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

--- represents a bond that is optionally present;

n is an integer from 0-4; and m is an integer from 0-4;

or a salt thereof.

In some embodiments, the PKC inhibitor is a staurosporine variant described in WO 1991/009034, the disclosure of which is incorporated herein by reference in its entirety. Examples of such staurosporine variants are represented by formula (II)

(II)

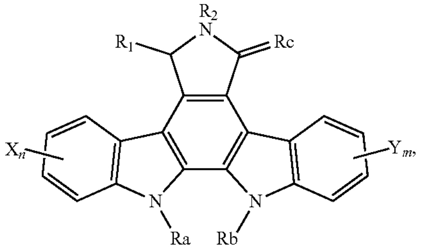

wherein $R_1$ is H, OH, optionally substituted alkoxy, optionally substituted acyloxy, optionally substituted amino, optionally substituted alkylamino, optionally substituted amido, halogen, oxo, or thiocarbonyl;

$R_2$ is H, optionally substituted $C_{1-6}$ alkyl, optionally substituted $C_{2-6}$ alkenyl, optionally substituted $C_{2-6}$ alkynyl, or optionally substituted acyl;

$R_a$ and $R_b$, together with the atoms to which they are bound, are joined to form an optionally substituted and optionally fused heterocycloalkyl ring;

$R_c$ is O or S;

each X is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

each Y is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

n is an integer from 0-4; and m is an integer from 0-4;

or a salt thereof.

Additional examples of such staurosporine variants are represented by formula (III)

(III)

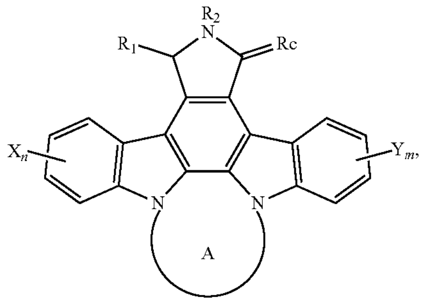

wherein $R_1$ is H, OH, oxo, or thiocarbonyl;

$R_2$ is H, optionally substituted $C_{1-6}$ alkyl, optionally substituted $C_{2-6}$ alkenyl, optionally substituted $C_{2-6}$ alkynyl, or optionally substituted acyl;

Ring A is an optionally substituted and optionally fused heterocycloalkyl ring;

$R_c$ is O or S;

each X is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

each Y is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

n is an integer from 0-4; and m is an integer from 0-4;

or a salt thereof.

Further examples of such staurosporine variants are represented by formula (IV)

(IV)

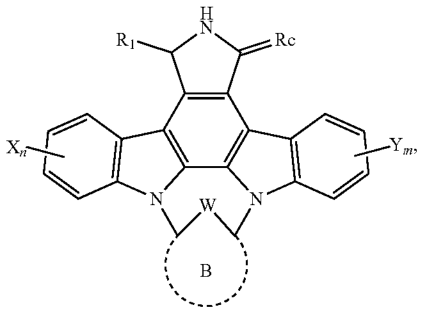

wherein $R_1$ is H, OH, or oxo;

Ring B is an optionally substituted heteroaryl or heterocycloalkyl ring;

$R_c$ is O or S;

W is O, NH, or S;

each X is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

each Y is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

n is an integer from 0-4; and m is an integer from 0-4;

or a salt thereof.

Additional examples of such staurosporine variants are represented by formula (V)

(V)

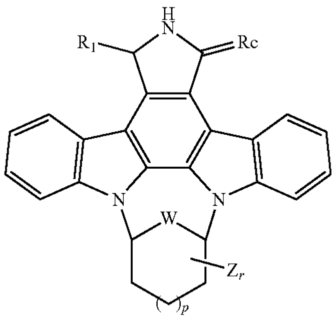

wherein $R_1$ is H, OH, or oxo;

$R_c$ is O or S;

W is O, NH, or S;

each Z is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl; and p is 0 or 1;

or a salt thereof.

Additional examples of such staurosporine variants are represented by formula (VI)

(VI)

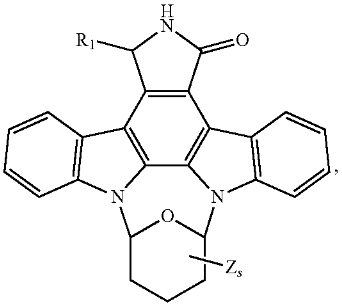

wherein $R_1$ is H, OH, or oxo;

each Z is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl; and s is an integer from 0-8;

or a salt thereof.

Further examples of such staurosporine variants are represented by formula (VII)

(VII)

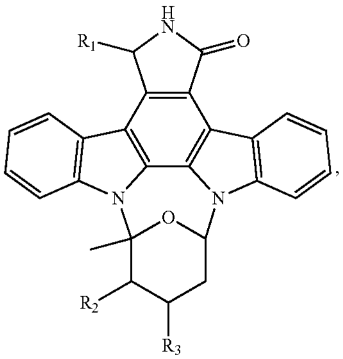

wherein $R_1$ is H, OH, or oxo;

$R_2$ is H, OH, optionally substituted alkoxy, or optionally substituted acyloxy; and $R_3$ is H, OH, optionally substituted alkoxy, optionally substituted acyloxy, optionally substituted amino, or optionally substituted amido or a salt thereof.

Additional examples of such staurosporine variants are represented by formula (VIII)

(VIII)

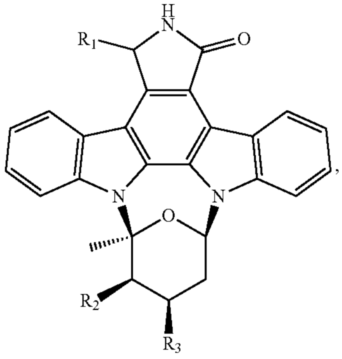, wherein $R_1$ is H, OH, or oxo;

$R_2$ is H, OH, optionally substituted alkoxy, or optionally substituted acyloxy; and $R_3$ is H, OH, optionally substituted alkoxy, optionally substituted acyloxy, optionally substituted amino, or optionally substituted amido or a salt thereof.

Further examples of such staurosporine variants are represented by formula (IX)

(IX)

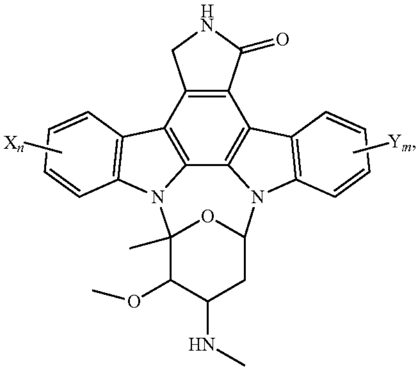

wherein each X is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

each Y is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

n is an integer from 0-4; and m is an integer from 0-4;

or a salt thereof.

Additional examples of such staurosporine variants are represented by formula (1)

(1)

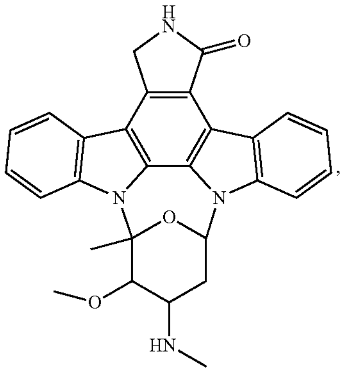, or a salt thereof.

In some embodiments, the PKC inhibitor is staurosporine, (2S,3R,4R,6R)-3-methoxy-2-methyl-4-(methylamino)-29-oxa-1,7,17-triazaoctacyclo[12.12.2.12,6.07,28.08,13.015,19.020,27.021,26]nonacosa-8,10,12,14,19,21,23,25,27-nonaen-16-one, represented by formula (2)

(2)

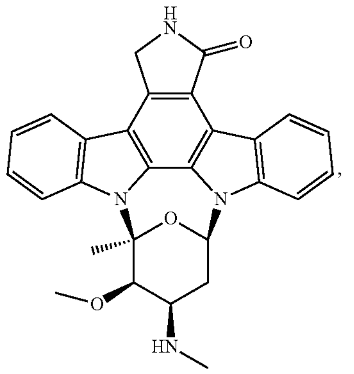

or a salt thereof.

Further examples of such staurosporine variants are represented by formula (X)

(X)

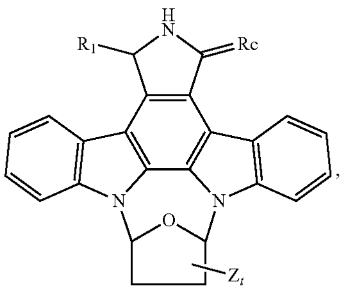

wherein $R_1$ is H, OH, or oxo;

each Z is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl; and t is an integer from 0-6;

or a salt thereof.

Additional examples of such staurosporine variants are represented by formula (XI)

(XI)

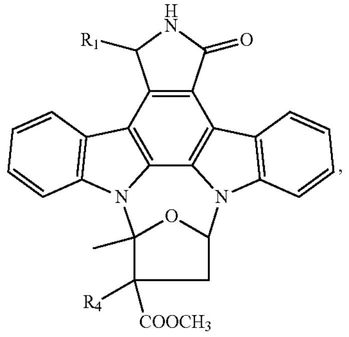

wherein $R_1$ is H, OH, or oxo; and $R_4$ is H, OH, optionally substituted alkoxy, or optionally substituted acyloxy;

or a salt thereof.

Further examples of such staurosporine variants are represented by formula (XII)

(XII)

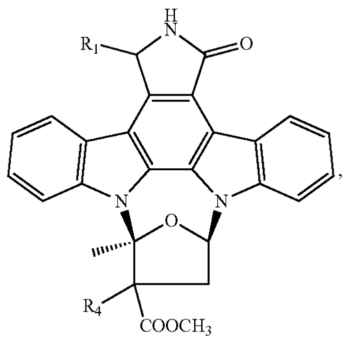

wherein $R_1$ is H, OH, or oxo; and $R_4$ is H, OH, optionally substituted alkoxy, or optionally substituted acyloxy;

or a salt thereof.

Additional examples of such staurosporine variants are represented by formula (XIII)

(XIII)

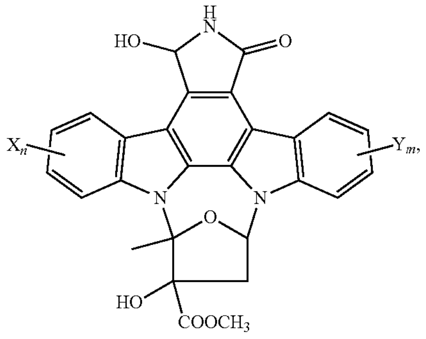

wherein each X is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

each Y is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

n is an integer from 0-4; and m is an integer from 0-4;

or a salt thereof.

Additional examples of such staurosporine variants are represented by formula (3)

(3)

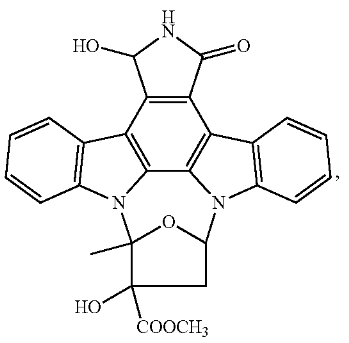

or a salt thereof.

Additional examples of such staurosporine variants are represented by formula (4)

(4)

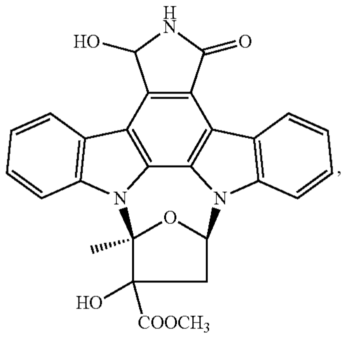

or a salt thereof.

Additional examples of such staurosporine variants are:

(5)

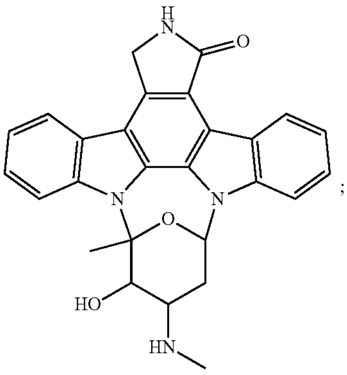

(6)

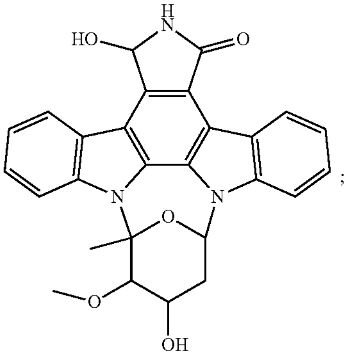

(7)

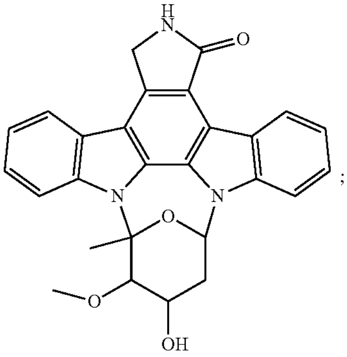

-continued
(8)
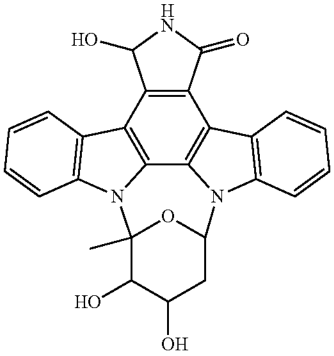
;
(9)
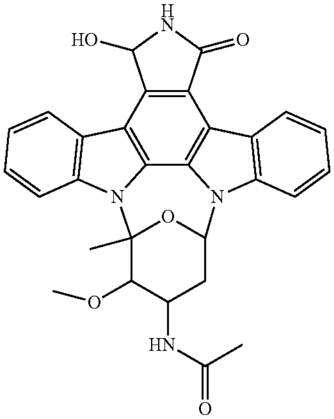
;
(10)
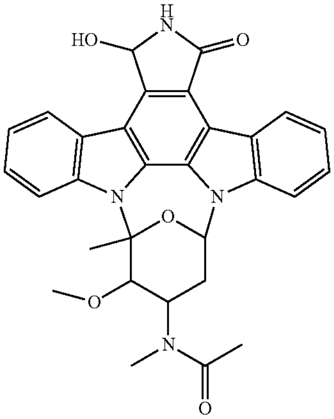
;
(11)
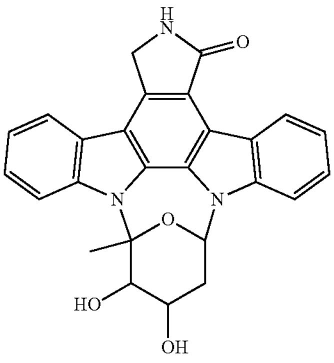
;
-continued
(12)
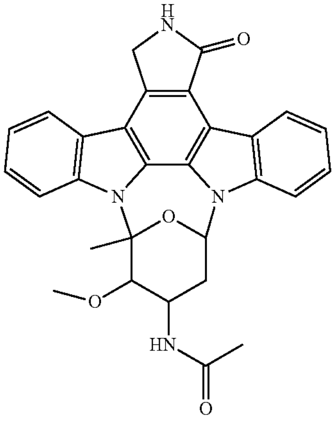
;
(13)
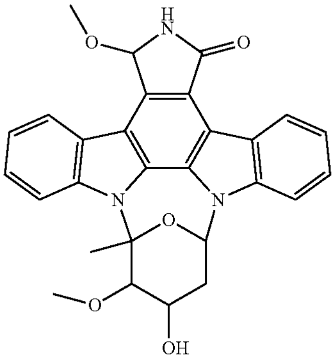
;
(14)
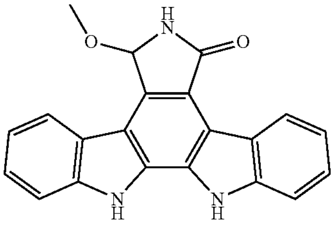
; and
(15)
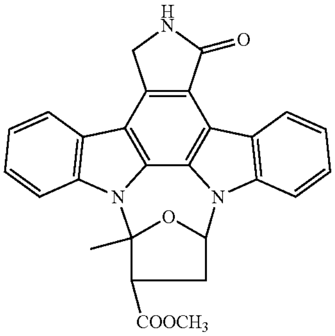
;
or a salt thereof.
In some embodiments, the PKC inhibitor is a staurosporine variant described in WO 1993/007153, the disclosure of which is incorporated herein by reference in its entirety. Examples of such staurosporine variants are represented by formula (XIV)

(XIV)

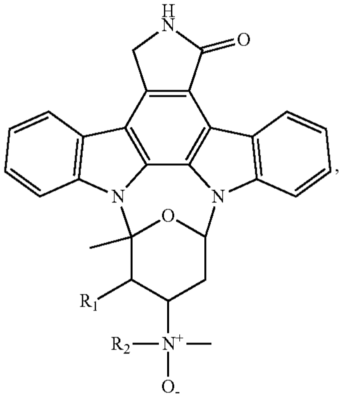, wherein $R_1$ is H or optionally substituted $C_{1-6}$ alkyl; and $R_2$ is optionally substituted $C_{1-6}$ alkyl;

or a salt thereof.

In some embodiments, the PKC inhibitor is a compound represented by formula (XV)

(XV)

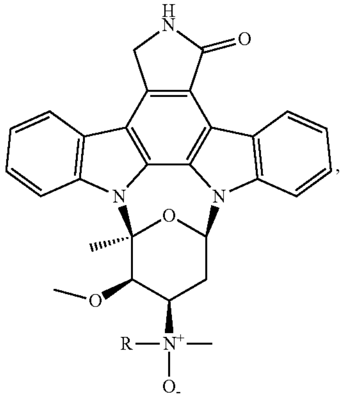, wherein $R_1$ is H or optionally substituted $C_{1-6}$ alkyl; and $R_2$ is optionally substituted $C_{1-6}$ alkyl;

or a salt thereof.

In some embodiments, the PKC inhibitor is a compound selected from:

(16)

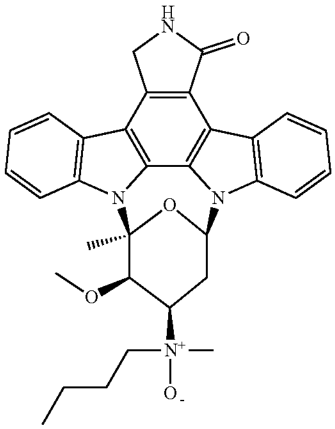

and

-continued (17)

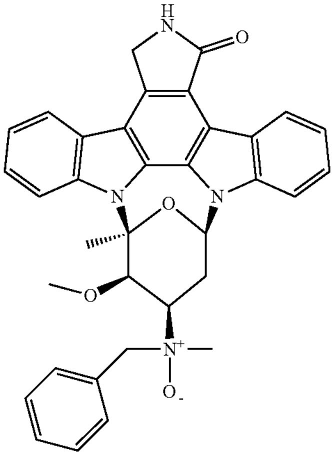, or a salt thereof.

In some embodiments, the PKC inhibitor is a staurosporine variant described in U.S. Pat. No. 5,093,330, the disclosure of which is incorporated herein by reference in its entirety. Examples of such staurosporine variants are represented by formula (XVI)

(XVI)

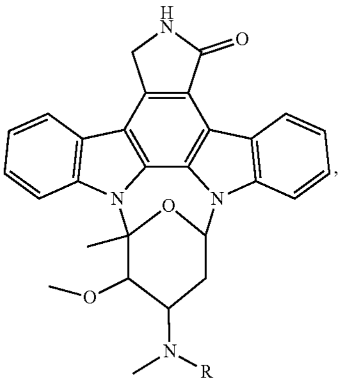, wherein R is H, optionally substituted alkyl, optionally substituted acyl, optionally substituted sulfonyl, optionally substituted sulfinyl, optionally substituted aryl, optionally substituted heteroaryl, optionally substituted cycloalkyl, and optionally substituted heterocycloalkyl;

or a salt or quaternized variant thereof.

In some embodiments, the PKC inhibitor is a compound represented by formula (XVII)

(XVII)

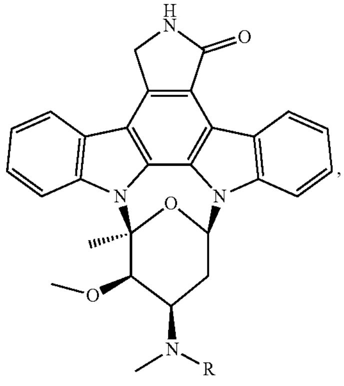

, wherein R is H, optionally substituted alkyl, optionally substituted acyl, optionally substituted sulfonyl, optionally substituted sulfinyl, optionally substituted aryl, optionally substituted heteroaryl, optionally substituted cycloalkyl, and optionally substituted heterocycloalkyl;

or a salt or quaternized variant thereof.

In some embodiments the PKC inhibitor is a compound selected from:

(18)

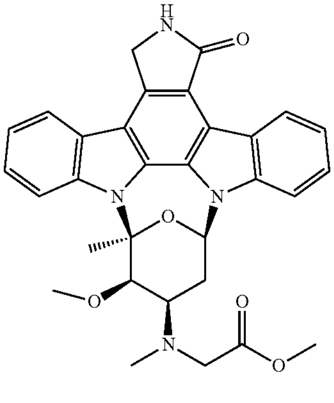

;

(19)

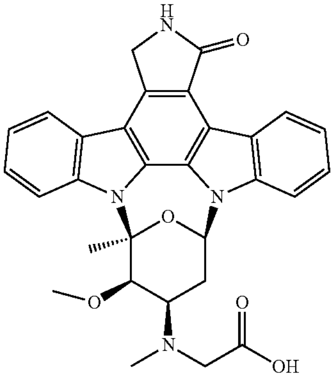

;

-continued (20)

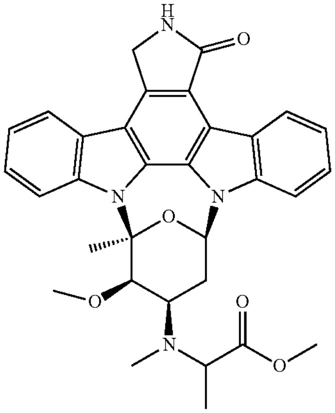

;

(21)

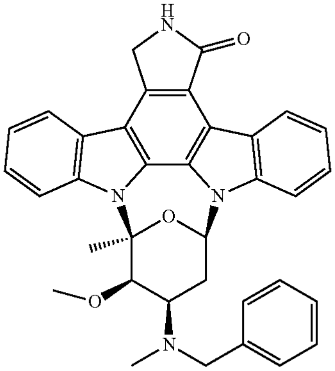

;

(22)

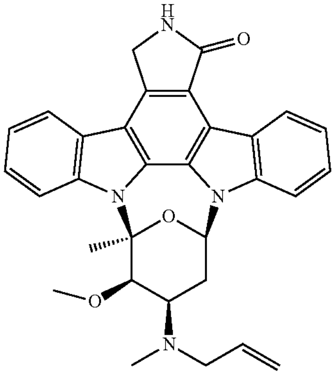

;

(23)

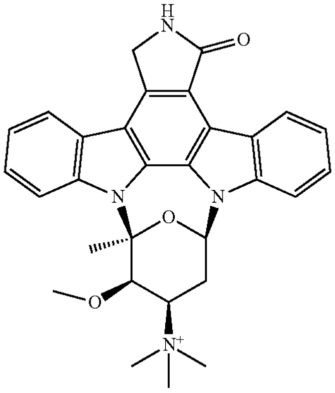

;

(24)
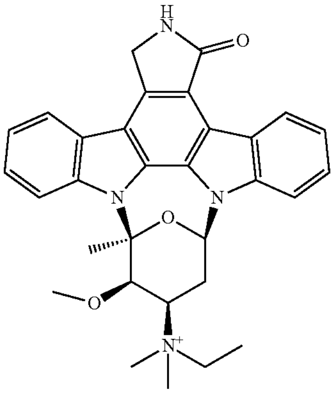
;
(25)
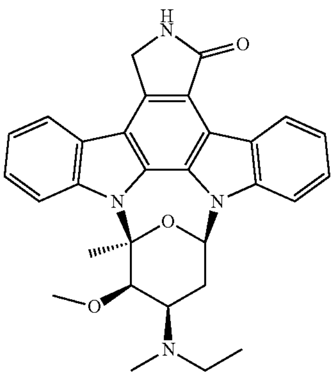
;
(26)
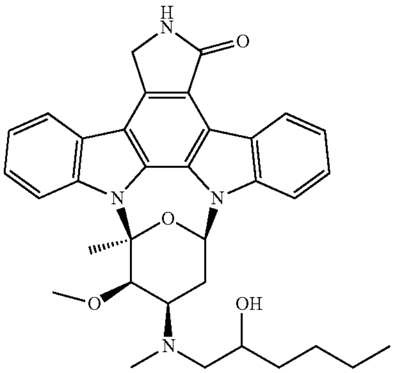
;
(27)
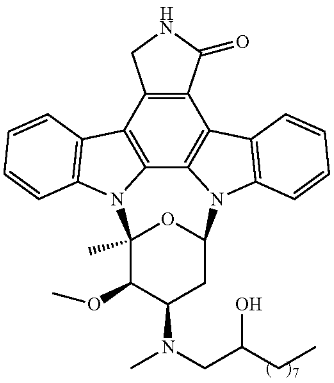
;
(28)
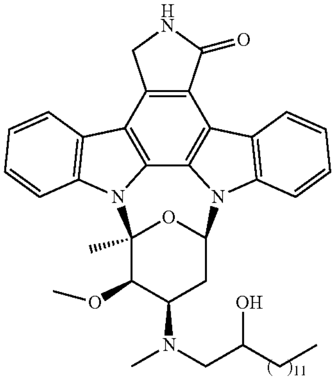
;
(29)
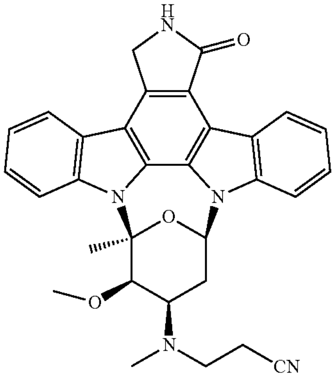
;
(30)
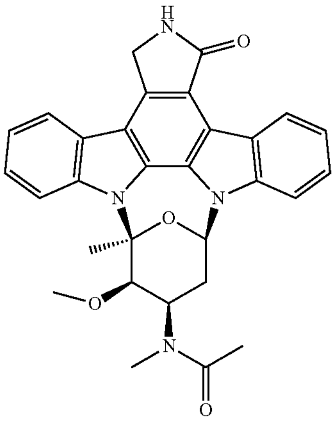
;
(31)
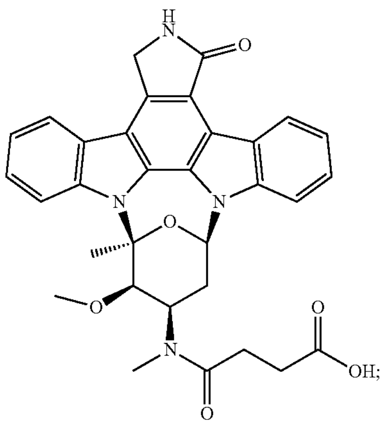

-continued
(32)
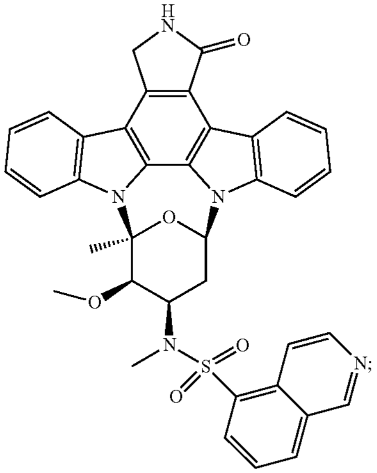
(33)
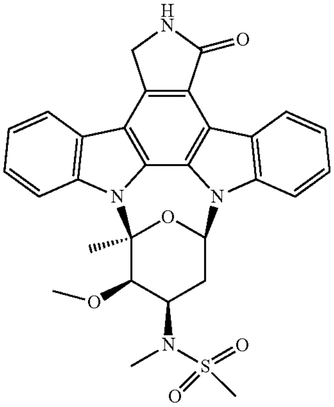
;
(34)
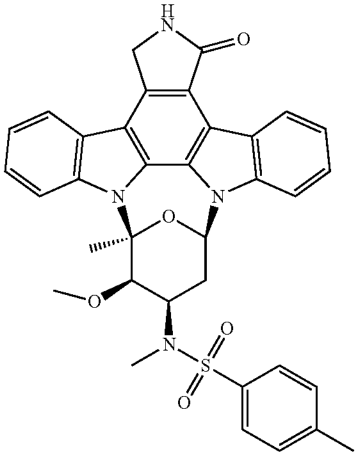
;
-continued
(35)
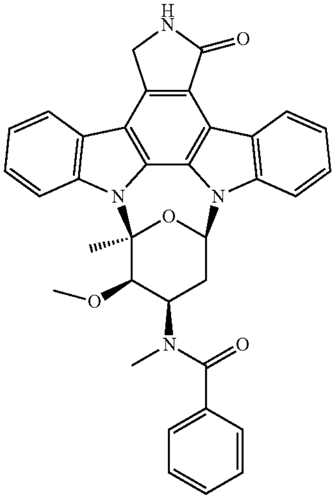
;
(36)
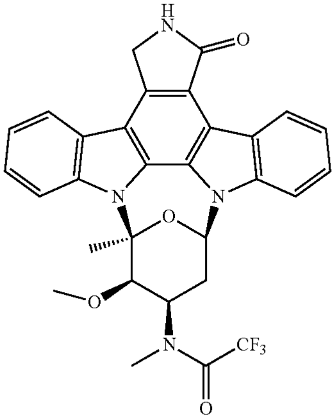
;
(37)
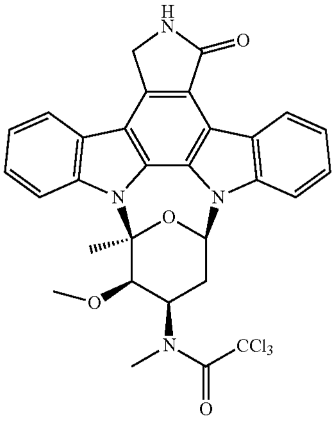
;

-continued
(38)
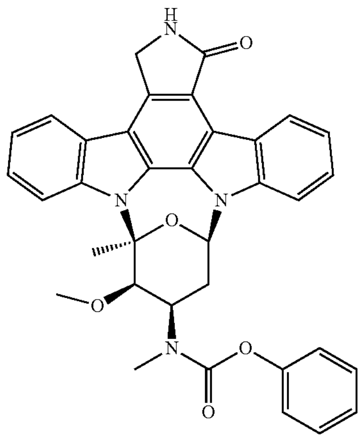
;
(39)
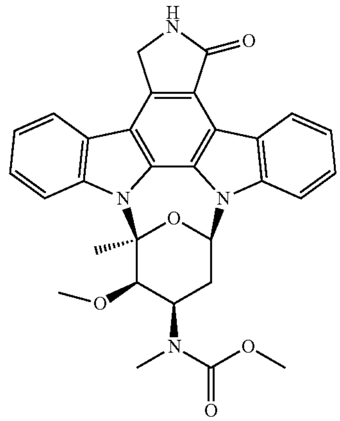
;
(40)
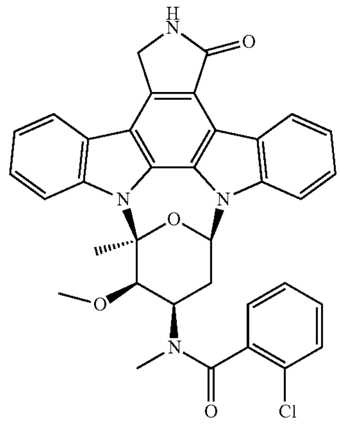
;
-continued
(41)
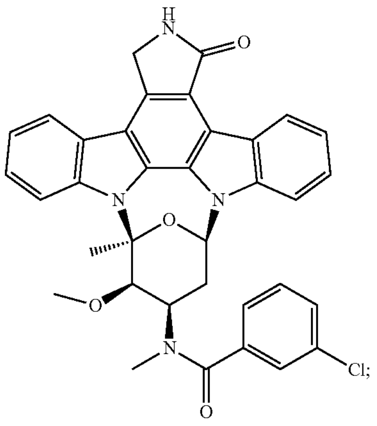
(42)
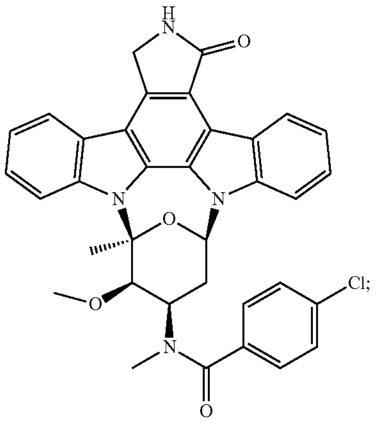
(43)
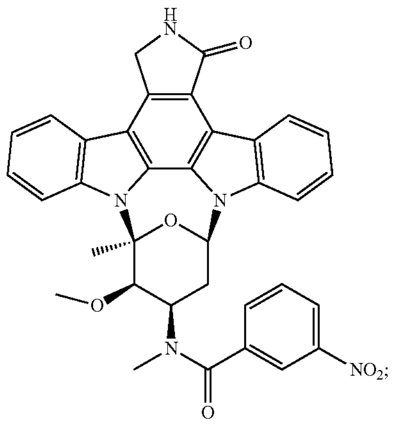

-continued
(44)
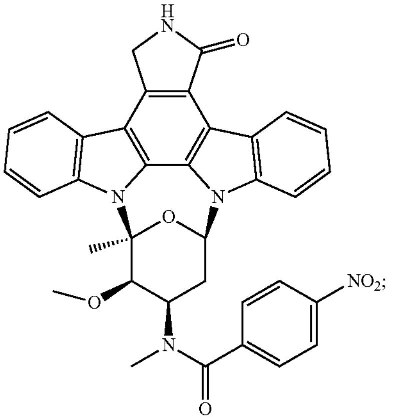
(45)
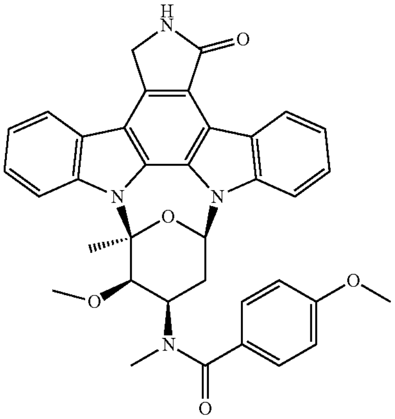
;
(46)
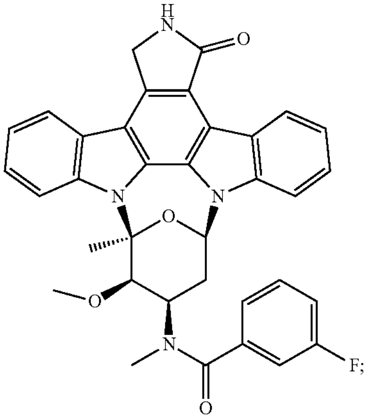
-continued
(47)
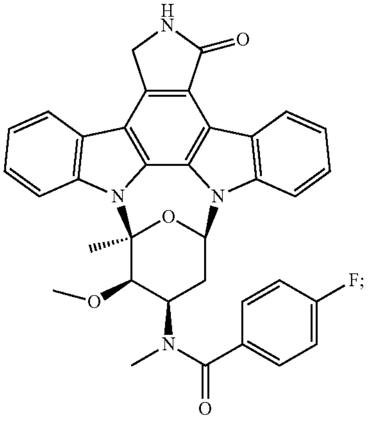
(48)
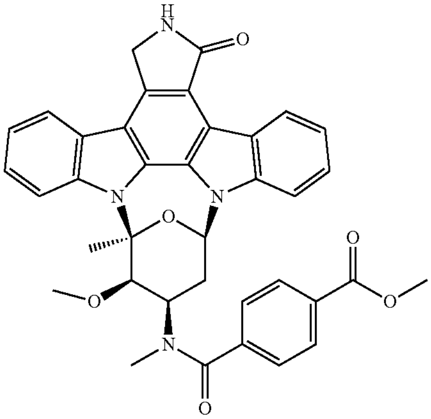
;
(49)
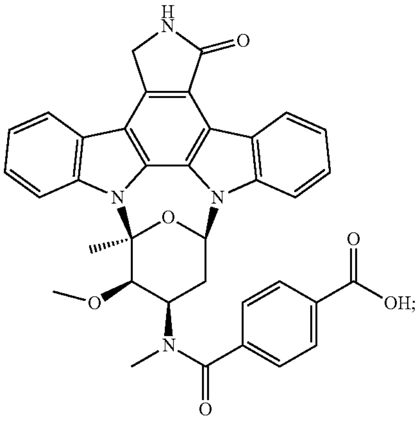

-continued
(50)
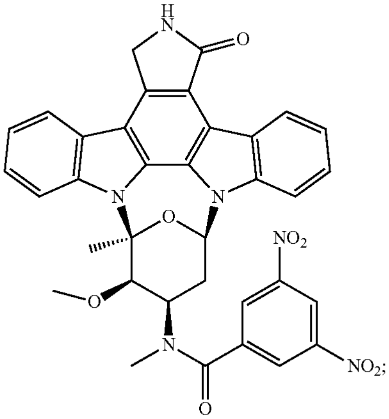
;
(51)
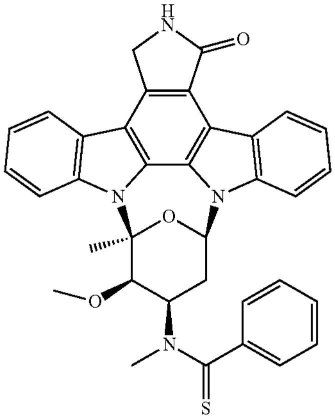
;
(52)
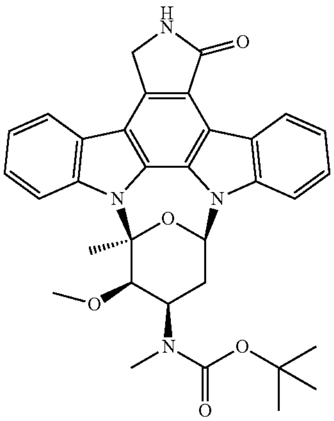
;
-continued
(53)
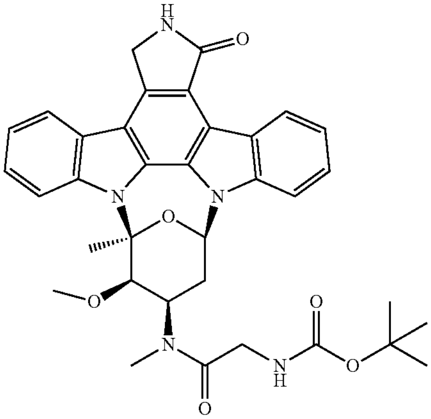
;
(54)
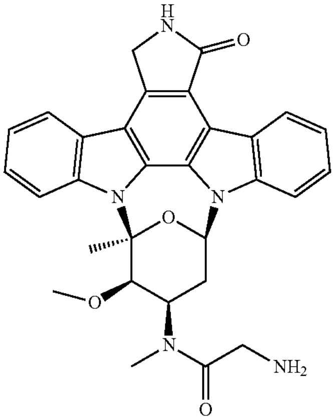
;
(55)
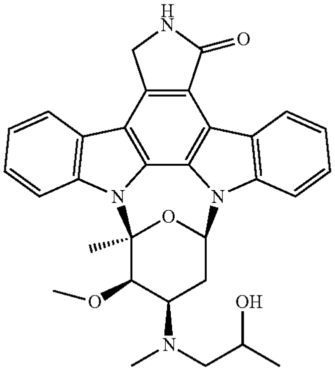
;
(56)
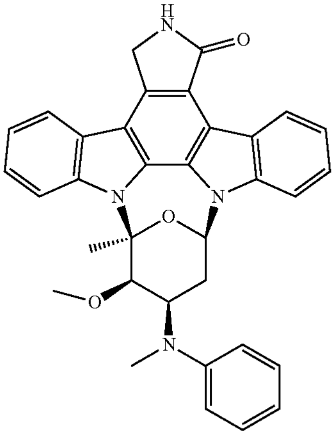
;

-continued
(57)
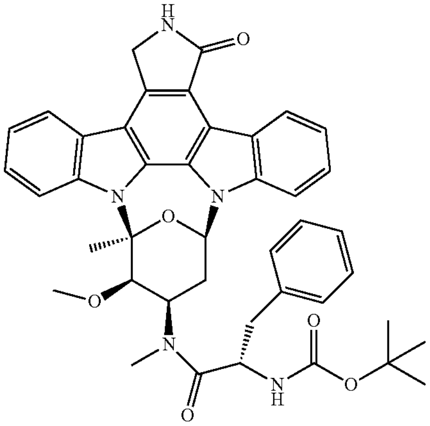
;
(58)
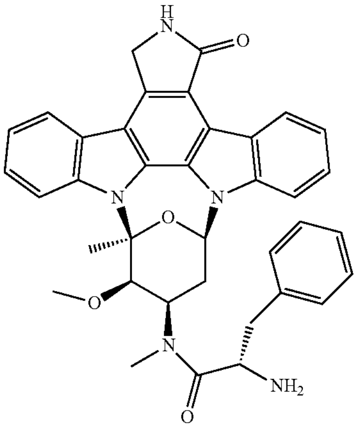
;
(59)
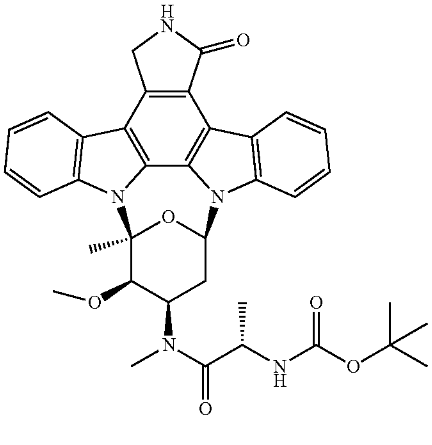
;
-continued
(60)
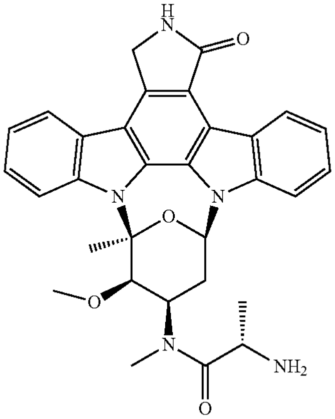
;
(61)
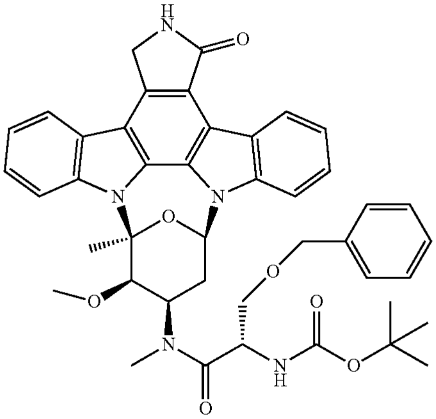
;
(62)
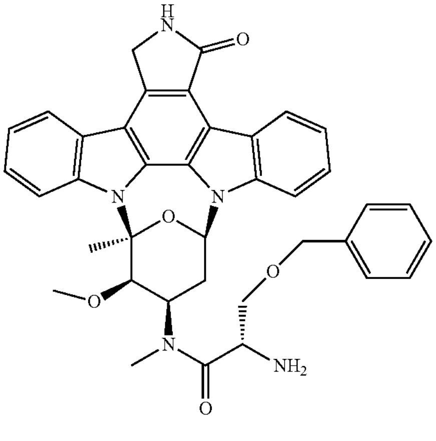
;

-continued
(63)
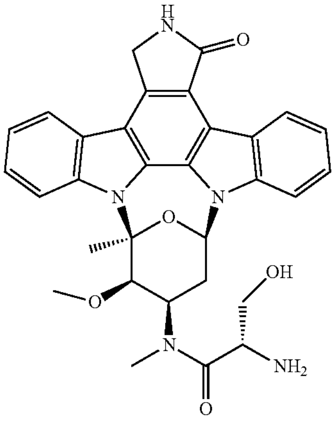
;
(64)
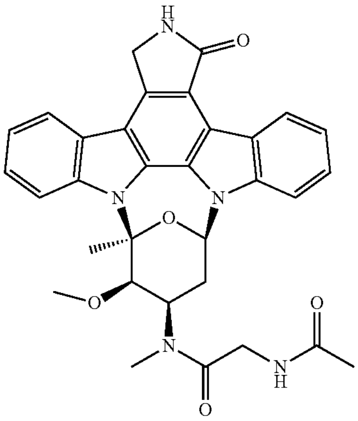
;
(65)
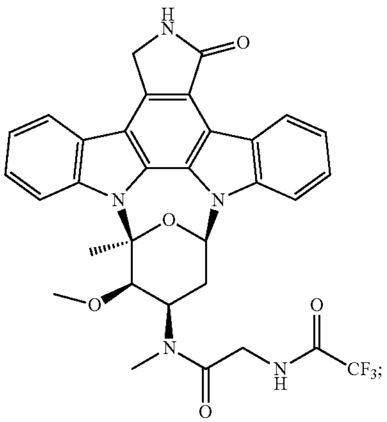
-continued
(66)
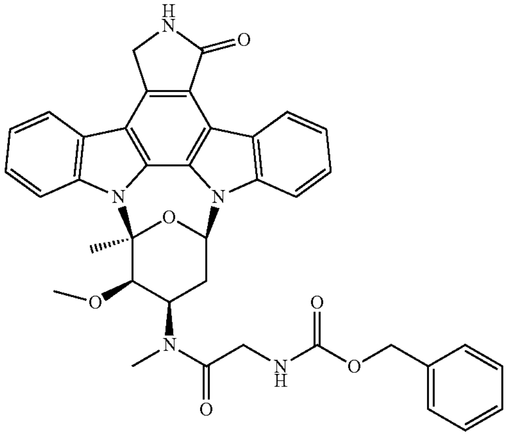
;
(67)
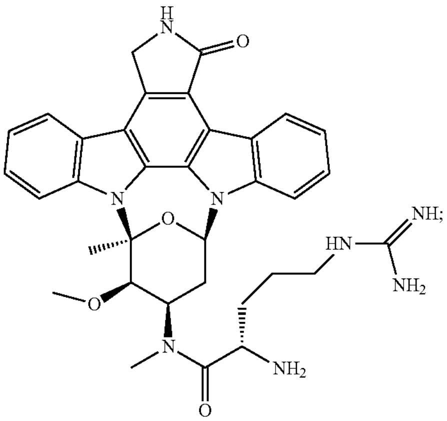
(68)
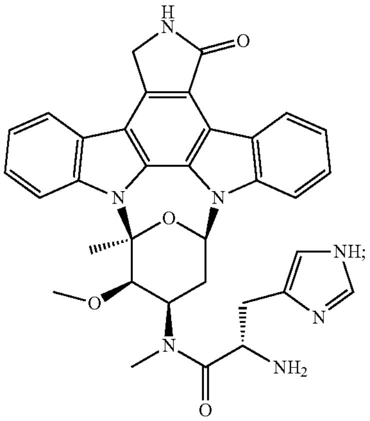

-continued (69)

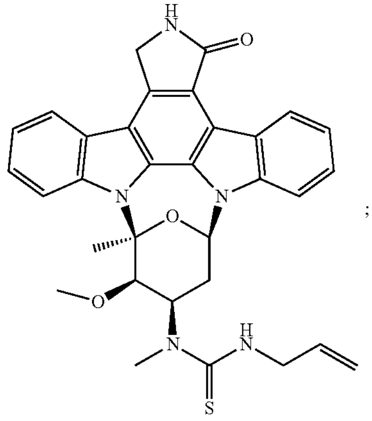

;

(70)

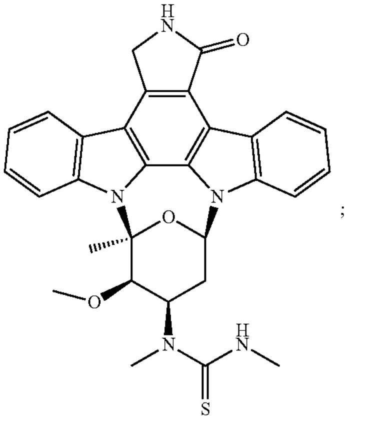

; and (71)

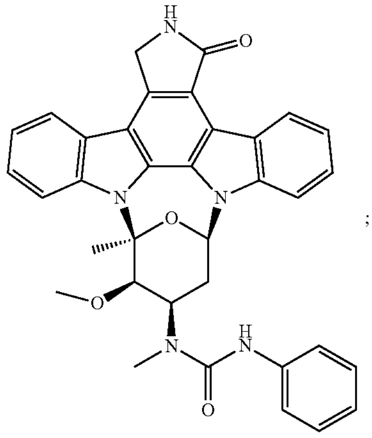

;

or a salt thereof.

In some embodiments, the PKC inhibitor is a staurosporine variant described in U.S. Pat. No. 5,264,431, the disclosure of which is incorporated herein by reference in its entirety. Examples of such staurosporine variants are represented by formula (XVIII)

(XVIII)

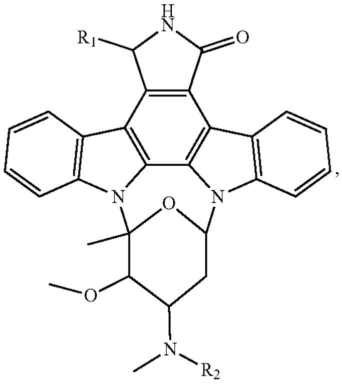

, wherein R is H, OH, $C_{1-6}$ alkoxy, or oxo; and $R_2$ is

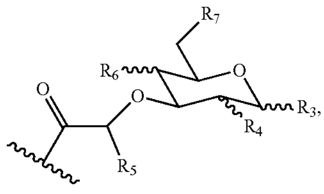

optionally wherein the configuration of the sugar moiety is derived from D-glucose, D-galactose, or D-mannose;

$R_3$ is H, OH, $C_{1-6}$ alkanoyloxy, $C_{1-6}$ alkoxy, benzyloxy, benzoyloxy or phenyloxy, each of which is optionally substituted in the phenyl moiety by halogen, hydroxyl, trifluoromethyl, $C_{1-6}$ alkyl, or $C_{1-6}$ alkoxy;

$R_4$ is OH, $C_{1-6}$ alkanoyloxy, benzoyloxy, benzyloxy, amino, $C_{1-6}$ alkylamino, di-$C_{1-6}$ alkylamino, $C_{1-6}$ alkoxycarbonylamino, $C_{2-20}$ alkanoylamino, benzoylamino, benzyloxycarbonylamino, or phenyloxycarbonylamino, each of which is optionally substituted in the phenyl moiety by halogen, hydroxyl, trifluoromethyl, $C_{1-6}$ alkyl, $C_{1-6}$ alkoxy;

$R_5$ is H or $C_{1-6}$ alkyl;

$R_6$ is hydroxyl which is free or esterified with an aliphatic $C_{2-22}$ carboxylic acid, or is $C_{1-6}$ alkoxycarbonyloxy, $C_{1-6}$ alkylsulfonyloxy, amino which is free or acylated with an aliphatic $C_{2-22}$ carboxylic acid, $C_{1-6}$ alkoxycarbonylamino, azido, benzoyloxy, benzyloxycarbonyloxy, benzoylamino, benzyloxycarbonylamino, or phenylsulfonyloxy, each of which is optionally substituted in the phenyl moiety by halogen, hydroxyl, trifluoromethyl, $C_{1-6}$ alkyl, or $C_{1-6}$ alkoxy; and $R_7$ is OH which is free or esterified with an aliphatic $C_{2-22}$ carboxylic acid, $C_{1-6}$ alkoxycarbonyloxy, $C_{1-6}$ alkylsulfonyloxy, azido, amino which is free or acylated with an aliphatic $C_{2-22}$ carboxylic acid, $C_{1-6}$ alkylamino, di-$C_{1-6}$ alkylamino, $C_{1-6}$ alkoxycarbonylamino, carbamoylamino, benzoyloxy, benzyloxycarbonyloxy, phenylsulfonyloxy, benzoylamino, benzylamino or benzyloxycarbonylamino, each of which is optionally substituted in the phenyl moiety by halogen, hydroxyl, trifluoromethyl, $C_{1-6}$ alkyl, $C_{1-6}$ alkoxy, or $C_{1-6}$ alkoxycarbonyl;

or a salt thereof.

In some embodiments, the PKC inhibitor is a compound represented by formula (XIX)

(XIX)

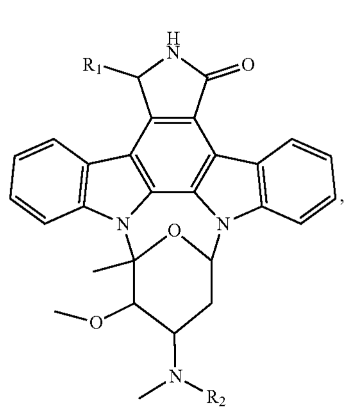

wherein R is H, OH, $C_{1-6}$ alkoxy, or oxo; and $R_2$ is

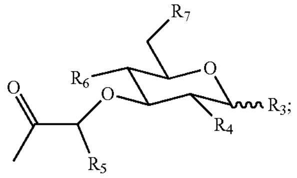

$R_3$ is H, OH, $C_{1-6}$ alkanoyloxy, $C_{1-6}$ alkoxy, benzyloxy, benzoyloxy or phenyloxy, each of which is optionally substituted in the phenyl moiety by halogen, hydroxyl, trifluoromethyl, $C_{1-6}$ alkyl, or $C_{1-6}$ alkoxy;

$R_4$ is OH, $C_{1-6}$ alkanoyloxy, benzoyloxy, benzyloxy, amino, $C_{1-6}$ alkylamino, di-$C_{1-6}$ alkylamino, $C_{1-6}$ alkoxycarbonylamino, $C_{2-20}$ alkanoylamino, benzoylamino, benzyloxycarbonylamino, or phenyloxycarbonylamino, each of which is optionally substituted in the phenyl moiety by halogen, hydroxyl, trifluoromethyl, $C_{1-6}$ alkyl, $C_{1-6}$ alkoxy;

$R_5$ is H or $C_{1-6}$ alkyl;

$R_6$ is hydroxyl which is free or esterified with an aliphatic $C_{2-22}$ carboxylic acid, or is $C_{1-6}$ alkoxycarbonyloxy, $C_{1-6}$ alkylsulfonyloxy, amino which is free or acylated with an aliphatic $C_{2-22}$ carboxylic acid, $C_{1-6}$ alkoxycarbonylamino, azido, benzoyloxy, benzyloxycarbonyloxy, benzoylamino, benzyloxycarbonylamino, or phenylsulfonyloxy, each of which is optionally substituted in the phenyl moiety by halogen, hydroxyl, trifluoromethyl, $C_{1-6}$ alkyl, or $C_{1-6}$ alkoxy; and $R_7$ is OH which is free or esterified with an aliphatic $C_{2-22}$ carboxylic acid, $C_{1-6}$ alkoxycarbonyloxy, $C_{1-6}$ alkylsulfonyloxy, azido, amino which is free or acylated with an aliphatic $C_{2-22}$ carboxylic acid, $C_{1-6}$ alkylamino, di-$C_{1-6}$ alkylamino, $C_{1-6}$ alkoxycarbonylamino, carbamoylamino, benzoyloxy, benzyloxycarbonyloxy, phenylsulfonyloxy, benzoylamino, benzylamino or benzyloxycarbonylamino, each of which is optionally substituted in the phenyl moiety by halogen, hydroxyl, trifluoromethyl, $C_{1-6}$ alkyl, $C_{1-6}$ alkoxy, or $C_{1-6}$ alkoxycarbonyl;

or a salt thereof.

In some embodiments, the PKC inhibitor is a compound selected from N-(1-α-O-Benzyl-2-N-acetylmuramyl)staurosporine, N-(2-N-Acetyl-muramyl)staurosporine, N-(6-0-Mesyl-1-α-O-benzyl-2-N-acetylmuramyl)staurosporine, N-(6-Azido-1-α-O-benzyl-2-N-acetyl-6-deoxymuramyl) staurosporine, N-(6-Amino-1-α-O-benzyl-2-N-acetyl-6-deoxymuramyl)staurosporine, N-(6-Amino-6-deoxy-2-N-acetylmuramyl)staurosporine, N-(6-O-Mesyl-2-N-acetylmuramyl)staurosporine, N-(2-N-Acetyl-demethylmuramyl)staurosporine, N-(1-α-O-Benzyl-2-N-acetylhomomuramyl)staurosporine, N-(1-α-O-Benzyl-2-N-acetyl-L-homomuramyl)staurosporine, the 1-α-anomer of N-(2-N-acetyl-L-homomuramyl)staurosporine, N-(1-α-O-Benzyl-4,6-O-diacetyl-2-N-acetylmuramyl)staurosporine, N-(1-α-O-Benzyl-4-O-acetyl-6-O-stearoyl-2-N-acetylmuramyl)staurosporin, N-(1-Deoxy-2-N-acetylmuramyl)staurosporine, the 1-α-anomer of N-(4-O-acetyl-6-O-stearoyl-2-N-acetylmuramyl)staurosporine, the 1-α-anomer of N-(4,6-O-diacetyl-2-N-acetylmuramyl)staurosporine, N-(1-α,4-O-diacetyl-6-O-stearoyl-2-N-acetylmuramyl)staurosporine, N-(1-α,4,6-O-Triacetyl-2-N-acetylmuramyl)staurosporine, N-(1-Deoxy-6-O-acetyl-2-N-acetylmuramyl)staurosporine, N-(1-Deoxy-6-O-mesyl-2-N-acetylmuramyl)staurosporine, N-(1-Deoxy-6-O-toluylsulfonyl-2-N-acetylmuramyl)staurosporine, N-(1-Deoxy-6-azido-2-N-acetylmuramyl)staurosporine, and N-(1-Deoxy-6-O-mesyl-2-N-acetylmuramyl) staurosporine, or a salt thereof.

In some embodiments, the PKC inhibitor is a staurosporine variant described in U.S. Pat. No. 5,461,146, the disclosure of which is incorporated herein by reference in its entirety. Examples of such staurosporine variants are represented by formula (XX)

(XX)

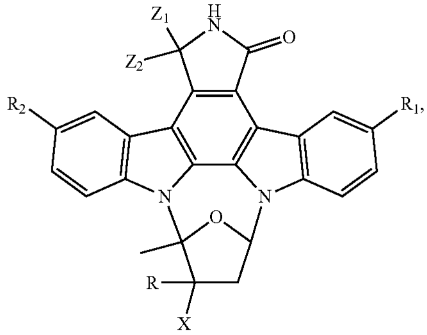

wherein $Z_1$ is H or OH;

$Z_2$ is H or OH;

$R_1$ is H, halogen, or optionally substituted alkyl;

$R_2$ is H or halogen;

R is OH or optionally substituted alkoxy; and

X is optionally substituted alkyl or optionally substituted acyl, optionally wherein X is $CH_2$—NH-serine, $CO_2CH_3$, $CH_2NHCO_2C_6H_5$, $CONHC_6H_5$, or $CH_2NHCO_2CH_3$, wherein $C_6H_5$ denotes a phenyl moiety;

or a salt thereof.

In some embodiments, the PKC inhibitor is a staurosporine variant described in U.S. Pat. No. 5,756,494, the disclosure of which is incorporated herein by reference in its entirety. Examples of such staurosporine variants are represented by formula (XXI)

(XXI)

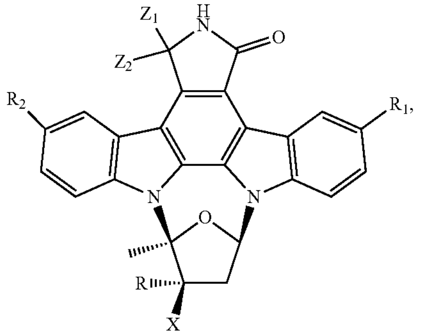

wherein $Z_1$ is H or OH;

$Z_2$ is H or OH;

$R_1$ is H, halogen, or optionally substituted alkyl;

$R_2$ is H or halogen;

R is OH or optionally substituted alkoxy; and

X is optionally substituted alkyl or optionally substituted acyl, optionally wherein X is $CH_2$—NH-serine, $CO_2CH_3$, $CH_2NHCO_2C_6H_5$, $CONHC_6H_5$, or $CH_2NHCO_2CH_3$, wherein $C_6H_5$ denotes a phenyl moiety;

or a salt thereof.

In some embodiments, the PKC inhibitor is a staurosporine variant described in US 2005/0020570, the disclosure of which is incorporated herein by reference in its entirety. Examples of such staurosporine variants are represented by formula (XXII), (XXIII), (XXIV or (XXV)

(XXII)

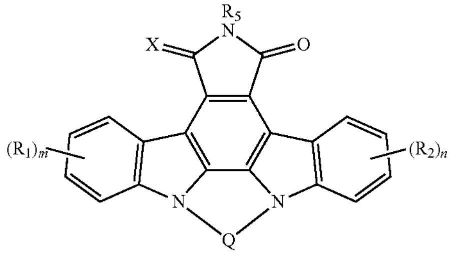

(XXIII)

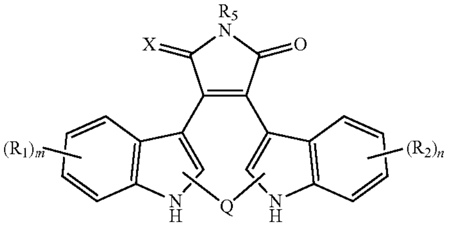

(XXIV)

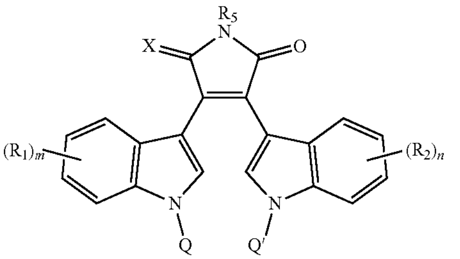

-continued (XXV)

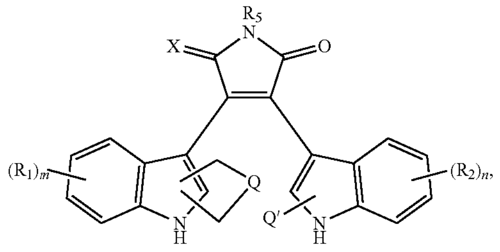

wherein each $R_1$ is, independently, optionally substituted alkyl, hydrogen, halogen, hydroxy, etherified or esterified hydroxy, amino, mono- or disubstituted amino, cyano, nitro, mercapto, substituted mercapto, carboxy, esterified carboxy, carbamoyl, N-mono- or N,N-di-substituted carbamoyl, sulfo, substituted sulfonyl, aminosulfonyl, or N-mono- or N,N-di-substituted aminosulfonyl;

each $R_2$ is, independently, optionally substituted alkyl, hydrogen, halogen, hydroxy, etherified or esterified hydroxy, amino, mono- or disubstituted amino, cyano, nitro, mercapto, substituted mercapto, carboxy, esterified carboxy, carbamoyl, N-mono- or N,N-di-substituted carbamoyl, sulfo, substituted sulfonyl, aminosulfonyl, or N-mono- or N,N-di-substituted aminosulfonyl;

each $R_5$ is, independently, H, an aliphatic, carbocyclic, or carbocyclic-aliphatic radical with up to 29 carbon atoms in each case, or a heterocyclic or heterocyclic-aliphatic radical with up to 20 carbon atoms in each case, and in each case up to 9 heteroatoms, or acyl with up to 30 carbon atoms; and each X is, independently, O, OH and H, or a pair of hydrogen atoms;

each Q is, independently, H, OH, halogen, etherified or esterified hydroxy, amino, mono- or disubstituted amino, cyano, nitro, mercapto, substituted mercapto, carboxy, esterified carboxy, carbamoyl, N-mono- or N,N-di-substituted carbamoyl, sulfo, substituted sulfonyl, aminosulfonyl or N-mono- or N,N-di-substituted aminosulfonyl;

each Q' is, independently, H, OH, halogen, etherified or esterified hydroxy, amino, mono- or disubstituted amino, cyano, nitro, mercapto, substituted mercapto, carboxy, esterified carboxy, carbamoyl, N-mono- or N,N-di-substituted carbamoyl, sulfo, substituted sulfonyl, aminosulfonyl or N-mono- or N,N-di-substituted aminosulfonyl;

each n is, independently, an integer from 0-4; and each m is, independently, an integer from 0-4;

or a salt thereof.

In some embodiments, the PKC inhibitor is a compound represented by formula (XXVI) or (XXVII)

(XXVI)

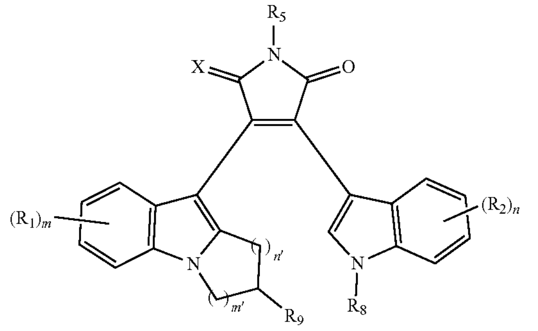

(XXVII)

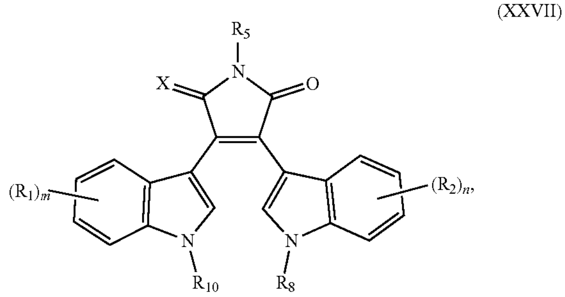

wherein each $R_1$ is, independently, optionally substituted alkyl, hydrogen, halogen, hydroxy, etherified or esterified hydroxy, amino, mono- or disubstituted amino, cyano, nitro, mercapto, substituted mercapto, carboxy, esterified carboxy, carbamoyl, N-mono- or N,N-disubstituted carbamoyl, sulfo, substituted sulfonyl, aminosulfonyl or N-mono- or N,N-di-substituted aminosulfonyl;

each $R_2$ is, independently, optionally substituted alkyl, hydrogen, halogen, hydroxy, etherified or esterified hydroxy, amino, mono- or disubstituted amino, cyano, nitro, mercapto, substituted mercapto, carboxy, esterified carboxy, carbamoyl, N-mono- or N,N-di-substituted carbamoyl, sulfo, substituted sulfonyl, aminosulfonyl or N-mono- or N,N-di-substituted aminosulfonyl;

each $R_5$ is, independently, H, an aliphatic, carbocyclic, or carbocyclic-aliphatic radical with up to 29 carbon atoms in each case, or a heterocyclic or heterocyclic-aliphatic radical with up to 20 carbon atoms in each case, and in each case up to 9 heteroatoms, or acyl with up to 30 carbon atoms;

each $R_8$ is, independently, acyl with up to 30 carbon atoms, an aliphatic, carbocyclic, or carbocyclic-aliphatic radical with up to 29 carbon atoms in each case, a heterocyclic or heterocyclic-aliphatic radical with up to 20 carbon atoms in each case, and in each case up to 9 heteroatoms;

each $R_9$ is, independently, optionally substituted acyl, optionally substituted alkyl, hydrogen, halogen, hydroxy, etherified or esterified hydroxy, amino, mono- or disubstituted amino, cyano, nitro, mercapto, substituted mercapto, carboxy, carbonyl, carbonyldioxy, esterified carboxy, carbamoyl, N-mono- or N,N-disubstituted carbamoyl, sulfo, substituted sulfonyl, aminosulfonyl or N-mono- or N,N-di-substituted aminosulfonyl;

each $R_{10}$ is, independently, acyl with up to 30 carbon atoms, an aliphatic, carbocyclic, or carbocyclic-aliphatic radical with up to 29 carbon atoms in each case, a heterocyclic or heterocyclic-aliphatic radical with up to 20 carbon atoms in each case, and in each case up to 9 heteroatoms;

each X is, independently, O, OH and H, or a pair of hydrogen atoms;

each n is, independently, an integer from 0-4;

each m is, independently, an integer from 0-4;

each n' is, independently, an integer from 0-4; and each m' is, independently, an integer from 0-4;

or a salt thereof.

In some embodiments, the PKC inhibitor is a staurosporine variant described in U.S. Pat. No. 5,624,949, the disclosure of which is incorporated herein by reference in its entirety. Examples of such staurosporine variants are represented by formula (XXVIII)

(XXVIII)

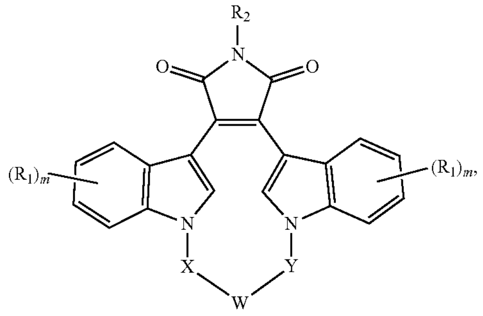

wherein $R_1$ is H or optionally substituted $C_{1-6}$ alkyl; and $R_2$ is optionally substituted $C_{1-6}$ alkyl;

or a salt thereof.

In some embodiments, the PKC inhibitor is a compound represented by formula (XXIX)

(XXIX)

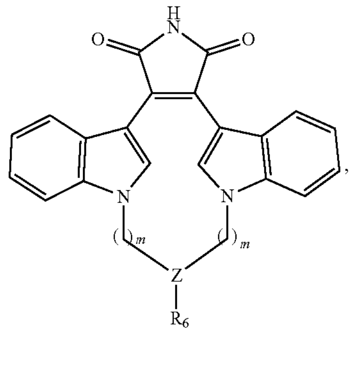

wherein $R_1$ is H or optionally substituted $C_{1-6}$ alkyl; and $R_2$ is optionally substituted $C_{1-6}$ alkyl;

or a salt thereof.

In some embodiments, the PKC inhibitor is a compound represented by formula (XXX)

(XXX)

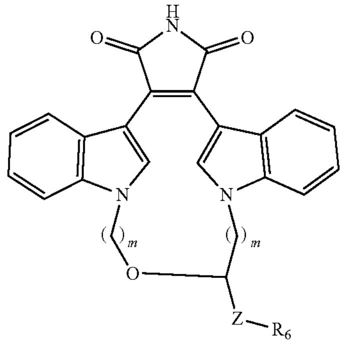

, wherein $R_1$ is H or optionally substituted 01-6 alkyl; and $R_2$ is optionally substituted $C_{1-6}$ alkyl;

or a salt thereof.

In some embodiments, the PKC inhibitor is a compound represented by formula (XXXI)

(XXXI)

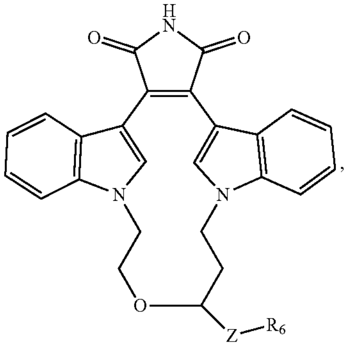

, wherein $R_1$ is H or optionally substituted $C_{1-6}$ alkyl; and $R_2$ is optionally substituted $C_{1-6}$ alkyl;

or a salt thereof.

In some embodiments, the PKC inhibitor is a compound selected from:

(72)

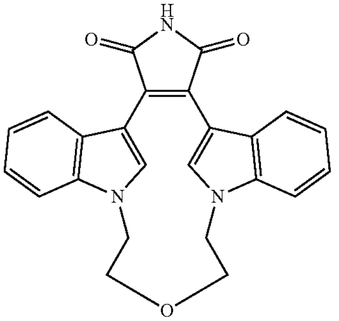

;

-continued (73)

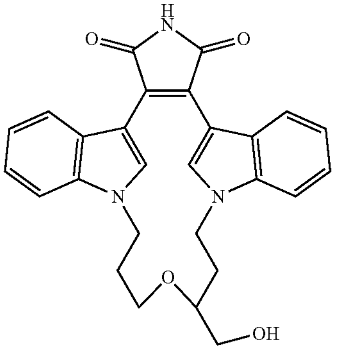

;

(74)

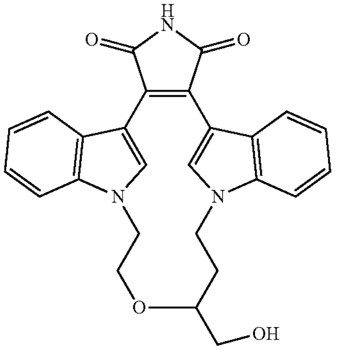

;

(75)

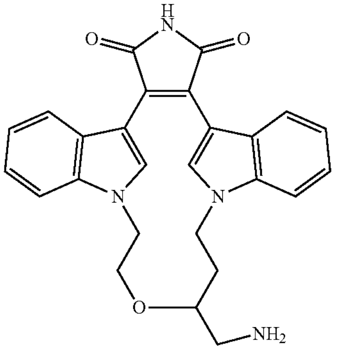

;

(76)

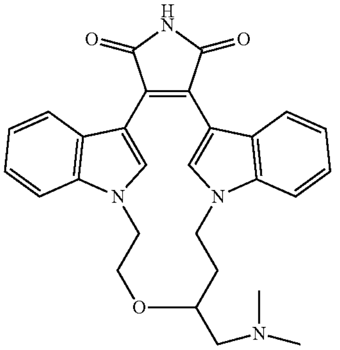

;

-continued
(77)
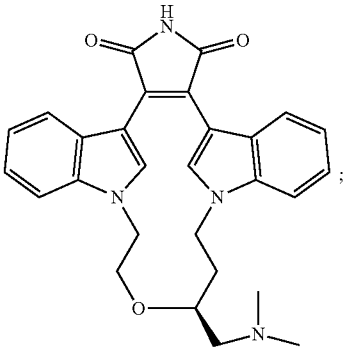
(78)
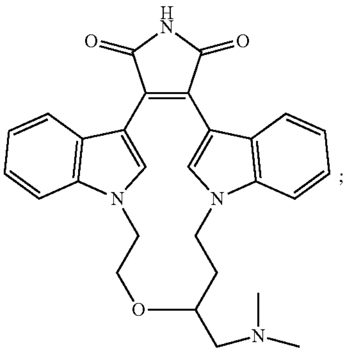
(79)
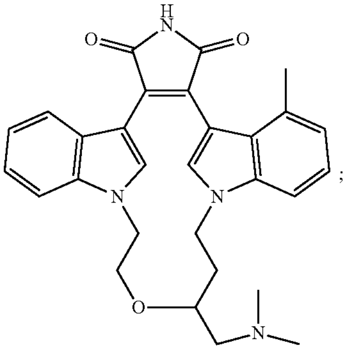
(80)
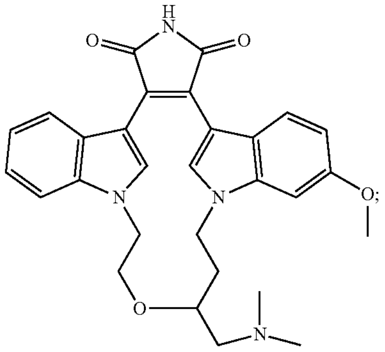
-continued
(81)
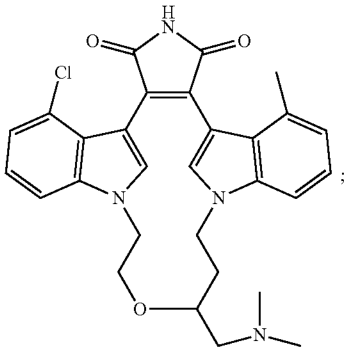
(82)
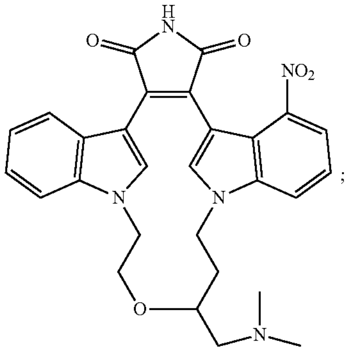
(83)
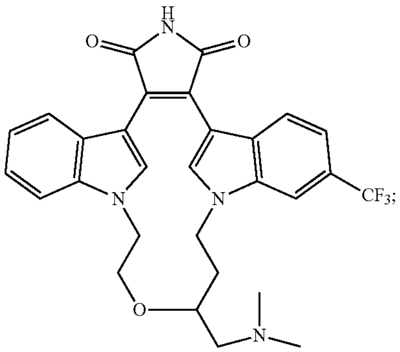
(84)
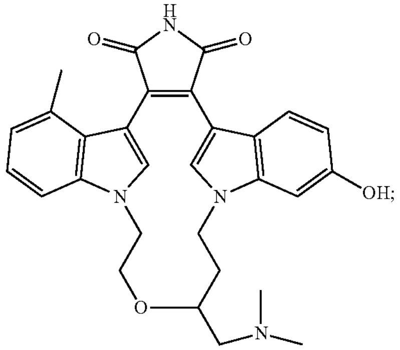

(85)
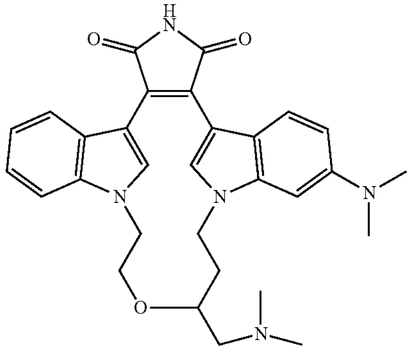
;
(86)
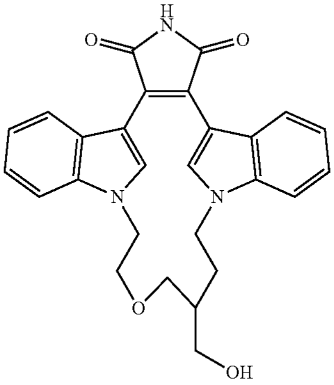
;
(87)
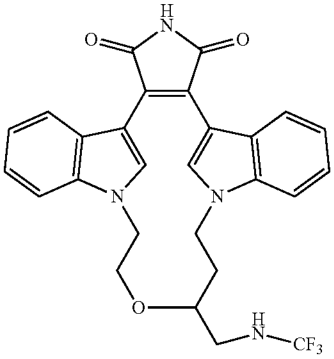
;
(88)
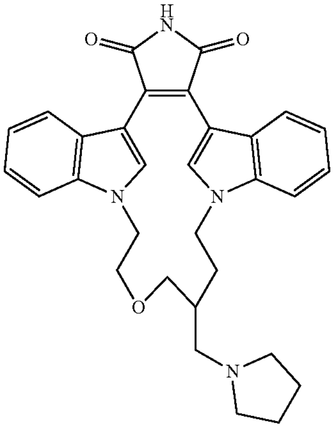
;
(89)
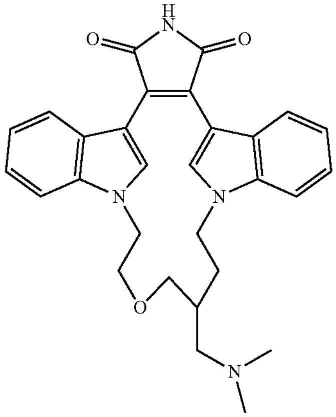
;
(90)
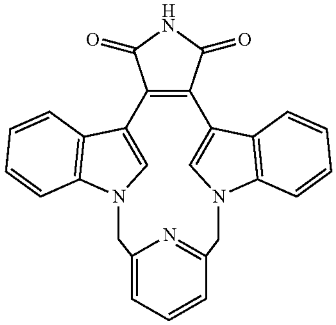
;
(91)
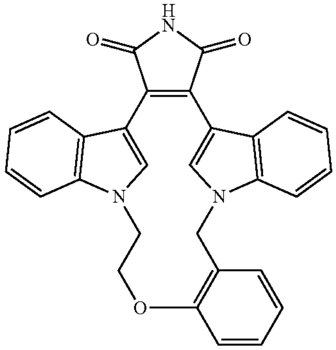
;
(92)
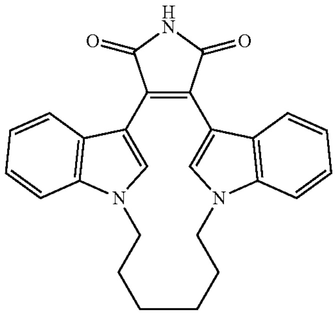
;

-continued
(93)
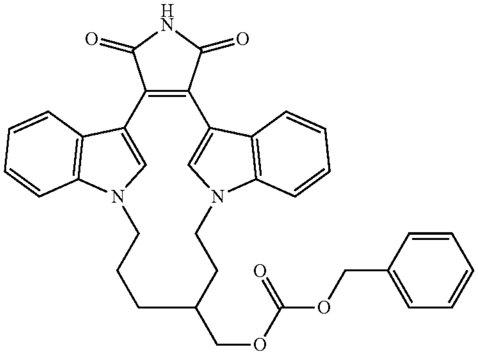
;
(94)
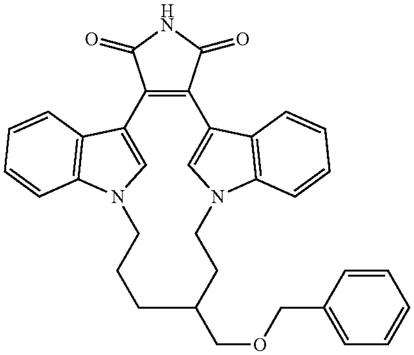
;
(95)
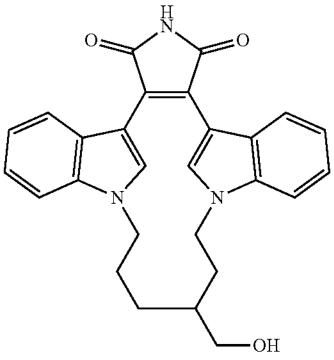
;
(96)
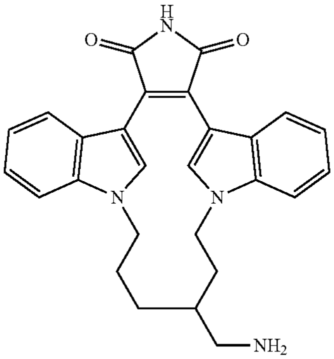
;
-continued
(97)
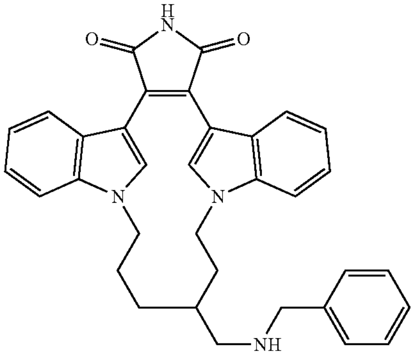
;
(98)
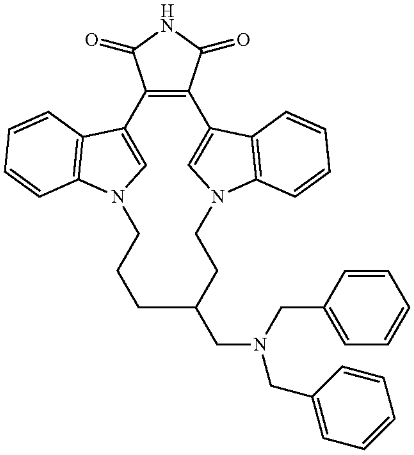
;
(99)
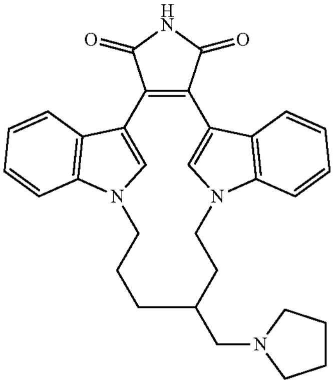
;
(100)
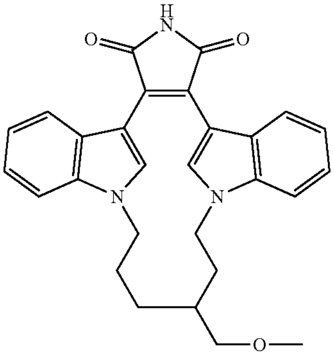
;

-continued
(101)
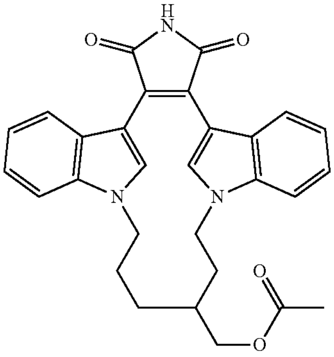
;
(102)
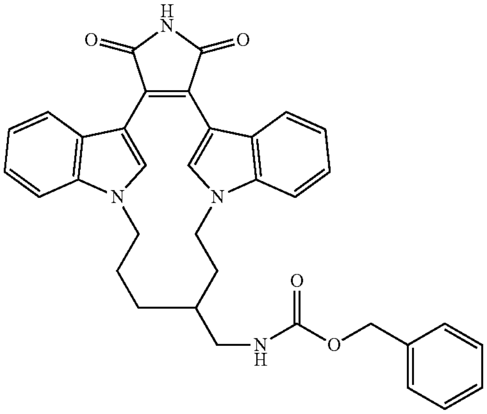
;
(103)
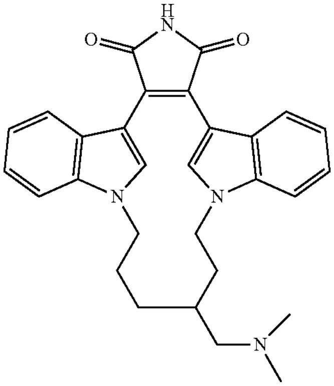
;
(104)
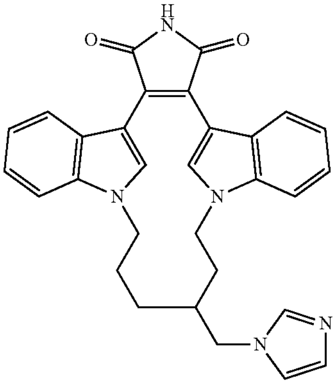
;
-continued
(105)
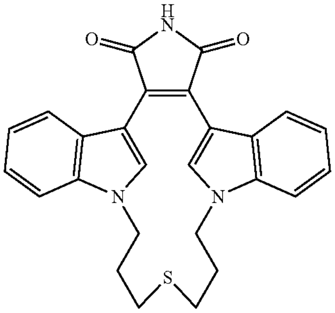
;
(106)
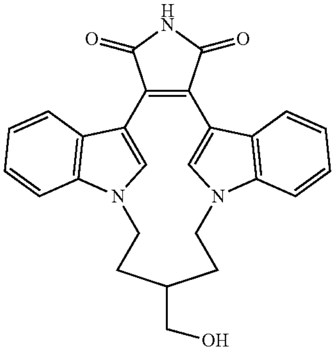
;
(107)
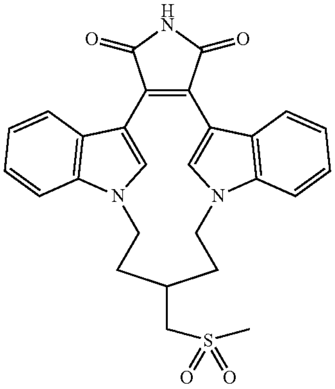
;
(108)
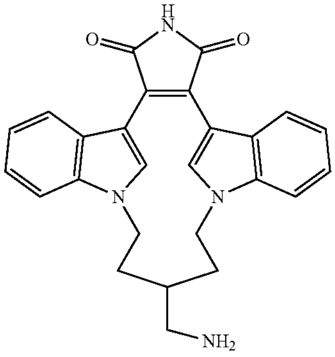
; and -continued (109)

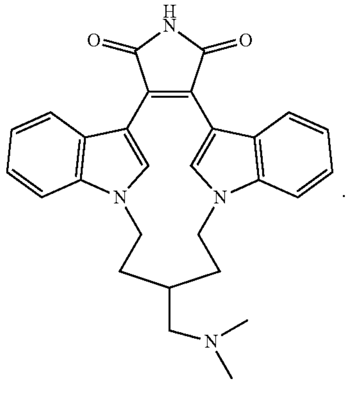

Interfering RNA

Exemplary PKC modulating agents that may be used in conjunction with the compositions and methods of the disclosure include interfering RNA molecules, such as short interfering RNA (siRNA), short hairpin RNA (shRNA), and/or micro RNA (miRNA), that diminish PKC gene expression. Methods for producing interfering RNA molecules are known in the art and are described in detail, for example, in WO 2004/044136 and U.S. Pat. No. 9,150,605, the disclosures of each of which are incorporated herein by reference in their entirety.

Spinoculation

In some embodiments of the disclosure, a cell targeted for transduction may be spun e.g., by centrifugation, while being cultured with a viral vector (e.g., in combination with one or more additional agents described herein). This "spinoculation" process may occur with a centripetal force of, e.g., from about 200×g to about 2,000×g. The centripetal force may be, e.g., from about 300×g to about 1,200×g (e.g., about 300×g, 400×g, 500×g, 600×g, 700×g, 800×g, 900×g, 1,000×g, 1,100×g, or 1,200×g, or more). In some embodiments, the cell is spun for from about 10 minutes to about 3 hours (e.g., about 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, 120 minutes, 125 minutes, 130 minutes, 135 minutes, 140 minutes, 145 minutes, 150 minutes, 155 minutes, 160 minutes, 165 minutes, 170 minutes, 175 minutes, 180 minutes, or more). In some embodiments, the cell is spun at room temperature, such as at a temperature of about 25° C.

Exemplary transduction protocols involving a spinoculation step are described, e.g., in Millington et al., PLoS One 4:e6461 (2009); Guo et al., Journal of Virology 85:9824-9833 (2011); O'Doherty et al., Journal of Virology 74:10074-10080 (2000); and Federico et al., Lentiviral Vectors and Exosomes as Gene and Protein Delivery Tools, Methods in Molecular Biology 1448, Chapter 4 (2016), the disclosures of each of which are incorporated herein by reference.

Target Cells

Cells that may be used in conjunction with the compositions and methods described herein include cells that are capable of undergoing further differentiation. For example, one type of cell that can be used in conjunction with the compositions and methods described herein is a pluripotent cell. A pluripotent cell is a cell that possesses the ability to develop into more than one differentiated cell type. Examples of pluripotent cells are ESCs, iPSCs, and CD34+ cells. ESCs and iPSCs have the ability to differentiate into cells of the ectoderm, which gives rise to the skin and nervous system, endoderm, which forms the gastrointestinal and respiratory tracts, endocrine glands, liver, and pancreas, and mesoderm, which forms bone, cartilage, muscles, connective tissue, and most of the circulatory system.

Cells that may be used in conjunction with the compositions and methods described herein include hematopoietic stem cells and hematopoietic progenitor cells. Hematopoietic stem cells (HSCs) are immature blood cells that have the capacity to self-renew and to differentiate into mature blood cells including diverse lineages including but not limited to granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). Human HSCs are CD34+. In addition, HSCs also refer to long term repopulating HSC (LT-HSC) and short-term repopulating HSC (ST-HSC). Any of these HSCs can be used in conjunction with the compositions and methods described herein.

HSCs and other pluripotent progenitors can be obtained from blood products. A blood product is a product obtained from the body or an organ of the body containing cells of hematopoietic origin. Such sources include unfractionated bone marrow, umbilical cord, placenta, peripheral blood, or mobilized peripheral blood. All of the aforementioned crude or unfractionated blood products can be enriched for cells having HSC or myeloid progenitor cell characteristics in a number of ways. For example, the more mature, differentiated cells can be selected against based on cell surface molecules they express. The blood product may be fractionated by positively selecting for CD34+ cells, which include a subpopulation of hematopoietic stem cells capable of self-renewal, multi-potency, and that can be re-introduced into a transplant recipient whereupon they home to the hematopoietic stem cell niche and reestablish productive and sustained hematopoiesis. Such selection is accomplished using, for example, commercially available magnetic anti-CD34 beads (Dynal, Lake Success, NY). Myeloid progenitor cells can also be isolated based on the markers they express. Unfractionated blood products can be obtained directly from a donor or retrieved from cryopreservative storage. HSCs and myeloid progenitor cells can also be obtained from by differentiation of ES cells, iPS cells or other reprogrammed mature cells types.

Cells that may be used in conjunction with the compositions and methods described herein include allogeneic cells and autologous cells. When allogeneic cells are used, the cells may optionally be HLA-matched to the subject receiving a cell treatment.

Viral Vectors for Transgene Expression

Viral genomes provide a rich source of vectors that can be used for the efficient delivery of exogenous genes into a mammalian cell. Viral genomes are particularly useful vectors for gene delivery as the polynucleotides contained within such genomes are typically incorporated into the nuclear genome of a mammalian cell by generalized or specialized transduction. These processes occur as part of the natural viral replication cycle, and do not require added proteins or reagents in order to induce gene integration. Examples of viral vectors are a retrovirus (e.g., Retroviridae family viral vector), adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, modified vaccinia Ankara (MVA), fowlpox and canarypox). Other viruses include Norwalk virus, togavirus, flavivirus, reoviruses, papovavirus, hepadnavirus, human papilloma virus, human foamy virus, and hepatitis virus, for example. Examples of retroviruses are: avian leukosis-sarcoma, avian C-type viruses, mammalian C-type, B-type viruses, D-type viruses, oncoretroviruses, HTLV-BLV group, lentivirus, alpharetrovirus, gammaretrovirus, spumavirus (Coffin, J. M., Retroviridae: The viruses and their replication, Virology, Third Edition (Lippincott-Raven, Philadelphia, (1996))). Other examples are murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., (U.S. Pat. No. 5,801,030), the teachings of which are incorporated herein by reference.

Retroviral Vectors

The delivery vector used in the methods and compositions described herein may be a retroviral vector. One type of retroviral vector that may be used in the methods and compositions described herein is a lentiviral vector. Lentiviral vectors (LVs), a subset of retroviruses, transduce a wide range of dividing and non-dividing cell types with high efficiency, conferring stable, long-term expression of the transgene. An overview of optimization strategies for packaging and transducing LVs is provided in Delenda, The Journal of Gene Medicine 6: S125 (2004), the disclosure of which is incorporated herein by reference.

The use of lentivirus-based gene transfer techniques relies on the in vitro production of recombinant lentiviral particles carrying a highly deleted viral genome in which the transgene of interest is accommodated. In particular, the recombinant lentivirus are recovered through the in trans coexpression in a permissive cell line of (1) the packaging constructs, i.e., a vector expressing the Gag-Pol precursors together with Rev (alternatively expressed in trans); (2) a vector expressing an envelope receptor, generally of an heterologous nature; and (3) the transfer vector, consisting in the viral cDNA deprived of all open reading frames, but maintaining the sequences required for replication, encapsidation, and expression, in which the sequences to be expressed are inserted.

A LV used in the methods and compositions described herein may include one or more of a 5'-Long terminal repeat (LTR), HIV signal sequence, HIV Psi signal 5'-splice site (SD), delta-GAG element, Rev Responsive Element (RRE), 3'-splice site (SA), elongation factor (EF) 1-alpha promoter and 3'-self inactivating LTR (SIN-LTR). The lentiviral vector optionally includes a central polypurine tract (cPPT) and a woodchuck hepatitis virus post-transcriptional regulatory element (WPRE), as described in U.S. Pat. No. 6,136,597, the disclosure of which is incorporated herein by reference as it pertains to WPRE. The lentiviral vector may further include a pHR' backbone, which may include for example as provided below.

The Lentigen LV described in Lu et al., Journal of Gene Medicine 6:963 (2004) may be used to express the DNA molecules and/or transduce cells. A LV used in the methods and compositions described herein may a 5'-Long terminal repeat (LTR), HIV signal sequence, HIV Psi signal 5'-splice site (SD), delta-GAG element, Rev Responsive Element (RRE), 3'-splice site (SA), elongation factor (EF) 1-alpha promoter and 3'-self inactivating L TR (SIN-LTR). It will be readily apparent to one skilled in the art that optionally one or more of these regions is substituted with another region performing a similar function.

Enhancer elements can be used to increase expression of modified DNA molecules or increase the lentiviral integration efficiency. The LV used in the methods and compositions described herein may include a nef sequence. The LV used in the methods and compositions described herein may include a cPPT sequence which enhances vector integration. The cPPT acts as a second origin of the (+)-strand DNA synthesis and introduces a partial strand overlap in the middle of its native HIV genome. The introduction of the cPPT sequence in the transfer vector backbone strongly increased the nuclear transport and the total amount of genome integrated into the DNA of target cells. The LV used in the methods and compositions described herein may include a Woodchuck Posttranscriptional Regulatory Element (WPRE). The WPRE acts at the transcriptional level, by promoting nuclear export of transcripts and/or by increasing the efficiency of polyadenylation of the nascent transcript, thus increasing the total amount of mRNA in the cells. The addition of the WPRE to LV results in a substantial improvement in the level of transgene expression from several different promoters, both in vitro and in vivo. The LV used in the methods and compositions described herein may include both a cPPT sequence and WPRE sequence. The vector may also include an IRES sequence that permits the expression of multiple polypeptides from a single promoter.

In addition to IRES sequences, other elements which permit expression of multiple polypeptides are useful. The vector used in the methods and compositions described herein may include multiple promoters that permit expression more than one polypeptide. The vector used in the methods and compositions described herein may include a protein cleavage site that allows expression of more than one polypeptide. Examples of protein cleavage sites that allow expression of more than one polypeptide are described in Klump et al., Gene Ther.; 8:811 (2001), Osborn et al., Molecular Therapy 12:569 (2005), Szymczak and Vignali, Expert Opin Biol Ther. 5:627 (2005), and Szymczak et al., Nat Biotechnol. 22:589 (2004), the disclosures of which are incorporated herein by reference as they pertain to protein cleavage sites that allow expression of more than one polypeptide. It will be readily apparent to one skilled in the art that other elements that permit expression of multiple polypeptides identified in the future are useful and may be utilized in the vectors suitable for use with the compositions and methods described herein.

The vector used in the methods and compositions described herein may, be a clinical grade vector.

Methods of Treatment

Exemplary diseases that may be treated using the compositions and methods of the disclosure Transgenes that may be introduced into a target cell and ultimately delivered to a patient (e.g., by administration of the target cell to a patient) using the compositions and methods of the disclosure include those that encode therapeutic proteins. The recipient of the transgene (e.g., the recipient of a cell transduced to express the transgene) may be suffering from a disease characterized by deficiency in the encoded protein. For example, transgenes that can expressed in a target cell and delivered to a patient in accordance with the compositions and methods of the disclosure include transgenes encoding beta-globin, which are particularly useful for the treatment of patients having beta-thalassemia. Exemplary nucleic acid and amino acid sequences of human beta-globin cDNA and protein are shown below.

Exemplary Wild-Type Human Beta-Globin cDNA Sequence:

```
                                   (SEQ ID NO: 1)
ATGGTGCATCTGACCCCGGAAGAAAAAAGCGCGGTG

ACCGCGCTGTGGGGCAAAGTGAACGTGGATGAAGT

GGGCGGCGAAGCGCTGGGCCGCCTGCTGGTGGTGT

ATCCGTGGACCCAGCGCTTTTTTGAAAGCTTTGGC

GATCTGAGCACCCCGGATGCGGTGATGGGCAACCC

GAAAGTGAAAGCGCATGGCAAAAAAGTGCTGGGCG

CGTTTAGCGATGGCCTGGCGCATCTGGATAACCTG

AAAGGCACCTTTGCGACCCTGAGCGAACTGCATTG

CGATAAACTGCATGTGGATCCGGAAAACTTTCGCC

TGCTGGGCAACGTGCTGGTGTGCGTGCTGGCGCAT

CATTTTGGCAAAGAATTTACCCCGCCGGTGCAGGC

GGCGTATCAGAAAGTGGTGGCGGGCGTGGCGAACG

CGCTGGCGCATAAATATCAT
```

Exemplary Wild-Type Human Beta-Globin Amino Acid Sequence:

```
                                   (SEQ ID NO: 2)
MVHLTPEEKSAVTALWGKVNVDEVGGEALGRLLVVYPW

TQRFFESFGDLSTPDAVMGNPKVKAHGKKVLGAFSDGL

AHLDNLKGTFATLSELHCDKLHVDPENFRLLGNVLVCV

LAHHFGKEFTPPVQAAYQKVVAGVANALAHKYH
```

Additional examples of transgenes that may be used in conjunction with the compositions and methods of the disclosure include hormones and growth and differentiation factors including, without limitation, insulin, glucagon, growth hormone (GH), parathyroid hormone (PTH), calcitonin, growth hormone releasing factor (GRF), thyroid stimulating hormone (TSH), adrenocorticotropic hormone (ACTH), prolactin, melatonin, vasopressin, β-endorphin, met-enkephalin, leu-enkephalin, prolactin-releasing factor, prolactin-inhibiting factor, corticotropin-releasing hormone, thyrotropin-releasing hormone (TRH), follicle stimulating hormone (FSH), luteinizing hormone (LH), chorionic gonadotropin (CG), vascular endothelial growth factor (VEGF), angiopoietins, angiostatin, endostatin, granulocyte colony stimulating factor (GCSF), erythropoietin (EPO), connective tissue growth factor (CTGF), basic fibroblast growth factor (bFGF), bFGF2, acidic fibroblast growth factor (aFGF), epidermal growth factor (EGF), transforming growth factor α (TGFα), platelet-derived growth factor (PDGF), insulin-like growth factors I and II (IGF-I and IGF-II), any one of the transforming growth factor β (TGFβ) superfamily comprising TGFβ, activins, inhibins, or any of the bone morphogenic proteins (BMP) BMPs 1 15, any one of the heregulin/neuregulin/ARIA/neu differentiation factor (NDF) family of growth factors, nerve growth factor (NGF), brain-derived neurotrophic factor (BDNF), neurotrophins NT-3, NT-4/5 and NT-6, ciliary neurotrophic factor (CNTF), glial cell line derived neurotrophic factor (GDNF), neurturin, persephin, agrin, any one of the family of semaphorins/collapsins, netrin-1 and netrin-2, hepatocyte growth factor (HGF), ephrins, noggin, sonic hedgehog and tyrosine hydroxylase.

Further examples of transgenes that may be used in conjunction with the compositions and methods of the disclosure include those that encode proteins that regulate the immune system including, without limitation, cytokines and lymphokines such as thrombopoietin (TPO), interleukins (IL) IL-1α, IL-1β, IL-2, IL-3, IL-4, IL-5, IL-6, IL-7, IL-8, IL-9, IL-10, IL-11, IL-12, IL-13, IL-14, IL-15, IL-16, and IL-17, monocyte chemoattractant protein (MCP-1), leukemia inhibitory factor (LIF), granulocyte-macrophage colony stimulating factor (GM-CSF), granulocyte colony stimulating factor (G-CSF), monocyte colony stimulating factor (M-CSF), Fas ligand, tumor necrosis factors α and β (TNFα and TNFβ), interferons (IFN) IFN-α, IFN-β, and IFN-γ, stem cell factor, flk-2/flt3 ligand. Transgenes encoding protein products produced by the immune system are also encompassed by the present disclosure. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered MHC molecules including single chain MHC molecules. Useful gene products also include complement regulatory proteins such as membrane cofactor protein (MCP), decay accelerating factor (DAF), CR1, CR2 and CD59.

Additional examples of suitable transgenes include those that encode any one of the receptors for the hormones, growth factors, cytokines, lymphokines, regulatory proteins and immune system proteins. Examples of such receptors include flt-1, flk-1, TIE-2; the trk family of receptors such as TrkA, MuSK, Eph, PDGF receptor, EGF receptor, HER2, insulin receptor, IGF-1 receptor, the FGF family of receptors, the TGFβ receptors, the interleukin receptors, the interferon receptors, serotonin receptors, α-adrenergic receptors, β-adrenergic receptors, the GDNF receptor, p75 neurotrophin receptor, among others. Further examples are transgenes encoding extracellular matrix proteins, such as integrins, counter-receptors for transmembrane-bound proteins, such as intercellular adhesion molecules (ICAM-1, ICAM-2, ICAM-3 and ICAM-4), vascular cell adhesion molecules (VCAM), and selectins E-selectin, P-selectin and L-selectin. The invention encompasses receptors for cholesterol regulation, including the LDL receptor, HDL receptor, VLDL receptor, and the scavenger receptor. Additional examples are transgenes encoding the apolipoprotein ligands for these receptors, including ApoAI, ApoAIV and ApoE.

Additional transgenes include those encoding antimicrobial peptides such as defensins and maginins, transcription factors such as jun, fos, max, mad, serum response factor (SRF), AP-1, AP-2, myb, MRG1, CREM, Alx4, FREAC1, NF-κB, members of the leucine zipper family, $C_2H_4$ zinc finger proteins, including Zif268, EGR1, EGR2, C6 zinc finger proteins, including the glucocorticoid and estrogen receptors, POU domain proteins, exemplified by Pit 1, homeodomain proteins, including HOX-1, basic helix-loop-helix proteins, including myc, MyoD and myogenin, ETSbox containing proteins, TFE3, E2F, ATF1, ATF2, ATF3, ATF4, ZF5, NFAT, CREB, HNF-4, C/EBP, SP1, CCAAT-box binding proteins, interferon regulation factor 1 (IRF-1), Wilms' tumor protein, ETS-binding protein, STAT, GATA-box binding proteins, e.g., GATA-3, and the forkhead family of winged helix proteins.

Other useful transgenes include those encoding carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, porphobilinogen deaminase, factor VII, factor VIII, factor IX, factor II, factor V, factor X, factor XII, factor XI, von Willebrand factor, superoxide dismutase, glutathione peroxidase and reductase, heme oxygenase, angiotensin converting enzyme, endothelin-1, atrial natriuretic peptide, pro-urokinase, urokinase, plasminogen activator, heparin cofactor II, activated protein C (Factor V Leiden), Protein C, antithrombin, cystathione beta-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, beta-glucosidase, pyruvate carboxylase, hepatic phosphorylase, phosphorylase kinase, glycine decarboxylase (also referred to as P-protein), H-protein, T-protein, Menkes disease protein, tumor suppressors (e.g., p53), cystic fibrosis transmembrane regulator (CFTR), the product of Wilson's disease gene PWD, Cu/Zn superoxide dismutase, aromatic amino acid decarboxylase, tyrosine hydroxylase, acetylcholine synthetase, prohormone convertases, protease inhibitors, lactase, lipase, trypsin, gastrointestinal enzymes including chymotrypsin, and pepsin, adenosine deaminase, α1 anti-trypsin, tissue inhibitor of metalloproteinases (TIMP), GLUT-1, GLUT-2, trehalose phosphate synthase, hexokinases I, II and III, glucokinase, any one or more of the individual chains or types of collagen, elastin, fibronectin, thrombospondin, vitronectin and tenascin, and suicide genes such as thymidine kinase and cytosine deaminase. Other useful proteins include those involved in lysosomal storage disorders, including acid β-glucosidase, α-galactosidase a, α-1-iduronidase, iduronate sulfatase, lysosomal acid α-glucosidase, sphingomyelinase, hexosaminidase A, hexomimidases A and B, arylsulfatase A, acid lipase, acid ceramidase, galactosylceramidase, α-fucosidase, α-, β-mannosidosis, aspartylglucosaminidase, neuramidase, galactosylceramidase, heparan-N-sulfatase, N-acetyl-α-glucosaminidase, Acetyl-CoA: α-glucosaminide N-acetyltransferase, N-acetylglucosamine-6-sulfate sulfatase, N-acetylgalactosamine-6-sulfate sulfatase, arylsulfatase B, β-glucuoronidase and hexosaminidases A and B.

Other useful transgenes include those encoding non-naturally occurring polypeptides, such as chimeric or hybrid polypeptides or polypeptides having a non-naturally occurring amino acid sequence containing insertions, deletions or amino acid substitutions. For example, single-chain engineered immunoglobulins could be useful in certain immunocompromised patients. Other useful proteins include truncated receptors which lack their transmembrane and cytoplasmic domain. These truncated receptors can be used to antagonize the function of their respective ligands by binding to them without concomitant signaling by the receptor. Other types of non-naturally occurring gene sequences include sense and antisense molecules and catalytic nucleic acids, such as ribozymes, which could be used to modulate expression of a gene.

Exemplary transgenes that can be expressed in a target cell, which may then be administered to a patient for the treatment of a disease characterized by a deficiency or dysfunction of the encoded product, include those encoding a protein product listed in Table 2, below.

TABLE 2

Exemplary disorders associated with gene deficiency or dysfunction

| Protein | Disease associated with deficiency in protein | Exemplary amino acid sequence of protein |
|---|---|---|
| acid α-glucosidase (GAA) | Pompe | NP_000143.2, NP_001073271.1, NP_001073272.1 |
| Methyl CpG binding protein 2 (MECP2) | Rett syndrome | NP_001104262.1, NP_004983.1 |
| Aromatic L-amino acid decarboxylase (AADC) | Parkinson's disease | NP_000781.1, NP_001076440.1, NP_001229815.1, NP_001229816.1, NP_001229817.1, NP_001229818.1, NP_001229819.1 |
| Glial cell-derived neurotrophic factor (GDNF) | Parkinson's disease | NP_000505.1, NP_001177397.1, NP_001177398.1, NP_001265027.1, NP_954701.1 |
| Glutamate decarboxylase 1 (GAD1) | Parkinson's disease | NP_000808.2, NP_038473.2 |
| Glutamate decarboxylase 2 (GAD2) | Parkinson's disease | NP_000809.1, NP_001127838.1 |
| Neurturin (NRTN) | Parkinson's disease | NP_004549.1 |
| neuropeptide Y (NPY) | Parkinson's disease, epilepsy | NP_000896.1 |
| Cystic fibrosis transmembrane conductance regulator (CFTR) | Cystic fibrosis | NP_000483.3 |
| Tumor necrosis factor receptor fused to an antibody Fe (TNFR:Fc) | Arthritis, Rheumatoid arthritis | SEQ ID NO. 1 of W02013025079 |

TABLE 2-continued

| Exemplary disorders associated with gene deficiency or dysfunction | | |
|---|---|---|
| Protein | Disease associated with deficiency in protein | Exemplary amino acid sequence of protein |
| Sarcoglycan α, β, γ, Δ, ε, or ζ (SGCA, SGCB, SGCG, SGCD, SGCE, or SGCZ) | Muscular dystrophy | SGCA NP_000014.1, NP_001129169.1 SGCB NP_000223.1 SGCG NP_000222.1 SGCD NP_000328.2, NP_001121681.1, NP_758447.1 SGCE NP_001092870.1, NP_001092871.1, NP_003910.1 SGCZ NP_631906.2 |
| α-1-antitrypsin (AAT) | Hereditary emphysema or α-1-antitrypsin deficiency | NP_000286.3, NP_001002235.1, NP_001002236.1, NP_001121172.1, NP_001121173.1, NP_001121174.1, NP_001121175.1, NP_001121176.1, NP_001121177.1, NP_001121178.1, NP_001121179.1 |
| Aspartoacylase (ASPA) | Canavan's disease | NP_000040.1, NP_001121557.1 |
| Nerve growth factor (NGF) | Alzheimer's disease | NP_002497.2 |
| Granulocyte-macrophage colonystimulating factory (GM-CSF) | Prostate cancer | NP_000749.2 |
| Cluster of Differentiation 86 (CD86 or B7-2) | Malignant melanoma | NP_001193853.1, NP_001193854.1, NP_008820.3, NP_787058.4, NP_795711.1 |
| Interleukin 12 (IL-12) | Malignant melanoma | NP_000873.2, NP_002178.2 |
| ATPase, $Ca^{2+}$ transporting, cardiac muscle, slow twitch 2 (SERCA2) | Chronic heart failure | NP_001672.1, NP_733765.1 |
| Dystrophin or Minidystrophin | Muscular dystrophy | NP_000100.2, NP_003997.1, NP_004000.1, NP_004001.1, NP_004002.2, NP_004003.1, NP_004004.1, NP_004005.1, NP_004006.1, NP_004007.1, NP_004008.1, NP_004009.1, NP_004010.1, NP_004011.2, NP_004012.1, NP_004013.1, NP_004014.1 |
| Ceroid lipofuscinosis neuronal 2 (CLN2) | Late infantile neuronal ceroidlipofuscinosis or Batten's disease | NP_000382.3 |
| N-acetylglucosaminidase, α (NAGLU) | Sanfilippo syndrome (MPSIIIB) | NP_000254.2 |
| Iduronidase, α -1 (IDUA) | MPSI-Hurler | NP_000194.2 |
| Iduronate 2-sulfatase (IDS) | MPSII-Hunter | NP_000193.1, NP_001160022.1, NP_006114.1 |
| Glucuronidase, β (GUSB) | MPSVII-Sly | NP_000172.2, NP_001271219.1 |
| Hexosaminidase A, α polypeptide (HEXA) | Tay-Sachs | NP_000511.2 |
| Retinal pigment epithelium-specific protein 65 kDa (RPE65) | Leber congenital amaurosis | NP_000320.1 |

TABLE 2-continued

| Exemplary disorders associated with gene deficiency or dysfunction | | |
|---|---|---|
| Protein | Disease associated with deficiency in protein | Exemplary amino acid sequence of protein |
| Factor IX (FIX) | Hemophilia B | NP_000124.1 |
| Adenine nucleotide translocator (ANT-I) | progressive external ophthalmoplegia | NP_001142.2 |
| ApaLI | mitochondrial heteroplasmy, myoclonic epilepsy with ragged red fibers (MERRF) or mitochondrial encephalomyopathy, lactic acidosis, and stroke-like episodes (ME LAS) | YP_007161330.1 |
| NADH ubiquinone oxidoreductase subunit 4 (ND4) | Leber hereditary optic | YP_003024035.1 |
| very long-acyl-CoA dehydrogenase (VLCAD) | very long-chain acyl-CoA dehydrogenase (VLCAD) deficiency | NP_000009.1, NP_001029031.1, NP_001257376.1, NP_001257377.1 |
| short-chain acyl-CoA dehydrogenase (SCAD) | short-chain acyl-CoA dehydrogenase (SCAD) deficiency | NP_000008.1 |
| medium-chain acyl-CoA dehydrogenase (MCAD) | medium-chain acyl-CoA dehydrogenase (MCAD) deficiency | NP_000007.1, NP_001120800.1, NP_001272971.1, NP_001272972.1, NP_001272973.1 |
| Myotubularin 1 (MTM1) | X-linked myotubular myopathy | NP_000243.1 |
| Myophosphorylase (PYGM) | McArdle disease (glycogen storage disease type V, myophosphorylase deficiency) | NP_001158188.1, NP_005600.1 |
| Lipoprotein lipase (LPL) | LPL deficiency | NP_000228.1 |
| sFLTOI (VEGF/PIGF (placental growth factor) binding domain of human VEGFRI/Flt-1 (hVEGFRI) fused to the Fe portion of human IgG(I) through a polyglycine linker) | Age-related macular degeneration | SEQ ID NO: 2, 8, 21, 23, or 25 of W02009105669 |
| Glucocerebrosidase (GC) | Gaucher disease | NP_000148.2, NP_001005741.1, NP_001005742.1, NP_001165282.1, NP_001165283.1 |
| Calsequestrin 2 (CASQ2) | Catecholaminergic polymorphic ventricular tachycardia (CPVT) | NP_001223.2 |
| UDP glucuronosyltransferase 1 family member A1 (UGT1A1) | Crigler-Najjar syndrome | NP_000454.1 |
| Glucose 6-phosphatase (G6Pase) | GSD-Ia | NP_000142.2, NP_001257326.1 |
| Omithine carbamoyltransferase (OTC) | OTC deficiency | NP_000522.3 |
| Cystathionine-β-synthase (CBS) | Homocystinuria | NP_000062.1, NP_001171479.1, NP_001171480.1 |
| Factor VIII (F8) | Haemophilia A | NP_000123.1, NP_063916.1 |
| Hemochromatosis (HFE) | Hemochromatosis | NP_000401.1, NP_620572.1, NP_620573.1, NP_620575.1, NP_620576.1, NP_620577.1, NP_620578.1, NP_620579.1, NP_620580.1 |
| Low density lipoprotein receptor (LDLR) | Phenylketonuria (PKU) | NP_000518.1, NP_001182727.1, NP_001182728.1, NP_001182729.1, NP_001182732.1 |
| Galactosidase, α (AGA) | Fabry disease | NP_000160.1 |
| Phenylalanine hydroxylase (PAH) | Hypercholesterolaemia or Phenylketonuria (PKU) | NP_000268.1 |
| Propionyl CoA carboxylase, alpha polypeptide (PCCA) | Propionic acidaemias | NP_000273.2, NP_001121164.1, NP_001171475.1 |

Selection of Donor Cells

In some embodiments, the subject undergoing treatment is the donor that provides cells (e.g., pluripotent cells, such as CD34+ HSCs or HPCs) which are subsequently modified to express one or more therapeutic proteins of the disclosure before being re-administered to the patient. In such cases, withdrawn cells (e.g., CD34+ HSCs or HPCs) may be re-infused into the subject following, for example, incorporation of a transgene encoding one or more therapeutic proteins of the disclosure, and/or disruption of an allelic variant harboring a deleterious mutation), such that the cells may subsequently home to hematopoietic tissue and establish productive hematopoiesis, thereby restoring expression of the transgene in the patient. In cases in which the subject undergoing treatment also serves as the cell donor, the transplanted cells (e.g., HSCs or HPCs) are less likely to undergo graft rejection. This stems from the fact that the infused cells are derived from the patient and express the same HLA class I and class II antigens as expressed by the patient. Alternatively, the subject and the donor may be distinct. In some embodiments, the subject and the donor are related, and may, for example, be HLA-matched. As described herein, HLA-matched donor-recipient pairs have a decreased risk of graft rejection, as endogenous T cells and NK cells within the transplant recipient are less likely to recognize the incoming hematopoietic stem or progenitor cell graft as foreign, and are thus less likely to mount an immune response against the transplant. Exemplary HLA-matched donor-recipient pairs are donors and recipients that are genetically related, such as familial donor-recipient pairs (e.g., sibling donor-recipient pairs). In some embodiments, the subject and the donor are HLA-mismatched, which occurs when at least one HLA antigen, in particular with respect to HLA-A, HLA-B and HLA-DR, is mismatched between the donor and recipient. To reduce the likelihood of graft rejection, for example, one haplotype may be matched between the donor and recipient, and the other may be mismatched.

Pharmaceutical Compositions and Dosing

In cases in which a subject is administered a population of cells that together express one or more therapeutic proteins of the disclosure, the number of cells administered may depend, for example, on the expression level of the desired protein(s), the patient, pharmaceutical formulation methods, administration methods (e.g., administration time and administration route), the patient's age, body weight, sex, severity of the disease being treated, and whether or not the patient has been treated with agents to ablate endogenous pluripotent cells (e.g., endogenous CD34+ cells, hematopoietic stem or progenitor cells, or microglia, among others). The number of cells administered may be, for example, from $1\times10^4$ cells/kg to $1\times10^{14}$ cells/kg, or more. Cells may be administered in an undifferentiated state, or after partial or complete differentiation into a target cell type. The number of pluripotent cells may be administered in any suitable dosage form.

EXAMPLES

The following examples are put forth so as to provide those of ordinary skill in the art with a description of how the compositions and methods described herein may be used, made, and evaluated, and are intended to be purely exemplary of the disclosure and are not intended to limit the scope of what the inventors regard as their disclosure.

Example One. Poloxamers, when Used at Low Concentrations, Serve to Increase Viral Transduction Efficiency This example describes a series of experiments designed to evaluate the effect of poloxamers, particularly poloxamer P407, on lentiviral transduction efficiency. Human CD34+ hematopoietic stem cells were mobilized into peripheral circulation and isolated from donor subjects. Cells were cultured in the presence of a lentiviral vector at a multiplicity of infection of 10. The lentiviral vector used in these experiments contained a transgene encoding green fluorescent protein (GFP), enabling the detection of transgene-expressing cells by monitoring fluorescence at about 510 nm.

During the transduction procedure, cells were exposed to the GFP-encoding lentiviral vector either alone or in combination with poloxamer P407 at a concentration of 7 μg/ml, 10 μg/ml, or 100 μg/ml. For cells transduced in the presence of poloxamer, the cells were exposed to the lentivirus and P407 simultaneously. After 18 hours of incubation, cells were washed to remove the lentivirus (and the poloxamer, for co-cultured cells). The proportion of transgene-expressing cells and the vector copy number of each population of cells was then assessed 12 days after the transduction procedure. The results of these studies are reported in FIGS. 1A and 1B, respectively.

Figure 1A:
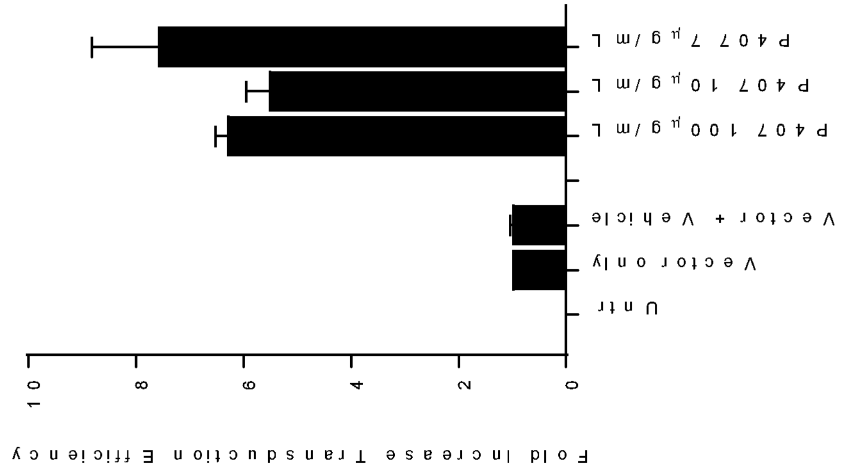
FIG. 1A is a graph showing the effect of poloxamer P407, when incubated with CD34+ hematopoietic stem cells at various concentrations, on lentiviral transduction efficiency, as described in Example One, below. Briefly, CD34+ cells were transduced with a lentiviral vector containing a transgene encoding green fluorescent protein (GFP). Cells were either untreated ("Untr") or incubated with: the lentivirus alone ("Vector only"), the lentivirus in combination with vehicle ("Vector+Vehicle"), or the lentivirus in combination with particular concentrations of P407, as indicated along the x axis. Values along the y axis represent fold increase in the quantity of transduced cells 12 days after exposure to each of the specified conditions relative to the quantity of transduced cells 12 days after treatment with lentiviral vector alone ("Vector only"). Quantities of transduced cells were determined by measuring expression of the encoded transgene, which was evaluated using flow cytometry to detect GFP-mediated fluorescence. Values along the y axis denote the mean±standard error of the mean (SEM) for n=4 independent experiments.

To assess the quantity of transgene-expressing cells, each population of cells was monitored using flow cytometry to detect GFP+ cells. As shown in FIG. 1A, surprisingly, lower concentrations of P407 appear to promote a general increase in the proportion of transgene-expressing cells. Vector copy number was evaluated using polymerase chain reaction techniques designed to measure the number of lentiviral genomes present in each cell. As shown in FIG. 1B, cells transduced with 7 μg/ml of P407 appeared to exhibit elevated vector copy numbers relative to cells transduced with 10 μg/ml.

Example Two. Effects of Poloxamers P407 and P338 on Lentiviral Transduction of Hematopoietic Stem Cells This example describes a series of experiments designed to compare the effects of poloxamers P407 and P338 on lentiviral transduction efficiency. Human CD34+ hematopoietic stem cells were mobilized into peripheral circulation and isolated from donor subjects. Cells were cultured in the presence of a lentiviral vector at a multiplicity of infection of from 5 to 20. The lentiviral vector used in these experiments contained a transgene encoding GFP, enabling the detection of transgene-expressing cells by monitoring fluorescence at about 510 nm.

During the transduction procedure, cells were exposed to the GFP-encoding lentiviral vector either alone or in combination with poloxamer P407 or poloxamer 338 at various concentrations. The proportion of transgene-expressing cells and the vector copy number of each population of cells was then assessed 12 days after the transduction procedure. The results of these studies are reported in FIGS. 2A-2C.

Figure 2A:
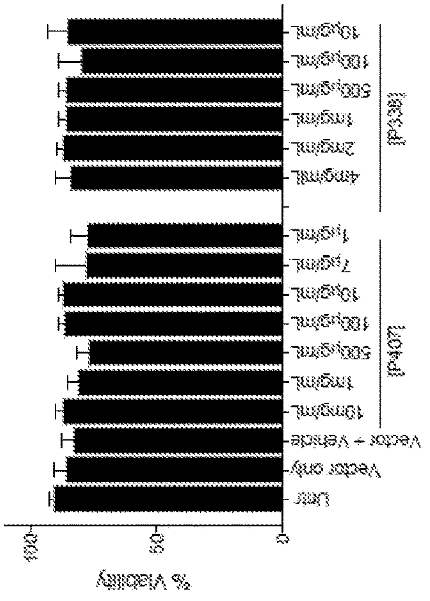
FIGS. 2A-2C are graphs showing the effect of poloxamers P407 and P338 on lentiviral transduction of human hematopoietic stem cells, as described in Example Two, below. CD34+ hematopoietic stem cells from peripheral mobilized blood were either untreated ("Untr") or incubated with a lentiviral vector containing a transgene encoding GFP. Among those cells incubated with a lentiviral vector, cells were either transduced with the vector alone ("Vector only," multiplicity of infection 5-20) or in the presence of various concentrations of poloxamer P407 (final concentration 1 μg/mL-10 mg/mL) or poloxamer P338 (final concentration 10 μg/mL-4 mg/mL).
Figure 2B:
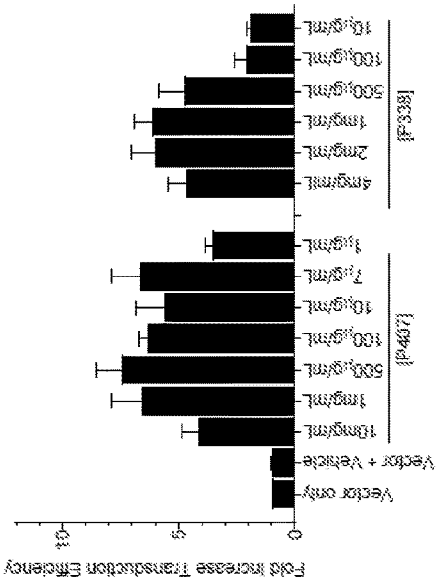
Figure 2C:
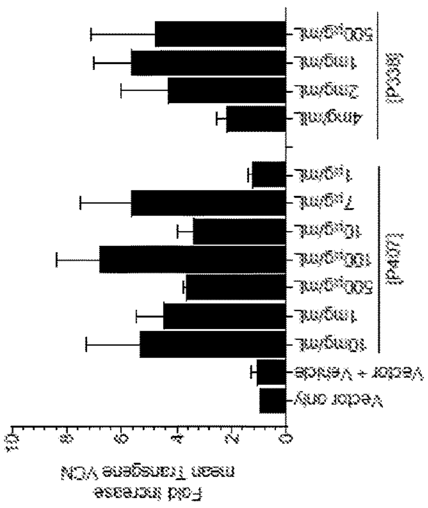

As shown in FIG. 2A, both CD34+ stem cells were tolerant of both poloxamer P407 and poloxamer P338, as neither poloxamer exerted a detrimental effect on cell viability at the concentrations tested. Surprisingly, lower concentrations of P407, such as concentrations less than 10 μg/ml, were found to enhance lentiviral transduction to a greater extent than the same or higher concentrations of poloxamer P338, as shown in FIGS. 2B and 2C.

Example Three. Poloxamers can be Used in Combination with Protamine Sulfate, Cyclosporine H, and/or Lithium Carbonate to Enhance Lentiviral Transduction This example describes a series of experiments designed to evaluate the effects of poloxamers, such as poloxamer P407, in combination with protamine sulfate on lentiviral transduction efficiency. Briefly, human CD34+ hematopoietic stem cells were mobilized into peripheral circulation and isolated from donor subjects in accordance with the method described in Examples One and Two, above. Cells were then transduced with a lentiviral vector encoding GFP in the presence of poloxamer P407 (7 μg/mL) or poloxamer P338 (1 mg/mL), each in combination with protamine sulfate (3.5 μg/mL). At 12 days post-transduction, the percentage of transduced cells was assessed by flow cytometry detection of transgene expression, and VCN was determined by droplet digital PCR detection of integrated transgene sequences in genomic DNA. The results of these experiments are shown in FIGS. 3A and 3B.

Figure 3B:
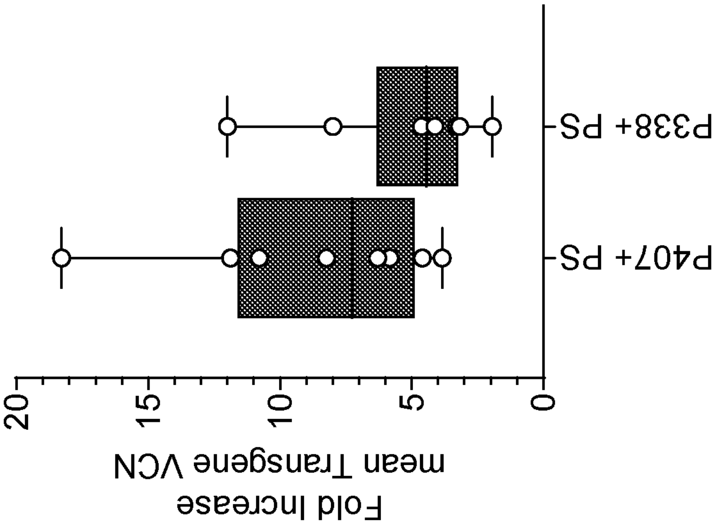
FIGS. 3A and 3B are graphs showing the effect of poloxamer P407 or poloxamer P338 in combination with protamine sulfate on lentiviral transduction of human hematopoietic stem cells, as described in Example Three, below. CD34+ hematopoietic stem cells from peripheral mobilized blood were transduced with a lentiviral vector encoding GFP in the presence of poloxamer P407 (7 μg/mL) or poloxamer P338 (1 mg/mL), in combination with protamine sulfate ("PS," 3.5 μg/mL). The plots summarize the fold change in the percentage of transduced cells as assessed by flow cytometry (FIG. 3A) and mean transgene copy number (VCN, FIG. 3B) induced by the addition of P407 or P338, in combination with protamine sulfate, relative to cells treated with vector alone. At 12 days post-transduction, percentage of transduced cells was assessed by flow cytometry detection of transgene expression, and VCN was determined by droplet digital PCR detection of integrated transgene sequences in genomic DNA. The data show mean±range of n=5-8 independent experiments with healthy human donor cells. Statistical analysis was conducted using a T-test ($p<0.05$).
Figure 3A:
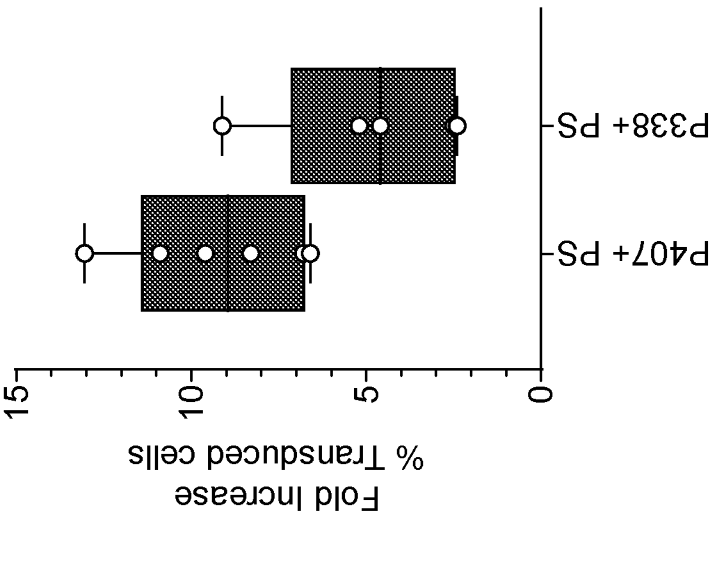

As FIGS. 3A and 3B show, poloxamer P407, in the presence of protamine sulfate, exhibited a surprisingly greater improvement in lentiviral transduction efficiency relative to poloxamer P338 in the presence of protamine sulfate.

Figure 4B:
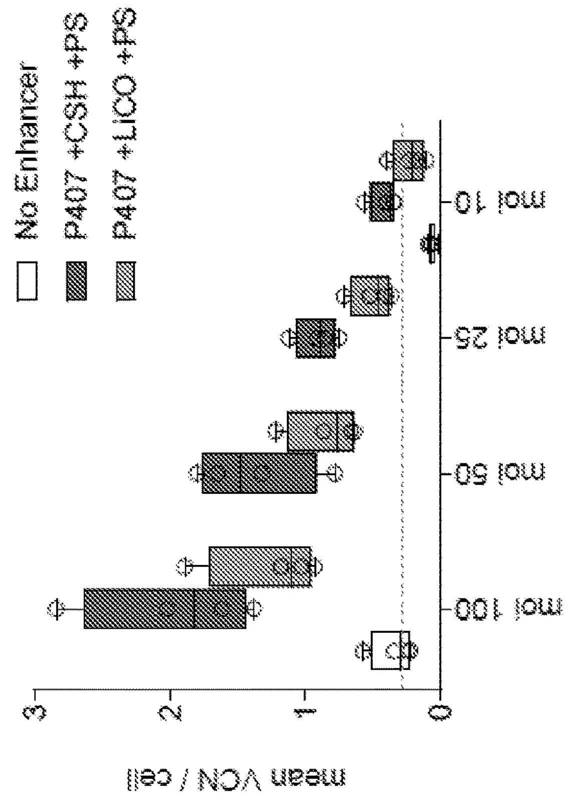
FIGS. 4A and 4B are graphs showing the effect of poloxamer P407 and protamine sulfate, in combination with either cyclosporine H or lithium carbonate, on lentiviral transduction of human hematopoietic stem cells, as described in Example Three, below. CD34+ stem cells freshly isolated from peripheral mobilized blood were transduced with a clinical therapeutic lentiviral vector in the presence of poloxamer P407 (7 μg/mL) in combination with protamine sulfate ("PS," 3.5 μg/mL) and either cyclosporine H ("CSH," 8 μM, dark grey) or lithium carbonate ($Li_2CO_3$, represented in the figures as "LiCO," 2 mM, light grey). Plots summarize the percentage of transduced colonies determined by droplet digital PCR detection of integrated transgene sequences in genomic DNA isolated from Colony Forming Units (CFU, FIG. 4A), and mean transgene copy number (VCN) per cell, detected 12 days post transduction, achieved when using a range of vector doses (moi, multiplicity of infection, FIG. 4B). White bars show transduction efficiency and VCN achieved by addition of vector alone. Data show mean±range of n=4 independent experiments with clinical scale isolation of healthy human donor CD34+ cells.
Figure 4A:
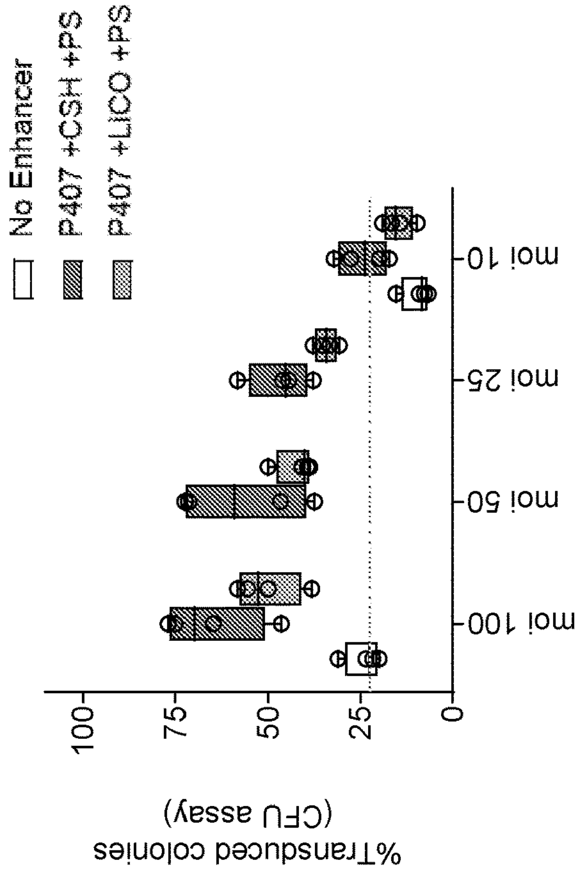

In addition to analyzing the effects of poloxamers in combination with protamine sulfate, a series of experiments was conducted in which poloxamer P407 was combined with protamine sulfate and either cyclosporine H or lithium carbonate ($Li_2CO_3$) in order to evaluate the effects of three-component combinations of agents on lentiviral transduction efficiency. In these experiments, CD34+ stem cells freshly isolated from peripheral mobilized blood were transduced with a clinical therapeutic lentiviral vector encoding a beta-globin transgene in the presence of poloxamer P407 (7 μg/mL) in combination with protamine sulfate (3.5 μg/mL) and either cyclosporine H (8 μM) or $Li_2CO_3$, (2 mM). The results of these experiments are shown in FIGS. 4A and 4B, as well as in Table 3, below.

TABLE 3

Effects of poloxamer P407, protamine sulfate, and either cyclosporine H or $Li_2CO_3$ on lentiviral transduction efficiency

| Transduction Conditions | Mean VCN (range) in eryth. LC (MOI 100)[1] | Mean VCN (range) in myel. LC (MOI 100)[2] | Mean (range) % Transduction (MOI 100)[3] | Range VCN per cell in total CFU/ only BFU (MOI 100)[4] | Range % transduction (MOI 10-20) | Range VCN per cell in CFU (MOI 10-20) | n |
|---|---|---|---|---|---|---|---|
| Vector only | 0.37 (0.18-0.82) | 0.24 (0.18-0.34) | 28.3 (22-31) | 0.4-3.9/ 0.8-6.7 | 13-28 | 0.15-0.36 | 5 |
| P407 + PS + CSH | 3.4 (3.02-4.05) | 1.81 (1.38-2.32) | 76.9 (65-94) | 2.1-3.4/ 0.8-4.1 | 35-65 | 0.76-1.44 | 4 |
| P407 + PS + $Li_2CO_3$ | 1.74 (0.73-2.9) | 1.37 (0.93-2.33) | 63 (50-78) | 0.9-3.1/ 1.2-2.6 | 33-64 | 0.56-0.90 | 4 |

[1, 2]Mean VCN (and VCN range) detected in bulk liquid cultures for erythroid and myeloid differentiation

[3]Range shows percentage of LV+ colonies detected of total colonies screened in CFU assays

[4]Shows the lower and upper range of VCN/cell detected within all LV+ colonies detected within a CFU assay, followed by the range of VCN detected within LV+ BFU-E colonies within each CFU assay (n = 4-5 independent healthy donors)

As the results in FIGS. 4A, 4B, and Table 3 show, poloxamers, such as poloxamer P407, can be used to enhance lentiviral transduction efficiency in the presence of additional agents, such as protamine sulfate, cyclosporine H, and $Li_2CO_3$.

OTHER EMBODIMENTS

Various modifications and variations of the described disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosure that are obvious to those skilled in the art are intended to be within the scope of the disclosure.

Other embodiments are in the claims.

The invention claimed is:

1. A method of transducing a eukaryotic cell to express a transgene, the method comprising contacting the cell with (i) a viral vector encoding the transgene and (ii) a poloxamer, wherein the concentration of the poloxamer, when contacted with the cell, is less than 10 μg/ml.

2. The method of claim 1, wherein the cell is:
(a) a mammalian cell;
(b) a pluripotent cell;
(c) a CD34+ cell;
(d) an embryonic stem cell;
(e) an induced pluripotent stem cell; or
(f) a hematopoietic stem cell (HSC) or a hematopoietic progenitor cell (HPC).

3. The method of claim 2, wherein the mammalian cell is a human cell.

4. The method of claim 1, further comprising contacting the cell with a substance that reduces activity and/or expression of protein kinase C (PKC).

5. The method of claim 4, wherein the substance that reduces activity and/or expression of PKC activates Akt signal transduction and/or is a PKC inhibitor or an agent that reduces translation of a ribonucleic acid (RNA) transcript encoding PKC.

6. The method of claim 5, wherein the agent comprises a nucleic acid, such as an interfering RNA or an antisense oligonucleotide.

7. The method of claim 5, wherein the PKC inhibitor is a compound represented by formula (I)

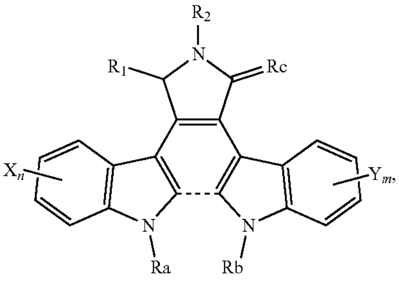

(I)

wherein $R_1$ is H, OH, optionally substituted alkoxy, optionally substituted acyloxy, optionally substituted amino, optionally substituted alkylamino, optionally substituted amido, halogen, optionally substituted $C_{1-6}$ alkyl, optionally substituted $C_{2-6}$ alkenyl, optionally substituted $C_{2-6}$ alkynyl, optionally substituted acyl, optionally substituted alkoxycarbonyl, oxo, thiocarbonyl, optionally substituted carboxy, or ureido;

$R_2$ is H, optionally substituted $C_{1-6}$ alkyl, optionally substituted $C_{2-6}$ alkenyl, optionally substituted $C_{2-6}$ alkynyl, or optionally substituted acyl;

$R_a$ and $R_b$ are each, independently, H, optionally substituted $C_{1-6}$ alkyl, optionally substituted $C_{2-6}$ alkenyl, or optionally substituted $C_{2-6}$ alkynyl, optionally substituted and optionally fused aryl, optionally substituted and optionally fused heteroaryl, optionally substituted and optionally fused cycloalkyl, or optionally substituted and optionally fused heterocycloalkyl, or $R_a$ and $R_b$, together with the atoms to which they are bound, are joined to form an optionally substituted and optionally fused heterocycloalkyl ring;

$R_c$ is O, $NR_d$, or S;

$R_d$ is H, optionally substituted $C_{1-6}$ alkyl, optionally substituted $C_{2-6}$ alkenyl, or optionally substituted $C_{2-6}$ alkynyl;

each X is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

each Y is, independently, halogen, optionally substituted haloalkyl, cyano, optionally substituted amino, hydroxyl, thiol, optionally substituted alkoxy, optionally substituted alkylthio, optionally substituted acyloxy, optionally substituted alkoxycarbonyl, optionally substituted carboxy, ureido, optionally substituted alkyl sulfonyl, optionally substituted aryl sulfonyl, optionally substituted heteroaryl sulfonyl, optionally substituted cycloalkyl sulfonyl, optionally substituted heterocycloalkyl sulfonyl, optionally substituted alkyl sulfanyl, optionally substituted aryl sulfanyl, optionally substituted heteroaryl sulfanyl, optionally substituted cycloalkyl sulfanyl, optionally substituted heterocycloalkyl sulfanyl, optionally substituted alkyl sulfinyl, optionally substituted aryl sulfinyl, optionally substituted heteroaryl sulfinyl, optionally substituted cycloalkyl sulfinyl, optionally substituted heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

--- represents a bond that is optionally present;

n is an integer from 0-4; and m is an integer from 0-4;

or a salt thereof.

8. The method of claim 1, wherein the concentration of the poloxamer, when contacted with the cell, is from about 10 ng/ml to about 9 μg/ml.

9. The method of claim 1, wherein the poloxamer:

(a) has an average molar mass of polyoxypropylene subunits of greater than 2,050 g/mol, 2,250 g/mol, 2,750 g/mol, 3,250 g/mol, or 3,625 g/mol;

(b) has an average molar mass of polyoxypropylene subunits of from about 2,050 g/mol to about 4,000 g/mol;

(c) has an average ethylene oxide content of greater than 40%, 50%, 60%, or 70% by mass;

(d) has an average molar mass of greater than 10,000 g/mol, 11,000 g/mol, 12,000 g/mol, or 12,500 g/mol;

(e) has an average molar mass of from about 10,000 g/mol to about 15,000 g/mol; or (f) is P407, P338, P288, or P188.

10. The method of claim 1, wherein the viral vector;

(a) is selected from the group consisting of a Retroviridae family virus, an adeno-associated virus, an adenovirus, a parvovirus, a coronavirus, a rhabdovirus, a paramyxovirus, a picornavirus, an alphavirus, a herpes virus, and a poxvirus; or (b) is a psuedotyped viral vector.

11. The method of claim 10, wherein:

(a) the Retroviridae family viral vector is a lentiviral vector; or (b) comprises a central polypurine tract, a woodchuck hepatitis virus post-transcriptional regulatory element, a 5'-LTR, HIV signal sequence, HIV Psi signal 5'-splice site, delta-GAG element, 3'-splice site, and a 3'-self inactivating LTR.

12. The method of claim 1, wherein;

(a) the contacting occurs ex vivo;

(b) the cell is further contacted with a cyclosporine, such as cyclosporine A or cyclosporine H;

(c) the cell is further contacted with an activator of prostaglandin E receptor signaling, such as prostaglandin E2;

(d) the cell is further contacted with a polycationic polymer, such as polybrene, protamine sulfate, polyethylenimine, or a polyethylene glycol/poly-L-lysine block copolymer; or (e) the cell is spun by centrifugation while being contacted with the viral vector.

13. A method of expressing a transgene in a subject, delivering a population of genetically modified cells to a subject, or providing cell therapy to a subject in need thereof, the method comprising administering to the subject a population of cells that have been modified in accordance with the method of claim 1 or progeny thereof.

14. The method of claim 13, wherein the cells are allogeneic, HLA-matched, or autologous with respect to the subject.

15. The method of claim 13, wherein:

(a) prior to the contacting, a population of precursor cells is isolated from the subject or a donor, and wherein the precursor cells are expanded ex vivo to yield the population of cells being administered to the subject;

(b) prior to isolation of the precursor cells from the subject or donor, the subject or donor is administered one or more pluripotent cell mobilization agents;

(c) prior to administering the population of cells to the subject, a population of endogenous pluripotent cells is ablated in the subject by administration of one or more conditioning agents to the subject;

(d) the method further comprises ablating a population of endogenous pluripotent cells in the subject by administering to the subject one or more conditioning agents prior to administering to the subject the population of cells; and/or (e) upon administration of the population of cells to the subject, the administered cells, or progeny thereof, differentiate into one or more cell types selected from megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells, T-lymphocytes, and B-lymphocytes.

16. The method of claim 15, wherein the precursor cells are CD34+ HSCs, and wherein the precursor cells are expanded without loss of HSC functional potential, or wherein prior to administering the population of cells to the subject, a population of endogenous pluripotent cells is ablated in the subject by administration of one or more conditioning agents to the subject.

17. The method of claim 13, wherein the subject has been diagnosed as having a deficiency of an endogenous protein encoded by the transgene.

18. The method of claim 17, wherein the subject has been diagnosed as having a disease set forth in Table 2.

19. The method of claim 1, wherein the transgene encodes a beta-globin protein.

20. A population of eukaryotic cells that have been modified in accordance with the method of claim 1.

* * * * *

SEQUENCE LISTING

```
<160> NUMBER OF SEQ ID NOS: 2

<210> SEQ ID NO 1
<211> LENGTH: 441
<212> TYPE: DNA
<213> ORGANISM: Homo sapiens

<400> SEQUENCE: 1

atggtgcatc tgaccccgga agaaaaaagc gcggtgaccg cgctgtgggg caaagtgaac      60

gtggatgaag tgggcggcga agcgctgggc cgcctgctgg tggtgtatcc gtggacccag     120

cgcttttttg aaagctttgg cgatctgagc accccggatg cggtgatggg caacccgaaa     180

gtgaaagcgc atggcaaaaa agtgctgggc gcgtttagcg atggcctggc gcatctggat     240

aacctgaaag gcacctttgc gaccctgagc gaactgcatt gcgataaact gcatgtggat     300

ccggaaaact ttcgcctgct gggcaacgtg ctggtgtgcg tgctggcgca tcattttggc     360

aaagaattta ccccgccggt gcaggcggcg tatcagaaag tggtggcggg cgtggcgaac     420

gcgctggcgc ataaatatca t                                               441


<210> SEQ ID NO 2
<211> LENGTH: 147
<212> TYPE: PRT
<213> ORGANISM: Homo sapiens

<400> SEQUENCE: 2

Met Val His Leu Thr Pro Glu Glu Lys Ser Ala Val Thr Ala Leu Trp
1               5                   10                  15

Gly Lys Val Asn Val Asp Glu Val Gly Gly Glu Ala Leu Gly Arg Leu
            20                  25                  30

Leu Val Val Tyr Pro Trp Thr Gln Arg Phe Phe Glu Ser Phe Gly Asp
        35                  40                  45

Leu Ser Thr Pro Asp Ala Val Met Gly Asn Pro Lys Val Lys Ala His
    50                  55                  60

Gly Lys Lys Val Leu Gly Ala Phe Ser Asp Gly Leu Ala His Leu Asp
65                  70                  75                  80

Asn Leu Lys Gly Thr Phe Ala Thr Leu Ser Glu Leu His Cys Asp Lys
                85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Gly Val Ala Asn Ala Leu Ala His
    130                 135                 140

Lys Tyr His
145
```